United States Patent
Jessell et al.

(10) Patent No.: US 6,566,092 B1
(45) Date of Patent: *May 20, 2003

(54) DNA ENCODING A VERTEBRATE HOMOLOG OF HEDGEHOG, VHH-1, EXPRESSED BY THE NOTOCHORD, AND USES THEREOF

(75) Inventors: Thomas M. Jessell; Jane Dodd, both of New York, NY (US); Henk Roelink, Seattle, WA (US); Thomas Edlund, Umea (SE)

(73) Assignee: The Trustees of Columbia University in the City of New York, New York, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/700,393
(22) PCT Filed: Feb. 24, 1995
(86) PCT No.: PCT/US95/02315
§ 371 (c)(1), (2), (4) Date: Feb. 27, 1997
(87) PCT Pub. No.: WO95/23223
PCT Pub. Date: Aug. 31, 1995

Related U.S. Application Data

(63) Continuation-in-part of application No. 08/202,040, filed on Feb. 25, 1994, now abandoned.

(51) Int. Cl.⁷ ........................ C12N 15/12; C12N 15/09; C12N 5/00; C12P 21/06
(52) U.S. Cl. ........................ 435/69.1; 435/6; 435/320.1; 435/325; 536/23.1; 536/23.5
(58) Field of Search ............................... 536/23.1, 23.5, 536/24.31; 435/6, 320.1, 325, 69.1

(56) References Cited

U.S. PATENT DOCUMENTS 5,196,316 A * 3/1993 Iwasaki et al.
5,789,543 A * 8/1998 Ingham et al. ............... 530/350
5,844,079 A * 12/1998 Ingham et al.

FOREIGN PATENT DOCUMENTS

WO  WO9518556  * 7/1995
WO  WO9617924  * 6/1996

OTHER PUBLICATIONS

Sambrook et al, "Molecular cloning: A Laboratory Manual" second edition (1989) pp 16.3–16.4, 17.2, 8.46–8.74, 9.2–9.3.*
Basler, K. and Struhl, G. (1994) "Compartment boundaries and the control of Drosophila limb pattern by hedgehog protein." *Nature* 386:208–214.
Chang, D.T., et al. (1994) "Products, genetic linkage and limb patterning activity of a murine hedgehog gene." *Development* 120:3339–3353.
Herberlain, U., et al., (1993) "TGFB homolog dpp and the segment polarity gene hedgehog are required for propagation of a morphogenetic wave in the Drosophila retina." *Cell* 75: 913–926.
Heemskerk, J. and DiNardo, S. (1994) "Drosophila hedgehog acts as a morphogen in cellular patterning." *Cell* 76:449–460.
Hidalgo, A. and Ingham, P. (1990) "Cell patterning in the Drosophila segment spatial regulation of the segment polarity gene patched." *Development* 110: 291–301.
Hynes, M., et al. (1995) "Control of neuronal diversity by the floor plate: contact–mediated induction of midbrain dopaminergic neurons." *Cell* 80: 95–101.
Ingham, P.W. (1993) "Localized hedgehog activity controls spatial limits of wingless transcription in the Drosphila embryo."
*Nature* 366: 560–582.
Jessell, T.M. and Dodd, J. (1992) "Floor plate–derived signals and the control of neural cell pattern in vertebrates." *Harvey Lect.* 85:87–128.
Krauss, S., et al. (1993) "A functionally conserved homolog of the Drosophila segment polarity gene hedgehog is expressed in tissues with polarizing activity in zebrafish embryos." *Cell* 75: 1431–1444.
Lee, J.J., et al. (1992) "Secretion and localization transcription suggest a role in positional signaling for products of the segmentation gene hedgehog."*Cell* 71: 33–50.
Ma, C., et al. (1993) "The segment polarity gene hedgehog is required for progression of the morphogenetic furrow in the developing Drosophila eye." *Cell* 75: 927–938.
Mohler, J. (1988) "Requirements for hedgehog, a segmental polarity gene, in patterning larval and adult cuticle of Drosophila." *Genetic* 120: 1061–1072.
Mohler, J. and Vani, K. (1992) "Molecular organization and embryonic expression of the hedgehog gene involved in cell–cell communication in segmental patterning of Drosophila." *Development* 115:957–971.

(List continued on next page.)

*Primary Examiner*—Marianne P. Allen
(74) *Attorney, Agent, or Firm*—John P. White; Cooper & Dunham LLP

(57) ABSTRACT

This invention provides an isolated nucleic acid molecule encoding a vhh-1 protein, an isolated protein which is a vhh-1 protein, vectors comprising an isolated nucleic acid molecule encoding a vhh-1 protein, mammalian cells comprising such vectors, antibodies directed to a vhh-1 protein, nucleic acid probes useful for detecting a nucleic acid molecule encoding a vhh-1 protein, pharmaceutical compositions related to the vhh-1 proteins, nonhuman transgenic animals which express a normal or a mutant vhh-1 protein. This invention further provides methods for inducing differentiation of floor plate cell, motor neuron, generating ventral neurons and treatments for alleviating abnormalities associated with the vhh-1 protein.

12 Claims, 81 Drawing Sheets

OTHER PUBLICATIONS

Nusslein–Volhard, C. and Wieschaus, E. (1992) "Mutations affecting segment number and polarity in Drosophila." *Nature* 287: 795–801.

Placzek, M., et al. (1990) "Orientation of commissural axons in vitro in response to a floor plate derived chemoattractant." *Development* 110: 19–30.

Placzek, M., et al. (1990) "Mesodermal control of neural cell identity: floor plate induction by the notochord." *Science* 250: 985–988.

Placzek, M., et al. (1991) "Control of dorso–ventral pattern in vertebrate neural development induction and polarizing properties of the floor plate." *Development* 113 (Suppl. 2): 105–122.

Placzek, M., et al. (1992) "Induction of floor plate differentiation by contact–dependent, homeogenetic signals." *Development* 117:205–218.

Roelink, H. and Nusse, R. (1991) "Expression of two members of the Wnt family during mouse development: restricted temporal and spatial patterns in the developing neural tube." *Genes & Dev.* 5: 381–388.

Roelink, H., et al. (1994) "Floor plate and motor neuron induction by vhh–1, a vertebrate homolog of hedgehog expressed by the notochord." *Cell* 76: 761–775.

Tabata, T. (1992) "The Drosophila hedgehog gene is expressed specifically in posterior compartment cells and is a target of engrailed regulation." *Genes Dev.* 6: 2835–2646.

Tashiro, S. (1993) "Structure and expression of hedgehog, a Drosophila segment–polarity gene required for cell–cell communication." *Gene* 124: 183–189.

Taylor, A.M., et al. (1993) "Contrasting distrubutions of patched and hedgehog proteins in the Drosophila embryo." *Mech. Dev.* 42: 89–96.

Yamada, T., et al. (1991)"Control of cell pattern in the developing nervous system: polarizing activity of the floor plate and notochord." *Cell* 64: 635–647; and.

Yamada, T., et al. (1993) "Control of cell pattern in the neural tube: motor neuron induction by diffusible factors from notochord and floor plate." *Cell* 73: 673–686.

Riddle, R.D. (1993) "Sonic hedgehog mediates the polarizing activity of the ZPA." *Cell* 75: 1401–1416; and.

Echelard, Y. (1993) "Sonic hedgehog, a member of a family of putative signaling molecules, is implicated in the regulation of CNS polarity." *Cell* 75: 1417–1430.

* cited by examiner

FIGURE 1A

```
TGG GTC TAC TAT GAA TCC AAA GCT CGC ATC CAC TGC TCT GTG AAA GCA      878
Trp Val Tyr Tyr Glu Ser Lys Ala Arg Ile His Cys Ser Val Lys Ala
        175                 180                 185

GAG AAC TCC GTG GCG GCC AAA TCT GAC GGC TGC TTC CCG GGA TCA GCC      926
Glu Asn Ser Val Ala Ala Lys Ser Asp Gly Cys Phe Pro Gly Ser Ala
        190                 195                 200

ACA GTG CAC CTG GAG CAG GGT GGC ACC AAG TTA GTG AAG GAT CTA AGT      974
Thr Val His Leu Glu Gln Gly Gly Thr Lys Leu Val Lys Asp Leu Ser
205                 210                 215                 220

CCC GGG GAC CGC GTG CTG GCG GCT GAC GAC CAG GGC CGG CTG CTG TAC     1022
Pro Gly Asp Arg Val Leu Ala Ala Asp Asp Gln Gly Arg Leu Leu Tyr
                225                 230                 235

AGC GAC TTC CTC ACC TTC CTG GAC CGC GAC GAA GGT GCC AAG AAG GTC     1070
Ser Asp Phe Leu Thr Phe Leu Asp Arg Asp Glu Gly Ala Lys Lys Val
                240                 245                 250

TTC TAC GTG ATC GAG ACG CGG GAG CCG CGG GAG CGT CTG CTG CTC ACT     1118
Phe Tyr Val Ile Glu Thr Arg Glu Pro Arg Glu Arg Leu Leu Leu Thr
                255                 260                 265

GCC GCG CAC CTG CTC TTC GTG GCG CCG CAC AAC GAC TCC GGG CCC ACT     1166
Ala Ala His Leu Leu Phe Val Ala Pro His Asn Asp Ser Gly Pro Thr
        270                 275                 280

CCG GGA CCG AGC CCA CTC TTC GCC AGC CGC GTG CGT CCG GGG CAG CGC     1214
Pro Gly Pro Ser Pro Leu Phe Ala Ser Arg Val Arg Pro Gly Gln Arg
285                 290                 295                 300

GTG TAC GTG GTG GCT GAA CGC GGC GGG GAC CGC CGG CTG CTG CCC GCC     1262
Val Tyr Val Val Ala Glu Arg Gly Gly Asp Arg Arg Leu Leu Pro Ala
                305                 310                 315

GCG GTG CAC AGC GTA ACG CTA CGA GAG GAG GCG GCG GGT GCG TAC GCG     1310
Ala Val His Ser Val Thr Leu Arg Glu Glu Ala Ala Gly Ala Tyr Ala
                320                 325                 330

CCG CTC ACG GCG GAC GGC ACC ATT CTC ATC AAC CGG GTG CTC GCC TCG     1358
Pro Leu Thr Ala Asp Gly Thr Ile Leu Ile Asn Arg Val Leu Ala Ser
                335                 340                 345

TGC TAC GCA GTC ATC GAG GAG CAC AGC TGG GCA CAC CGG GCC TTC GCG     1406
Cys Tyr Ala Val Ile Glu Glu His Ser Trp Ala His Arg Ala Phe Ala
350                 355                 360

CCC TTC CGC CTG GCG CAC GCG CTG CTG GCC GCG CTG GCA CCC GCC CGC     1454
Pro Phe Arg Leu Ala His Ala Leu Leu Ala Ala Leu Ala Pro Ala Arg
365                 370                 375                 380

ACG GAC GGC GGG GGC GGG GGC AGC ATC CCT GCC CCG CAA TCT GTA GCG     1502
Thr Asp Gly Gly Gly Gly Gly Ser Ile Pro Ala Pro Gln Ser Val Ala
                385                 390                 395

GAA GCG AGG GGC GCA GGG CCG CCT GCG GGC ATC CAC TGG TAC TCG CAG     1550
Glu Ala Arg Gly Ala Gly Pro Pro Ala Gly Ile His Trp Tyr Ser Gln
                400                 405                 410
```

FIGURE 1B

```
TTAAAATCAG GCTCTTTTTG TCTTTTAATT GCCGTCTCGA GACCCAACTC CGATGTGTTC   60

CGTTACCAGC GACCGGCAGC CTGCCATCGC AGCCCCTGTC TGGGTGGGGA TCGGAGACAA  120

GTCCCCTGCA GCAACAGCAG GCAAGGTTAT ATAGGAAGAG AAAGAGCCAG GCAGCGCCAG  180

AGGGAACGAA CGAGCCGAGC GAGGAAGGGA GAGCCGAGCG CAAGGAGGAG CGCACACGCA  240

CACACCCGCG CGTACCAGCT CGCGCACAGA CCGGCGCGGG GACGGCTCGC AAGTCCTCAG  300

GTTCCGCGGA CGAG ATG CTG CTG CTG CTG GCC AGA TGT TTT CTG GTG GCC        350
              Met Leu Leu Leu Leu Ala Arg Cys Phe Leu Val Ala
               1               5                      10

CTT GCT TCC TCG CTG CTG GTG TGC CCC GGA CTG GCC TGT GGG CCC GGC        398
Leu Ala Ser Ser Leu Leu Val Cys Pro Gly Leu Ala Cys Gly Pro Gly
         15              20                      25

AGG GGG TTT GGA AAG AGG CAG CAC CCC AAA AAG CTG ACC CCT TTA GCC        446
Arg Gly Phe Gly Lys Arg Gln His Pro Lys Lys Leu Thr Pro Leu Ala
         30              35                      40

TAC AAG CAG TTT ATC CCC AAC GTA GCC GAG AAG ACC CTA GGG GCC AGC        494
Tyr Lys Gln Phe Ile Pro Asn Val Ala Glu Lys Thr Leu Gly Ala Ser
 45              50                      55                  60

GGC CGA TAT GAA GGG AAG ATC ACA AGA AAC TCC GAA CGA TTT AAG GAA        542
Gly Arg Tyr Glu Gly Lys Ile Thr Arg Asn Ser Glu Arg Phe Lys Glu
                 65                      70                  75

CTC ACC CCC AAT TAC AAC CCC GAC ATC ATA TTT AAG GAT GAG GAA AAC        590
Leu Thr Pro Asn Tyr Asn Pro Asp Ile Ile Phe Lys Asp Glu Glu Asn
                 80                      85                  90

ACT GGA GCA GAC CGG CTG ATG ACT CAG AGG TGC AAA GAC AAG TTA AAT        638
Thr Gly Ala Asp Arg Leu Met Thr Gln Arg Cys Lys Asp Lys Leu Asn
                 95                     100                 105

GCC TTG GCC ATC TCC GTG ATG AAC CAG TGG CCT GGA GTG AAG CTT CGA        686
Ala Leu Ala Ile Ser Val Met Asn Gln Trp Pro Gly Val Lys Leu Arg
         110                 115                     120

GTG ACT GAG GGC TGG GAT GAG GAC GGC CAT CAT TCA GAG GAG TCT CTA        734
Val Thr Glu Gly Trp Asp Glu Asp Gly His His Ser Glu Glu Ser Leu
125              130                     135                     140

CAC TAT GAG GGT CGA GCA GTG GAC ATC ACC ACG TCT GAC AGG GAC CGC        782
His Tyr Glu Gly Arg Ala Val Asp Ile Thr Thr Ser Asp Arg Asp Arg
                 145                     150                     155

AGC AAG TAT GGC ATG CTG GCT CGC CTG GCT GTG GAG GCT GGA TTC GAC        830
Ser Lys Tyr Gly Met Leu Ala Arg Leu Ala Val Glu Ala Gly Phe Asp
                 160                     165                     170
```

FIGURE 1C

```
CTG CTG TAC CAC ATT GGC ACC TGG CTG TTG GAC AGC GAG ACC CTG CAT    1598
Leu Leu Tyr His Ile Gly Thr Trp Leu Leu Asp Ser Glu Thr Leu His
        415                 420                 425

CCC TTG GGA ATG GCA GTC AAG TCC AGC TGAAGTCCGA CGGGACCGGG          1645
Pro Leu Gly Met Ala Val Lys Ser Ser
        430                 435

CAGGGGGCGT GGGGGCGGGC GGGGCGGGAA GCGACTGCCA GATAAGCAAC CGGGAAAGCG  1705

CACGGAAGGA                                                         1715
```

FIGURE 2A-1

```
         1
     hh  MDNHSSVPWA SAASVTCLSL DAKCHSSSSS SSSKSAASSI SAIPQEETQT
         51
  zf vhh .MRLLTRVLL VSLLTLSLVV SGLACGPGRG YGRRRHPKKL
  R  vhh ........... MLLLLARCFL VALASSLLVC PGLACGPGRG FGKRQHPKKL
     hh  MRHIAHTQRC LSRLTSLVAL LLIVLPMVFS PAHSCGPGRG LG.RHRARNL
         101
  zf vhh TPLAYKQFIP NVAEKTLGAS GRYEGKITRN SERFKELTPN YNPDIIFKDE
  R  vhh TPLAYKQFIP NVAEKTLGAS GRYEGKITRN SERFKELTPN YNPDIIFKDE
     hh  YPLVLKQTIP NLSEYTNSAS GPLEGVIRRD SPKFKDLVPN YNRDILFRDE
         151
  zf vhh ENTGADRLMT QRCKDKLNSL AISVMNHWPG VKLRVTEGWD EDGHHFEESL
  R  vhh ENTGADRLMT QRCKDKLNAL AISVMNQWPG VKLRVTEGWD EDGHHSEESL
     hh  EGTGADRLMS KRCKEKLNVL AYSVMNEWPG IRLLVTESWD EDYHHGQESL
         201
  zf vhh HYEGRAVDIT TSDRDKSKYG TLSRLAVEAG FDWVYYESKA HIHCSVKAEN
  R  vhh HYEGRAVDIT TSDRDRSKYG MLARLAVEAG FDWVYYESKA RIHCSVKAEN
     hh  HYEGRAVTIA TSDRDQSKYG MLARLAVEAG FDWVSYVSRR HIYCSVKSDS
```

FIGURE 2A-2

```
       251
zf vhh SVAAKSGGCF PGSALVSLQD GGQKAVKDLN PGDKVLAADS AGNLVFSDFI
R  vhh SVAAKSDGCF PGSATVHLEQ GGTKLVKDLS PGDRVLAADD QGRLLYSDFL
   hh  SISSHVHGCF TPESTALLES GVRKPLGELS IGDRVLSMTA NGQAVYSEVI
       301
zf vhh MFTDRDSTTR RVFYVIETQE PVEKITLTAA HLLFVL.DNS TEDLHTMTAA
R  vhh TFLDRDEGAK KVFYVIETRE PRERLLLTAA HLLFVAPHND SGPTPGPSPL
   hh  LFMDRNLEQM QNFVQLHT.D GGAVLTVTPA HLVSVWQPES ....QKLTFV
       351
zf vhh YASSVRAGQK VMVVD.DSGQ LKSVIVQRIY T....EEQRG SFAPVTAHGT
R  vhh FASRVRPGQR VYVVA.ERGG DRRLLPAAVH SVTLREEAAG AYAPLTADGT
   hh  FADRIEEKNQ VLVRDVETGE LRPQRVVKVG SV.....RSKG VVAPLTREGT
       401
zf vhh IVVDRILASC YAVIEDQGLA HLAFAPARLY YVVSSFLFPQ NSSSRSNATL
R  vhh ILINRVLASC YAVIEEHSWA HRAFAPFRLA HALLAALAPA RTDGGGGGSI
   hh  IVVNSVAASC YAVINSQSLA HWGLAPMRLL STLEAWLPAK EQLHSSPKVV
       451
zf vhh .......... ...QQEGVHW YSRLLYQMGT WLLDSNMLHP LGMSVNSS*
R  vhh PAPQSVAEAR GAGPPAGIHW YSQLLYHIGT WLLDSETLHP LGMAVKSS*
   hh  SSAQ...... ...QQNGIHW YANALYKVKD YVLPQSWRHD *
```

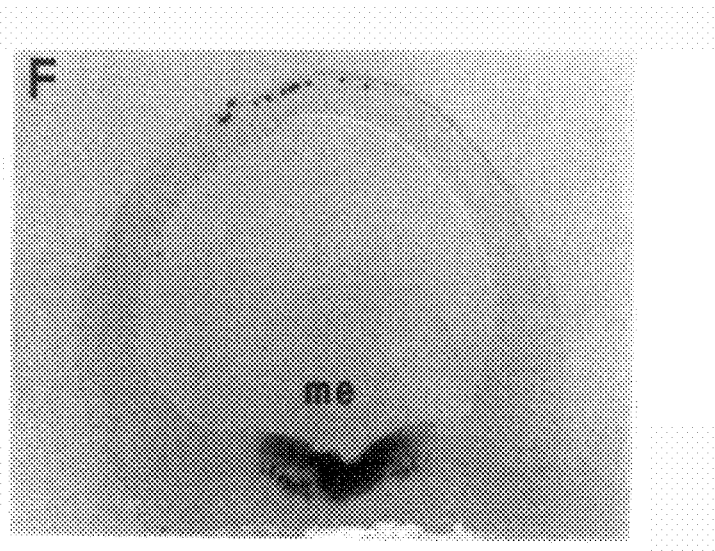
*FIGURE 8F*
*FIGURE 8G*
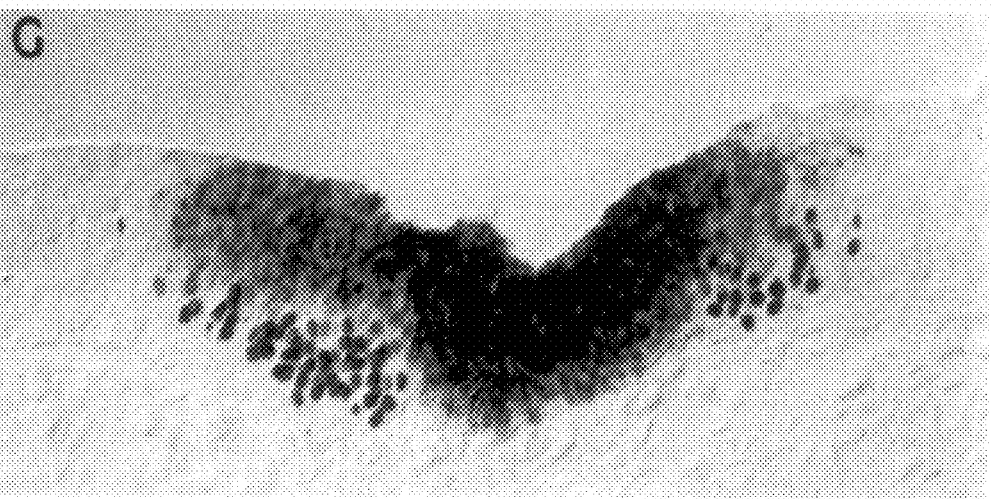
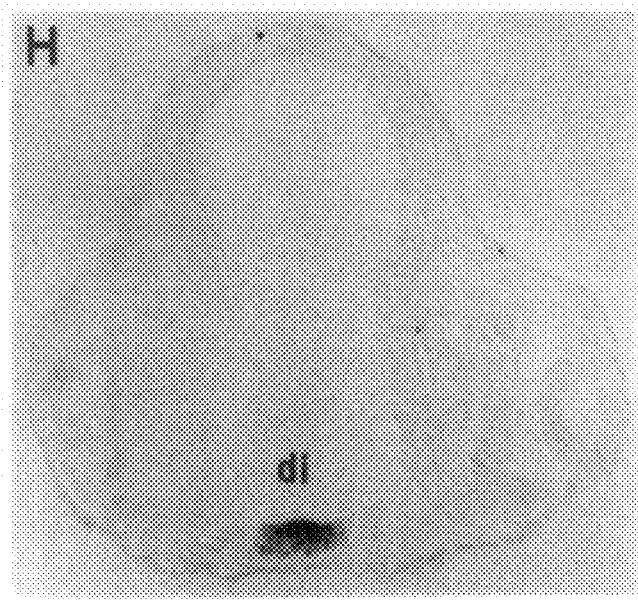
*FIGURE 8H*

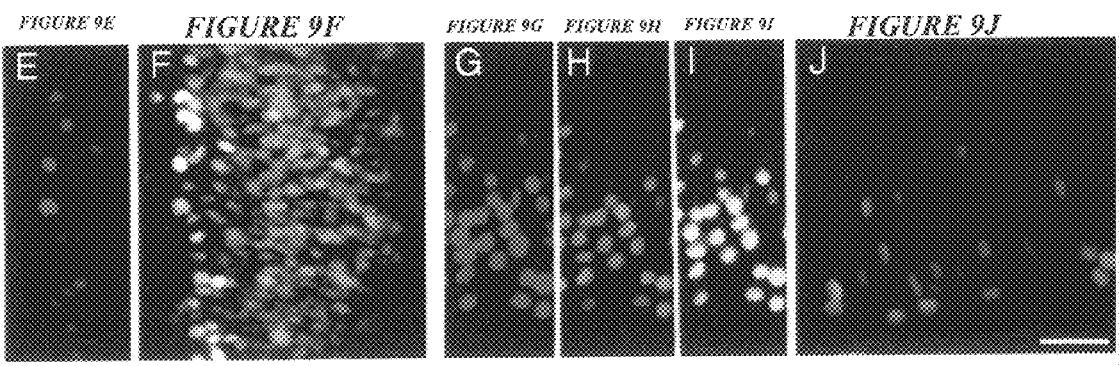

FIGURE 10B 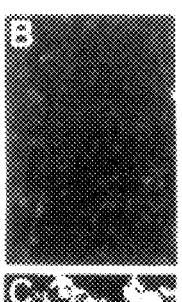 FIGURE 10D 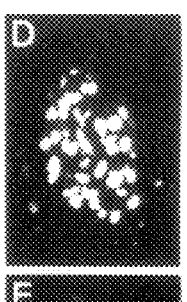 FIGURE 10F 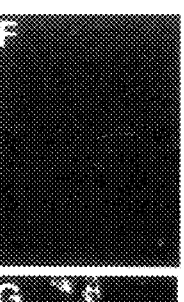 FIGURE 10H 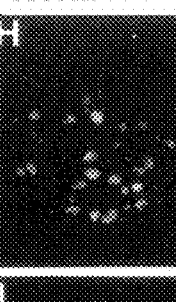 FIGURE 10J 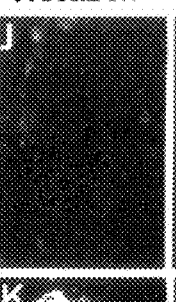 FIGURE 10L 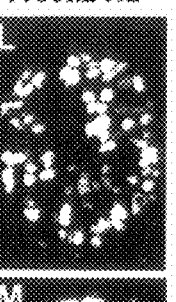
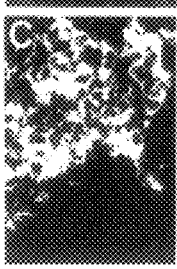 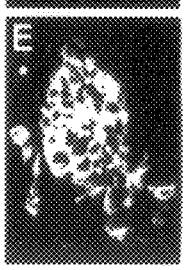  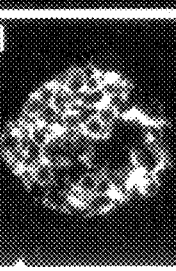  
FIGURE 10C  FIGURE 10E  FIGURE 10G  FIGURE 10I  FIGURE 10K  FIGURE 10M

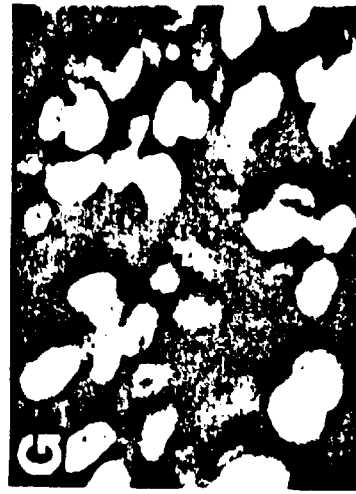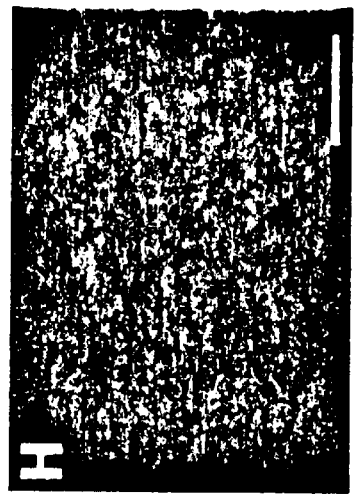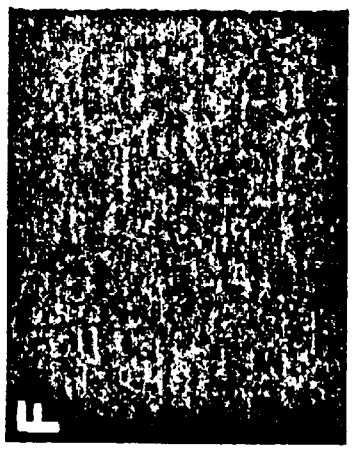

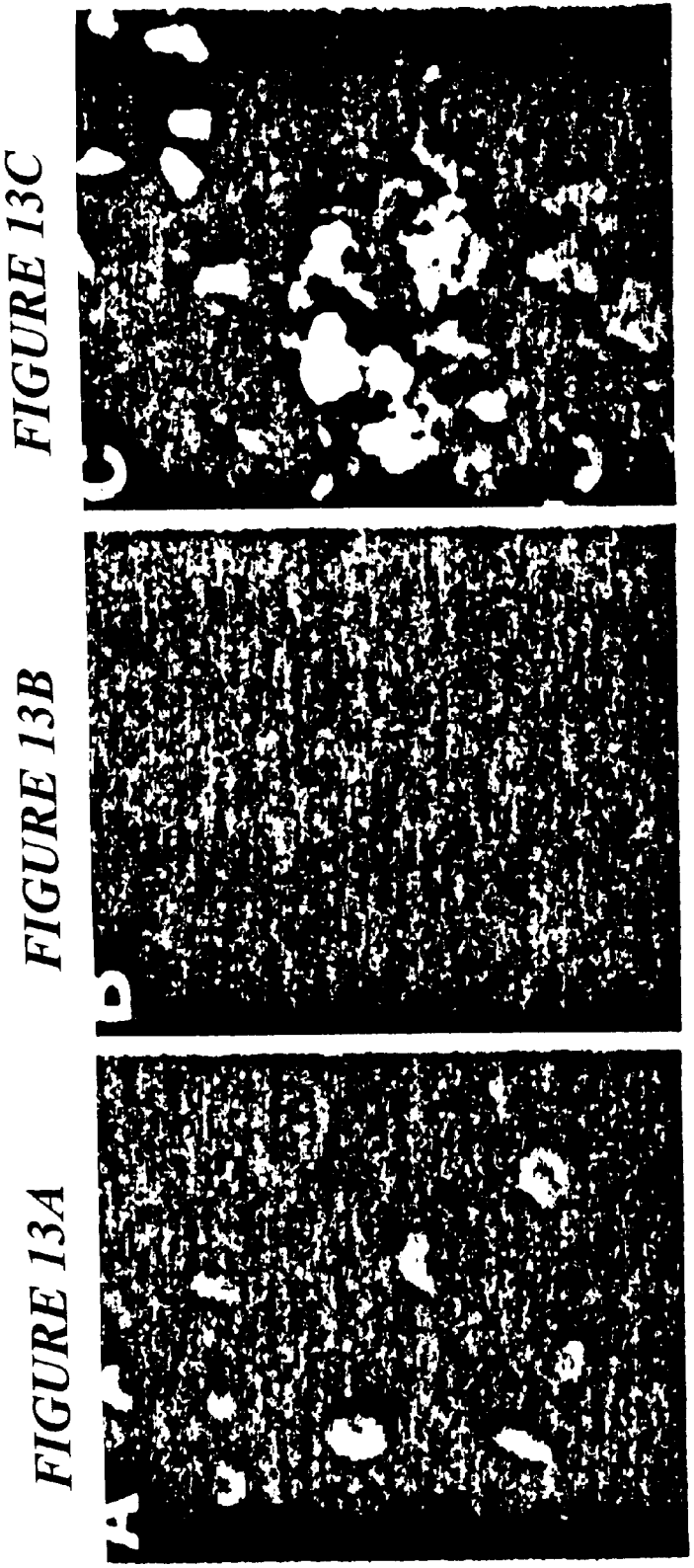

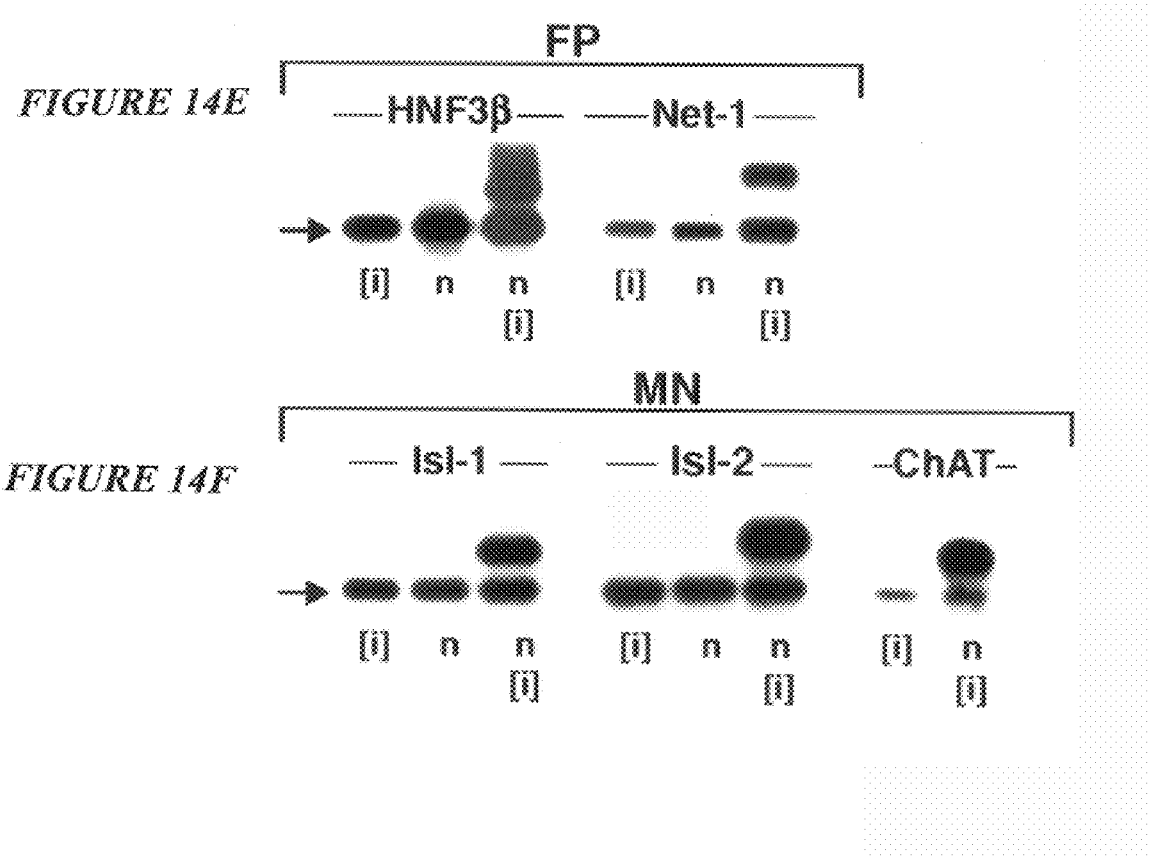

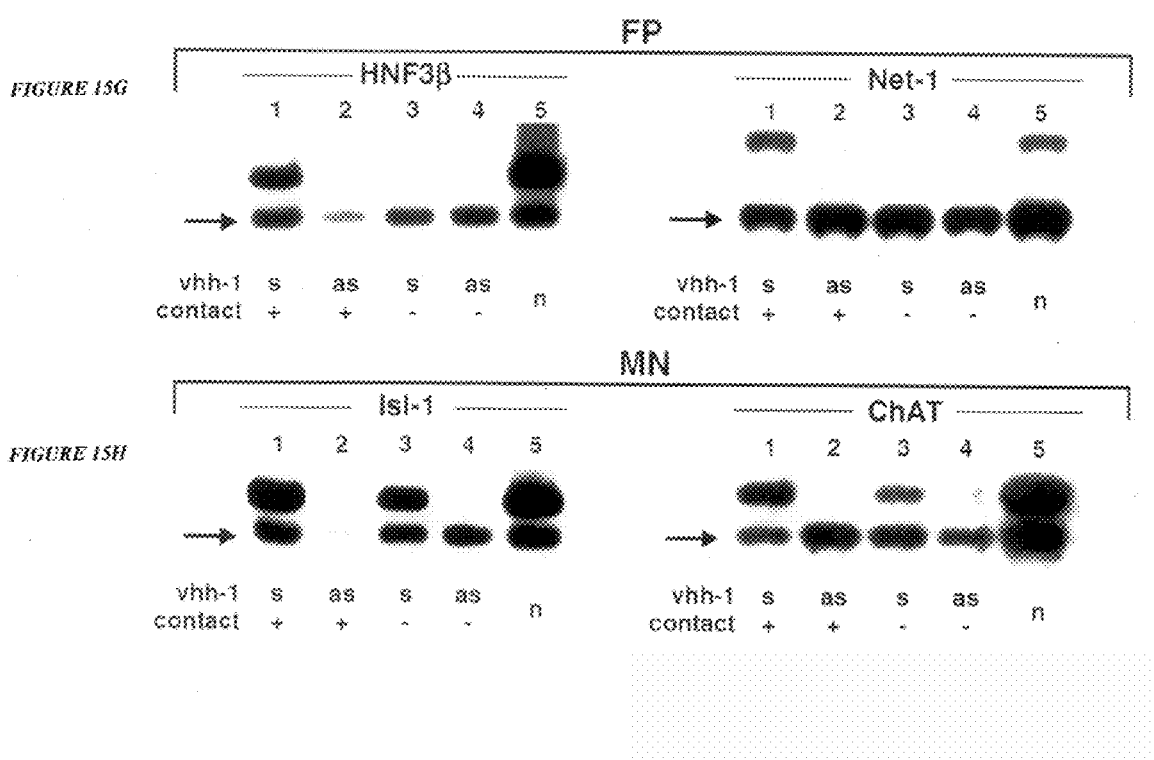

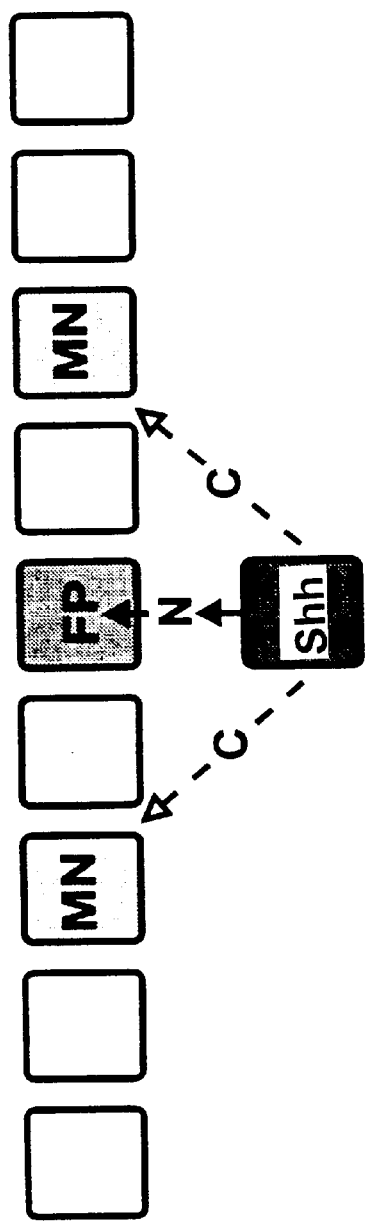
FIGURE 17A floor plate and motor neuron induction by different proteolytic fragments of shh/vhh-1
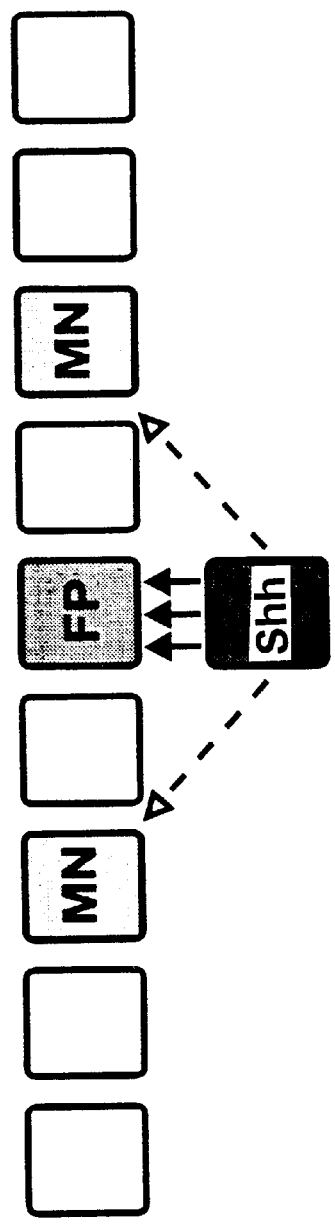
FIGURE 17B floor plate and motor neuron induction by different concentrations of shh/vhh-1

FIGURE 18P
FIGURE 18Q

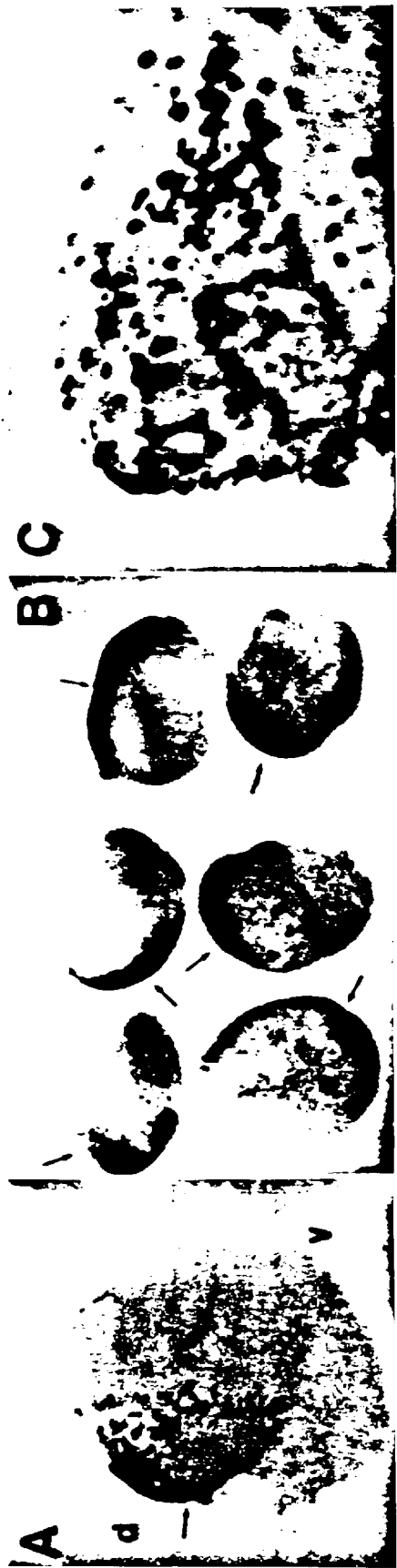

FIGURE 21A FIGURE 21B FIGURE 21C
FIGURE 21D FIGURE 21E FIGURE 21F

FIGURE 22A
FIGURE 22B
FIGURE 22C

FIGURE 22D
FIGURE 22E
FIGURE 22F

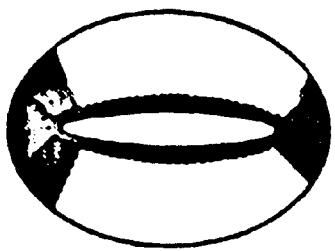
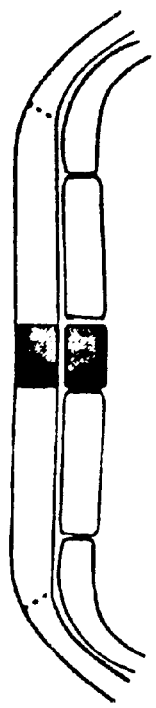
*FIGURE 23B*
expression in injected embryos

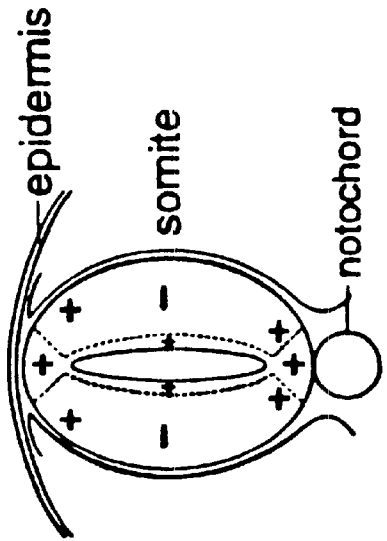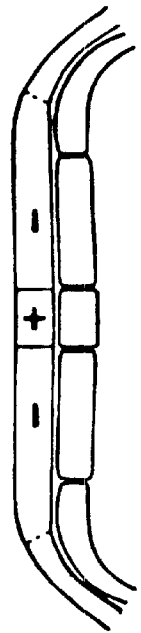
FIGURE 23C
competence of neural tissue molecular interactions

SEQUENCE LISTING

<160> NUMBER OF SEQ ID NOS: 18

<210> SEQ ID NO 1
<211> LENGTH: 1715
<212> TYPE: DNA
<213> ORGANISM: RAT

<400> SEQUENCE: 1

| | | | | | |
|---|---|---|---|---|---|
| ttaaaatcag | gctcttttg | tcttttaatt | gccgtctcga | gacccaactc | cgatgtgttc | 60 |
| cgttaccagc | gaccggcagc | ctgccatcgc | agccctgtc | tgggtgggga | tcggagacaa | 120 |
| gtcccctgca | gcaacagcag | gcaaggttat | ataggaagag | aaagagccag | gcagcgccag | 180 |
| agggaacgaa | cgagccgagc | gaggaaggga | gagccgagcg | caaggaggag | cgcacacgca | 240 |
| cacacccgcg | cgtaccagct | cgcgcacaga | ccggcgcggg | gacggctcgc | aagtcctcag | 300 |
| gttccgcgga | cgagatgctg | ctgctgctgg | ccagatgttt | tctggtggcc | cttgcttcct | 360 |
| cgctgctggt | gtgccccgga | ctggcctgtg | ggcccggcag | ggggtttgga | aagaggcagc | 420 |
| accccaaaaa | gctgacccct | ttagcctaca | agcagtttat | ccccaacgta | gccgagaaga | 480 |
| ccctaggggc | cagcggccga | tatgaaggga | agatcacaag | aaactccgaa | cgatttaagg | 540 |
| aactcacccc | caattacaac | cccgacatca | tatttaagga | tgaggaaaac | actggagcag | 600 |
| accggctgat | gactcagagg | tgcaaagaca | agttaaatgc | cttggccatc | tccgtgatga | 660 |
| accagtggcc | tggagtgaag | cttcgagtga | ctgagggctg | ggatgaggac | ggccatcatt | 720 |
| cagaggagtc | tctacactat | gagggtcgag | cagtggacat | caccacgtct | gacagggacc | 780 |
| gcagcaagta | tggcatgctg | gctcgcctgg | ctgtggaggc | tggattcgac | tgggtctact | 840 |
| atgaatccaa | agctcgcatc | cactgctctg | tgaaagcaga | gaactccgtg | gcggccaaat | 900 |
| ctgacggctg | cttcccggga | tcagccacag | tgcacctgga | gcagggtggc | accaagttag | 960 |
| tgaaggatct | aagtcccggg | gaccgcgtgc | tggcggctga | cgaccagggc | cggctgctgt | 1020 |
| acagcgactt | cctcaccttc | ctggaccgcg | acgaaggtgc | caagaaggtc | ttctacgtga | 1080 |
| tcgagacgcg | ggagccgcgg | gagcgtctgc | tgctcactgc | cgcgcacctg | ctcttcgtgg | 1140 |
| cgccgcacaa | cgactccggg | cccactccgg | gaccgagccc | actcttcgcc | agccgcgtgc | 1200 |

-continued

| | | | | |
|---|---|---|---|---|
| gtccggggca | gcgcgtgtac | gtggtggctg | aacgcggcgg | ggaccgccgg ctgctgcccg | 1260 |
| ccgcggtgca | cagcgtaacg | ctacgagagg | aggcggcggg | tgcgtacgcg ccgctcacgg | 1320 |
| cggacggcac | cattctcatc | aaccgggtgc | tcgcctcgtg | ctacgcagtc atcgaggagc | 1380 |
| acagctgggc | acaccgggcc | ttcgcgccct | tccgcctggc | gcacgcgctg ctggccgcgc | 1440 |
| tggcacccgc | ccgcacggac | ggcggggcg | ggggcagcat | ccctgccccg caatctgtag | 1500 |
| cggaagcgag | gggcgcaggg | ccgcctgcgg | gcatccactg | gtactcgcag ctgctgtacc | 1560 |
| acattggcac | ctggctgttg | gacagcgaga | ccctgcatcc | cttgggaatg gcagtcaagt | 1620 |
| ccagctgaag | tccgacggga | ccgggcaggg | ggcgtggggg | cgggcggggc gggaagcgac | 1680 |
| tgccagataa | gcaaccggga | aagcgcacgg | aagga | | 1715 |

<210> SEQ ID NO 2
<211> LENGTH: 437
<212> TYPE: PRT
<213> ORGANISM: RAT

<400> SEQUENCE: 2

Met Leu Leu Leu Leu Ala Arg Cys Phe Leu Val Ala Leu Ala Ser Ser
 1               5                  10                  15

Leu Leu Val Cys Pro Gly Leu Ala Cys Gly Pro Gly Arg Gly Phe Gly
                20                  25                  30

Lys Arg Gln His Pro Lys Lys Leu Thr Pro Leu Ala Tyr Lys Gln Phe
            35                  40                  45

Ile Pro Asn Val Ala Glu Lys Thr Leu Gly Ala Ser Gly Arg Tyr Glu
        50                  55                  60

Gly Lys Ile Thr Arg Asn Ser Glu Arg Phe Lys Glu Leu Thr Pro Asn
 65                  70                  75                  80

Tyr Asn Pro Asp Ile Ile Phe Lys Asp Glu Glu Asn Thr Gly Ala Asp
                 85                  90                  95

Arg Leu Met Thr Gln Arg Cys Lys Asp Lys Leu Asn Ala Leu Ala Ile
            100                 105                 110

Ser Val Met Asn Gln Trp Pro Gly Val Lys Leu Arg Val Thr Glu Gly
        115                 120                 125

Trp Asp Glu Asp Gly His His Ser Glu Glu Ser Leu His Tyr Glu Gly
130                 135                 140

Arg Ala Val Asp Ile Thr Thr Ser Asp Arg Asp Arg Ser Lys Tyr Gly
145                 150                 155                 160

Met Leu Ala Arg Leu Ala Val Glu Ala Gly Phe Asp Trp Val Tyr Tyr
                165                 170                 175

Glu Ser Lys Ala Arg Ile His Cys Ser Val Lys Ala Glu Asn Ser Val
            180                 185                 190

Ala Ala Lys Ser Asp Gly Cys Phe Pro Gly Ser Ala Thr Val His Leu
        195                 200                 205

Glu Gln Gly Gly Thr Lys Leu Val Lys Asp Leu Ser Pro Gly Asp Arg
    210                 215                 220

Val Leu Ala Ala Asp Gln Gly Arg Leu Leu Tyr Ser Asp Phe Leu
225                 230                 235                 240

Thr Phe Leu Asp Arg Asp Glu Gly Ala Lys Lys Val Phe Tyr Val Ile
                245                 250                 255

Glu Thr Arg Glu Pro Arg Glu Arg Leu Leu Leu Thr Ala Ala His Leu
            260                 265                 270

Leu Phe Val Ala Pro His Asn Asp Ser Gly Pro Thr Pro Gly Pro Ser
        275                 280                 285

```
Pro Leu Phe Ala Ser Arg Val Arg Pro Gly Gln Arg Val Tyr Val Val
    290                 295                 300

Ala Glu Arg Gly Gly Asp Arg Arg Leu Leu Pro Ala Ala Val His Ser
305                 310                 315                 320

Val Thr Leu Arg Glu Glu Ala Ala Gly Ala Tyr Ala Pro Leu Thr Ala
                325                 330                 335

Asp Gly Thr Ile Leu Ile Asn Arg Val Leu Ala Ser Cys Tyr Ala Val
                340                 345                 350

Ile Glu Glu His Ser Trp Ala His Arg Ala Phe Ala Pro Phe Arg Leu
            355                 360                 365

Ala His Ala Leu Leu Ala Ala Leu Ala Pro Ala Arg Thr Asp Gly Gly
    370                 375                 380

Gly Gly Gly Ser Ile Pro Ala Pro Gln Ser Val Ala Glu Ala Arg Gly
385                 390                 395                 400

Ala Gly Pro Pro Ala Gly Ile His Trp Tyr Ser Gln Leu Leu Tyr His
                405                 410                 415

Ile Gly Thr Trp Leu Leu Asp Ser Glu Thr Leu His Pro Leu Gly Met
            420                 425                 430

Ala Val Lys Ser Ser
            435

<210> SEQ ID NO 3
<211> LENGTH: 20
<212> TYPE: DNA
<213> ORGANISM: DROSOPHILA

<400> SEQUENCE: 3
gaggattggg tcgtcatagg                                            20

<210> SEQ ID NO 4
<211> LENGTH: 20
<212> TYPE: DNA
<213> ORGANISM: DROSOPHILA

<400> SEQUENCE: 4
cttcaaggat tccatctcaa                                            20

<210> SEQ ID NO 5
<211> LENGTH: 22
<212> TYPE: DNA
<213> ORGANISM: DROSOPHILA

<400> SEQUENCE: 5
agctgggacg aggactacca tc                                         22

<210> SEQ ID NO 6
<211> LENGTH: 22
<212> TYPE: DNA
<213> ORGANISM: DROSOPHILA

<400> SEQUENCE: 6
tgggaactga tcgacgaatc tg                                         22

<210> SEQ ID NO 7
<211> LENGTH: 418
<212> TYPE: PRT
<213> ORGANISM: ZEBRAFISH

<400> SEQUENCE: 7
```

-continued

```
Met Arg Leu Leu Thr Arg Val Leu Leu Val Ser Leu Leu Thr Leu Ser
 1               5                  10                 15

Leu Val Val Ser Gly Leu Ala Cys Gly Pro Gly Arg Gly Tyr Gly Arg
                20                  25                 30

Arg Arg His Pro Lys Lys Leu Thr Pro Leu Ala Tyr Lys Gln Phe Ile
            35                  40                  45

Pro Asn Val Ala Glu Lys Thr Leu Gly Ala Ser Gly Arg Tyr Glu Gly
        50                  55                  60

Lys Ile Thr Arg Asn Ser Glu Arg Phe Lys Glu Leu Thr Pro Asn Tyr
 65                  70                  75                  80

Asn Pro Asp Ile Ile Phe Lys Asp Glu Glu Asn Thr Gly Ala Asp Arg
                 85                  90                  95

Leu Met Thr Gln Arg Cys Lys Asp Lys Leu Asn Ser Leu Ala Ile Ser
                100                 105                 110

Val Met Asn His Trp Pro Gly Val Lys Leu Arg Val Thr Glu Gly Trp
            115                 120                 125

Asp Glu Asp Gly His His Phe Glu Glu Ser Leu His Tyr Glu Gly Arg
        130                 135                 140

Ala Val Asp Ile Thr Thr Ser Asp Arg Asp Lys Ser Lys Tyr Gly Thr
145                 150                 155                 160

Leu Ser Arg Leu Ala Val Glu Ala Gly Phe Asp Trp Val Tyr Tyr Glu
                165                 170                 175

Ser Lys Ala His Ile His Cys Ser Val Lys Ala Glu Asn Ser Val Ala
            180                 185                 190

Ala Lys Ser Gly Gly Cys Phe Pro Gly Ser Ala Leu Val Ser Leu Gln
        195                 200                 205

Asp Gly Gly Gln Lys Ala Val Lys Asp Leu Asn Pro Gly Asp Lys Val
        210                 215                 220

Leu Ala Ala Asp Ser Ala Gly Asn Leu Val Phe Ser Asp Phe Ile Met
225                 230                 235                 240

Phe Thr Asp Arg Asp Ser Thr Thr Arg Arg Val Phe Tyr Val Ile Glu
                245                 250                 255

Thr Gln Glu Pro Val Glu Lys Ile Thr Leu Thr Ala Ala His Leu Leu
                260                 265                 270

Phe Val Leu Asp Asn Ser Thr Glu Asp Leu His Thr Met Thr Ala Ala
            275                 280                 285

Tyr Ala Ser Ser Val Arg Ala Gly Gln Lys Val Met Val Val Asp Asp
        290                 295                 300

Ser Gly Gln Leu Lys Ser Val Ile Val Gln Arg Ile Tyr Thr Glu Glu
305                 310                 315                 320

Gln Arg Gly Ser Phe Ala Pro Val Thr Ala His Gly Thr Ile Val Val
                325                 330                 335

Asp Arg Ile Leu Ala Ser Cys Tyr Ala Val Ile Glu Asp Gln Gly Leu
            340                 345                 350

Ala His Leu Ala Phe Ala Pro Ala Arg Leu Tyr Tyr Val Ser Ser
        355                 360                 365

Phe Leu Phe Pro Gln Asn Ser Ser Arg Ser Asn Ala Thr Leu Gln
    370                 375                 380

Gln Glu Gly Val His Trp Tyr Ser Arg Leu Leu Tyr Gln Met Gly Thr
385                 390                 395                 400

Trp Leu Leu Asp Ser Asn Met Leu His Pro Leu Gly Met Ser Val Asn
                405                 410                 415

Ser Ser
```

```
<210> SEQ ID NO 8
<211> LENGTH: 471
<212> TYPE: PRT
<213> ORGANISM: DROSOPHILA

<400> SEQUENCE: 8

Met Asp Asn His Ser Ser Val Pro Trp Ala Ser Ala Ser Val Thr
 1               5                  10                  15

Cys Leu Ser Leu Asp Ala Lys Cys His Ser Ser Ser Ser Ser Ser
                20                  25                  30

Ser Lys Ser Ala Ala Ser Ser Ile Ser Ala Ile Pro Gln Glu Thr
            35                  40                  45

Gln Thr Met Arg His Ile Ala His Thr Gln Arg Cys Leu Ser Arg Leu
        50                  55                  60

Thr Ser Leu Val Ala Leu Leu Leu Ile Val Leu Pro Met Val Phe Ser
65                  70                  75                  80

Pro Ala His Ser Cys Gly Pro Gly Arg Gly Leu Gly Arg His Arg Ala
                85                  90                  95

Arg Asn Leu Tyr Pro Leu Val Leu Lys Gln Thr Ile Pro Asn Leu Ser
               100                 105                 110

Glu Tyr Thr Asn Ser Ala Ser Gly Pro Leu Glu Gly Val Ile Arg Arg
           115                 120                 125

Asp Ser Pro Lys Phe Lys Asp Leu Val Pro Asn Tyr Asn Arg Asp Ile
       130                 135                 140

Leu Phe Arg Asp Glu Glu Gly Thr Gly Ala Asp Arg Leu Met Ser Lys
145                 150                 155                 160

Arg Cys Lys Glu Lys Leu Asn Val Leu Ala Tyr Ser Val Met Asn Glu
                165                 170                 175

Trp Pro Gly Ile Arg Leu Leu Val Thr Glu Ser Trp Asp Glu Asp Tyr
            180                 185                 190

His His Gly Gln Glu Ser Leu His Tyr Glu Gly Arg Ala Val Thr Ile
        195                 200                 205

Ala Thr Ser Asp Arg Asp Gln Ser Lys Tyr Gly Met Leu Ala Arg Leu
    210                 215                 220

Ala Val Glu Ala Gly Phe Asp Trp Val Ser Tyr Val Ser Arg Arg His
225                 230                 235                 240

Ile Tyr Cys Ser Val Lys Ser Asp Ser Ser Ile Ser Ser His Val His
                245                 250                 255

Gly Cys Phe Thr Pro Glu Ser Thr Ala Leu Leu Glu Ser Gly Val Arg
            260                 265                 270

Lys Pro Leu Gly Glu Leu Ser Ile Gly Asp Arg Val Leu Ser Met Thr
        275                 280                 285

Ala Asn Gly Gln Ala Val Tyr Ser Glu Val Ile Leu Phe Met Asp Arg
    290                 295                 300

Asn Leu Glu Gln Met Gln Asn Phe Val Gln Leu His Thr Asp Gly Gly
305                 310                 315                 320

Ala Val Leu Thr Val Thr Pro Ala His Leu Val Ser Val Trp Gln Pro
                325                 330                 335

Glu Ser Gln Lys Leu Thr Phe Val Phe Ala Asp Arg Ile Glu Glu Lys
            340                 345                 350

Asn Gln Val Leu Val Arg Asp Val Glu Thr Gly Glu Leu Arg Pro Gln
        355                 360                 365

Arg Val Val Lys Val Gly Ser Val Arg Ser Lys Gly Val Val Ala Pro
```

```
              370            375            380
Leu Thr Arg Glu Gly Thr Ile Val Asn Ser Val Ala Ala Ser Cys
385                 390                 395                 400

Tyr Ala Val Ile Asn Ser Gln Ser Leu Ala His Trp Gly Leu Ala Pro
                405                 410                 415

Met Arg Leu Leu Ser Thr Leu Glu Ala Trp Leu Pro Ala Lys Glu Gln
                420                 425                 430

Leu His Ser Ser Pro Lys Val Val Ser Ser Ala Gln Gln Gln Asn Gly
                435                 440                 445

Ile His Trp Tyr Ala Asn Ala Leu Tyr Lys Val Lys Asp Tyr Val Leu
            450                 455                 460

Pro Gln Ser Trp Arg His Asp
465                 470
```

<210> SEQ ID NO 9
<211> LENGTH: 23
<212> TYPE: DNA
<213> ORGANISM: HNF3B

<400> SEQUENCE: 9
tcaccatggc catccagcag tcg                                            23

<210> SEQ ID NO 10
<211> LENGTH: 23
<212> TYPE: DNA
<213> ORGANISM: HNF3B

<400> SEQUENCE: 10
cagcaggtgc tgcgctggag agg                                            23

<210> SEQ ID NO 11
<211> LENGTH: 17
<212> TYPE: DNA
<213> ORGANISM: Netrin-1

<400> SEQUENCE: 11
tgggcagcac cgaggac                                                   17

<210> SEQ ID NO 12
<211> LENGTH: 17
<212> TYPE: DNA
<213> ORGANISM: Netrin-1

<400> SEQUENCE: 12
ccttccatcc ctcaata                                                   17

<210> SEQ ID NO 13
<211> LENGTH: 22
<212> TYPE: DNA
<213> ORGANISM: Isl-1

<400> SEQUENCE: 13
tcaaacctac tttggggtct ta                                             22

<210> SEQ ID NO 14
<211> LENGTH: 24
<212> TYPE: DNA
<213> ORGANISM: Isl-1

<400> SEQUENCE: 14
atcgccgggg atgagctggc ggct                                           24

```
<210> SEQ ID NO 15
<211> LENGTH: 17
<212> TYPE: DNA
<213> ORGANISM: Isl-2

<400> SEQUENCE: 15
tgctgaacga gaagcag                                                  17

<210> SEQ ID NO 16
<211> LENGTH: 19
<212> TYPE: DNA
<213> ORGANISM: Isl-2

<400> SEQUENCE: 16
tggtaggtct gcacctcca                                                19

<210> SEQ ID NO 17
<211> LENGTH: 24
<212> TYPE: DNA
<213> ORGANISM: ChAT

<400> SEQUENCE: 17
tccatacgcc gatttgatga gggc                                          24

<210> SEQ ID NO 18
<211> LENGTH: 24
<212> TYPE: DNA
<213> ORGANISM: ChAT

<400> SEQUENCE: 18
ctattgcttg tcaaataggt ctca                                          24
```

DNA ENCODING A VERTEBRATE HOMOLOG OF HEDGEHOG, VHH-1, EXPRESSED BY THE NOTOCHORD, AND USES THEREOF

This application is a continuation-in-part of U.S. patent application Ser. No. 08/202,040, filed Feb. 25, 1994, now abandoned the contents of which are hereby incorporated by reference.

The invention disclosed herein was made with U.S. Government support under Grant Number NS-30532 from the National Institute of Health, U.S. Department of Health and Human Servies. Accordingly, the U.S. Government has certain rights in this invention.

BACKGROUND OF THE INVENTION

Throughout this application various publications are referred to by partial citations within parenthesis. Full citations for these publications may be found at the end of the specification immediately preceding the claims. The disclosures of these publications, in their entireties, are hereby incorporated by reference into this application in order to more fully describe the state of the art to which this invention pertains.

In vertebrate embryos, the neural tube displays distinct cell types at defined dorsoventral positions. Floor plate cells differentiate at the ventral midline; motor neurons appear in ventrolateral regions; and sensory relay neurons, neural crest, and roof plate cells appear dorsally. The generation of cell pattern in the neural tube depends on signals that derive from surrounding tissues. A clear example of this is the influence of axial mesoderm on the development of ventral cell types.

The differentiation of floor plate cells, motor neurons, and other ventral cell types requires inductive signals from axial mesodermal cells of the notochord. In the absence of the notochord, floor plate cells and motor neurons do not differentiate (Placzek et al., 1990b; Bovolenta and Dodd, 1991; Clarke et al., 1991; van Straaten and Hekking, 1991; Yamada et al., 1991; Ruiz i Altaba, 1992; Goulding et al., 1993; Ruiz i Altaba et al., 1993a; Halpern et al., 1993) Conversely, notochord grafts can induce the ectopic differentiation of floor plate cells and motor neurons in vivo and in vitro (van Straaten et al., 1988; Placzek et al., 1990b, 1991, 1993, Yamada et al., 1991, 1993; Ruiz l Altaba, 1992; Goulding et al., 1993). Floor plate cells themselves also possess both floor plate and motor neuron inducing activity (Yamada et al., 1991, 1993; Hatta et al., 1991; Placzek et al., 1993). In vitro assays have provided evidence that floor plate induction requires a contact-mediated signal, whereas motor neurons can be induced by diffusible signals (Yamada et al., 1993; Placzek et al., 1990b, 1993).

The differentiation of floor plate cells and motor neurons is associated with the expression of different classes of transcription factors. Floor plate cells express three members of the hepatocyte nuclear factor HNF-3/fork head gene family (Weigel and Jackie, 1990, Lai et al., 1991): Pintallavis (XFKH1/XFD1/1), HNF-3β, and HNF-3α (Dirksen and Jamrich, 1992; Knochel et al., 1992; Ruiz l Altaba and Jessell, 1992; Bolce et al., 1993; Monaghan et al., 1993; Ruiz l Altaba et al., 1993a; Sasaki and Hogan, 1993; Strahle e al., 1993). Ectopic expression of Pintallavis and HNF-3β leads to the appearance of floor plate markers in cells in the dorsal region of the neural tube (Ruiz i Altaba et al., 1992, 1993b; A.R.A. et al., unpublished data; Sasaki and Hogan, 1994) suggesting that members of this family may specify floor plate cell fate. The differentiation of motor neurons is associated with expression of islet-1, a member of the LIM homeobox gene family (Ericson et a!., 1992; Yamada et al., 1993). In addition to their possible functions in cell faze determination, these transcription factors provide markers that can be used in conjunction with cell surface molecules to monitor floor plate and motor neuron differentiation.

Cell patterning in the dorsal neural tube appears to be regulated by members of two families of secreted proteins that also have prominent roles in insect development. The transforming growth factor β (TGFβ) family member dorsalin-1 is expressed in the dorsal neural tube and can induce the differentiation of neural crest cells in neural plate explants in vitro (Basler et al., 1993). Members of the wnt family are also expressed in the dorsal neural tube (Roelink and Nusse, 1991; Nusse and Varmus, 1992; Parr et al., 1993). In Drosophila, the TGFβ family member decapentaplegic (dpp) regulates the dorsoventral pattern of the Drosophila embryo (see Ferguson and Anderson, 1992) and the differentiation and patterning of cells in imaginal discs (Spencer et al., 1982; Posakony et al., 1991; Campbell et al., 1993, Heberlein et al., 1993). similarly, wingless (wg), a member of the wnt gene family, controls cell fates during segmentation and imaginal disc development (Morata and Lawrence, 1977; Nusslein-Volhard and Wieschaus, 1980; Baker, 1988; Martinez-Arias et al., 1988; Struhl and Basler, 1993).

A third Drosophila gene important in the specification of cell identity is hedgehog (hh) (Nusslein-Volhard and Wieschaus, 1980). hh acts with dpp and wg to control cell fate and pattern during segmentation and imaginal disc development (Hidalgo and Ingham, 1990; Ingham, 1993; Ma e tal., 1993; Heberlein et al., 1993; Basler and Struhl, 1994; Heemskerk and DiNardo, 1994). hh encodes a novel protein (Lee et al., 1992; Mohler and Vani, 1992; Tabata et al., 1992; Tashiro et al., 1993) that enters the secretory pathway (Lee et al., 1992), and genetic evidence indicates the hh function is not cell autonomous (Mohler, 1988; Heberlein et al., 1993; Ma et al., 1993; Basler and Struhl, 1994), consistent with the possibility that hh acts as a signaling molecule.

The importance of hh in cell patterning in insects prompted applicants to search for vertebrate homologs and to examine their potential functions during early neural development. Applicants disclose here the cloning of a vertebrate homolog of hh, vhh-1, from rat. Recent independent studies have identified a vertebrate homolog of hh, sonic hedgehog (shh), that is closely related to vhh-1 and appears to regulate cell patterning in the neural tube and limb bud (Echelard et al., 1993; Krauss et al., 1993, Riddle et al., 1993). Here, applicants present evidence that vhh-1 is involved in the induction of ventral neural cell types. vhh-1 is expressed in midline structures (in particular, the node, notochord, and floor plate) at a time when these cells have inducing activity. COS cells expressing the rat vhh-1 gene induce floor plate and motor neuron differentiation in neural plate explants in vitro. Moreover, widespread expression of the rat vhh-1 gene in frog embryos leads to ectopic expression of the floor plate markers in the neural tube. These results suggest that vhh-1 expression in the notochord provides an inductive signal that is involved in the differentiation of floor plate cells, motor neurons, and possibly other cell types in the ventral neural tube.

SUMMARY OF THE INVENTION

This invention provides an isolated nucleic acid molecule encoding a vertebrate vhh-1 protein. In one embodiment of this invention, the nucleic acid molecule encoding a frog vhh-1 protein. In another embodiment, the nucleic acid molecule encoding a mammalian vhh-1 protein. In a further embodiment, the nucleic acid molecule encoding a rat vhh-1 protein. In a still further embodiment, the nucleic acid molecule encoding a human vhh-1 protein.

This invention provides a nucleic acid molecule comprising a nucleic acid molecule of at least 15 nucleotides capable of specifically hybridizing with a unique sequence included within the sequence of a nucleic acid molecule encoding a vertebrate vhh-1 protein.

This invention also provides monoclonal and polyclonal antibodies directed to a vhh-1 protein.

This invention provides a transgenic, nonhuman mammal comprising the isolated nucleic acid molecule encoding a vhh-1 protein.

This invention provides a method of producing a purified vertebrate vhh-1 protein which comprises: (a) inserting nucleic acid molecule encoding the vertebrate vhh-1 protein in a suitable vector; (b) introducing the resulting vector in a suitable host cell; (c) selecting the introduced host cell for the expression of the vertebrate vhh-1 protein; (d) culturing the selected cell to produce the vhh-1 protein; and (e) recovering the vhh-1 protein produced.

This invention provides a method of inducing the differentiation of floor plate cells comprising contacting floor plate cells with a purified vertebrate vhh-1 protein at a concentration effective to induce the differentiation of floor plate cells.

This invention provides a method of inducing the differentiation of floor plate cells in a subject comprising administering to the subject a purified vertebrate vhh-1 protein at an amount effective to induce the differentiation of floor plate cells in the subject.

This invention provides a method of inducing the differentiation of motor neuron comprising contacting the floor plate cells with a purified vertebrate vhh-1 protein at a concentration effective to induce the differentiation of motor neuron.

This invention provides a method of inducing the differentiation of motor neuron in a subject comprising administering to the subject a purified vertebrate vhh-1 protein at an amount effective to induce the differentiation of motor neuron in the subject.

This invention provides a method of generating ventral neurons comprising contacting progenitor cells with a purified vertebrate vhh-1 protein at a concentration effective to generate ventral neurons.

This invention provides a method of generating ventral neurons from progenitor cells in a subject comprising administering to the subject a purified vertebrate vhh-1 protein at an amount effective to generate ventral neurons from progenitor cells in the subject.

This invention provides a pharmaceutical composition comprising a vertebrate vhh-1 proein and a pharmaceutically acceptable carrier. En an embodiment, the vhh-protein is a rat protein. In another embodiment, the vhh-protein is a human protein.

This invention provides a method for generating motor neurons from undifferentiated precursor neurons consisting of introducing an amount of a pharmaceutical composition comprising the human vhh-1 protein effective to generate motor neurons from undifferentiated precursor neurons. The generation of motor neurons can alleviate acute nervous system injury or chronic neurodegenerative diseases, such as Amyotropic lateral sclerosis (ALS).

This invention provides a method of generating motor neurons from undifferentiated precursor neurons wherein the acute nervous system injury is localized to specific central axons which comprises surgical implantation of a pharmaceutical compound comprising the human vhh-1 protein and a pharmaceutically acceptable carrier effective to generate motor neurons from undifferentiated motor neurons located proximal to the injured axon(s).

BRIEF DESCRIPTION OF THE FIGURES

FIGS. 1A–C

Figure 2B:
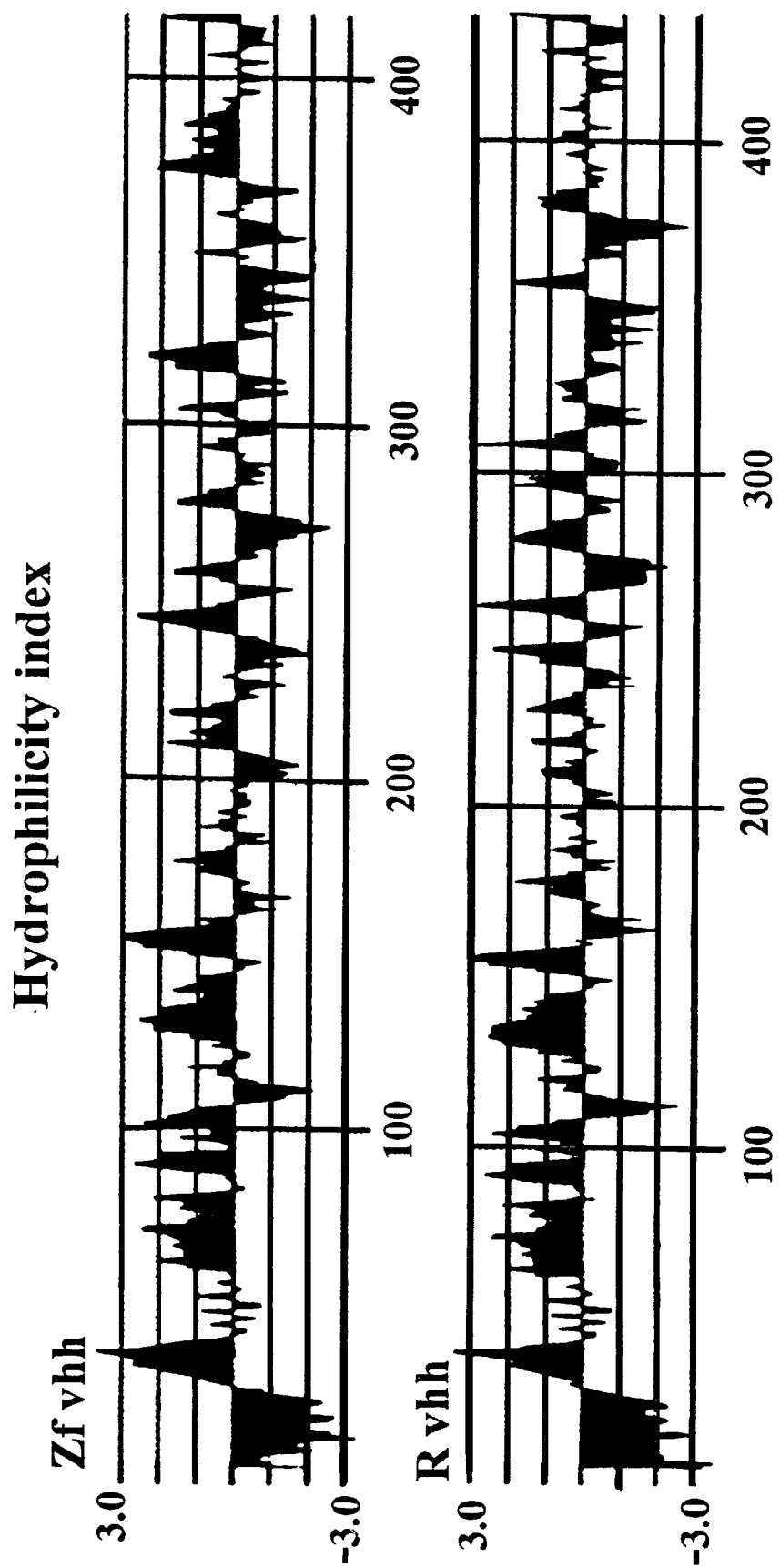

DNA Sequence (the DNA sequence as described by SEQ ID NO: 1) of Rat Vhh-1 Protein with Corresponding Deduced Amino Acid Sequence.

FIGS. 2A-1 and 2A-2

Deduced Amino Acid Sequences of Zebrafish and Rat Homologs of the Drosophila Hh Protein alignment of the zebrafish (Z1 vhh SEQ ID NO:1) and rat (R vhh) proteins SEQ ID NO:2 with the Drosophila hh protein SEQ ID NO:8. Residues identical in all sequences are shown in bold. Gaps introduced to optimize the alignment are shown by ellipses. The vhh-1 sequence shows no homology with other proteins in the National Center for Biotechnology Information blast peptide sequence data base with the exception of resides 113–211, which show 39% conservation with the outer surface protein A of Borella burgdorferi, a lyme disease spirochete (Eiffert et al., 1992).

FIG. 2B

Analysis of the hydrophilicity (Kyle and Doolittle, 1982) of the zebrafish and rat proteins. The $NH_2$-terminus of the protein is to the left. Negative values indicate hydrophobic residues. The $NH_2$-terminal hydrophobic region is likely to serve as a signal sequence (von Heijne, 1985). Immediately following the putative signal sequence cleavage site is a basic region that conforms to the requirements for a heparin-binding site (Cardin and Weintraub, 1989).

FIG. 3A

Localization of Rat vhh-1 mRNA by In Situ Hybridization vhh-1 mRNA expression in an E9.5 rat embryo. Labeled cells are found in the node (nd) and in the axial mesoderm laid down at the midline of the embryo in the wake of the node. Anterior is up. Scale bar is 165 $\mu$m.

FIG. 3B

Localization of vhh-1 mRNA expression in an E10.5 rat embryo shown in side view vhh-1 mRNA expression is present in the notochord (n in [C–E]) and in floor plate cells in more rostral regions of the spinal cord, hindbrain (h), and midbrain (m). Cells in the ventral diencephalon (d) also express vhh-1 mRNA at high levels. In addition, a group of cells in the dorsal midbrain express vhh-1 mRNA. Endodermal cells in the gut (g) also express the gene. At later stages a small group of cells in the rostral telencephalon also express vhh-1 mRNA (data not shown). Scale bar is 400 $\mu$m.

FIG. 3C

Cross section showing the neural olate and surrounding tissues in an E10 rat embryo. vhh-1 mRNA expression is confined to a group of cells that lie under the midline of the neural plate. Scale bar is 100 $\mu$m.

FIG. 3D

Cross section showing the neural plate and surrounding tissues in an E10 rat embryo. vhh-1 mRNA expression is confined to the notochord (n). Scale bar is 100 $\mu$m.

FIG. 3E

Cross section through an E11 rat embryo showing the spinal cord and surrounding tissues. vhh-1 mRNA expression is detected in cells at the ventral midline of the spinal cord, corresponding to the floor plate (f) and to the notochord (n), which by this stage is displaced from the ventral midline of the nervous system. The border of the spinal cord is marked. Scale bar is 180 µm.

FIG. 4A

Ectopic Expression of F-Spondin and HNF-3β in the Dorsal Neural Tube of Frog Embryos injected with a Plasmid Expressing Rat vhh-1. Cross section of neurula stage (approximately stage 16) Xenopus embryo expressing rat vhh-1 mRNA from a plasmid driven by a CMV promoter. The rat vhh-1 gene is detected predominantly in one half of the neural plate. Lateral arrows denote the lateral extent of the neural plate. Abbreviations: np. neural plate: n, notochord, s, somite.

FIG. 4B

Lateral views of tadpole stage (approximately stage 34) embryos showing the pattern of F-spondin mRNA expression in an embryo injected with CMV plasmid encoding antisense vhh-1. F-spondin is expressed in the floor plate (fp) at the ventral midline of the neural tube and in the hypochord (h) located ventral to the notochord (n). Scale bar is 200 µm.

FIG. 4C

Lateral views of tadpole stage (approximately stage 34) embryos showing the pattern of F-spondin mRNA expression in an embryo injected with CMV plasmid encoding sense vhh-1. Ectopic expression of F-spondin mRNA is detected in the dorsal neural tube and in the dorsal ventricular zone adjacent to the floor plate (first and last arrowheads) (Ruiz i Altaba et al. 1993a). Ectopic F-spondin expression occurs in the posterior hindbrain and in the spinal cord. Scale bar is 200 µm.

FIG. 4D

Cross section of tadpole stage (approximately stages 32–36) embryos injected with CMV plasmid encoding antisense vhh-1 and showing the expression of F-spondin mRNA. Embryos injected with CMV plasmids encoding antisense vhh-1 show a normal pattern of F-spondin mRNA expression, restricted to the floor plate (fp). Scale bar is 10 µm.

FIG. 4E

Cross section of tadpole stage (approximately stages 32–36) embryos injected with CMV plasmid encoding sense vhh-1 and showing the expression of F-spondin mRNA. Ectopic expression of F-spondin in embryos injected with CMV plasmids encoding sense vhh-1 is detected in roof plate cells in the hindbrain. Scale bar is 10 µm.

FIG. 4F

Cross section of tadpole stage (approximately stages 32–36) embryos injected with CMV plasmid encoding sense vhh-1 and showing the expression of F-spondin mRNA. Ectopic expression of F-spondin in embryos injected with CMV plasmids encoding sense vhh-1 is detected in the roof plate cells of the spinal cord. Scale bar is 10 µm.

FIG. 4G

Cross section of tadpole stage (approximately stages 32–36) embryos injected with CMV plasmid encoding antisense vhh-1 and showing the expression of HNF-3β protein. Embryos injected with a CMV plasmid encoding antisense vhh-1 show the normal pattern of HNF-3β protein expression, restricted to the floor plate (fp). Scale bar is 10 µm.

FIG. 4H

Cross section of tadpole stage (approximately stages 32–36) embryos injected with CMV plasmid encoding sense vhh-1 and showing the expression of HNF-3β protein. Ectopic expression of HNF-3β protein in the roof plate of the hindbrain (H) is detected in embryos expressing vhh-1 mRNA. Scale bar is 10 µm.

FIG. 4I

Cross section of tadpole stage (approximately stages 32–36) embryos injected with CMV plasmid encoding sense vhh-land showing the expression of HNF-3β protein. Ectopic expression of HNF-3β protein in the roof plate of the spinal cord is detected in embryos expressing vhh-1 mRNA. HNF-3β protein expression is also detected in very low levels in the notochord (n). Ectopic expression of these floor plate markers was also detected in the dorsal midbrain (data not shown). Scale bar is 10 µm.

FIG. 5A

Induction of Floor Plate differentiation in neural plant explants by vhh-1. Pattern of expression of the FP3 antigen in a cross section of the ventral region of an E11 rat spiral cord. FP3 expression is restricted to floor plate cells (f). The notochord (h) is unlabeled. Scale bar is 35 µm.

FIG. 5B

Induction of Floor Plate differentiation in neural plant explants by vhh-1. Pattern of expression of the FP4 antigen in a cross section of the ventral region of an E11 rat spinal cord. FP4 expression in the spinal cord is restricted to floor plate cells (f). The notochord (n) also expresses FP4. Scale bar is 35 µm.

FIG. 5C

Induction of Floor Plate differentiation in neural plant explants by vhh-1. Expression of FP3 by cells in rat neural plate explants that have been grown in contact with stage b chick notochord for 96 hours. Neural cells in proximity to the notochord express FP3. Scale bar is 45 µm.

FIG. 5D

Induction of Floor Plate differentiation in neural plant explants by vhh-1. Expression of FP4 by cells in rat neural plate explants grown in contact with stage 6 chick notochord for 96 hours. Neural cells in proximity to the notochord express FP4. Scale bar is 45 µm.

FIG. 5E

Induction of Floor Plate differentiation in neural plant explants by vhh-1. Phase-contrast micrograph showing expression of FP3 in neural plate cells grown in contact with COS cells transfected with cDNA encoding sense vhh-1. Intense expression of FP3 is detected at regions of contact between the neural plate explant and COS cell aggregate. Scale bar is 50 µm.

FIG. 5F

Induction of Floor Plate differentiation in neural plant explants by vhh-1. Fluorescence micrograph showing expression of FP3 in neural plate cells grown in contact with COS cells transfected with cDNA encoding sense vhh-1. Intense expression of FP3 is detected at regions of contact between the neural plate explant and COS cell aggregate. Scale bar is 50 µm.

FIG. 5G

Induction of Floor Plate differentiation in neural plant explants by vhh-1. Phase-contrast micrograph showing expression of FP4 in neural plate cells grown in contact with COS cells transfected with cDNA encoding sense vhh-1. FP4 expression is detected at regions of contact between the neural plate (np) explant and COS cells (c). The junction between COS cells and neural plate explant is shown by the dotted line. Scale bar is 60 µm.

FIG. 5H

Induction of Floor Plate differentiation in neural plant explants by vhh-1. Fluorescence micrograph showing expression of FP4 in neural plate cells grown in contact with COS cells transfected with cDNA encoding sense vhh-1. FP4 expression is detected at regions of contact between the neural plate (np) explant and COS cells (c). The junction between COS cells and neural plate explant is shown by the dotted line. Scale bar is 60 µm.

FIG. 5J

Induction of Floor Plate differentiation in neural plant explants by vhh-1. Neural plate explants grown in contact with COS cells transfected with cDNA encoding antisense vhh-1 and labeled with anti-FP3 antibodies.

The FP3 antigen is not expressed. Scale bar is 60 µm.

FIG. 5K

Induction of Floor Plate differentiation in neural plant explants by vhh-1. Neural plate explants grown in contact with COS cells transfected with cDNA encoding antisense vhh-1 and labeled with anti-FP4 antibodies. The FP4 antigen is not expressed. Scale bar is 60 µm.

FIG. 6A

Induction of Motor Neuron Differentiation in Neural Explants by vhh-1. Section through a stage 17 chick spinal cord showing the expression of Islet-1$^+$ motor neurons in ventral spinal cord. Islet-1$^+$ cells are also detected in dorsal root ganglion neurons located next to the spinal cord. Scale bar is 70 µm.

FIG. 6B

Induction of Motor Neuron Differentiation in Neural Explants by vhh-1. Phase-contrast micrographs explants grown for 44 hours on a monolayer of COS cells transfected with cDNA encoding sense vhh-1. The field shows three explants containing Islet-1$^+$ cells. COS cells nuclei (COS) visible under the neural plate explants. The border between the neural plate explants and COS cell monolayer is shown. Scale bar is 70 µm.

FIG. 6C

Induction of Motor Neuron Differentiation in Neural Explants by vhh-1. Florescence micrographs explants grown for 44 hours on a monolayer of COS cells transfected with cDNA encoding sense vhh-1. The field shows three explants containing Islet-1$^+$ cells. COS cells nuclei (COS) visible under the neural plate explants. The border between the neural plate explants and COS cell monolayer is shown. Scale bar is 70 µm.

FIG. 6D

Induction of Motor Neuron Differentiation in Neural Explants by vhh-1. Section through a stage 17 chick spinal cord showing the distribution of SC1 in floor plate cells (f), motor neurons (m), and notochord (n). Scale bar is 70 µm.

FIG. 6E

Figure 5A:
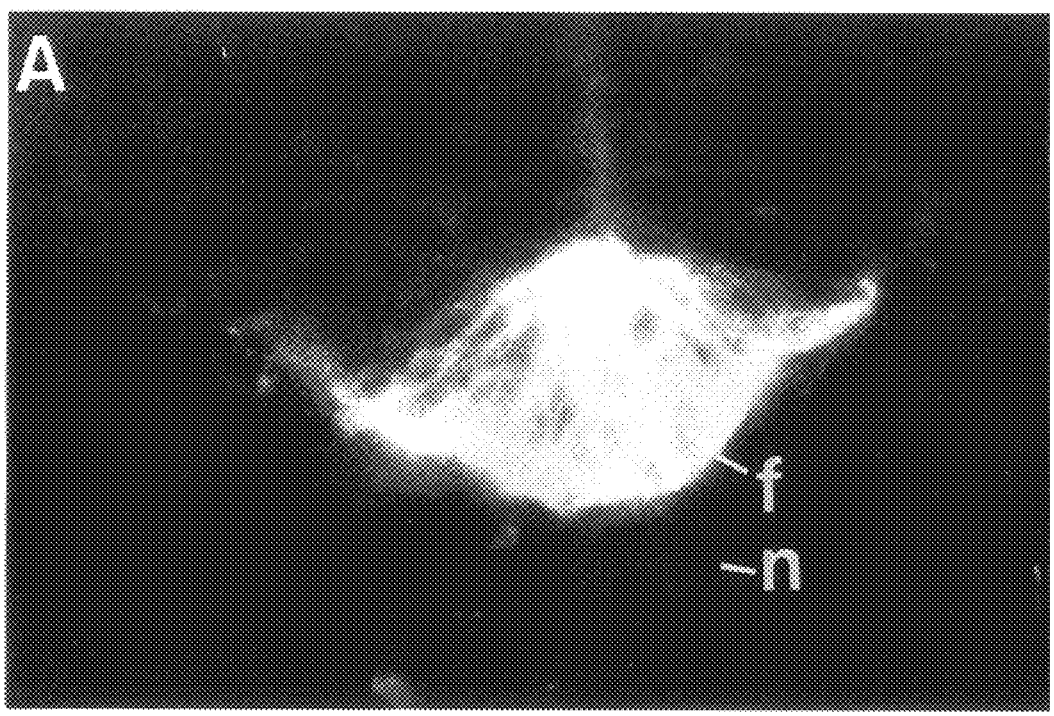
Figure 5B:
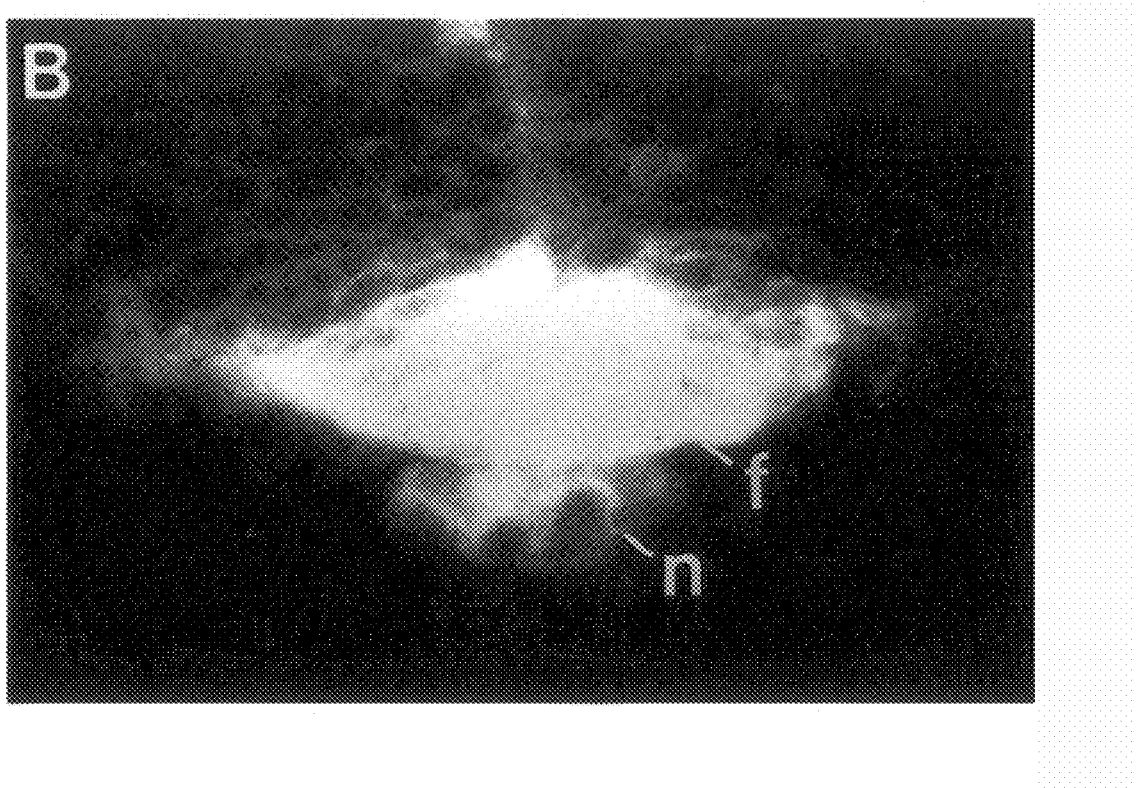
Figure 5C:
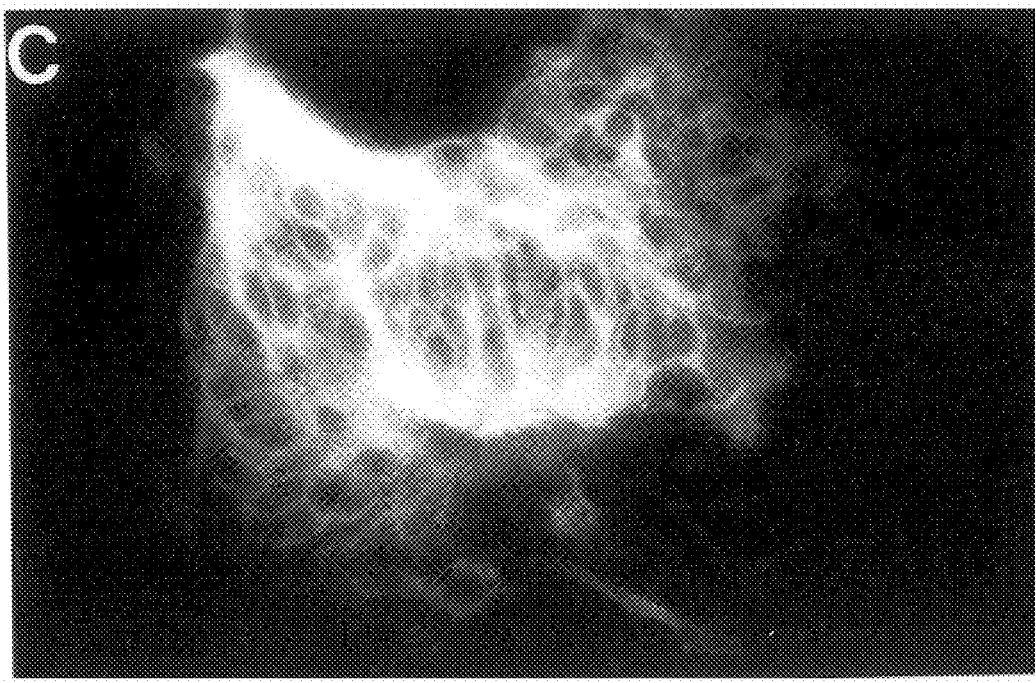
Figure 5D:
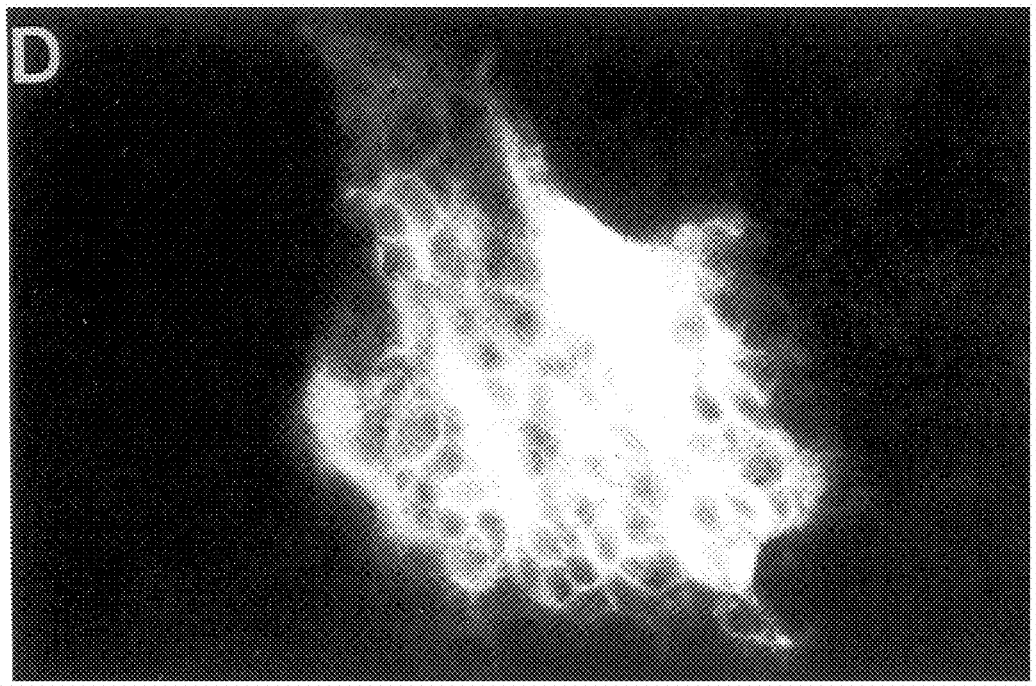
Figure 5E:
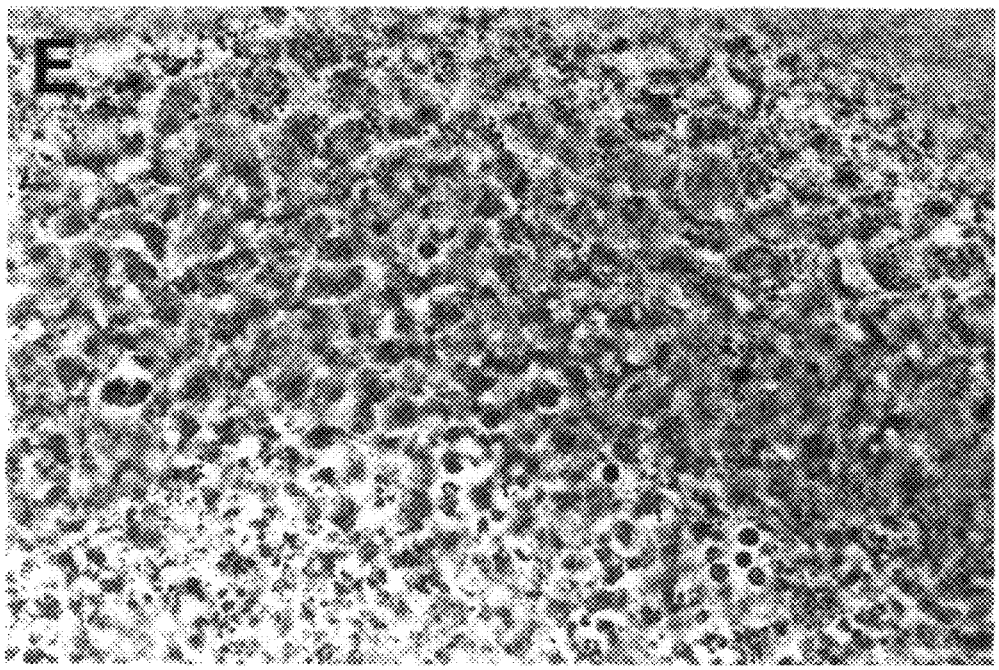
Figure 5F:
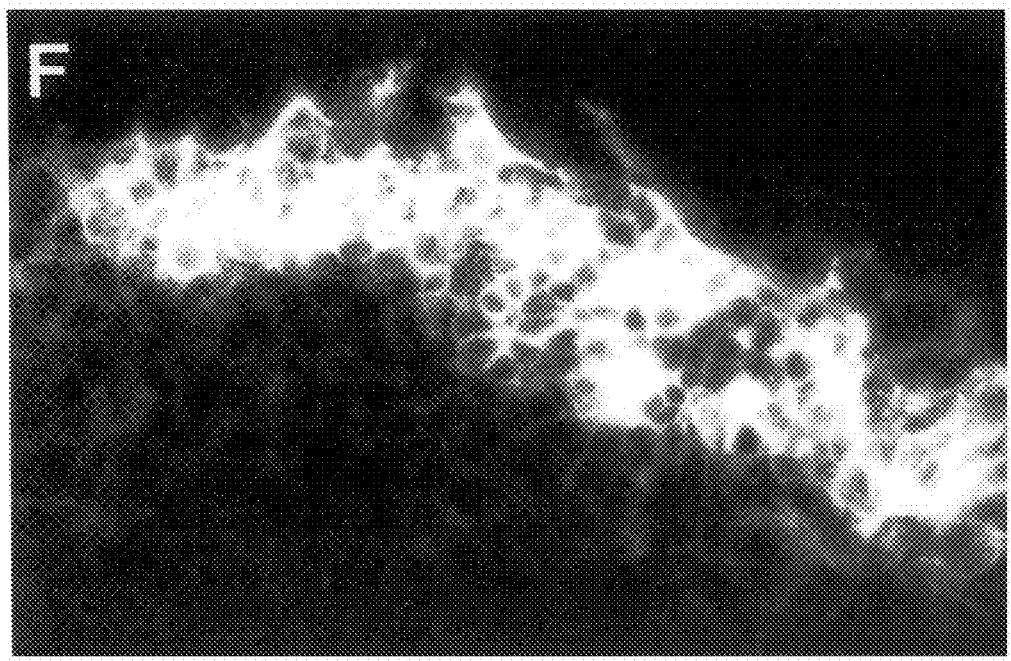
Figure 5G:
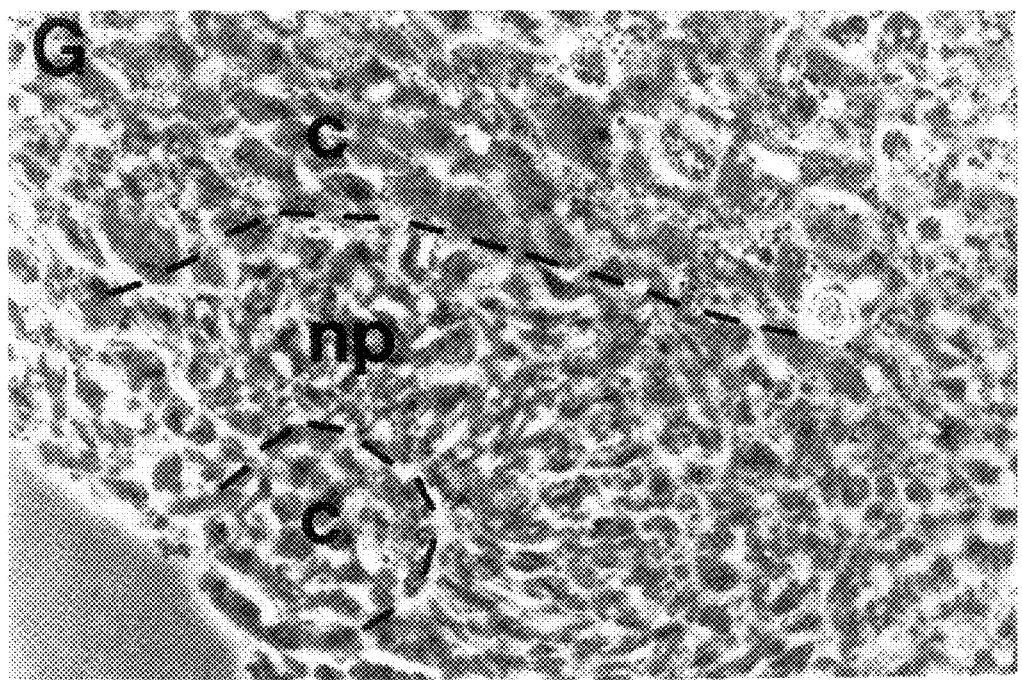
Figure 5H:
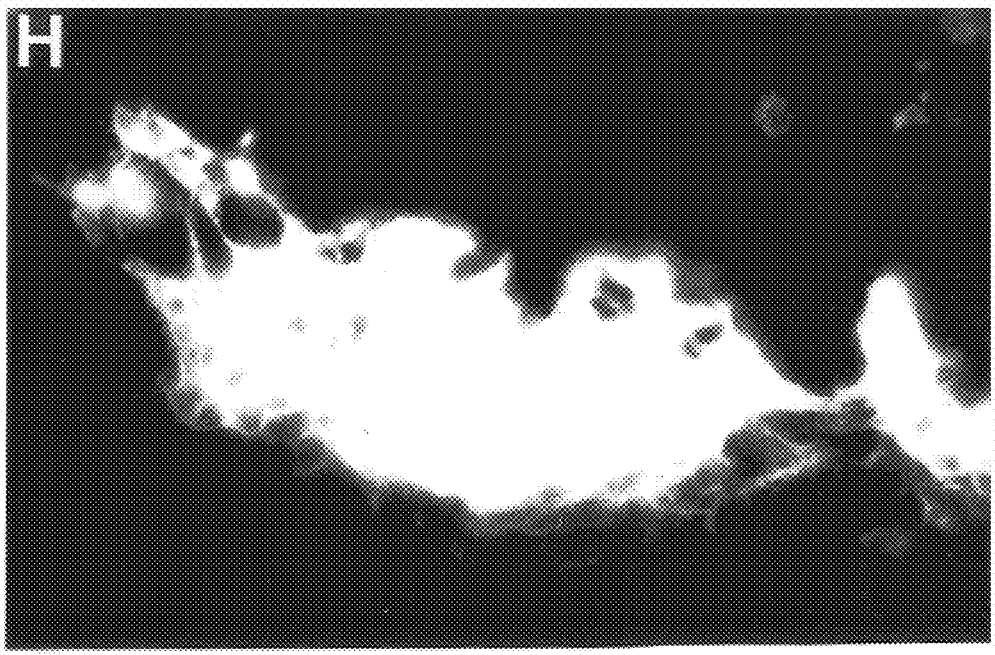

Induction of Motor Neuron Differentiation in Neural Explants by vhh-1. Confocal image of a single field in a chick neural plate explant grown 44 hours on COS cells transfected with the vhh-1 gene and labelled with antibodies against SC1 All SC1$^+$ cells express Islet-1 in their nuclei (Compare with FIG. 5F). Clusters of SC1$^+$/Islet-1$^-$ cells were not detected in these explants (data not shown). Scale bar is 13 µm.

FIG. 6F

Induction of Motor Neuron Differentiation in Neural Explants by vhh-1. Confocal image of a single field in a chick neural plate explant grown 44 hours on COS cells transfected with the vhh-1 gene and labelled with antibodies against Islet-1. Scale bar is 13 µm.

FIG. 6G

Neural plate explants grown for 48 hours on a monolayer of COS cells transfected with a gene encoding ant-sense vhh-1 and labelled with anti-Islet-1 antibodies. No expression of Islet-1 is detected. Scale bar is 70 µm.

FIG. 6H

Neural plate explants grown for 48 hours on a monolayer of COS cells transfected with a gene encoding antisense vhh-1 and labelled with anti-SC1 antibodies. No expression of SC1 is detected. This image is of a confocal section through an explant. Scale bar is 13 µm.

FIG. 7A

Cells in Posterior Limb Bud Mesenchyme Express mRNA Encoding vhh-1 and Can Enduce Floor Plate Differentiation in Neural Plate Explants. Section through limb bud of an E11 rat embryo showing expression of mRNA encoding vhh-1 in mesenchymal cells located in the posterior (p) region of the limb bud. Mesenchymal cells in the anterior (a) region of the cell do not express mRNA encoding vhh-1. Ectodermal cells do not express vhh-1 mRNA. Scale bar is 270 µm.

FIG. 7B

Cells in Posterior Limb Bud Mesenchyme Express mRNA Encoding vhh-1 and Can Enduce Floor Plate Differentiation in Neural Plate Explants. Phase-contrast micrograph showing expression of FP3 by neural plate cells grown in contact with chick posterior limb mesenchyme. Neural plate cells express FP3. Scale bar is 60 µm.

FIG. 7C

Cells in Posterior Limb Bud Mesenchyme Express mRNA Encoding vhh-1 and Can Enduce Floor Plate Differentiation in Neural Plate Explants. Fluorescence micrograph showing expression of FP3 by neural plate cells grown in contact with chick posterior limb mesenchyme. Neural plate cells express FP3. Scale bar is 60 µm.

FIG. 7D

Induction of Motor Neuron Differentiation in Neural Explants by vhh-1. Phase-contrast micrograph of neural plate explants grown in contact with anterior limb bud mesenchyme. No expression of FP3 is detected. Scale bar is 60 µm.

FIG. 7E

Induction of Motor Neuron Differentiation in Neural Explants by vhh-1. Fluorescence micrograph of neural plate explants grown in contact with anterior limb bud mesenchyme. No expression of FP3 is detected. Scale bar is 60 µm.

Figure 8A:
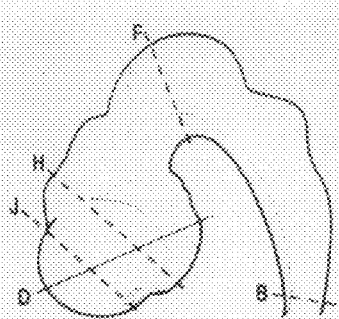

FIG. 8A vhh-1/shh and Islet-1 are expressed in Adjacent Ventral Domains in the Embryonic Chick Central Nervous System.

(A) Sagittal view showing the domain of vhh-1/shh expression in the central nervous system of a HH stage 18/19 chick embryo (shaded area). The dashed lines indicate the axial levels and planes of the sections shown in panels B–K.

(B–K) The domains of vhh-1/shh mRNA (blue-black) and Islet-1 (brown) express in adjacent domains of the ventral CNS.

Figure 8B:
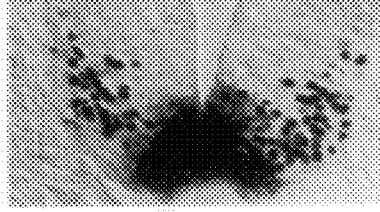

FIG. 8B (B) A transverse section through the caudal rhombencephalon showing vhh-1/shh expression at the ventral midline in the floor plate and Islet-1 expression, laterally, in motor neurons.

Figure 8C:
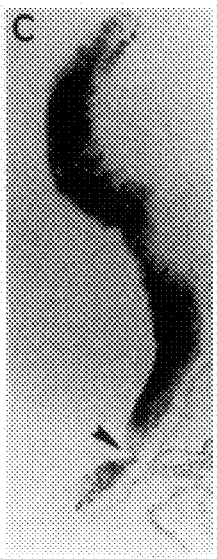

FIG. 8C (C) A sagittal section of the neural tube showing vhh-1/shh and Islet-1 expression in the ventral mesencephalon, diencephalon and telencephalon. In the mesencephalon and rostral diencephalon, cells that express Islet-1 are located adjacent to the ventral domain of expression of vhh-1/shh. vhh-1/shh expression is detected in the basal telencephalon, rostral to the optic chiasm (arrow head) and here, Islet-1 cells are found ventral and rostral to the domain of vhh-1/shh expression. Note that there is a region at the rostral-most tip of the ventral diencephalon, abutting the optic chiasm, that does not express vhh-1/shh.

Figures 8D, 8E:
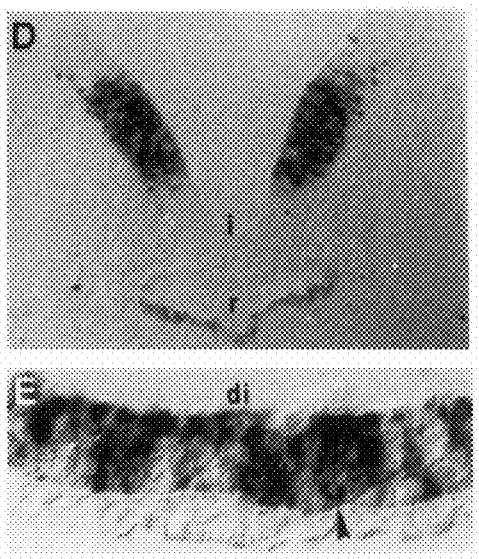

FIG. 8D (D) A transverse section through the mid-diencephalon at the level of infundibulum (i). Cells that express vhh-1/shh form two bilateral stripes. Cells that express Islet-1 are located at the lateral edge of the domain of vhh-1/shh expression. Islet-1$^+$ cells are absent from the ventral midline at the level of the infundibulum. Cells at the ventral region of Rathke's pouch (r) express Islet-1.

FIG. 8E (E) In the rostral diencephalon at HH stage 13, cells that express Islet-1 are interspersed with cells that express vhh-1/shh. The double labeling method does not resolve whether any cells coexpress vhh-1/shh and Islet-1 at this stage.

FIG. 8F (F) A transverse section through the mesencephalon showing ventral midline expression of vhh-1 and Islet-1. At this axial level, a small number of Islet-1$^+$ sensory neurons can also be detected dorsally, in the trigeminal mesencephalic nucleus.

FIG. 8G (G) Higher magnification of (F) showing that the domain of vhh-1/shh expression expands lateral to the midline and that Islet-1 cells are located lateral to the midline domain of vhh-1/shh expression.

FIG. 8H (H) A transverse section at the level of the rostral diencephalon showing ventral midline expression of vhh-1 and Islet-1.

Figure 8I:
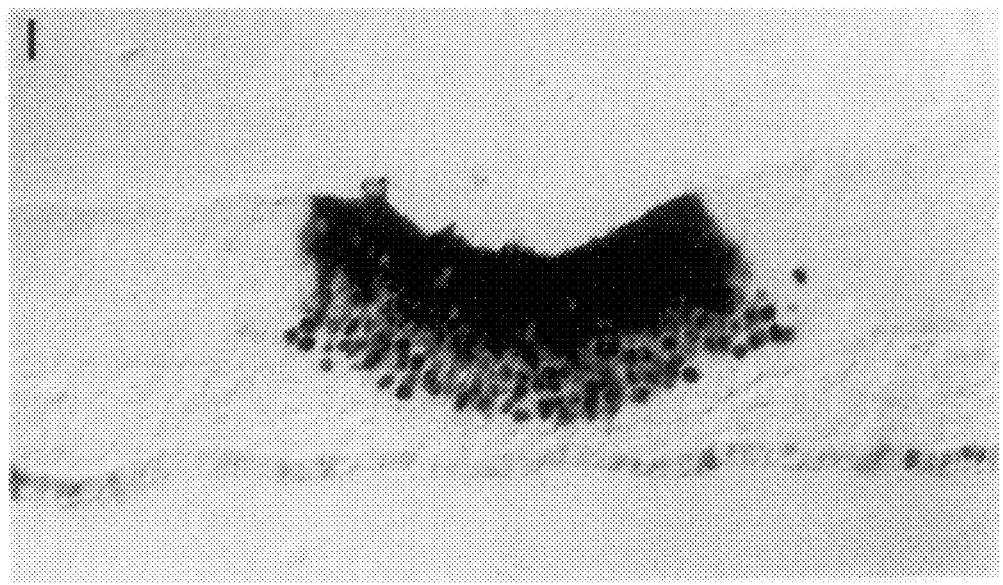

FIG. 8I (I) Higher magnification of (H) showing the ventral midline of the rostral diencephalon. Both vhh-1/shh and Islet-1 are expressed at the midline of the rostral diencephalon. vhh-1/shh is expressed in the ventricular zone whereas Islet-1$^+$ cells are located basally.

Figure 8J:
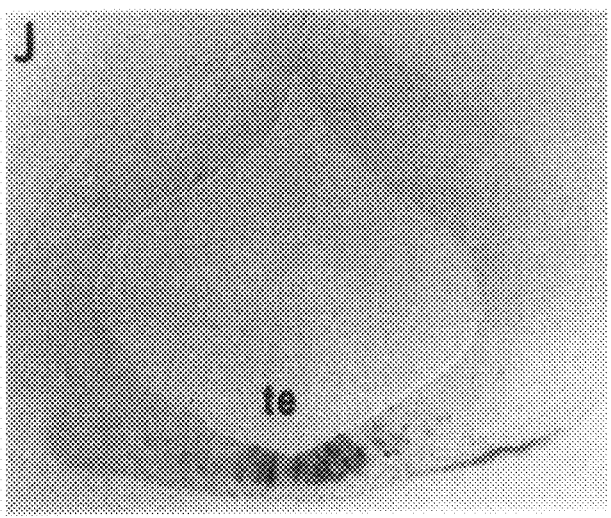

FIG. 8J (J) A transverse section at the level of the caudal telencephalon showing vhh-1/shh and Islet-1 cells in the floor of the telencephalon.

Figure 8K:
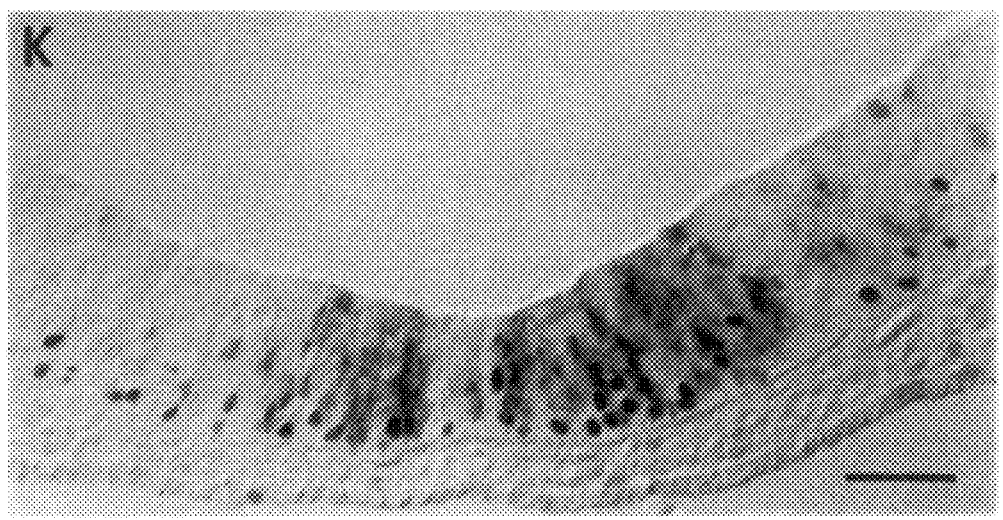

FIG. 8K (K) Higher magnification of (J). In the ventral telencephalon cells that express vhh-1/shh and Islet-1 are more dispersed then at caudal regions of the ventral CNS. The lack of vhh-1/shh expression by cells at the ventral midline suture of the telencephalon is a consistent observation. Whole-mount in situ hybridization was performed using a chick Islet-2 probe (Tsuchida et al., 1994). Chick Islet-2 mRNA was not expressed at rhombencephalic, mesencephalic, diencephalic or telencephalic levels, indicating that immunoreactivity detected with the Islet-1 antisera corresponds to the Islet-1 protein (data not shown). Abbreviations: i: infundibulum, di: diencephalon, me: mesencephalon, te: telencephalon. Scale bar: B, G, I, K=50 µm; C, F, H, J=200 µm; D=100 µm, E=25 µm.

Figure 9A:
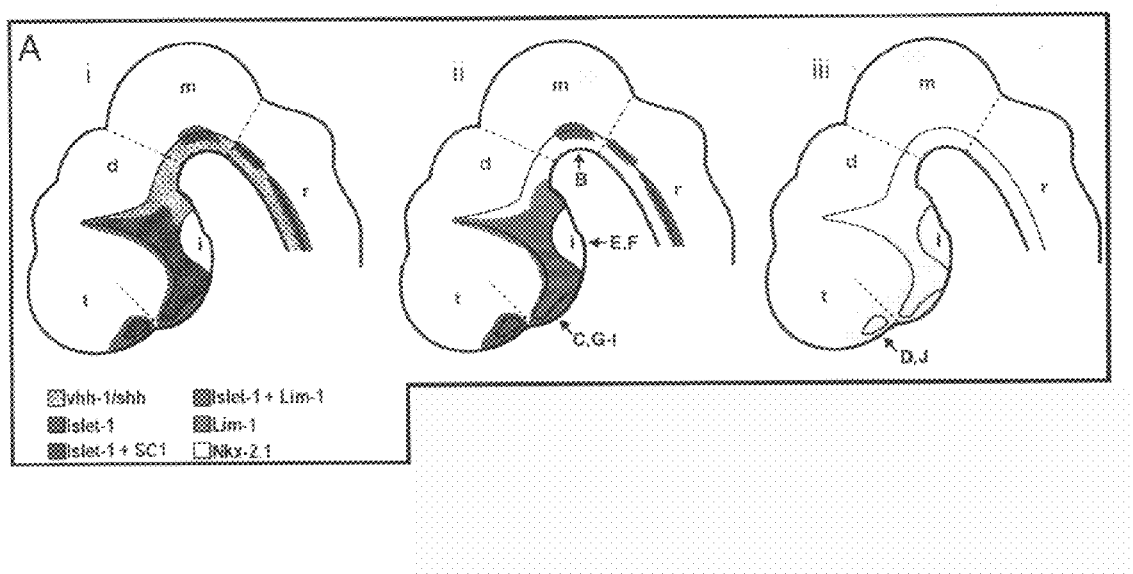
Figure 9B:
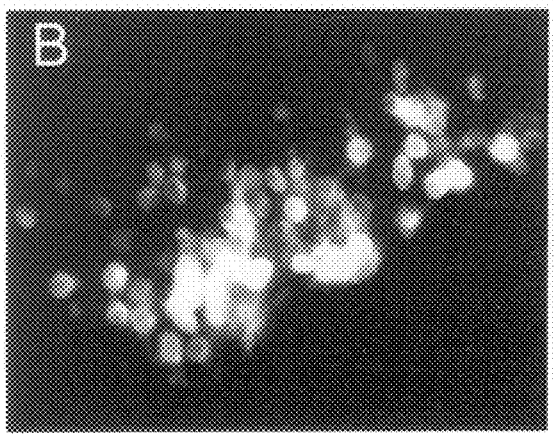

FIG. 9A (A) Diagram of a sagittal section of the neural tube of a HH stage 18/19 chick embryo showing the domains of expression of cell type markers, (i) summary diagram of the domains of expression vhh-1/shh (stippled) and Islet-1 (red) derived from the whole-mount labeling shown in FIG. 8. (ii) Summary diagram showing the coexpression of markers in Islet-1$^+$ neurons. In the rhombencephalon (r) and mesencephalon (m), ventral Islet-1$^+$ neurons coexpress the surface immunoglobulin protein SC1 (green domain). In the ventral diencephalon, Islet-1$^+$ neurons are absent from the most caudal region, although Lim-1$^+$ cells (brown) are expressed. In the region of the mid-diencephalon, rostral to the zona limitans interthalamica (Puelles et al., 1987), and also at the ventral midline of the rostral diencephalon, most Islet-1$^+$ neurons coexpress Lim-1 (blue domain). In the intervening region of the mid-diencephalon above the infundibulum (i), Islet-1 and Lim-1 are expressed in separate but intermingled neuronal populations (domain indicated by brown and red stripes). In the ventral telencephalon, Islet-1$^+$ neurons (red domain) do not express SC1 or Lim-1. For simplicity, the domain of neuroepithelia Lim-1 expression that occupies the entire dorsoventral extent of the mid-diencephalon, rostral to the zona limitans interthalamica is not depicted n this diagram. (iii) Summary diagram showing the ventral domain of expression of Nkx 2.1 protein. Small arrows indicate the plane of sections shown in panels B–J.

FIG. 9B

Ventral detail of a transverse section through the mesencephalon showing that motor neurons of oculomotor (III) nucleus coexpress Islet-1 (red) and SC1 (green) Oculomotor neurons are the most rostrally located group of Islet-1$^+$ cells that coexpress SC1. Somatic visceral and brachial motor neurons at more caudal levels also express SC1 (see also Simon et al., 1994).

Figure 9C:
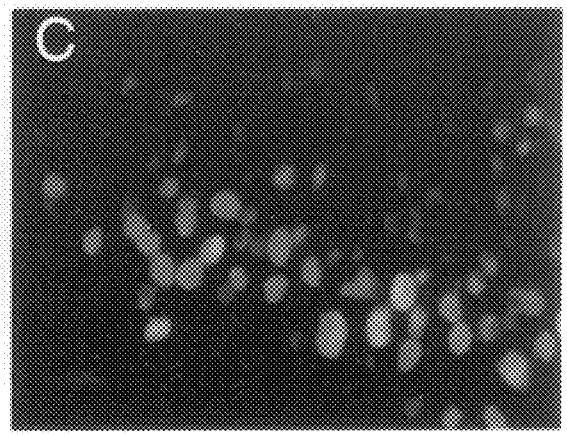

FIG. 9C (C) Ventral detail of a transverse section through the rostral diencephalon showing that Islet-1$^+$ neurons do not express SC1. SC-1-labeled axons in (C) derive from neurons located more rostrally that do not express Islet-1.

Figure 9D:
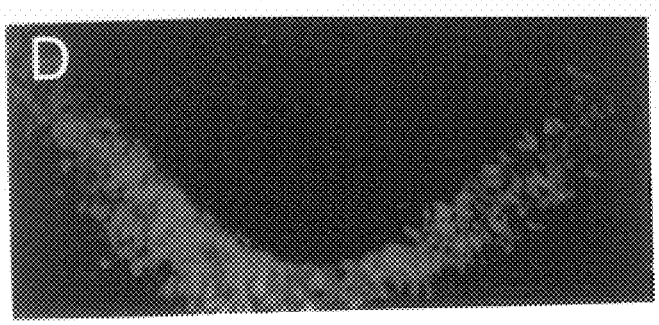

FIG. 9D (D) Detail of a transverse section through the ventral telencephalon showing expression of Nkx 2.1 in most cells.

FIGS. 9E, 9F (E, F) Detail of a transverse section through the lateral region of the mid-diencephalon dorsal to the infundibulum (see FIG. 8D for a low power view) showing that all virtually all undifferentiated neuroepithelial cells express Lim-1 at low levels (F) and that Islet-1$^+$ neurons (E) (red) also coexpress Lim-1 (yellow cells in (F)).

FIGS. 9G, 9H, 9I (G, H, I), Ventral detail of a transverse section through the rostral diencephalon showing that Islet-1$^+$ neurons (I) (red) express Lim-1 (H) (green). (I) shows a double exposure of (G) and (H) to indicate the extent of overlap of labeled cells.

FIG. 9J (J) Ventral detail of a coronal section through the ventral telencephalon showing that Islet-1$^+$ neurons do not express Lim-1, as shown by the absence of yellow cells in this double exposure of Islet-1 (rhodamine) and Lim-1 (FITC). Abbreviations: r: rhombencephalon, m: mesencephalon, d: diencephalon, t: telencephalon and i: infundibulum. The sections shown in (B–J) are from HH stage 18–19 embryos. Scale bar: B=160 µm; C, E–I=25 µm; and D, J=20 µm.

Figure 10A:
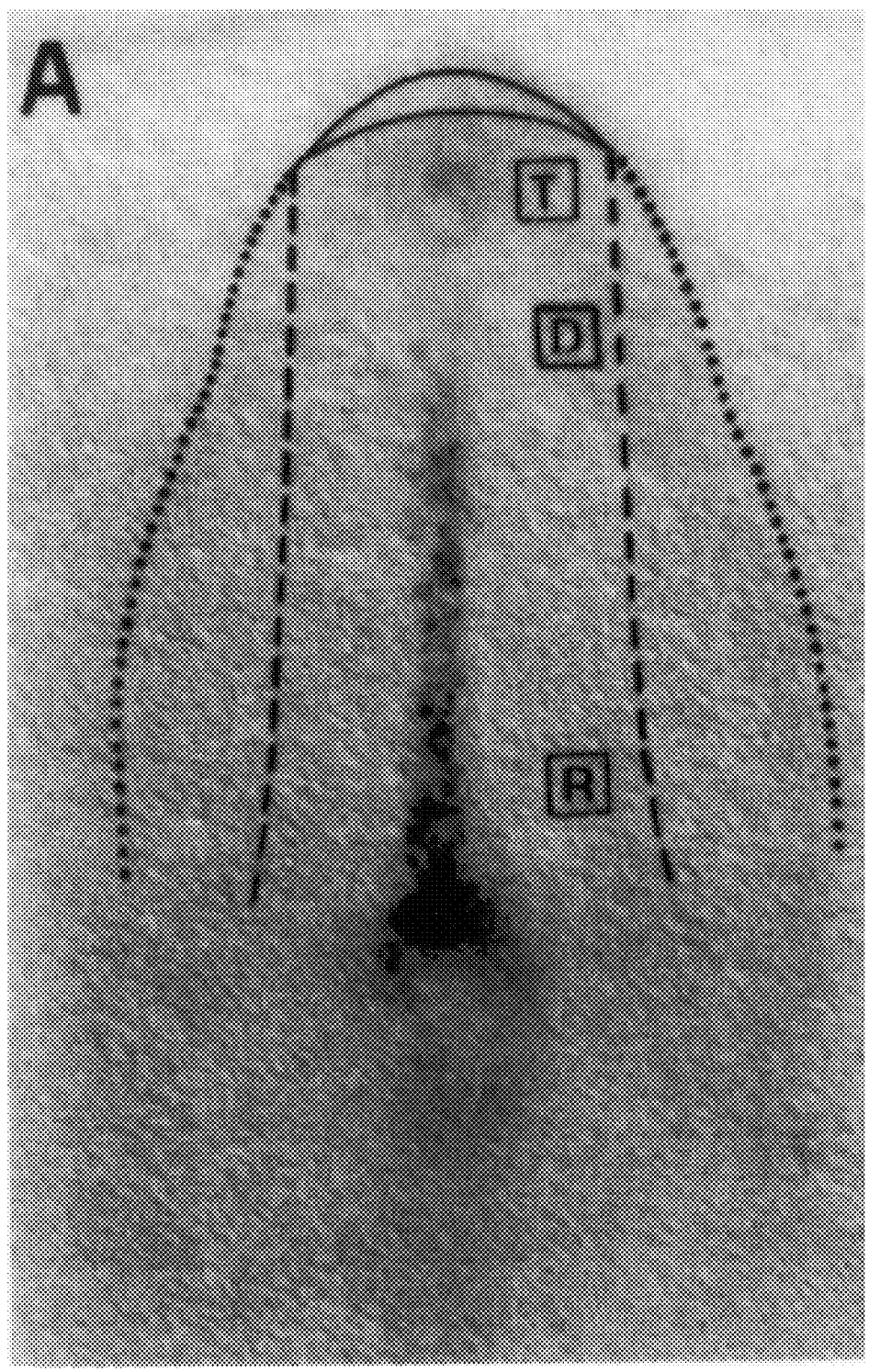

FIG. 10A vhh-1/shh induces Islet-1+ Neurons in Explants Derived from Different Rostrocaudal Levels of the Neural Plate.

(A) Expression of vhh-1/shh mRNA in the cells at the midline of a HH stage 6 chick embryo shown by whole mount in situ hybridization. Sections through such embryos shows that vhh-1/shh mRNA is expressed both in neural ectoderm and in the underlying mesoderm (data not shown). The position of the prospective telencephalic (T), diencephalic (D) and rhombencephalic (R) regions of the neural plate isolated for in vitro assays is indicated. The head-fold is at the top and the approximate neuroectodermal/ectodermal border is indicated by a dashed line. Dotted line indicates approximate border of the epiblast. Immunofluorescence micrographs in B–M show explants cultivated for approximately 65 hours on COS cells transfected with antisense or sense vhh-1 cDNA.

FIGS. 10B and 10C (B, C) Section of a rhombencephalic level explant grown on COS cells transfected with ancisense vhh-1/shh. No Islet-1+ cells are detected (B) even though β-tubulin+ neurons have differentiated (C)

FIGS. 10D and 10E (D, E) Section of a rhombencephalic level explant grown on COS cells transfected with sense vhh-1/shh. Numerous Islet-1+ cells are detected (D) virtually all of which coexpress β-tubulin (E).

FIGS. 10F and 10G (F, G) Section of a diencephalic level explant grown on COS cells transfected with antisense vhh-1/shh. No Islet-1+ cells are detected (F) even though β-tubulin+ neurons are present (G).

FIGS. 10H and 10I (H, I) Section of a diencephalic level explant arrow on COS cells transfected with sense vhh-1/shh. Numerous Islet-1+ cells are present, and these coexpress β-tubulin+ (I).

FIGS. 10J and 10K (J, K) Section through a telencephalic level explant grown on COS cells transfected with antisense vhh-1/shh. No Islet-1+ cells are detected (J) despite the differentiation of β-tubulin+ neurons (K)

FIGS. 10L and 10M (L, M) Section of a telencephalic level explant grown on COS cells transfected with sense vhh-1/shh. Numerous Islet-1+ cells are present (L), and these coexpress β-tubulin (M). Scale bar: A=250 μm and B–M=25 μm.

FIGS. 11A and 11B

SC1 Expression Distinguishes the Islet-1+ Neurons Induced by vhh-1/shh in Explants Derived from Rostral and Caudal Levels of the Neural Plate. (A, B) Immunofluorescence micrographs of a section through a rhombencephalic level neural plate explant exposed to vhh-1/shh. Double-label images of the same section shows that Islet-1+ cells (A) express SC1 (B). Arrows in (A) and (B) indicate the same cell.

FIGS. 11C and 11D (C, D) Patches of cells in rhombencephalic level explants express SC1 (D) but not Islet-1 (C). These SC1+ cells coexpress FP1 (data not shown) indicating that they are floor plate cells.

FIGS. 11E and 11F (E, F), Immunofluorescence micrographs of a section through a diencephalic level neural plate explant exposed to vhh-1/shh. Islet-1+ cells (E) do not coexpress SC1 (F).

FIGS. 11G and 11H (G, H) Immunofluorescence micrographs of a section through a telencephalic level neural plate explant exposed to vhh-1/shh. Islet-1+ cells (G) do not express SC1 (H). Scale bar: A, B, E-H=10 μm and C, D=25 μm.

FIG. 12A

Expression of Nkx 2.1 and Lim-1 Distinguishes Ventral Neurons Induced by vhh-1/shh in Diencephalic and Telencephalic Level Neural Plate Explants.

(A–C) Expression of Nkx 2.1 in neural plate explants from different axial levels exposed to vhh-1/shh. (A) Absence of expression of Nkx 2.1 in a rhombencephalic level neural plate explant exposed to vhh-1/shh.

Figure 12C:
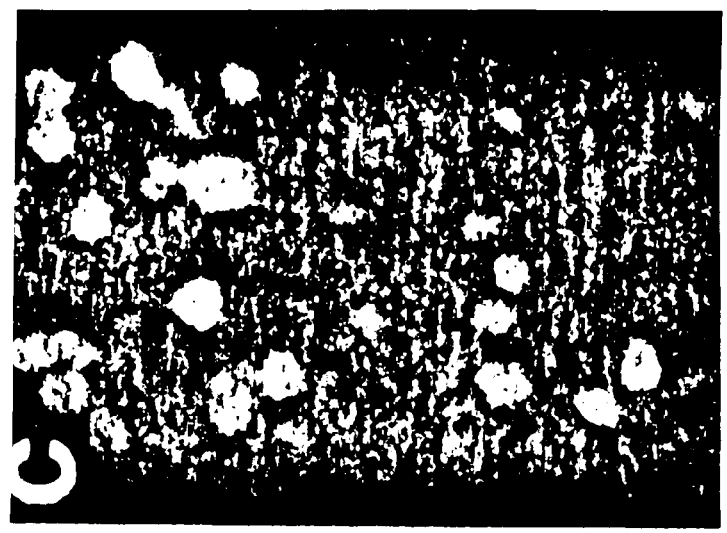
Figure 12B:
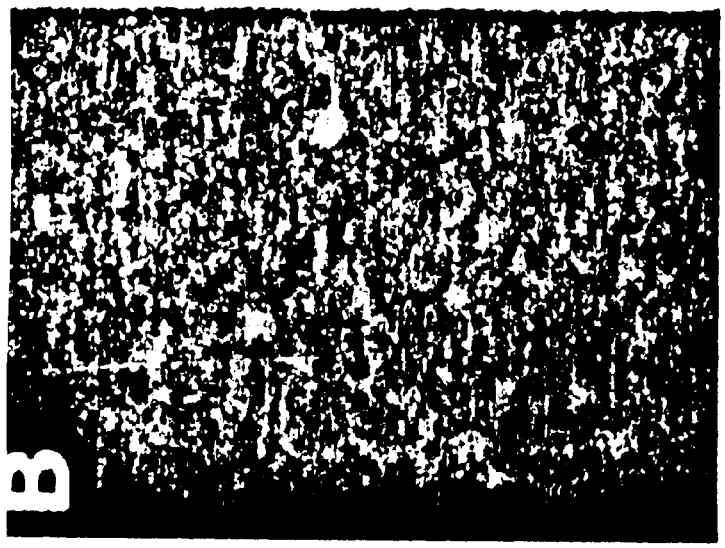

FIG. 12B (B) Expression of Nkx 2.1 in diencephalic level neural plate explant exposed to vhh-1/shh.

FIG. 12C (C) Expression of Nkx 2.1 in a telencephalic level neural plate explant exposed to vhh-1/shh. No expression of Nkx 2.1 was observed in neural plate explants that had not been exposed to vhh-1/shh (not shown).

Figure 12A:
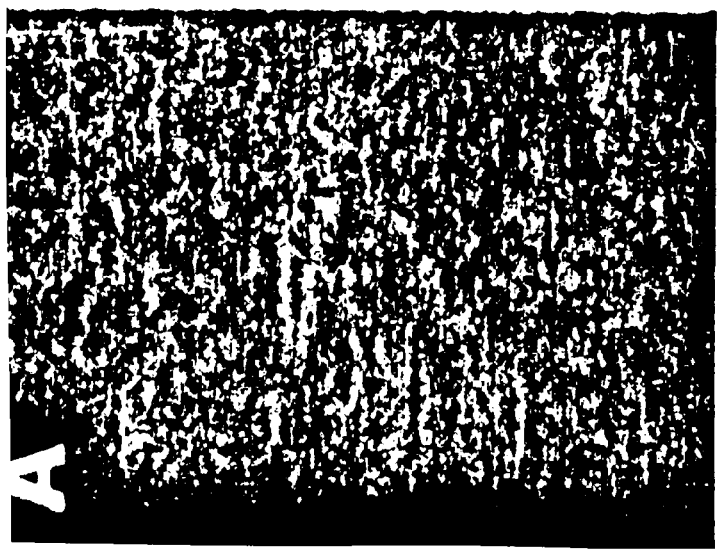
Figure 12F:
Figure 12E:
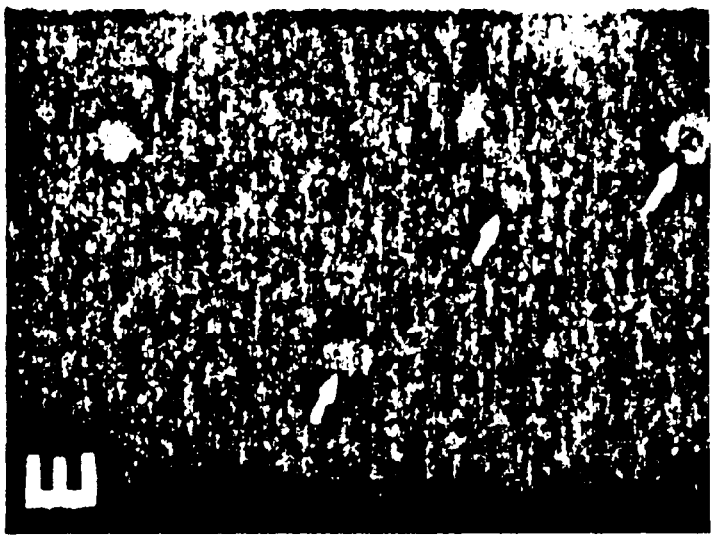
Figure 12D:

FIG. 12D (D) Lim-1+ cells are present in diencephalic level neural plate explants that have not been exposed to vhh-1/shh.

FIGS. 12E and 12F (E, F) Many Islet-1+ cells (E) in diencephalic level explants exposed to vhh-1/shh express Lim-1 (F). Arrows indicate some of the cells that coexpress Islet-1 and Lim-1. Note that Islet-1/Lim-1− and Islet-1−/Lim-1+ cells are also present.

Figure 12I:
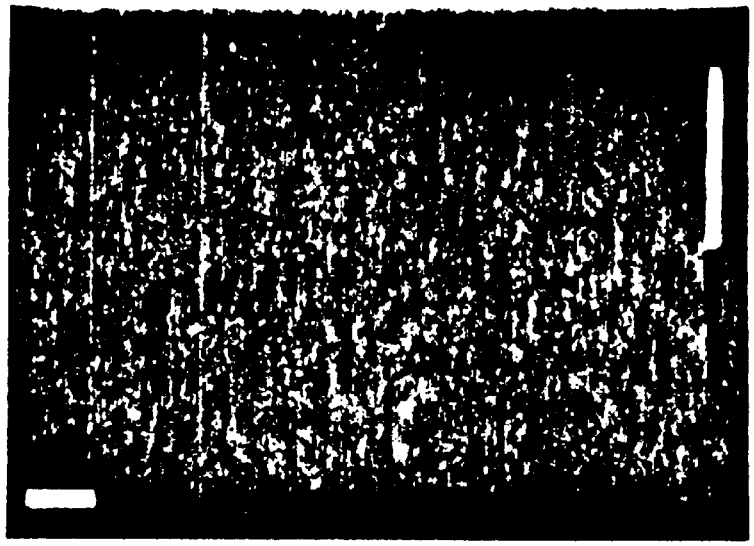
Figure 12H:
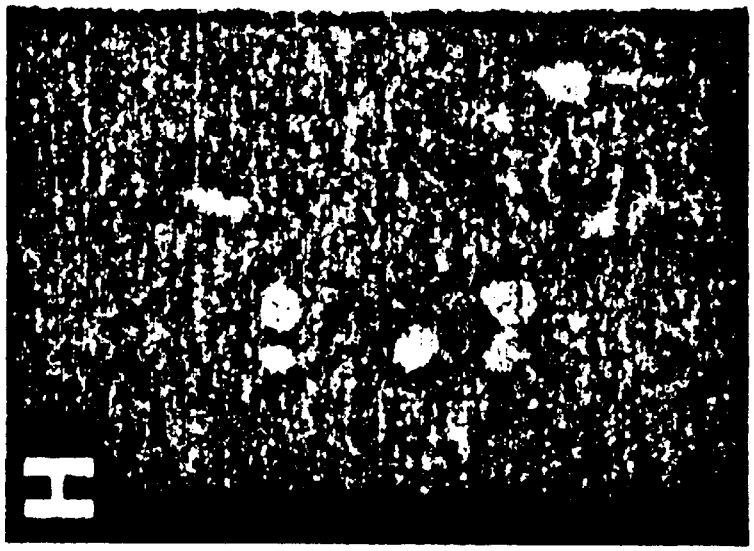
Figure 12G:
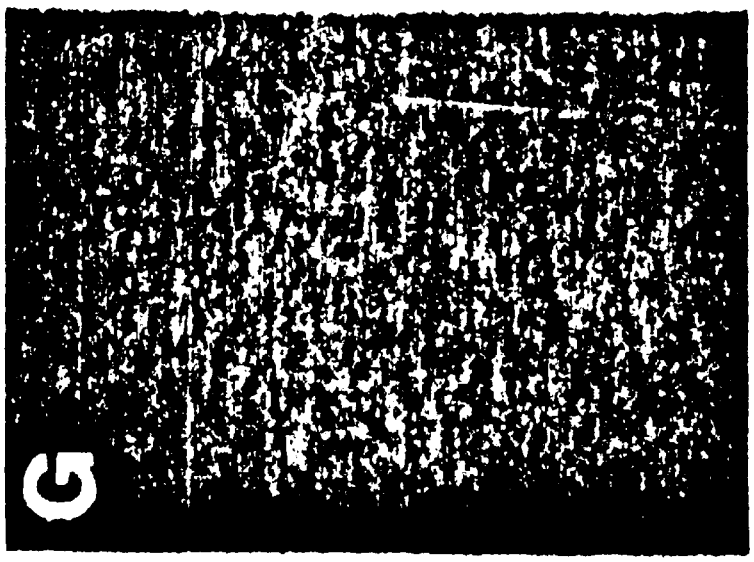

FIG. 12G (G) No Lim-1+ cells are detected in telencephalic level neural plate explants that have not been exposed to vhh-1/shh.

FIGS. 12H and 12I (H, I) Islet-1+ cells (H) in telencephalic level neural plate explants exposed to vhh-1/shh do not express Lim-1 (I). Note that no Lim-1+ cells are present in telencephalic level explants even after exposure to vhh-1/shh. Similar results were obtained in over 20 explants. Scale bar: 20 μm.

FIG. 13A

Floor plate and Midline Rostral Diencephalic Cells Mimic the Ability of vhh-1/shh to Induce Ventral Neurons at Different Levels of the Neuraxis.

(A) Islet-1+ neurons are induced by floor plate in rhombencephalic level neural plate explants. These cells coexpress SC1 (data not shown).

FIG. 13B (B) Nkx 2.1 is not induced by floor plate in rhombencephalic level explants.

FIG. 13C (C) Rostral diencephalic tissue induces Islet-1+ cells (green) in telencephalic level neural plate explants. Diencephalic tissue of murine origin is delineated by anti-nestin immunoreactivity (red) and contains a few Islet-1+ neurons (yellow cells). The induced telencephalic Islet-1+ neurons do not express SC1 (data not shown). About 10–20% of cells in the telencephalic explants expressed Islet-1.

Figure 13F:
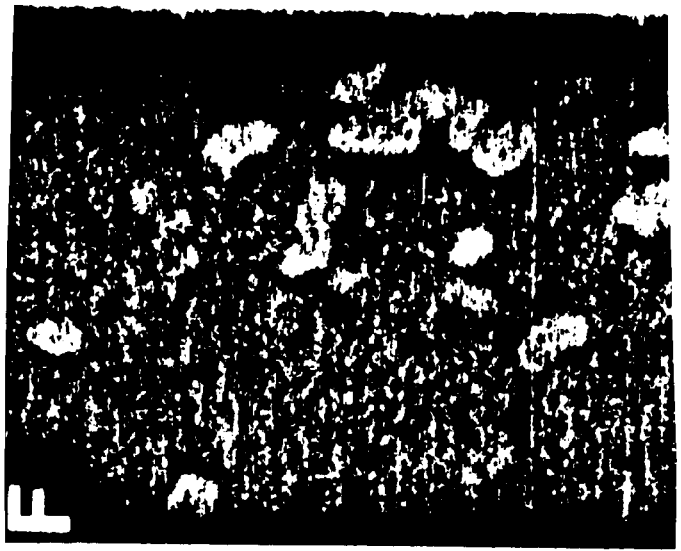
Figure 13E:
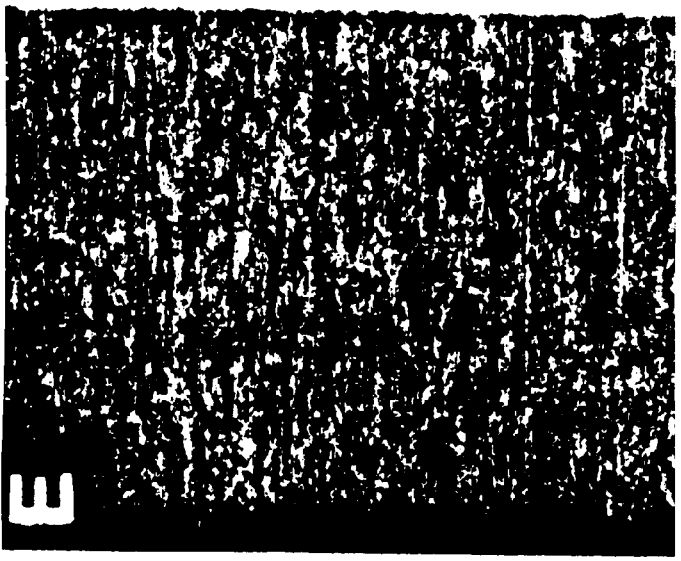
Figure 13D:
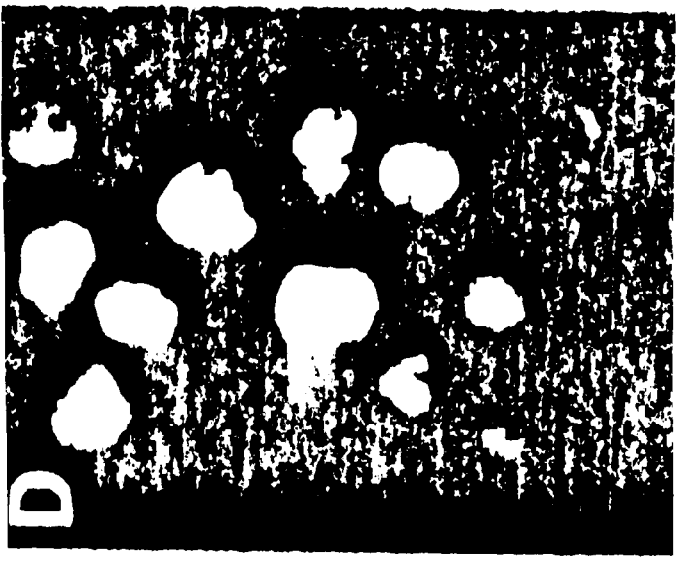

FIGS. 13D and 13E (D, E) Floor plate tissue induces Islet-1+ neurons (D) in telencephalic level explants. These neurons do not coexpress SC1 (E). The floor plate tissue is not depicted in this field.

FIG. 13F (F) Floor plate induces Nkx 2.1+ cells in telencephalic level explants. Scale bar: A, B=15 μm, C=30 μm, D, E=10 μm and F=12 μm.

FIG. 14A

Induction of Floor Plate and Motor Neuron Differentiation by the Notochord is Distinguished by Dependence on Cell Contact.

(A) Neural plate explant grown for 36 h in the absence of the notochord and labelled with antibodies that detect HNF3β and Isl-1 and/or Isl-2 (Isl+ cells). No HNF3β+ or Isl+ cells are detected.

Figure 14A:
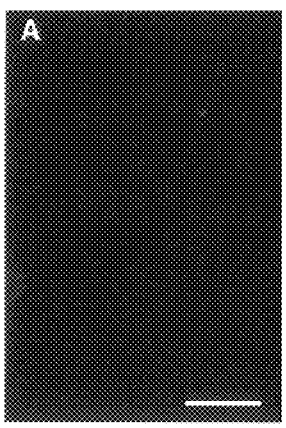
Figure 14B:
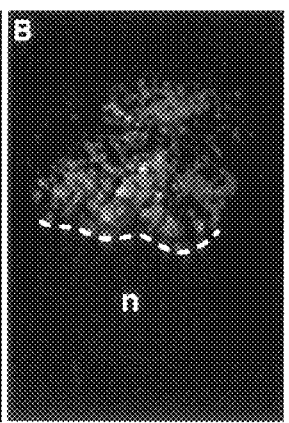

FIG. 14B (B) Neural plate explant grown for 36 h in contact with notochord (n). HNF3β+ (red) and Isl+ (green) cells are induced. HNF3β+ cells are located closer to the notochord/neural plate junction ( - - - ) than are Isl+ cells.

Figure 14C:
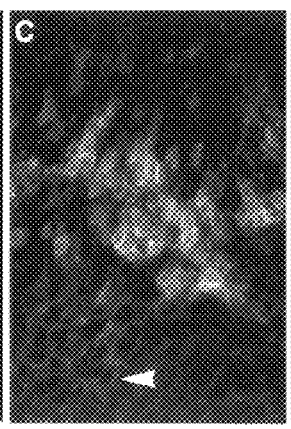

FIG. 14C (C) Isl+ cells (green) induced in neural plate explants by contact with the notochord coexpress the surface immunoglobulin-like protein SC1 (red). Patches of SC1+ cells that do not express Isl proteins (arrowhead) correspond to floor plate cells (34).

Figure 14D:
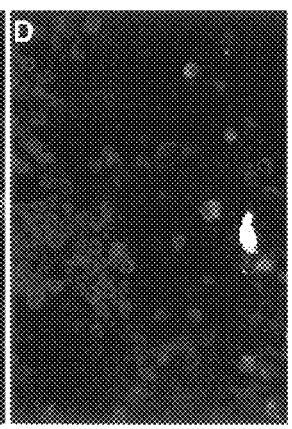

FIG. 14D (D) Contact with the notochord induces Isl-2+ cells (green) in neural plate explants. HNF3β+ cells (red) are also induced.

FIG. 14E (E) RT-PCR analysis of HNF3β and Netrin-1 mRNA induction by contact with the notochbrd. Lower bands marked by arrow indicate competitive templates introduced to control for the efficiency of the RT-PCR reactions. Intermediate neural plate explants ([i]) and notochord (n) do not express either gene when cultured alone for 36 h. Contact with the notochord (n+[i]) induces HNF3β and Netrin-1 expression (upper bands).

FIG. 14F (F) RT-PCR analysis of Isl-1, Isl-2 and CHAT mRNA induction by contact with the notochord. Intermediate neural plate explants ([i]) and notochord (n) do not express Isl-1, Isl-2 or ChAT (8) when cultured alone for 36 h. Contact with the notochord (n+[i]) induces the expression of all three genes (upper bands). Lower bands marked by arrow indicate internal standards introduced to control for the efficiency of the RT-PCR reactions. Results in E and F were obtained from RNA from the same set of explants. Similar results were obtained in 6 experiments.

Figure 14G:
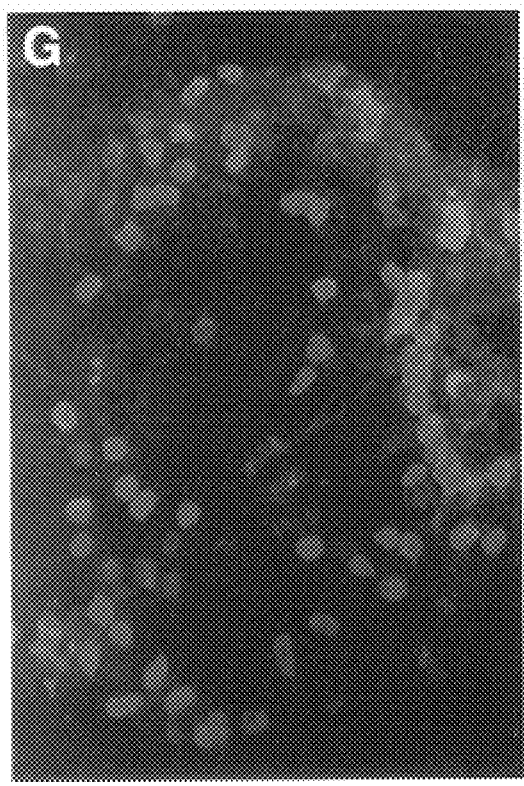

FIG. 14G (G) Neural plate explants separated from the notochord by a Nucleopore filter and grown in vitro for 36 h contain Isl+ (green) but not HNF3β+ (red) cells.

Figure 14H:
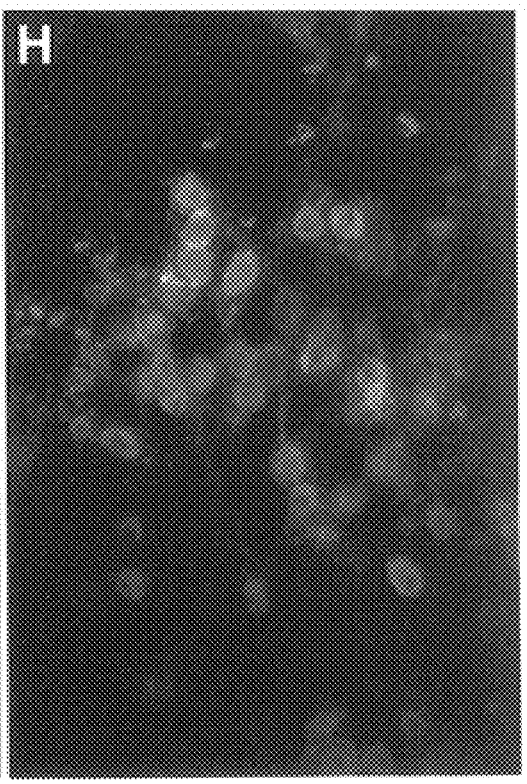

FIG. 14H (H) Isl+ cells (green) present in neural plate explants grown transfilter to the notochord express SC1 (red) indicating that they are motor neurons. Patches of SC1+/Isl- cells were not detected, indicating the absence of floor plate differentiation. Similar results were obtained in 4 separate experiments using either Nucleopore or dialysis membrane filters. Scale bar: A, C, H=20 μm; B=100 μm; D, G=33 μm.

FIG. 15A

COS Cells that Express Shh/vhh-1 Exhibit Contact-Dependent Floor Plate and Diffusible Motor Neuron-Inducing Activities.

(A) Neural plate explant grown in contact with vhh-1-transfected COS cells for 36 h contains HNF3β+ (red) and Isl+ (green) cells. The two cell groups are intermingled. Apparent yellow cells represent the superimposition of two distinct nuclei in the confocal section.

Figure 15A:
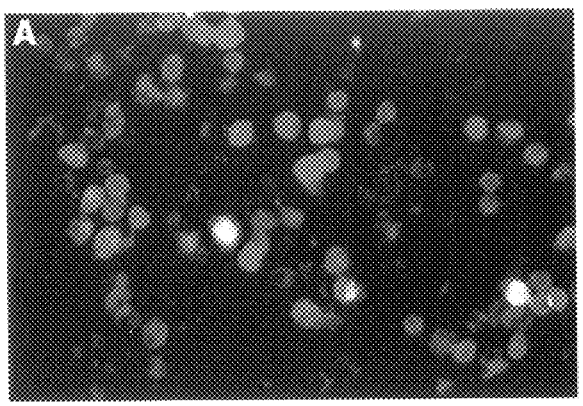
Figure 15B:

FIG. 15B (B) Isl+ neurons (green) in neural plate explants grown in contact with vhh-1-transfected COS cells express SC1 (red). Isl+ neurons that do not coexpress SC1 probably represent newly-differentiated motor neurons (34).

Figure 15C:
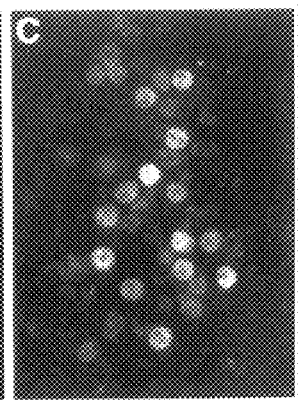

FIG. 15C (C) Many Isl-1+ neurons in intermediate neural plate explants grown in contact with vhh-1-transfected COS cells coexpress Isl-2 (orange cells).

Figure 15D:
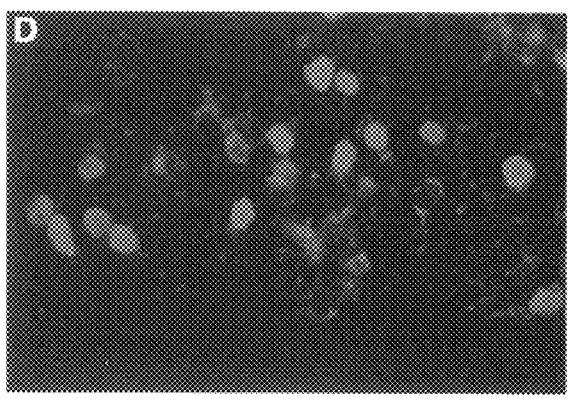

FIG. 15D (D) Neural plate explant separated from vhh-1-transfected COS cells in a collagen gel and grown for 36 h contains Isl+ (green) but not HNF3β+ (red) cells.

Figure 15E:
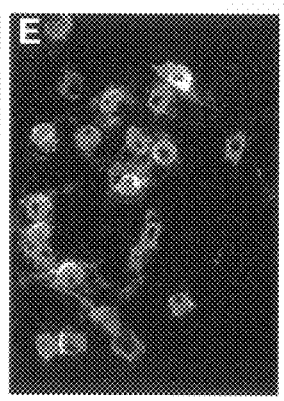

FIG. 15E (E) Isl+ neurons (green) induced at a distance from vhh-1-transfected COS cells coexpress SC1 (red) and are motor neurons.

Figure 15F:
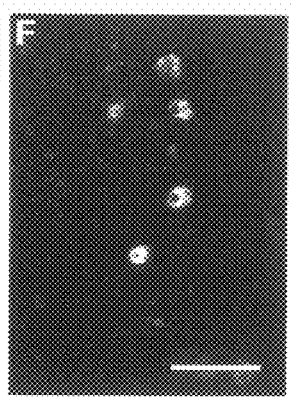

FIG. 15F (F) Isl-1+ neurons (green) induced at a distance from vhh-1-transfected COS cells coexpress Isl-2 (red), as shown by orange-labeled nuclei. Intermediate neural plate explants grown in contact with or at a distance from COS cells transfected with antisense vhh-1 cDNA did not contain HNF3β+, Isl-1+ or Isl-2+ cells (Table 2 and data not shown).

FIG. 15G (G) RT-PCR analysis of floor plate induction by vhh-1-transfected COS cells. HNF3β and Netrin-1 expression is induced in neural plate explants grown in contact with vhh-1-transfected COS cells (lanes 1) but not with antisense vhh-1-transfected COS cells (lanes 2). HNF3β and Netrin-1 expression is not induced in neural plate explants grown at a distance from vhh-1-transfected (lanes 3) or antisense vhh-1-transfected (lanes 4) COS cells. In the same experiment, notochord grown in contact with neural plate explants induces both HNF36 and Netrin-1 expression (lanes 5).

FIG. 15H (H) RT-PCR analysis of motor neuron induction by vhh-1-transfected COS cells. Isl-1 and ChAT expression is induced in neural plate exolants grown in contact with vhh-1-transfected COS cells (lanes 2). Isl-1 and CHAT expression are also induced in neural plate explants grown at a distance from vhh-1-transfected COS cells (lanes 3). Isl-1 and ChAT expression is not induced in neural plate explants exposed to COS cells transfected with antisense vhh-1 (lanes 2 and 4). Notochord grown in contact with neural plate explants induces both Isl-1 and CHAT (lanes 5). Results shown in Panels A–H have been replicated in 6 different experiments. Scale bar: A, D=16 μm; C, F=33 μm.

FIG. 16A

Induction of Floor Plate and Motor Neuron Differentiation by Transfection of vhh-1 into Neural Plate Explants.

(A) RT-PCR analysis of floor plate and motor neuron marker expression in neural plate explants analyzed 48 h after transfection with a CMV vhh-1-transfected explants (vhh-1) but not in mock-transfected (⁻) explants. Isl-1 was also detected in vhh-1-transfected neural plate explants grown in the absence of NT3 but at lower levels (data not shown). Cells that expressed HNF3β and Isl immunoreactivity could also be detected (data not shown) although there was an extremely high background, possibly because of cell damage as a consequence of the transfection protocol.

Figure 16A:
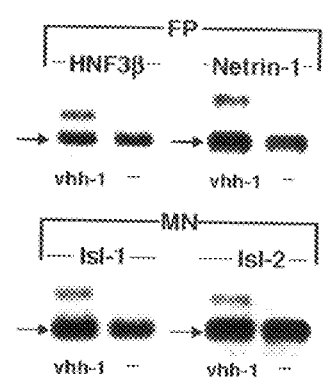
Figure 16B:
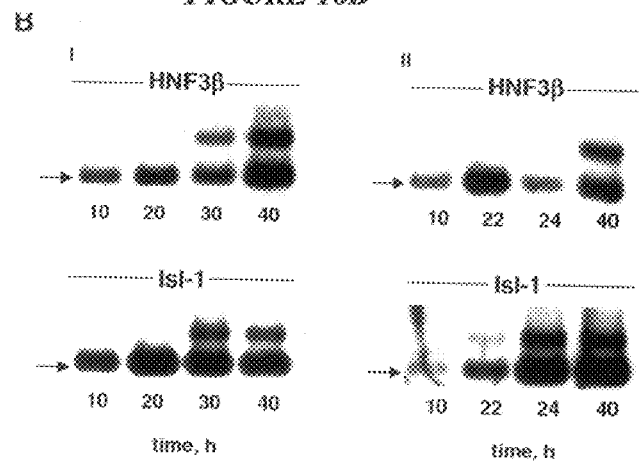

FIG. 16B (B) Time course of HNF3β and Isl-1 expression in neural plate explants transfected with a CMV vhh-1 cDNA expression construct. (i) In this experiment neither Isl-1 nor HNF3β are expressed 10 h or 20 h after transfection (lanes 1 and 2) but are detected at 30 h and 40 h (lanes 3 and 4). Netrin-1 and Isl-2 are also expressed after 30 h (data not shown). (ii) In this experiment Isl-1 expression is not apparent at 10 h (lane 1) and can first be detected at 22 h (lane 2). In contrast, HNF3β expression is not detected at either 22 h or 24 h (lanes 2 and 3) although the gene is expressed at 40 h (lane 4). Results showing that Isl-1 expression occurs before or coincident with HNF3β expression were obtained in 4 separate experiments. In a further 3 experiments, Isl-1 expression was detected although HNF3β could not be detected. Isl-1 was also detected in vhh-1-transfected neural plate explants grown in the absence of NT3 (data not shown; see below).

FIG. 17A

Independent Induction of Floor Plate and Motor Neuron Differentiation by Shh/vhh-1. Diagrams depict two possible mechanisms by which shh/vhh-1 derived from the notochord (dark shading) could induce floor plate (FP) and motor neuron (MN) differentiation independently.

(A) Floor plate and motor neuron differentiation could be mediated by different fragments of shh/vhh-1 that are generated by autoproteolysis (28). The amino terminal (N) fragment of hedgehog remains largely associated with the cell surface whereas the carboxy terminal fragment (C) is freely diffusible (28). Thus, in this diagram N is depicted as mediating the contact-dependent induction of floor plate differentiation and C, the longer range, contact-independent induction of motor neurons.

FIG. 17B (B) Floor plate and motor neuron differentiation could be mediated by different. concentrations of the same molecular species of shh/vhh-1. Since neural plate cells that are located immediately above the notochord differentiate into floor plate cells, the diagram indicates that a high concentration of shh/vhh-1 (→) is required to elicit floor plate differentiation. Lower concentrations of shh/vhh-1 (→) initiate motor neuron differentiation independent of floor plate differentiation.

FIGS. 18A, 18B, 18C

Embryonic midline expression of vhh-1, Pintallavis, goosecoid, and HNF-3β. All panels show Nomarski images of whole-mount in situ hybridizations (A–E, J–M, O, Q) or histological section (F–I, N, P) labeled with an antisense vhh-1 RNA probe (A, D, F–H, J–N, Q), an antisense Pintallavis RNA probe (B, E, I), an antisense goosecoid RNA probe (C) or antibodies directed against HNF-3β (O, P).

(A–C) Expression of vhh-1 (A) Pintallavis (B; and goosecoid (C) in early (stage 10) gastrula embryos. Note the absence of vhh-1 mRNA from the early dorsal blastopore lip (dbp) or organizer region (A) which expresses Pintallavis and goosecoid (B, C). Panels show vegetal views with dorsal side up (A, C) or slightly to the right (B).

Figure 18A:
Figure 18B:
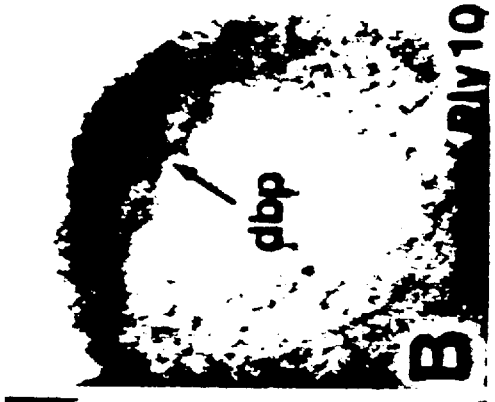
Figure 18C:
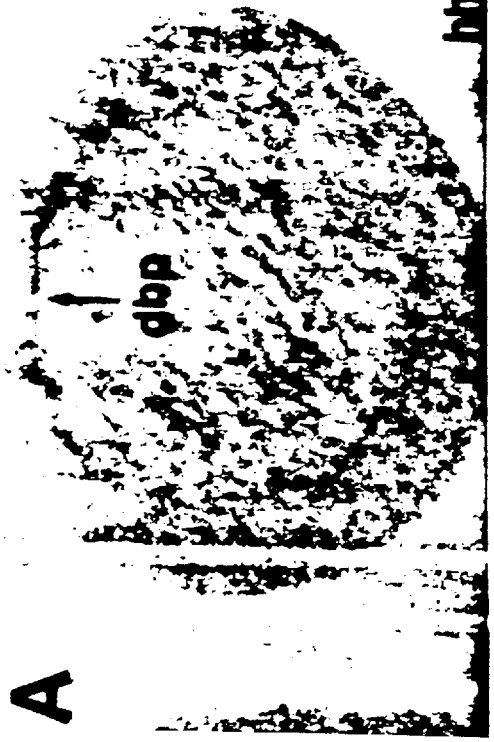
Figure 18D:
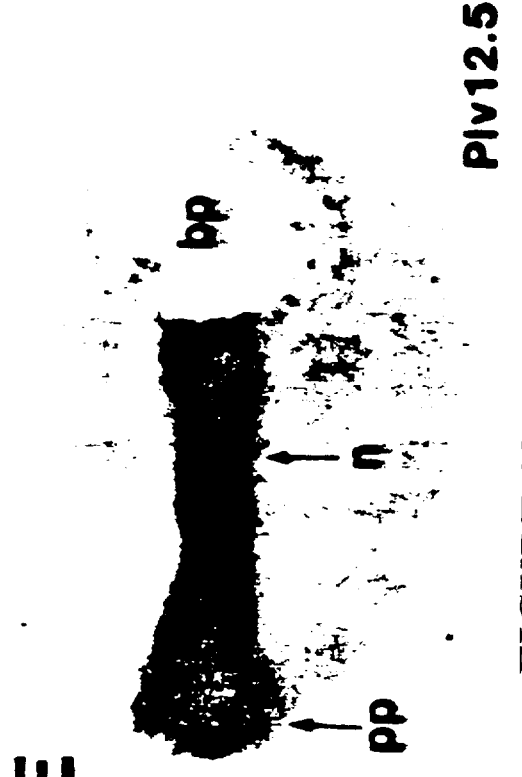
Figure 18E:

FIGS. 18D and 18E (D, E) vhh-1 is expressed in cells of the notochord (n) as it forms but is absent from the future tailbud region, near the blastopore (bp; D). Pintallavis, in contrast, is expressed throughout the notochord, including cells near the blastopore (E). Both vhh-1 and Pintallavis are also expressed in the prechordal plate (pp) a: anterior, p: posterior. Panels show dorsal views with anterior end to the left.

FIGS. 18F, 18G, 18H and 18I

Transverse sections of midline regions of gastrula and neurula stage embyros labelled in whole mount with an antisense vhh-1 RNA probe (F–H) or an antisense Pintallavis RNA probe (I). Expression of vhh-1 is detected in notochord (n) but not in neural plate (np) cells during early gastrula stages (stage approximately 11, F). Within the notochord, expression of vhh-1 is confined mainly to dorsal cells that underly the neural plate. At late gastrula stages (stage approximately 12.5–13, G), expression of vhh-1 within the notochord is detected at high levels in the most dorsal cells and expression is also detected in cells of the deep (d) but not superficial (s) cells of the neural plate (Schroeder, 1970). At early neurula stages (stage approximately 15), vhh-1 is expressed in median deep (md) neural plate cells forming a triangle over the notochord (n) but not in adjacent intermediate deep (id) or median superficial (ms) cells (H). Levels of expression in the notochord are very low. Following neural tube closure (stage approximately 20) expression of vhh-1 is still restricted to md cells (not shown). In older embryos (from stage approximately 24) md and ms cells intermix at the ventral midline of the neural tube and vhh-1 expression is detected in all ventral midline cells of the floor plate (stage approximately 36; N). Pintallavis mRNA is also detected in deep (d) but not superficial (s) cells of the neural plate (I) and in midline endodermal cells (en) underlying the notochord which will form the hypochord. Note the even distribution of Pintallavis expression throughout the notochord in comparison to that of vhh-1 shown in (F, G). s: somites. In all panels, dorsal side is up.

FIGS. 18J, 18K, 18L and 18M (J–M) Expression of vhh-1 mRNA in neurula (stage 15, J), tailed (stages approximately 20, approximately 26, K and L) and tappole (stage approximately 36, M) embryos labelled in whole mount. At the early neurula stage (stage approximately 15, J), vhh-1 is expressed in the floor plate (fp), prechordal plate mesoderm (pp) and adjacent anterior endoderm at high levels whereas its expression in the notochord (n) is lower that at earlier stages. Within the notochord there appears to be a gradual loss of vhh-1 mRNA from anterior to posterior regions. vhh-1 is also expressed in cells of the ventral forebrain overlying the prechordal plate. At early tailbud stages (stage approximately 20, K), vhh-1 is detected at high levels in the floor plate of the hindbrain and midbrain (m), in the entire ventral diencephalon (d) and prechordal plate mesoderm (pp) which underlies the forebrain. vhh-1 mRNA is also detected in pharyngeal endoderm (pe) anterior to the prechordal plate. No expression is detected in the notochord (n) or telencephalon (t). Note the sharp boundary between cells expressing vhh-1 in the ventral diencephalon and those not expressing vhh-1 in the ventral telencephalon. At late tailbud stages (stage approximately 26, L), vhh-1 is still expressed in the floor plate (fp) and midline cells of the ventral diencephalon (vd) but not in the telencephalon (t). vhh-1 expression is undetectable in the notochord (n) but it remains in the prechordal plate and in areas of the anterior endoderm (en). As the brain develops, there is expression in posterior diencephalic cells in more lateral areas (unlabelled arrow in L) Expression in the lateral diencephalon comprises a broad bilateral stripe. vhh-1 expression is also observed in an anterior position, ventral to the telencephalon (t) and dorsal to the cement gland, corresponding to the olfactory placode (op).

Expression of vhh-1 mRNA is detected in tadpoles (stage approximately 36, M) at high levels in the floor plate (fp) throughout its length, a dorsal-posterior diencephalic region and in broad bilateral diencephalic (d) stripes. At later stages, (stage>40) expression is detected in a small group of cells in the ventral telencephalon (not shown). vhh-1 is reexpressed at tadpole stages in the notochord (n). The tailbud (tb) does not express vhh-1 but expression is detected in cells forming the hypochord (located ventral to the notochord), notochord and floor plate as soon as these leave the tailbud (not shown). In the head, vhh-1 is widely expressed in the gill endoderm (ge) and in the frontonasal region, adjacent to the telencephalon (t) At later stages (stage approximately 51), vhh-1 expression was also detected in the posterior mesenchyme of the hind limb buds and in various regions of the brain, including the floor plate and hypothalamic areas (not shown). All panels show lateral views with dorsal side up and anterior end to the left.

FIG. 18O

Expression of HNF-3β protein in a tadpole (stage approximately 36) stage embryo. The expression of HNF-39 is nuclear. Within the central nervous system, cells that express HNF-3β are found in the floor plate (fp) at the ventral midline of the midbrain (m), hindbrain and spinal cord. HNF-3β is not expressed in the ventral region of the rostral diencephalon (d), or in the telencephalon (t). However, expression of HNF-3β as that of vhh-1 (L, M) and F-spondin (Ruiz i Altaba et al., 1993a), is detected in more lateral cells with large nuclei, possibly neurons, in the posterior diencephalon (unlabelled arrows in O). HNF-3β is also expressed in anterior endodermal cells lining the gill and foregut cavities and in posterior endodermal cells at lower levels (not shown). Expression of HNF-3β protein and mRNA (Ruiz i Altaba et al., 1993b) are coincident. Numbers refer to rhombomeres. Rhombomere 4 is located adjacent to the otic vesicle. The panel shows a lateral view with dorsal side up and anterior end to the left.

Figure 18G:
Figure 18I:
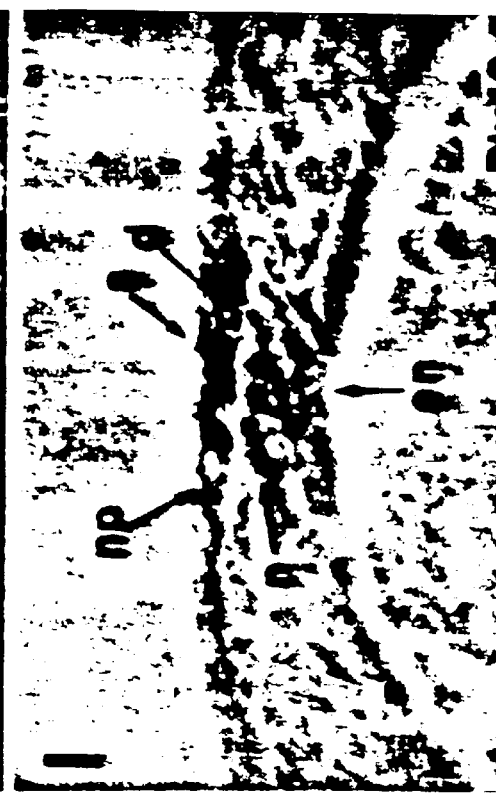
Figure 18F:
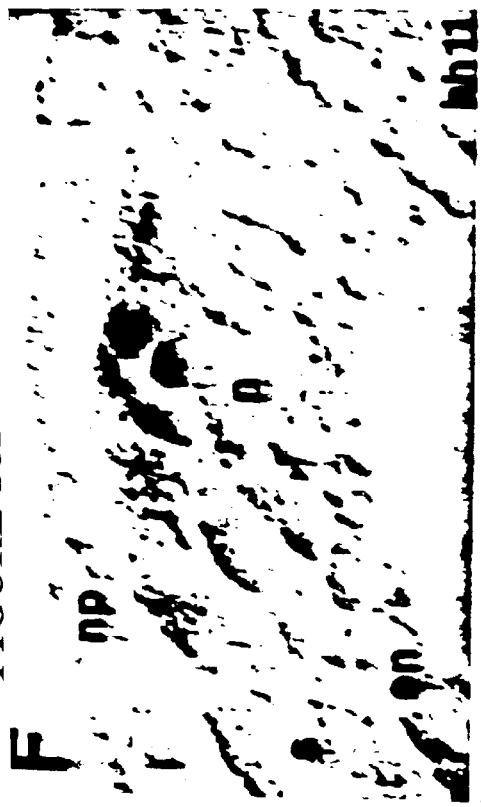
Figure 18H:
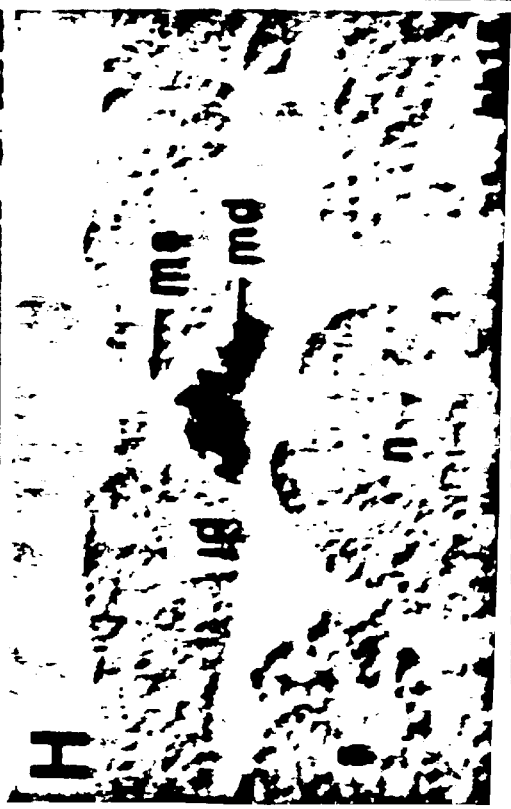
Figure 18J:
Figure 18K:
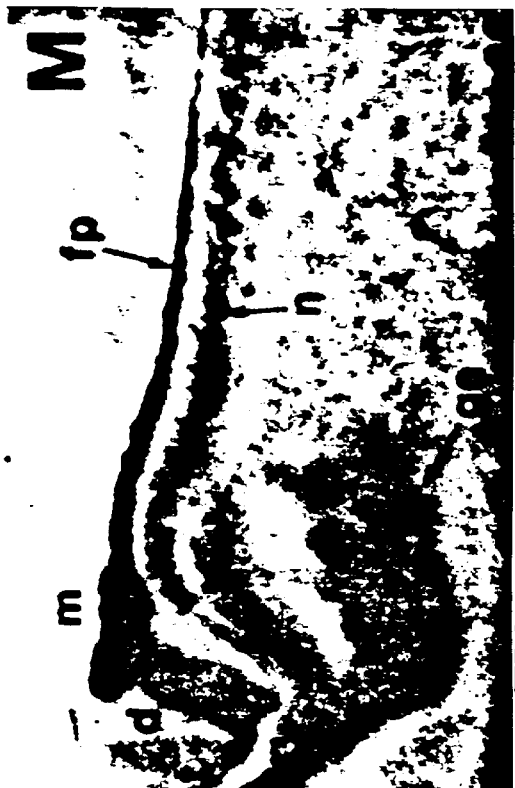
Figure 18L:
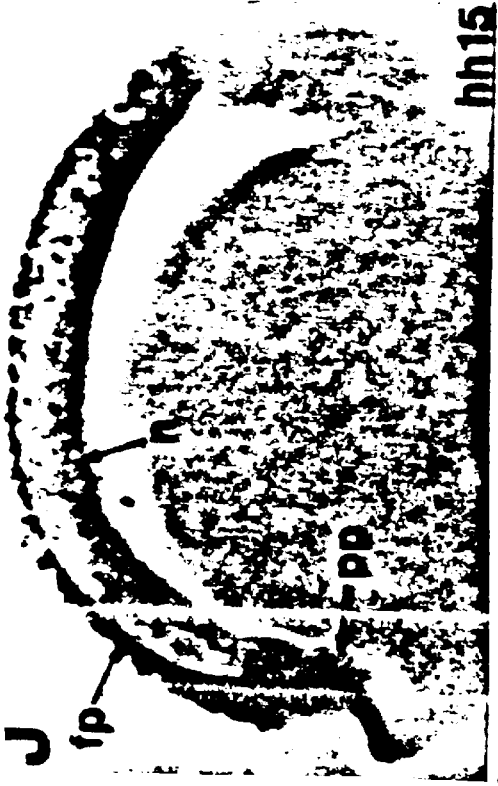
Figure 18M:
Figure 18N:

FIGS. 18N and 18P (N, P) Histological sections of tadpole (stage approximately 36) stage embryos showing the expression of vhh-1 (N) and HNF-3β (P) in the floor plate (fp) of the spinal cord (sc). vhh-1, but not HNF-3β, is also expressed at high levels throughout the notochord (n). Cells expressing HNF-3β are detected in the floor plate and in the immediately adjacent ventral ventricular zone (P, see also Ruiz i Altaba et al., 1993a, b), a region that does not express other floor plate markers such as vhh-1 (N) or F-spondin (Ruiz i Altaba et al., 1993a). Within the hindbrain, the expression of HNF-3β shows pronounced rhombomeric variations. HNF-3β in rhombomeres 3 and 5 is expressed exclusively in floor plate cells whereas in rhombomeres 2, 4 and 6 expression extends to adjacent ventricular cells (O and not shown). The appearance of these non-floor plate cells expressing HNF-3β may occur after the competence of neural tube cells to become floor plate is lost. Dorsal side is up.

FIG. 18Q (Q) Expression of vhh-1 in a tadpole stage (stage approximately 36) exogastrulae. In complete exogastrulae vhh-1 mRNA is expressed in the notochord (n) and prechordal plate at early stages (not shown) and in the notochord and anterior. endoderm, including the gill endoderm (ge) at later stages. Expression is also detected in the hypochord (not shown). In no case was expression of vhh-1 detected in the ectodermal sac containing the neural ectoderm (ne). This panel shows a lateral view with the anterior end of both the ectoderm and endomesoderm to the right. In situ hybridization with sense vhh-1 RNA probes resulted in the absence of any specific labelling (not shown). Scale bar=500 μm for A–C, E, M, ); 450 μm for D, J, L; 80 μm for F–I, 300 μm for K, N; 150 μm for P and 70 μm for Q.

FIGS. 19A, 19B, 19C

Widespread ectopic expression of vhh-1 and HNF-3β from injected plasmids.

(A–C) Expression of vhh-1 mRNA from injected vhh-1 plasmids (see Methods). A) In frog embryos injected with frog vhh-1 and analyzed at early gastrula (stage approximately 11.5) stage, ectoplc vhh-1 mRNA is detected at high levels in large patches in dorsal (d) ectodermal cells. B) Similarly, rat vhh-1 mRNA expression after injection of rat vhh-1 plasmids is detected in neural ectoderm (arrows) in late gastrula-early neurula stage (stage approximately 12.5–15) embryos. At tadpole (stage approximately 38) stages, rat vhh-1 mRNA is detected in a mosaic manner (C).

FIGS. 19D, 19E, 19F

Expression of HNF-3β protein after injection of HNF-3β plasmid.

(D) Expression of nucleic HNF-3β protein in large patches of neural and non-neural ectoderm in gastrula (stage approximately 12) stage embryos.

(E) Histological section through the dorsal tissues of gastrula stage embryos as that in (D) showing that predominant localization of labelled cells (arrows) in the ectoderm. Expression in the underlying mesoderm is confined to scattered single cells. The endogenous HNF-3β gene is not transcribed in mesodermal or ectodermal cells at these stages (Ruiz i Altaba et al., 1993b).

(F) At tadpole (stage approximately 36) stages, HNF-3β protein is detected in a mosaic pattern similar to that observed for vhh-1 in addition to expression of the endogenous gene in the endoderm and the floor plate (fp). However, HNF-3β expression is often detected in the dorsal hindbrain (dh) at high levels (Table 6). One possible explanation for this may be the activation of the endogenous HNF-3β gene in the dorsal neural tube by plasmid-driven HNF-3β (see Text) Arrows point to regions of expression. v: ventral A,C,F) show lateral views with anterior end up (A) or to the left (C, F). (D) shows a dorsal view with anterior end up. In most embryos in (B) and in the section shown in (E) dorsal side is up. Scale bar=680 μm for A, D, F; 1.5 mm. for B; 450 μm for C; 100 μm for E.

FIGS. 20A, 20B, 20C

Widespread expression of vhh-1 induces the ectopic expression of HNF-3β

Figure 18O:
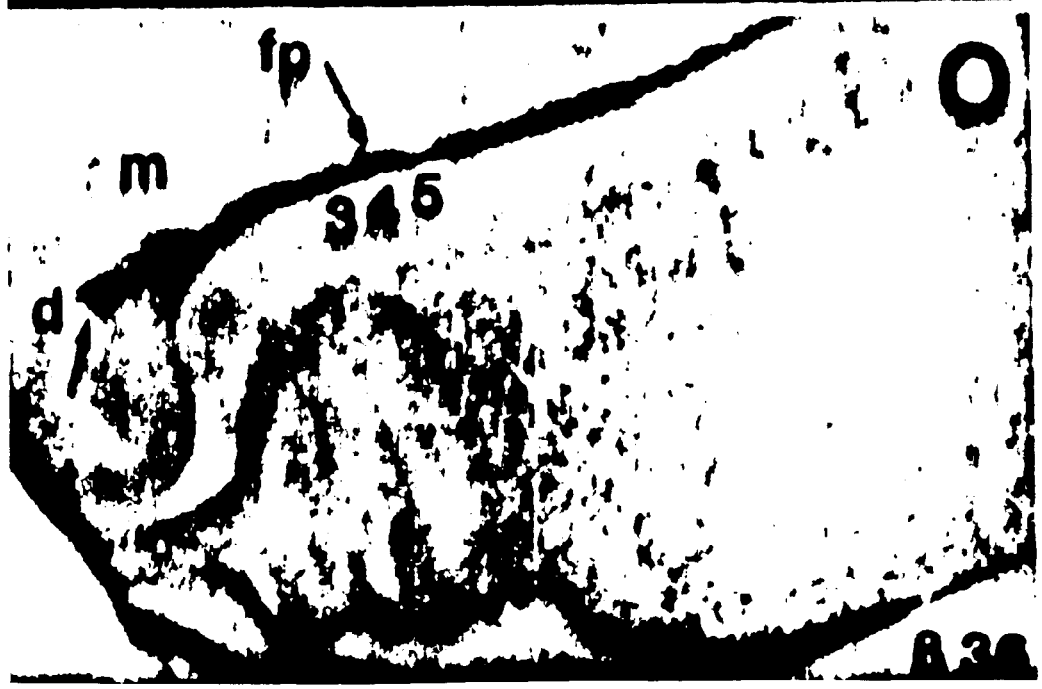

(A–C) Lateral views of the brain of injected tadpole (stages approximately 28, A and approximately 36, B, C) stage embryos labelled with anti-HNF-3β antibodies. The endogenous expression of HNF-3β is detected in the floor plate (fp). Numbers refer to rhombomeres identified by the presence of boundaries under Nomarski optics and the variation of the ventral domain of HNF-3β expression (see FIG. 18O). Restrictions in ectopic floor plate marker expression were also found within the hindbrain. A comparison of the location of TNP-R rpl .c in relation to morphologically visible rhombomeric boundaries revealed preferential ectopic expression in the dorsal region of rhombomere 4, located opposite the otic vesicle, but not in the adjacent rhombomeres 3 and 5. A bias in the ectopic expression of HNF-3β in even versus odd rhombomeres is consistent with evidence that these two rhombomeres display properties not shared by even numbered rhombomeres (Lumsden and Keynes, 1989; Bradley, et al., 1992; Winning and Sargent, 1994).

Figure 20A:
Figure 20B:
Figure 20C:
Figure 20D:
Figure 20E:
Figure 20F:

FIGS. 20D, 20E and 20F (D, E, F) Histological sections of embryos comparable to those in (B, C) showing expression of endogenous HNF-3β protein in the floor plate (fp) overlying the notochord (n) and in adjacent cells and ectopic expression restricted to dorsal midline regions including the roof plate (rp) (E, E) and adjacent dorsal alar plate region (arrow in D). A branched neurocoel (bne) is often detected associated with ectopic HNF-3β expression in dorsal cells (E). Ectopic expression is also detected in the otic vesicle (ov) and rarely in cells outside of the neural tube in between the otic vesicle and the dorsal neural tube (F). Within the otic vesicle, highest expression is detected in dorsal regions at late tadpole stages whereas at earlier. stages, expression is uniform throughout the otic placode. (A–C) show lateral views with anterior end to the left and in (D–F) dorsal side is up. Cells in the otic vesicle express ectopic (HNF-3β but not vhh-1 and cells in the epidermis express ectopic vhh-1 but not HNF-3β (D, F and not shown). This suggests that aspects of the molecular interactions between vertebrate hedgehog and winged-helix genes are present in non-neural tissues. Arrowheads point to the sites of ectopic expression. Scale bar=400 μm for A, B; 200 μm for C; 75 μm for D. E: 100 μm for F.

FIG. 21A

Widespread expression of rat vhh-1 induces the ectopic expression of frag vhh-1

(A) Expression of frog vhh-1 at the late gastrula (stage approximately 13) stage after injection of rat-vhh-1 plasmid. Endogenous expression is detected in the notochord (n) anterior to the blastopore (bp). Ectopic expression is also detected in a few scattered cells (see text).

FIGS. 21B and 21C (B, C) Expression of frog vhh-1 in tadpole (stage approximately 36) stage embryos after widespread expression of rat vhh-1. In addition to the endogenous expression in the floor plate (fp) and notochord (n), ectopic expression is detected in dorsal regions in the hindbrain and spinal cord (B, C) and in a continuous D–V stripe in the anterior spinal cord (B) Sites of expression along the entire D–V extent of the neural tube were detected only in embryos showing one or more dorsally restricted ectopic expression sites.

FIGS. 21D, 21E and 21F (D–F) Histological sections of the neural tube of tadpole stage embryos comparable to those in (B, C) showing the normal expression of vhh-1 in the floor plate (fp) and the dorsal restriction of ectopic vhh-1 expression (D, F) and expression in a medial septum in embryos showing extreme malformations (E). These defects are more prominent at tailbud than at tadpole stages. Branched neurocoels (bne) are often associated with ectopic vhh-1 expression in dorsal midline regions (F). The dorsal ectopic expression of frog vhh-1 detected after injection of rat vhh-1 is unlikely to reflect cross-hybridization with residual plasmid-derived rat vhh-1 mRNA since this would not be expected to be dorsally restricted. (A) shows a dorsal view with anterior end to the upper left side. B, C) show lateral views with anterior end to the left. In (D, F) dorsal side is up. Arrowheads point to the sites of ectopic expression. Scale bar=600 μm for A–C; 75 μm for D–F.

FIGS. 22A and 22B

Widespread expression of HNF-3β induces the ectopic expression of vhh-1 and F-Spondin.

(A, B) Expression of vhh-1 mRNA in tadpole (stage approximately 36) stage embryos injected with HNF-3β plasmids. Endogenous expression is detected in the floor plate (fp), notochord (n), diencephalon (d) and anterior endoderm. Ecotopic expression is detected in dorsal hindbrain, midbrain and diencephalic regions (A) and in the dorsal spinal cord (B). Analysis of the restriction of ectopic vhh-1 expression along the A–P axis of the hindbrain was not carried out because it was difficult to distinguish rhombomere boundaries after processing embryos for in situ hybridization.

Figures 19D, 19E, 19F:
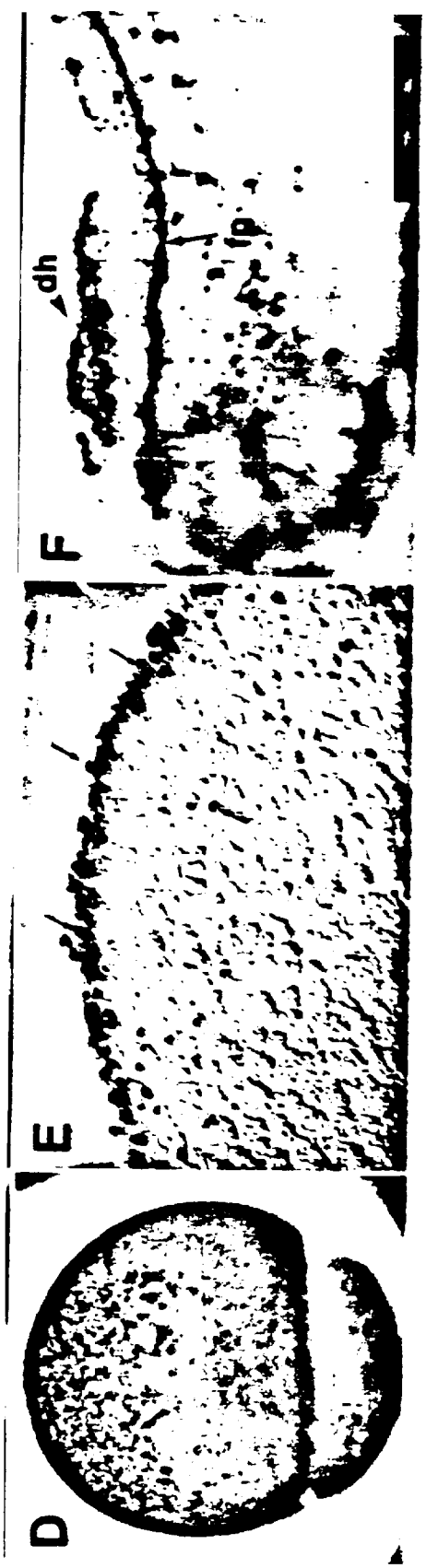

FIG. 22C (C) Histological section of a tadpole (stage approximately 36) stage embryo injected with HNF-3S plasmids, similar to that shown in FIG. 19F, displaying expression of HNF-3β protein in the dorsal neural tube. Endogenous expression is detected in the nuclei of floor plate (fp) cells.

FIG. 22D (D) Histological section through the diencephalon (d) of a tadpole (stage approximately 36) stage embryo similar to that shown in (A) displaying endogenous expression of vhh-1 in the ventricular zone of the ventral diencephalon. Ectopic expression is detected in dorsal ventricular cells.

FIGS. 22E and 22F (E, F) Expression of F-spondin in the floor plate (fp) of normal tadpole (stage approximately 36) embryos (E) and in a sibling embryo injected with HNF-3β plasmid (F) Ecotopic expression is detected in the dorsal ventricular zone. ov: otic vesicle. A, B) show lateral views with anterior end to the left. In (C–F) dorsal side is up. Arrowheads point to the sites of ectopic expression. Scale bar=580 μm for A; 1 mm for B; 75 μm for C–F.

FIG. 23A

Summary of the normal and ectopic expression of floor plate markers, and the molecular interactions implicated in floor plate differentiation.

(A) Summary of the normal expression of Pintallavis and vhh-1 at neural plate stages (left) and of HNF-3β, vhh-1 and F-spondin at neural tube stages (right). Note the normal restriction of floor plate marker expression to the midline.

Figure 23A:
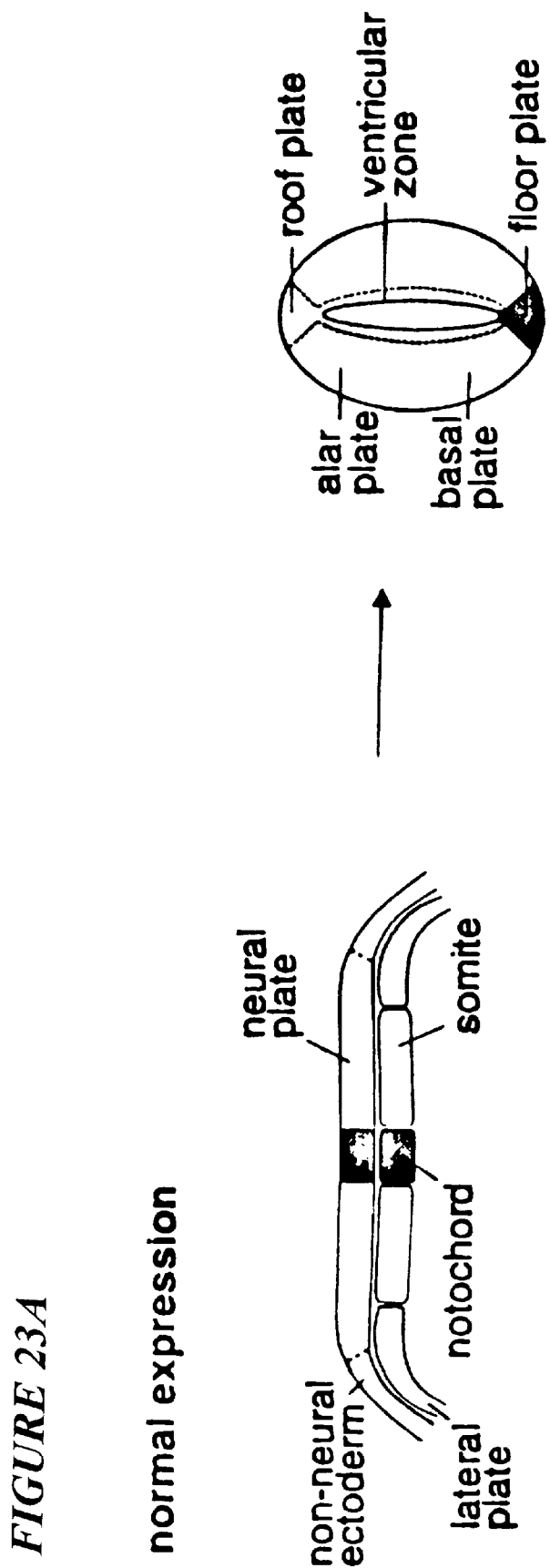

FIG. 23B (B) Summary of the expression of Pintallavis, HNF-3β, and vhh-1 at neural plate stages (left) and of HNF-3β, vhh-1 and F-spondin at neural tube stages (right) in injected embryos. Ectopic expression is induced by widespread expression of HNF-3β or vhh-1 and detected preferentially in dorsal regions and in the ventricular zone at neural tube stages. See text and Table 6 for other detals.

FIG. 23C (C) Summary of the ability (+) or inability (–) of neural cells in the neural plate (left) and neural tube (right) to response to widespread expression of vhh-1 or HNF-3β.

Figure 23D:
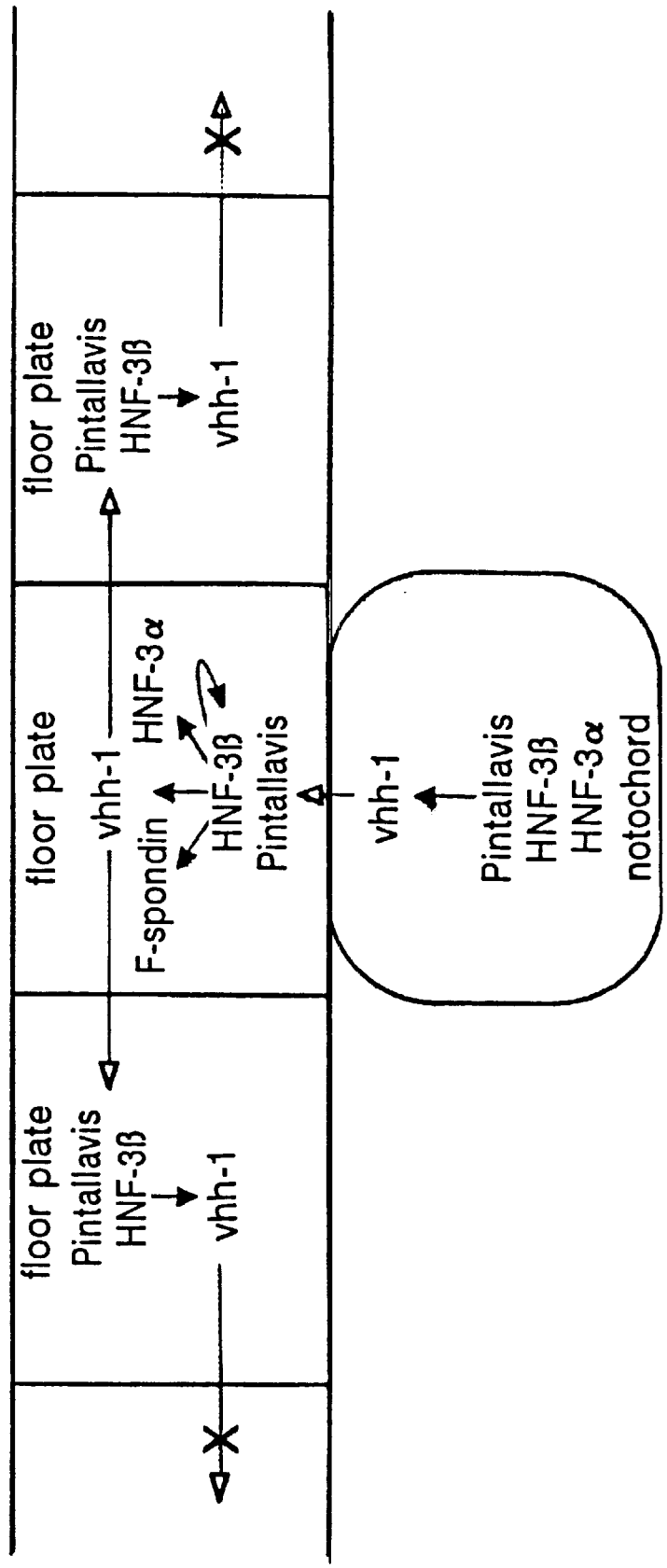

FIG. 23D (D) Proposed molecular interactions involved in the induction and differentiation of floor plate cells. Intercellular signalling mediated by vhh-1 is depicted by arrows with unfilled heads. Intracellular interactions mediated by winged-helix transcription factors are depicted by filled arrows. The limits on the spread of floor plate differentiation through the neural plate by homeogenetic induction are shown by interrupted dashed arrows. See text for details.

FIG. 24

Schematic diagram of a cross section through the hindbrain of a tadpole stage embryo (stage approximately 36) showing the different zones which localize ectopic floor plate marker expression in (A). The different regions shown are also representative of the midbrain and spinal cord but all sites located in the dorsal alar plate were scored in the hindbrain. Note that in all cases the roof plate is the major site of expression even though this region contains a small proportion of cells in the neural tube. The basis for the variations in the incidence of ectopic vhh-1 and HNF-3β in different regions (e.g. DAP versus VZ) is not clear. It is possible that expression of injected plasmids in the dorsal ectoderm differentially affects neighboring neural tube (RP and DAP) cells. Ectodermal cells expressing vhh-1 but not HNF-3β might be expected to affect adjacent neural tube cells since only vhh-1 can act intercellularly. RP=roof plate, DAP=dorsal alar plate immediately adjacent to the roof plate, AP+BP=alar basal plates minus dorsal most region and alar plate, VZ=ventricular zone, V=ventral region adjacent to the floor plate, FP=floor plate.

DETAILED DESCRIPTION OF THE INVENTION

This invention provides an isolated DNA molecule encoding a vertebrate vhh-1 protein. As used herein, the term "isolated nucleic acid molecule" means a non-naturally occurring nucleic acid molecule that is, a molecule which does not occur in nature. Examples of such an isolated nucleic acid molecule are isolated cDNA or genomic DNA molecules encoding a vertebrate vhh-1 protein. This invention provides an isolated nucleic acid molecule encoding a vertebrate vhh-1 protein wherein the nucleic acid molecule is a DNA molecule. This invention further provides an isolated DNA molecule encoding a vertebrate vhh-1 protein, wherein the DNA molecule is a cDNA molecule.

In an embodiment, the nucleic acid molecule encodes a frog vhh-1 protein. In another embodiment, the nucleic acid molecule encodes a mammalian vhh-1 protein.

A preferred embodiment of a nucleic acid encoding a vertebrate vhh-1 protein is a nucleic acid molecule encoding the rat vhh-1 protein. Such a molecule may have coding sequences the same or substantially the same as the coding sequences shown in FIGS. 1A–1A (Seq I.D. No. 1).

Another preferred embodiment of an isolated nucleic acid molecule encoding a vertebrate vhh-1 protein is a nucleic acid molecule encoding the human vhh-1 protein. This invention provides an isolated nucleic acid molecule encoding a vertebrate vhh-1 protein, wherein the isolated nucleic acid molecule encodes a human vhh-1 protein.

This invention further provides an isolated nucleic acid molecule encoding the human vhh-1 protein, wherein the nucleic acid molecule is DNA.

One means of isolating a vertebrate vhh-1 protein is to probe a mammalian genomic library with a natural or artificially designed DNA probe, using methods well known in the art. In one embodiment of this invention, the rat vhh-1 protein and the nucleic acid molecules encoding them are isolated from a rat cDNA library. DNA and cDNA molecules which encode rat vhh-1 protein are used to obtain complementary genomic DNA, cDNA or RNA from human, mammalian or other animal sources, or to isolate related cDNA or genomic clones by the screening of cDNA or genomic libraries, by methods described in more detail below. Transcriptional regulatory elements from the 5' untranslated region of the isolated clone, and other stability, processing, transcription, translation, and tissue specificity determining regions from the 3' and 5' untranslated regions of the isolated gene are thereby obtained.

The human homolog of the rat vhh-1 gene is isolated using the rat vhh-1 probe described hereinabove and cloning techniques known to one of skill in the art, such as homology screening of genomic or cDNA libraries or PCR amplification techniques. The vhh-1 gene is expressed in the lungs of older embryos, therefore the preferred method of cloning the human vhh-1 gene involves screening the clontech human fetal lung cDNA library to obtain the human clone. The rat vhh-1 has been used to identify the chick and frog vhh-1 genes (see below for the frog gene data) and will therefore be sufficiently conserved to identify the human vhh-1 gene.

This invention provides a vector comprising a nucleic acid molecule encoding a vertebrate vhh-1 protein. Examples of vectors are viruses such as bacteriophages (including but not limited to phage lambda), animal viruses (including but not limited to baculovirus, vaccinia virus, Herpes virus, and Murine Leukemia virus), cosmids, plasmids and other recombination vectors are well known in the art. Nucleic acid molecules are inserted into vector genomes by methods well known to those skilled in the art. To obtain these vectors, insert and vector DNA can both be exposed to a restriction enzyme to create complementary ends on both molecules which base pair with each other and are then ligated together with a ligase. Alternatively, linkers can be ligated to the insert DNA which correspond to a restriction site in the vector DNA, which is then digested with the restriction enzyme which cuts at that site. Other means are also known to one of skill in the art.

This invention provides a plasmid comprising the vector comprising an isolated nucleic acid molecule encoding a vertebrate vhh-1 protein. Examples of such plasmids are plasmids comprising cDNA having a coding sequence the same or substantially the same as: the coding sequence shown in FIGS. 1A–1C (Seq. I.D. No. 1) and designated clone pMT21 2hh #7 deposited under ATCC Accession No. 75686 and designated clone cmv vhh #7 deposited under ATCC Accession No. 75685.

Expression vectors can be adapted for expression in a bacterial cell, a yeast cell, an insect cell, a Xenopus oocyte or a mammalian cell which additionally are operatively linked to regulatory elements necessary for expression of the inserted gene in the bacterial, yeast, insect, frog or mammalian cells. DNA having coding sequences substantially the sane as the coding sequence shown n FIGS. 1A–1C can be inserted into the vectors for expression using the methods discussed hereinabove or other methods known to one of skill in the art. Regulatory elements required for expression include promoter sequences to bind RNA polymerase and transcription initiation sequences for ribosome binding. For example, a bacterial expression vector includes a promoter such as the lac promoter and for transcription initiation the Shine-Dalgarno sequence and the start codon AUG. Similarly, a eukaryotic expression vector includes a heterologous or homologous promoter for RNA polymerase II, a downstream polyadenylation signal, the start codon AUG, and a termination codon for detachment of the ribosome operatively linked to the recombinant gene. Furthermore, an insect expression vector such as baculovirus AcMNPV uses the strong viral expression signals for the virus' polyhedron gene to drive transcription of the recombinant gene. One such example of a plasmid comprising regulatory elements for expression in oocytes operatively linked to the recombinant vhh-1 gene is the plasmid designated cmv vhh #7 and deposited under ATCC Accession No. 75685. Such vectors may be obtained commercially or assembled from the sequences described by methods well known in the art, for example the methods described above for constructing vectors in general. Expression vectors are useful to produce cells that express the vhh-1 protein. Certain uses for such cells are described in more detail below.

Deposits were made on Feb. 24, 1994 of both the pMT21 2hh #7 and cmv vhh #7 plasmids with the American Type Culture Collection (ATCC), 12301 Parklawn Drive, Rockville, Md. 20852 (current address now 10801 University Boulevard, Manassas, Va. 20110-2209, U.S.A. The two deposits were made pursuant to, and in satisfaction of, the provisions of the Budapest Treaty on the International Recognition of the Deposit of Microorganisms for the Purpose of Patent Procedure with the ATCC.

Plasmid, pMT21 2hh #7, is produced by cloning a 2.6 kilobase fragment of the rat vhh-1 gene which contains the complete coding region and both 3' and 5' untranslated regions into the XhoI site of the plasmid pMT 21. The 2.6 kilobase can be regenerated by XhoI digestion.

Plasmid cmv vhh #7 also contains the 2.6 kilobase fragment of the rat vhh-1 gene which has the complete coding region and both 3' and 5' untranslated regions. The 2.6 kilobase XhoI insert is cloned into the SalI site such that the XhoI sites are destroyed. The insert is under the control of an upstream CMV promoter and further upstream by a Hox 2.6 enhancer. Downstream from the insert is a 0.8 kilobase poly A site of SV40 and then linked to a hvaromvcin gene (PGK HYG). NotI digest will linearize the plasmid.

This invention provides a mammalian cell comprising an expression plasmid encoding a vertebrate vhh-1 protein. This invention also provides a mammalian cell comprising an expression plasmid encoding a mammalian vhh-1 protein. This invention further provides a Cos cell comprising an expression plasmid encoding a vertebrate vhh-1 protein.

Numerous mammalian cells may be used as hosts, including, but not limited to, the mouse fibroblast cell NIH3T3, CHO cells, HeLa cells, Cos cells, and 293 cells. Expression plasmids such as that described supra may be used to transfect mammalian cells by methods well known in the art such as calcium phosphate precipitation, or DNA encoding the vhh-1 protein may be otherwise introduced into mammalian cells, e.g., by microinjection, to obtain mammalian cells which comprise DNA, e.g., cDNA or a plasmid, encoding a vertebrate vhh-1 protein.

This invention provides a nucleic acid molecule probe comprising a nucleic acid molecule of at least 15 nucleotides capable of specifically hybridizing with a unique sequence included within the sequence of a nucleic acid molecule comprising the gene encoding the vertebrate vhh-1 protein and its noncoding 3' arid 5' nucleotides.

As used herein, the phrase "specifically hybridizing" means the ability of a nucleic acid molecule to recognize a nucleic acid sequence complementary to its own and to form double-helical segments through hydrogen bonding between complementary base pairs. As used herein, a "unique sequence" is a sequence specific to only the nucleic acid molecules encoding the vertebrate vhh-1 protein. Nucleic acid probe technology is well known to those skilled in the art who will readily appreciate that such probes may vary greatly in length and may be labeled with a detectable label, such as a radioisotope or fluorescent dye, to facilitate detection of the probe. Detection of nucleic acid molecules encoding the vertebrate vhh-1 protein is useful as a diagnostic test for any disease process in which levels of expression of the corresponding vhh-1 protein is altered. DNA probe molecules are produced by insertion of a DNA molecule which encodes vertebrate vhh-1 protein or fragments thereof into suitable vectors, such as plasmids or bacteriophages, followed by insertion into suitable bacterial host cells and replication and harvesting of the DNA probes, all using methods well known in the art. For example, the DNA may be extracted from a cell lysate using phenol and ethanol, digested with restriction enzymes corresponding to the insertion sites of the DNA into the vector (discussed above), electrophoresed, and cut out of the resulting gel. Examples of such DNA molecules are shown in FIGS. 1A–1C. The probes are useful for 'in situ' hybridization or in order to locate tissues which express this gene family, or for other hybridization assays for the presence of these genes or their mRNA in various biological tissues. In addition, synthesized oligonucleotides (produced by a DNA synthesizer) complementary to the sequence of a DNA molecule which encodes a vertebrate vhh-1 protein are useful as probes for this gene, for its associated mRNA, or for the isolation of related genes by homology screening of genomic or cDNA libraries, or by the use of amplification techniques such as the Polymerase Chain Reaction.

A preferred embodiment of a nucleic acid molecule probe of a vertebrate vhh-1 protein is a DNA molecule probe.

This invention provides a purified vertebrate vhh-1 protein. In an embodiment, the purified vhh-1 protein is a frog vhh-1 protein. In another embodiment, the purified vhh-1 protein is a mammalian protein. In a further embodiment, the purified vhh-1 protein is a rat protein. In a still further embodiment, the purified vhh-1 protein is a human protein.

This invention further provides a purified unique polypeptide fragment of the vertebrate vhh-1 protein.

As used herein, the term "unique polypeptide fragment" encompasses any polypeptide with the same amino acid sequence as any unique amino acid sequence as shown in FIGS. 1A–1C (Sequence ID No. 2). One means for obtaining an isolated polypeptide fragment or a vertebrate vhh-1 protein is to treat isolated vhh-1 protein with commercially available peptidases and then separate the polypeptide fragments using methods well known to those skilled in the art. Polypeptide fragments are often useful as antigens used to induce an immune response and subsequently generate antibodies against the polypeptide fragment and possibly the whole polypeptide.

As used herein, the term "purified protein" is intended to encompass a protein molecule free of other cellular components. One means for obtaining purified vhh-1 protein is to express DNA encoding the vhh-1 protein in a suitable host, such as a bacterial, yeast, insect, or mammalian cell, using methods well known to those skilled in the art, and recovering the vhh-1 protein after it has been expressed in such a host, again using methods well known in the art. The vhh-1 protein may also be isolated from cells which express the vhh-1 protein, in particular from cells which have been transfected with the expression vectors described below in more detail.

This invention provides a monoclonal antibody directed to a vertebrate vhh-1 protein.

This invention further provides a monoclonal antibody, directed to an epitope of a vertebrate vhh-1 protein and having an amino acid sequence substantially the same as an amino acid sequence for an epitope of a vertebrate vhh-1 protein.

This invention further provides a monoclonal antibody, wherein the monoclonal antibody is directed to the frog vhh-1 protein.

This invention further provides a monoclonal antibody, wherein the monoclonal antibody is directed to the rat vhh-1 protein.

This invention further provides a monoclonal antibody, wherein the monoclonal antibody is directed to the mammalian vhh-1 protein.

This invention further provides a monoclonal antibody, wherein the monoclonal antibody is directed to the human vhh-1 protein.

Monoclonal antibody directed to a vertebrate vhh-1 protein may comprise, for example, a monoclonal antibody directed to an epitope of a vertebrate vhh-1 protein present on the surface of a cell, the epitope having an amino acid sequence substantially the same as an amino acid sequence for a cell surface epitope of the vertebrate vhh-1 protein included in the amino acid sequence shown in FIGS. 1A–1C. Amino acid sequences may be analyzed by methods well known to those skilled in the art to determine whether they produce hydrophobic or hydrophilic regions in the proteins which they build. In the case of cell membrane proteins, hydrophobic regions are well known to form the part of the protein that is inserted into the lipid bilayer which forms the cell membrane, while hydrophilic regions are located on the cell surface, in an aqueous environment. Therefore antibodies to the hydrophilic amino acid sequences shown in FIGS. 1A–1C will bind to a surface epitope of a vertebrate vhh-1 protein, as described. Antibodies directed to vertebrate vhh-1 protein may be serum-derived or monoclonal and are prepared. using methods well known in the art. For example, monoclonal antibodies are prepared using hybridoma technology by fusing antibody producing B cells from immunized animals with myeloma cells and selecting the resulting hybridoma cell line producing the desired antibody. Cells such as NIH3T3 cells or 293 cells may be used as immunogens to raise such an antibody. Alternatively, synthetic peptides may be prepared using commercially available machines and the amino acid sequences shown in FIGS. 1A–1C.

As a still further alternative, DNA, such as a cDNA or a fragment thereof, may be cloned and expressed and the resulting polypeptide recovered and used as an immunogen. These antibodies are useful to detect the presence of vertebrate vhh-1 encoded by the isolated DNA, or to inhibit the function of the vhh-1 protein in living animals, in humans, or in biological tissues or fluids isolated from animals or humans.

This invention provides polyclonal antibodies directed to a vertebrate vhh-1 protein.

Animal model systems which elucidate the physiological and behavioral roles of vertebrate vhh-1 protein are produced by creating transgenic animals in which the expression of a vhh-1 protein is either increased or decreased, or the amino acid sequence of the expressed vhh-1 protein is altered, by a variety of techniques. Examples of these techniques include, but are not limited to: 1) Insertion of normal or mutant versions of DNA encoding a rat vhh-1 or homologous animal versions of these genes, especially the human homolog of the vhh-1 gene, by microinjection, retroviral infection or other means well known to those skilled in the art, into appropriate fertilized embryos in order to produce a transgenic animal (Hogan B. et al. Manipulating the Mouse Embryo, A Laboratory Manual, Cold Spring Harbor Laboratory (1986)) or, 2) Homologous recombination (Capecchi M. R. Science 244:1288–1292 (1989); Zimmer, A. and Gruss, P. Nature 338:150–153 (1989)) of mutant or normal, human or animal versions of these genes with the native gene locus in transgenic animals to alter the regulation of expression or the structure of these vhh-1 proteins. The technique of homologous recombination is well known in the art. It replaces the native gene with the inserted gene and so is useful for producing an animal that cannot express native gene encoding the vhh-1 protein but does express, for example, an inserted mutant gene encoding a mutant vhh-1 protein, which has replaced the native vhh-1 gene in the animal's genome by recombination, resulting in underexpression of the vhh-1 protein. Microinjection adds genes to the genome, but does not remove them, and so is useful for producing an animal which expresses its own and added vhh-1 protein, resulting in overexpression of the vhh-1 protein.

This invention provides a transgenic nonhuman mammal which comprises an isolated DNA molecule encoding a vertebrate vhh-1 protein.

One means available for producing a transgenic animal, with a mouse as an example, is as follows: Female mice are mated, and the resulting fertilized eggs are dissected out of their oviducts. The eggs are stored in an appropriate medium such as M2 medium (Hogan B. et al. Manipulating the Mouse Embryo, A Laboratory Manual, Cold Spring Harbor Laboratory (1986)). DNA or cDNA encoding a vertebrate vhh-1 protein is purified from a vector (such as plasmid pMT21 2hh #7 described above) by methods well known in the art. Inducible promoters may be fused with the coding region of the DNA to provide an experimental means to regulate expression of the trans-gene. Alternatively or in addition, tissue specific regulatory elements may be fused with the coding region to permit tissue-specific expression of the trans-gene. The DNA, in an appropriately buffered solution, is put into a microinjection needle (which may be made from capillary tubing using a pipet puller) and the egg to be injected is put in a depression slide. The needle is inserted into the pronucleus of the egg, and the DNA solution is injected. The injected egg is then transferred into the oviduct of a pseudopregnant mouse (a mouse stimulated by the appropriate hormones to maintain pregnancy but which is not actually pregnant), where it proceeds to the uterus, implants, and develops to term. As noted above, microinjection is not the only method for inserting DNA into the egg cell, and is used here only for exemplary purposes.

Since the normal action of vhh-1 protein-specific drugs is to mimic, activate or inhibit the vhh-1 protein, the transgenic animal model systems described above are useful for testing the biological activity of drugs directed to mimic or alter the vhh-1 protein activity even before such drugs become available. These animal model systems are useful for predicting or evaluating possible therapeutic applications of drugs which mimic, activate or inhibit the rat vhh-1 protein by alleviating abnormalities observed in the transgenic animals associated with decreased or increased expression of the native vhh-1 gene or vhh-1 trans-gene. Thus, a model system is produced in which the biological activity of drugs specific for the vhh-1 protein are evaluated before such drugs become available. The transgenic animals which over or under produce the vhh-1 protein indicate by their physiological state whether over or under production of the vhh-1 protein is therapeutically useful. It is therefore useful to evaluate drug action based on the transgenic model system. Therefore, an animal which underexpresses vhh-1 protein is useful as a test system to investigate whether the actions of a pharmaceutical compound comprising vhh-1 is in fact therapeutic. Another use is that if overexpression is found to lead to abnormalities, then a drug which acts as an antagonist to the vhh-1 protein is indicated as worth developing, and if a promising therapeutic application is uncovered by these animal model systems, activation or inhibition of the vhh-1 protein is achieved therapeutically either by producing agonist or antagonist drugs directed against the vertebrate vhh-1 protein or by any method which increases or decreases the activity of the vhh-1 protein.

This invention provides a transgenic nonhuman mammal which comprises an isolated DNA molecule encoding a rat vhh-1 protein.

This invention further provides the transgenic nonhuman mammal which comprises an isolated DNA molecule encoding a vertebrate vhh-1 protein, wherein the DNA encoding a vertebrate vhh-1 protein additionally comprises tissue specific regulatory elements.

This invention provides a transgenic nonhuman mammal which comprises the isolated DNA molecule encoding a human vhh-1 protein.

This invention provides a method of determining the physiological effects of expressing varying levels of a vertebrate vhh-1 protein which comprises producing a panel of transgenic nonhuman animals each expressing a different amount of vertebrate vhh-1 protein. Such animals may be produced by introducing different amounts of DNA encoding a rat vhh-1 protein into the oocytes from which the transgenic animals are developed.

This invention provides a method of producing a purified vertebrate vhh-1 protein which comprises: (a) inserting nucleic acid molecule encoding the vertebrate vhh-1 protein in a suitable vector; (b) introducing the resulting vector in a suitable host cell; (c) selecting the introduced host cell for the expression of the vertebrate vhh-1 protein; (d) culturing the selected cell to produce the vhh-1 protein; and (e) recovering the vhh-1 protein produced.

This invention further provides the above-described method to produce purified frog, mammalian, rat and human vhh-1 proteins.

These methods for producing vhh-1 proteins involve methods well known in the art. For example, isolated nucleic acid molecule encoding frog, rat or human 1-protein is inserted in a suitable vector, such as an expression vector. A suitable host cell, such as a bacterial cell, or a eukaryotic cell such as a yeast cell, or an insect cell is transfected with the vector. The vertebrate protein is isolated from the culture medium by affinity purification or by chromatography or by other methods well known in the art.

This invention provides a method of inducing the differentiation of floor plate cells comprising contacting floor plate cells with a purified vertebrate vhh-1 protein at a concentration effective to induce the differentiation of floor plate cells.

This invention provides a method of inducing the differentiation of floor plate cells in a subject comprising administering to the subject a purified vertebrate vhh-1 protein at an amount effective to induce the differentiation of floor plate cells in the subject.

This invention provides a method of inducing the differentiation of motor neuron comprising contacting the floor plate cells with a purified vertebrate vhh-1 protein at a concentration effective to induce the differentiation of motor neuron.

This invention provides a method of inducing the differentiation of motor neuron in a subject comprising administering to the subject a purified vertebrate vhh-1 protein at an amount effective to induce the differentiation of motor neuron in the subject.

This invention provides a method of generating ventral neurons comprising contacting progenitor cells with a purified vertebrate vhh-1 protein at a concentration effective to generate ventral neurons.

This invention provides a method of generating ventral neurons from progenitor cells in a subject comprising administering to the subject a purified vertebrate vhh-1 protein at an amount effective to generate ventral neurons from progenitor cells in the subject.

This invention provides a pharmaceutical composition comprising an effective amount of a vertebrate vhh-1 protein and a pharmaceutically acceptable carrier.

This invention provides a pharmaceutical composition comprising an effective amount of a mammalian vhh-1 protein and a pharmaceutically acceptable carrier.

This invention provides a pharmaceutical composition comprising an effective amount of a human vhh-1 protein and a pharmaceutically acceptable carrier.

As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. Once the candidate drug has been shown to be adequately bio-available following a particular route of administration, for example orally or by injection (adequate therapeutic concentrations must be maintained at the site of action for an adequate period to gain the desired therapeutic benefit), and has been shown to be non-toxic and therapeutically effective, in appropriate disease models, the drug may be administered to patients by that route of administration determined to make the drug bio-available, in an appropriate solid or solution formulation, to gain the desired therapeutic benefit.

Delivery of pharmaceutical compositions to sites of vhh-1 protein action propose a complex problem. vhh-1 induces nondifferentiated motor neuron precursor cells to differentiate into motor neurons. Since the regeneration of motor neurons for the purpose of alleviating abnormalities associated with acute nervous system injury or chronic neurodegenerative diseases requires differentiation of motor neuron precursor cells which reside in the central nervous system (CNS), pharmaceutical compounds comprising the vhh-1 protein or drugs or substances that alter vhh-1 protein action must be delivered into the CNS. vhh-1 does not pass through the blood-brain barrier and therefore pharmaceutical compositions comprising same must be given intra cerebrally, surgically implanted within the CNS, or complexed to a carrier molecule (such as transferrin) capable of crossing the blood-brain barrier. A neurotrophic factor, NGF, has been chronically infused into the brain by a mechanical pump device which allow consistent delivery of NGF into the CNS (Koliatos et al. 1991 and Olsen et al. 1992). In the case of acute nervous system injury involving specific central axon(s), slow release implants containing vhh-1 in a known biodegradable polymer matrix could be surgically implanted at the site of the injured axon(s) effective to regenerate motor neurons from motor neuron precursor cells proximal to the injured axon. Another neurotrophic factor, NGF, has successfully been implanted in such a manner to prevent degeneration of cholinergic neurons (Hoffman et al. 1990 and Maysinger et al. 1992). Another method of implanting a source of vhh-1 next to an injured axon requires the transfection of cells incapable of proliferation and further encapsulated to avoid infiltration of the CNS wherein such cells comprise a plasmid encoding the human vhh-1 gene and therefore express vhh-1. Aebischer et al. (1991) successfully implanted encapsulated growth factor producing cells to avoid infiltration of brain tissue. Neurotrophic factors have successfully been conjugated to carrier molecules that shuttle the factor into the CNS. One such example is NGF which has been conjugated to a carrier molecule, monoclonal anti-transferrin receptor antibodies, effective to deliver the neurotrophic factor into the CNS (Friden et al. 1993).

This invention provides a method for treating a human subject afflicted with an abnormality associated with the lack of one or more normally functioning motor neuron(s) which comprises introducing an amount of a pharmaceutical composition comprising an amount of a human vhh-1 protein and a pharmaceutically acceptable carrier effective to generate motor neurons from undifferentiated motor neuron precursor cells in a human, thereby treating a human subject afflicted with an abnormality associated with a lack of one or more normally functioning motor neuron(s)

This invention provides a method for treating a human subject afflicted with an abnormality associated with the lack of one or more normally functioning motor neuron(s) which comprises introducing an amount of a pharmaceutical composition comprising an amount of a human vhh-1 protein and a pharmaceutically acceptable carrier effective to generate motor neurons from undifferentiated motor neuron precursor cells in a human, thereby treating a human subject afflicted with an abnormality associated with a lack of one or more normally functioning motor neuron(s)

This invention provides a method of treating a human subject afflicted with a neurodegenerative disease which comprises introducing an amount of a pharmaceutical composition comprising an amount of a human vhh-1 protein and a pharmaceutically acceptable carrier effective to generate motor neurons from undifferentiated motor neuron precursor cells in a human, thereby treating a human subject afflicted with a neurodegenerative disease.

This invention provides a method of treating a human subject afflicted with a neurodegenerative disease, wherein the chronic neurodegenerative disease is Amyotrophic lateral sclerosis (ALS), which comprises introducing an amount of a pharmaceutical composition comprising an amount of a human vhh-1 protein and a pharmaceutically acceptable carrier effective to generate motor neurons from undifferentiated motor neuron precursor cells in a human, thereby treating a human subject afflicted with Amyotrcphic lateral sclerosis (ALS).

A method of treating a human subject afflicted with an acute nervous system injury which comprises introducing an amount of a pharmaceutical composition comprising an amount of a human vhh-1 protein and a pharmaceutically acceptable carrier effective to generate motor neurons from undifferentiated motor neuron precursor cells in a human, thereby treating a human subject afflicted with an acute nervous system injury.

A method of treating a human subject afflicted with an acute nervous system injury, wherein an acute nervous system injury is localized to a specific central axon which comprises surgical implantation of an amount of a pharmaceutical composition comprising the human vhh-1 protein and a pharmaceutically acceptable carrier effective to generate motor neurons from undifferentiated motor neuron precursor cells located proximal to the injured axon in a human, thereby alleviating an acute nervous system injury localized to a specific central axon.

Elucidation of the molecular structures of the neurotrophic factor designated as the vhh-1 protein is an important step in the understanding of new neurotrophic factors. This disclosure reports the isolation, amino acid sequence, and functional expression of a cDNA clone from rat brain which encodes a vhh-1 protein. Analysis of the rat vhh-1 protein structure and function provides a possible model for the development of drugs useful for the treatment of acute nervous system injury or chronic neurodegenerative diseases such as amyotrophic lateral sclerosis (ALS).

Specifically, this invention relates to the first isolation of a cDNA clone encoding a rat vhh-1 protein. The vertebrate vhh-1 gene is expressed in restricted regions of the embryo, in particular the, notochord and floor plate, two cell groups which have been shown to induce ventral cell types including the floor plate and motor neurons. The vertebrate gene for this vhh-1 protein has been characterized in vivo and in vitro to elucidate the role of vhh-1 in inducing the developmental differentiation of motor neurons and floor plate in embryos. The vhh-1 protein is likely to be useful in the treatment of degenerative disorders of the central nervous system, in particular motor neuron degeneration, and this may be useful in the treatment of a number of clinical disorders that result in motor dysfunction. In addition, the rat vhh-1 protein has been expressed in COS cells by transfecting the cells with the plasmid pMT21 2hh #7.

The invention will be better understood by reference to the Experimental Details which follow, but those skilled in the art will readily appreciate that the specific experiments detailed are only illustrative, and are not meant to limit the invention as described herein, which is defined by the claims which follow thereafter.

EXPERIMENTAL DETAILS

Animals

Zebrafish embryos were obtained from the colony at the Department of Microbiology, Umea University, Sweden, Pregnant female rats (Hilltop) were delivered by Caesarean section and embryos staged according to somite number. Fertile white leghorn chicken eggs were obtained from SPAFAS, Incorporated (Norwich, Conn.). chick embryos were staged according to Hamburger and Hamilton (1951). Frog (Xenopus laovis) eggs and embryos were reared and staged according to Nieuwkoop and Faber (1957) and Ruiz i Altaba (1993).

Isolation of Vertebrate Genes Related to hh

Plaques ($10^4$) of a 9–16 hr. postfertilization λZAPII zebrafish library were screened at low stringency with Drosophila hh cDNA (provided by J. Mohler) and with DNA fragments generated by polymerase chain reaction using the hh sequence (Lee et al., 1992) as a template. Two sets of polymerase chain reaction primers were used 5'-GAGGATTGGGTCGTCATAGG-3' SEQ ID NO:3 (positions β52–β71 in the Drosophila hh cDNA) and 5'-CTTCAAGGATTCCATCTCAA-3' SEQ ID NO:4 (positions 1799–1818); 5'AGCTGGGACGAGGACTACCATC-3' SEQ ID NO:5 (positions 945–966) and 5'TGGGAACTGATCGACGAATCTG-3' SEQ ID NO:6 (positions 1147–1128). Clones isolated with the second primer set were subcloned and sequenced on both strands by the dideoxy chain termination method (Sanger et al., 1977). DNA and derived amino acid sequences were analyzed on a VAX computer using the Genus software package.

To identify rat hh-related cDNA clones, approximately $2.5 \times 10^5$ colonies of a rat E13 floor plague cDNA library in pMT21 were screened with the zebrafish vhh-1 probe in HM mix (5×Denhardt's solution. 10% dextran sulphate, 2×SSC, 2×SSPE, 0.5% SDS, and 50 μg/ml denatured herring sperm DNA) at 60%C Xhol cDNA inserts from hybridizing clones were subcloned in pBluscript II KS(−) and sequenced on both strands by the dideoxy chain termination methods (Sanger et al., 1977). Sequence analysis and compilations were performed on a VAX computer using GCG software.

In Situ Hybridization

Whole-mount in situ hybridization analysis of mRNA expression were performed with digoxigenin-labeled probes essentially as described by Harland (1991) and Krauss et al.

(1991) with minor modifications (Ruiz l Altaba et al., 1993b) and for cryostat sections as described by Schaeren-Wiemers and Gerfin-Moser (1993). For each species, the probe used included coding and noncoding regions. Control hybridizations contained sense strand probes or antisense probesdirected against other genes. The frog F-spondin gene (Ruiz i Altaba et al., 1993b) was transcribed with T7 RNA polymerase after digestion with HindIII) to generate an antisense probe.

Expression of vhh-1 in COS cells

Cos cells were grown overnight until 90% confluent and transfected with 1 μg of DNA per 35 mm dish with 12 μg/ml lipofectamino reagent (GIBCO BRL) in Dulbeccos' modified Eagle's medium (DMEM). After 5 hours, cells were washed and incubated in DMEM containing 10% FCS for 18 hours. The medium was then replaced by fresh DMEM containing 10% FCS and cells were incubated for 24–48 hours. COS cells were dissociated 24 hours after transfection with enzyme-free dissociation medium (Specially Media, Incorporated), peeled, and resuspended in OptiMEM containing 10% FCS. Aggregates were made by hanging a 20 μl drop containing 200–400 cells from the lid of a tissue culture plate. After 24 hours, cell aggregates were placed in contact with rat neural plate explants.

Neural Plate Explant Cultures

Rat neural plate tissue was isolated from the intermediate and dorsal regions of the neural plate of E9–E10 embryos (at the level of prospective somites 15–19) as described by Placzek et al. (1990a, 1993). Chick neural plate tissue was dissected from Hamburger-Hamilton stage 10 chick embryos as described (Yamada et al., 1993). Notochord explants were isolated by dissection from stage 6 chick embryos after dispose treatment. Rat neural plate explants were embedded within three-dimensional collagen gels and culture as described (Tessier-Lavigne et al., 1988; Placzek, et al., 1993). Conjugates were made by wrapping the neural plate explants around COS cell aggregates to maximize the extent of contact.

Chick intermediate neural plate explants, about one-third the size of those used by Yamada et al., (1993), were placed on a monolayer of control or transfected COS cells grown for 44 hours in 35 mm tissue culture dishes. A cushion of collagen gel was placed on top of the explant to maintain the position of the explant and the contact with COS cells and cultures were incubated for 44 hours as described (Yamada et al., 1993).

Limb Bud Explant Cultures

Chick limb bud tissue was dissected from Hamburger-Hamilton stage 20 embryos Mesenchymal tissue that corresponds to the region that expressed shh (Riddle et al., 1993) and defined to have ZPA activity (Honig and Summerball, 1985) and adjacent ectoderm was dissected from posterior limb tissue. Similar sized explants were dissected from anterior limb tissue. Explants were treated as described (Placzek et al., 1993). Rat tissues were wedged between mesenchymal and ectodermal layers of the limb bud explants or were opposed to the mesenchymal layer.

Exression of vhh-1 in Frog Embryos

X. laevis embryos at the 1-or-2-cell stage were injected with 100–200 pg of supercoiled plasmid DNA. In all cases injections were performed in the animal hemisphere that is fated to give rise to ectodermal derivatives, including the nervous system (Dale and Slack, 1987). Expression to the vhh-1 cDNA in the sense or antisense orientation in the injected plasmids was driven by the CMV promoter containing the Hox-B4 region A enhancer element (Whitnig et al., 1991). The region A element does not affect the tissue specificity or the level of expression of downstream genes (A.R.A., H.R., AND T.M.J., unpublished data). Expression of vhh-1 transcripts from the injected plasmids was monitored by whole-mount in situ hybridization using an antisense RNA probe.

Immunocytochemistry

Rabbit antibodies against the frog HNF-38 protein were used at 1:5000 to 1:8000 dilution for whole-mount labelling (Dent et al., 1989; Patel et al., 1989) FP3 was detected using monoclonal antibody (MAb) 6G3 (mouse 1 gG) and FP4 was detected using MAb K1/2E7 (mouse igG1; Placzek et al., 1993). Islet-1 was detected using rabbit anti-islet-1 antibodies diluted 1:1000 (Thor et al., 1991; Korzh et al., 1993) and MAb 4D5 (mouse IgG, raised by S. Morton against a rat islet-1 fusion protein; Thore et al., 1991). The SC1 protein was detected with a MAb provided by H. Tanaka. For identification of FP3 and FP4 in the same explants, serial sections were labeled with antibodies to FP3 and FP4.

EXPERIMENTAL RESULTS

Isolation and Characterization of Vertebrate Homologs of the Drosophila hh Gene

To isolate vertebrate homologs of the Drosophila hh gene, zebrafish and rat embryo cDNA libraries were screened with polymerase chain reaction fragments derived from the Drosophila hh cDNA. Five clones isolated from a 9–16 hr postfertilization zebrafish embryo library encoded two distinct hh-related cDNAs, one of which, vhh-1, is described here. The longest vhh-1 cDNA contained a 2.6 kb insert with a single long open reading frame that encodes a protein of 418 amino acids (FIGS. 2A-1 and 2A-2). Zebrafish vhh-1 mRNA expression was confined primarily to midline structures, in particular, the notochord and floor plate. The zebrafish vhh-1 cDNA was used to screen an embryonic day 13 (E13) rat floor plate cDNA library. Sixteen independent cDNA clones were isolated with inserts ranging in size from 0.8 to 2.7 kb. Partial sequencing of each of these cDNA clones revealed that they derived from the same gene. Sequencing of one 2.7 kb clone revealed a single long open reading frame that predicts a protein of 437 amino acids.

The rat vhh-1 cDNA encodes a protein with 71% identity to the zebrafish vhh-1 protein, 94% identity to mouse shh (Echelard et al., 1993), 82% identity to which shh (Riddle et al., 1993), and 47% identity to Drosophila hh (FIGS. 2A-1 and 2A-2). The sequence of the zebrafish shh (Krauss e al., 1993) with the exception of a region at its COOH-terminal end over residues 437–466 (residues aligned to the fly hh sequence; see FIGS. 2A-1 and 2A-2). Zebrafish vhh-1 is identical in the region of divergence to the zhhE protein isolated by Beachy and colleagues (P. Beachy, personal communication). The greatest degree of conservation between the vertebrate and fly proteins occurs over the $NH_2$-terminal 200 amino acids. Both zebrafish and rat vhh-1 proteins contain a hydrophobic $NH_2$-terminus that is likely to serve as a signal sequence (FIG. 2B), suggesting that the processed protein is secreted. The similarity in sequence and expression pattern (see below) of the zebrafish and rat vhh-1 genes and the mouse and chick shh genes suggests that they are homologs.

Expression of the vhh-1 Gene during Embryogenesis

Figure 3A:
Figure 3B:
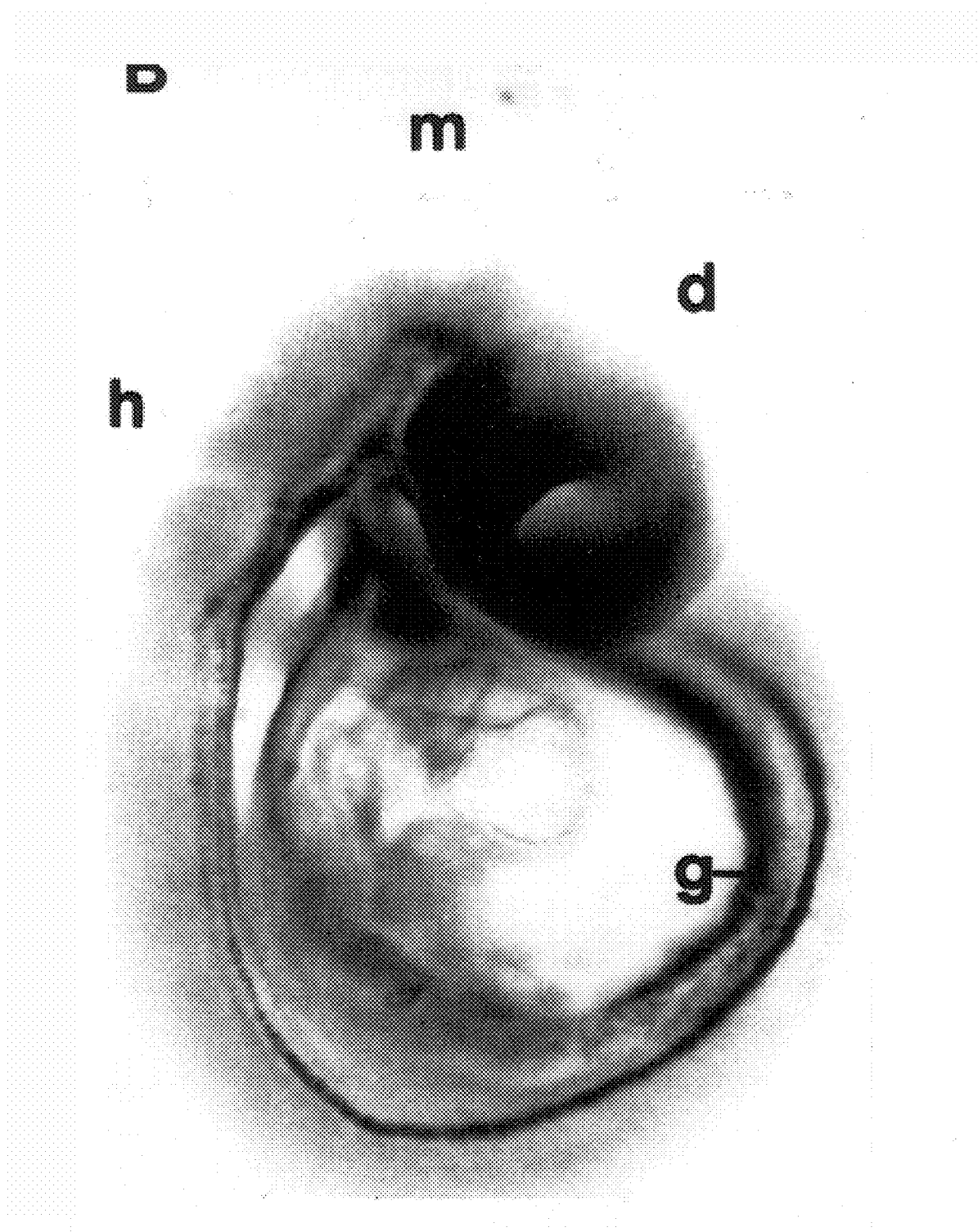
Figure 3C:
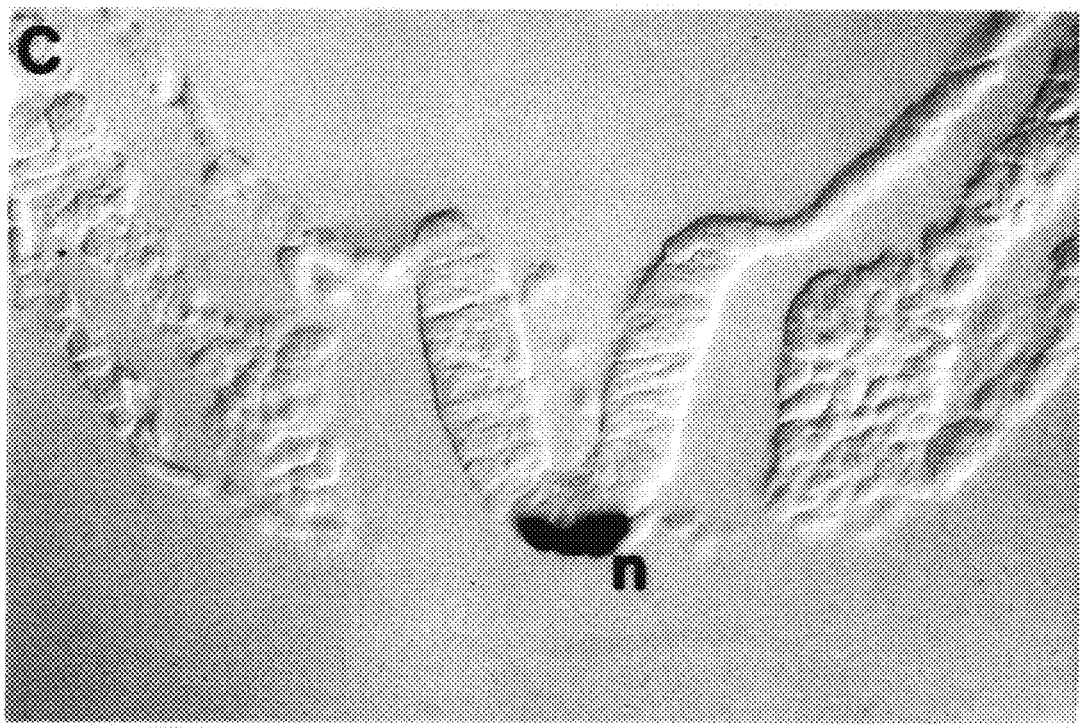
Figure 3D:
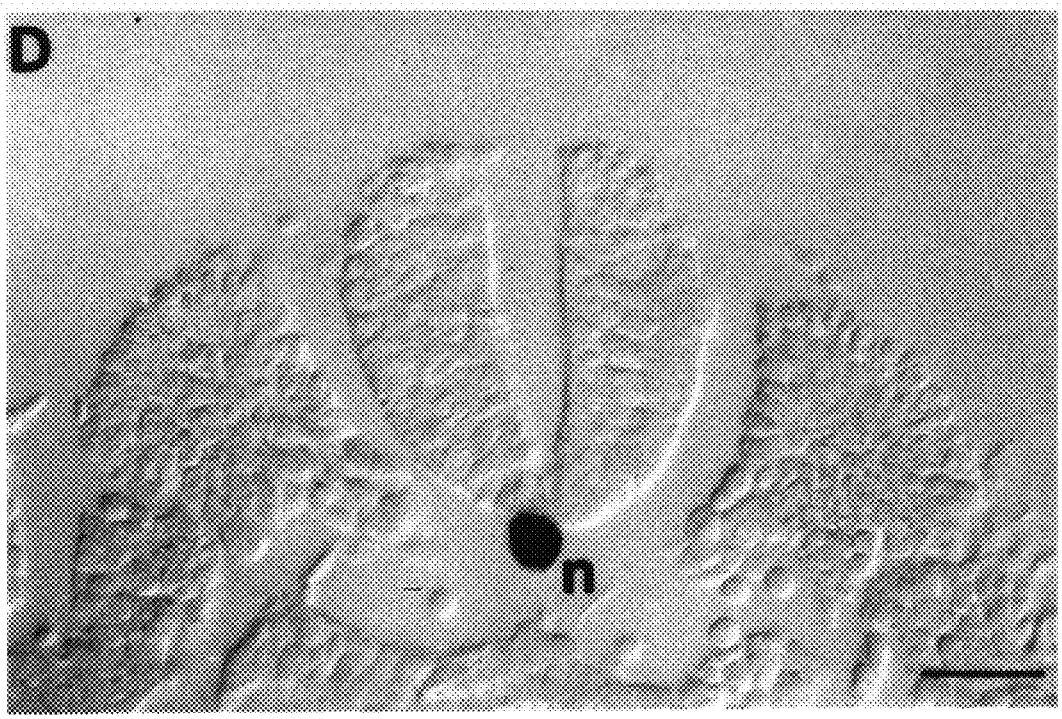
Figure 3E:
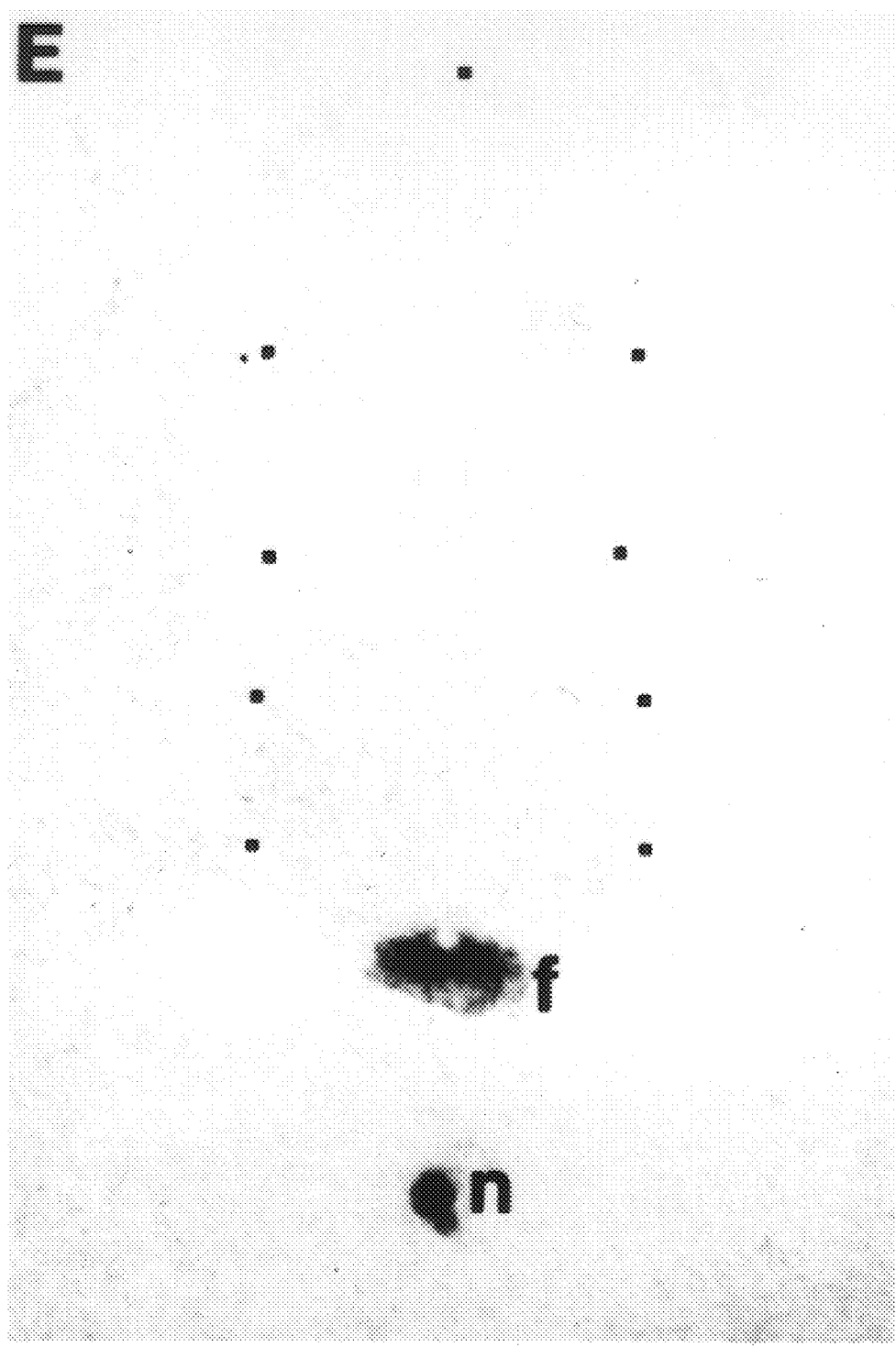

The patterns of expression of the zebrafish and rat vhh-1 genes are similar, and applicants report here only the expression of the rat gene. Applicants first assayed vhh-1 mRNA expression in gastrulating rat embryos at E9. At this time vhh-1 mRNA was found in the node and in axial mesodermal cells laid down in the wake of the regressing node (FIG. 3A). vhh-1 mRNA expression persists in midline mesodermal cells as they differentiate into the notochord (FIGS. 3B and 3C) and is detectable in this structure until E15, the latest stage examined (FIGS. 3D and 3E). Cells of the neural plate and newly closed neural tube do not express vhh-1 mRNA (FIGS. 3C and 3D). However, floor plate cells at the rostral region of the spinal cord expressed the gene by E10.5 (FIG. 3B), and soon after vhh-1 mRNA was detectable in the floor plate at all rostrocaudal levels, persisting until at least E 15 (FIG. 3E). In the spinal chord and hindbrain, vhh-1 mRNA expression was restricted to the floor plate as assessed by comparison with other rat floor plate markers (data not shown, Placzek et al., 1993; Ruiz i Altaba et al., 1993b). In the forebrain, vhh-1 expression is also located more laterally in the ventral diencephalon and is absent from the ventral midline at the level of the infundibulum (data not shown). Within the diencephalon, vhh-1 mRNA expression extends dorsally up to the boundary between the ventral and dorsal thalamus (data not shown). In the rostral diencephalon, vhh-1 expression is detected ventrally in the region of the developing hypothalamus. The sole dorsal site of neural expression of vhh-1 mRNA is a group of cells at the roof of the midbrain that is first detectable at E10.5 (FIG. 3B).

Vhh-1 mRNA was detected in two additional regions of rat embryos from E10.5 to E15. Endodermal cells located in the ventral half of the early gut tube expressed vhh-1 mRNA (FIG. 3B). The intensity of expression of the gene in endodermal derived tissues increases at later stages of development, and by E15–E15 it is expressed at high levels in gut and lung epithelia (data now shown). vhh-1 mRNA was also expressed in posterior mesenchymal cells of the developing limb bud at E11–E14 (see FIG. 7A), which corresponds to the region defined as the zone of polarizing activity (ZPA).

The expression of vhh-1 in the node, notochord, and floor plate, cell groups with floor plate inducing activity, raises the possibility that this gene encodes a floor plate-inducing activity, raises the possibility that this gene encodes a floor plate-inducing molecule. In the following sections were describe the effects of vhh-1 on the differentiation of ventral neural cell types in vivo and in vitro.

Figure 4A:
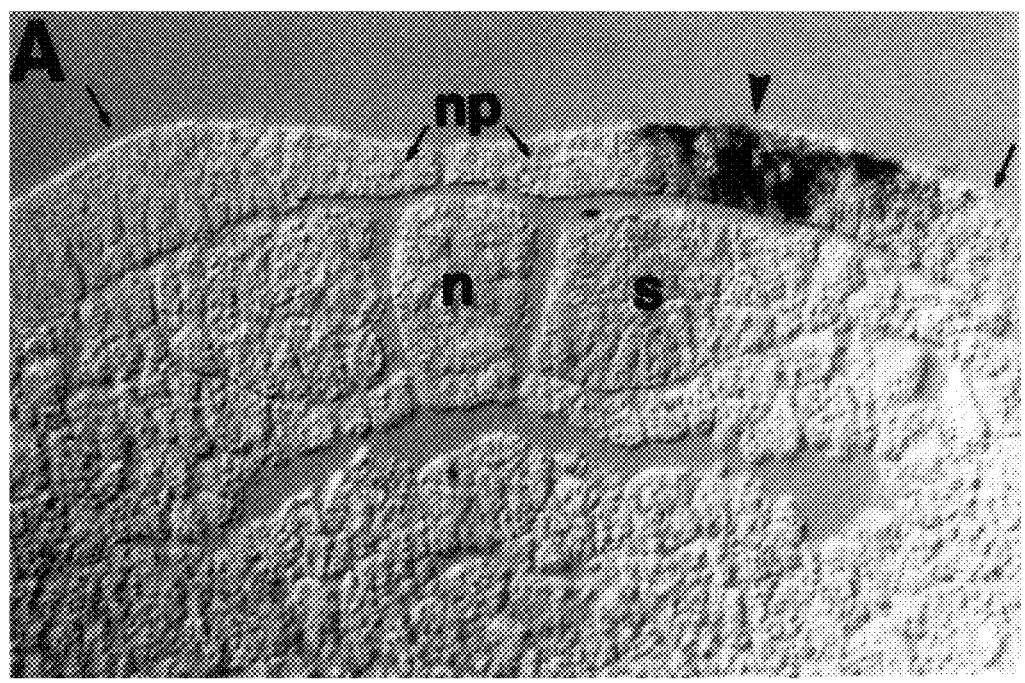

Ectonic Expression of the vhh-1 Gene in Frog Embryos Leads to Floor Plate Differentiation In the Dorsal Neural Tube Applicants monitored the consequences of ectopic expression of the vhh-1 gene in developing frog embryos. Ectopic expression of vhh-1 was achieved by injecting a plasmid vector containing the rat vhh-1 cDNA under the control of a cytomegalovirus (CMV) promoter. AT neural plate stages (stages 13–17), rat vhh-1 mRNA was expressed in large patches of cells located primarily in the region of the anterior epidermis and neural plate (11 of 11 embryos examined) (FIG. 4A). By the tadpole stage (stages 32–38), however, vhh-1 mRNA was mosaic and detected in smaller groups of cells (data not shown). Of injected embryos, 31% (23 of 74 examined) showed ectopic expression of vhh-1 in the neural tube. Within the neural plate and neural tube, there was no consistent restriction in the domain of neural expression of the CMV-driven rat vhh-1 gene (FIG. 4A; data not shown).

Figure 4B:
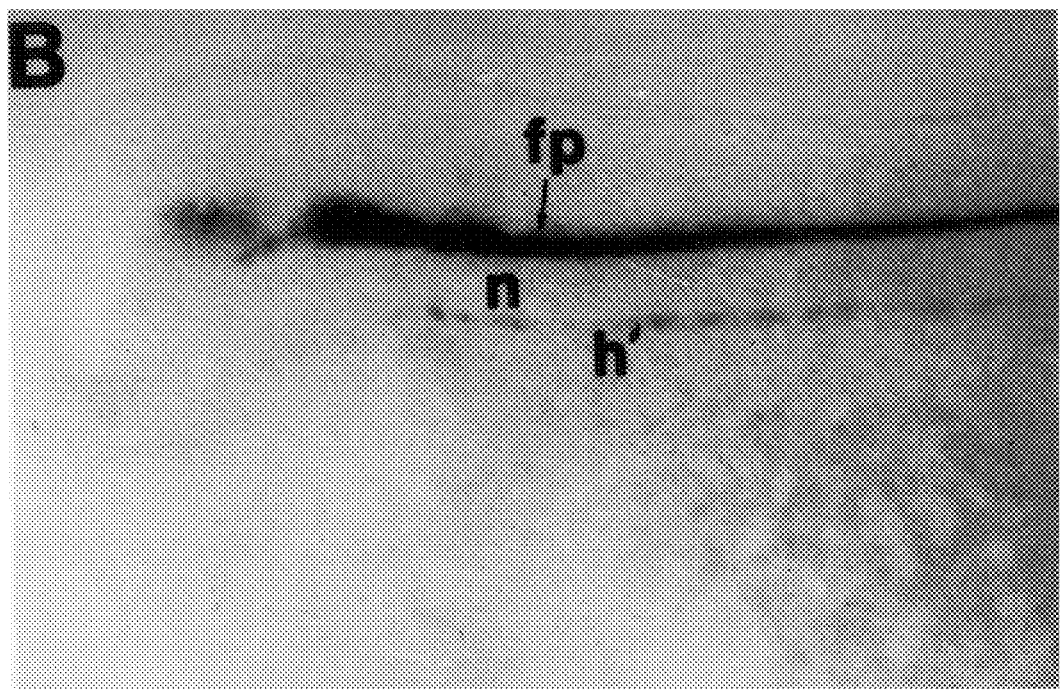
Figure 4C:
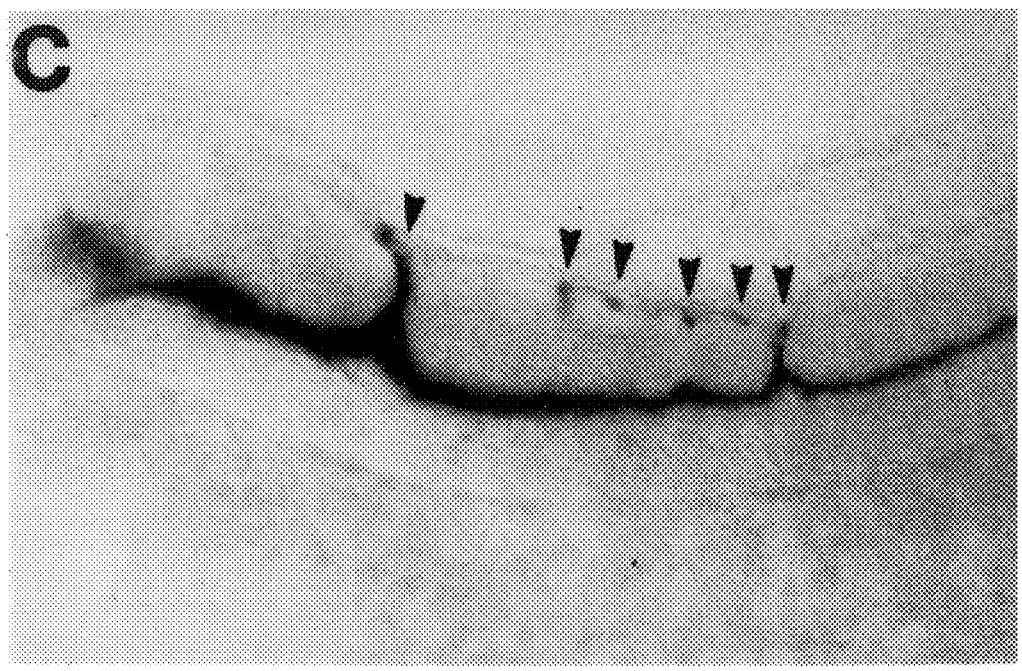
Figure 4D:
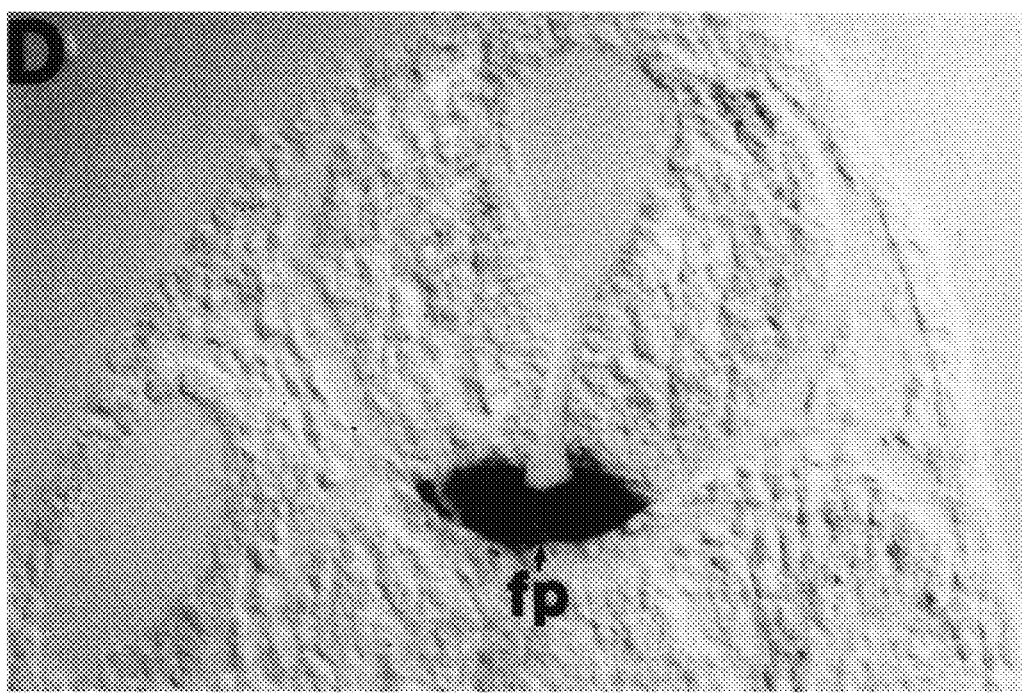
Figure 4E:
Figure 4F:
Figure 4G:
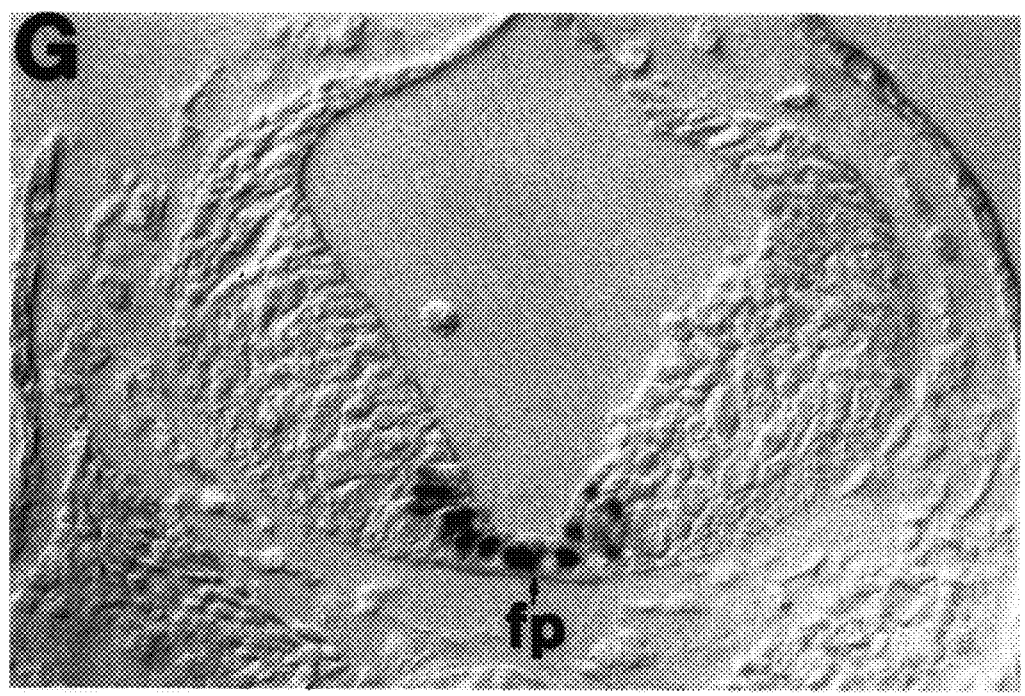
Figure 4H:
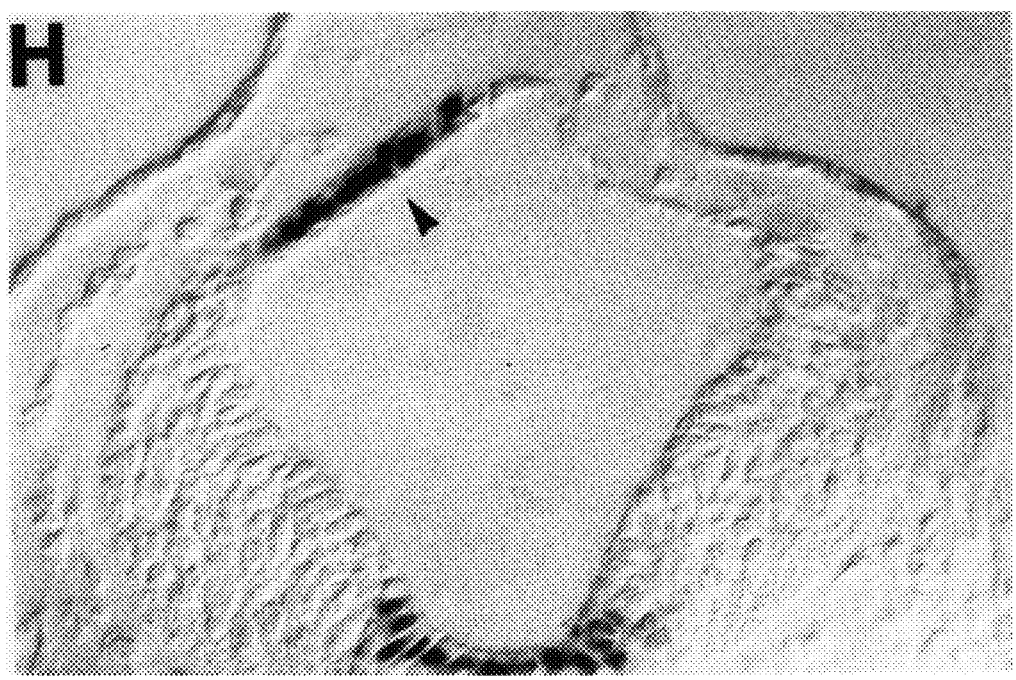
Figure 4I:
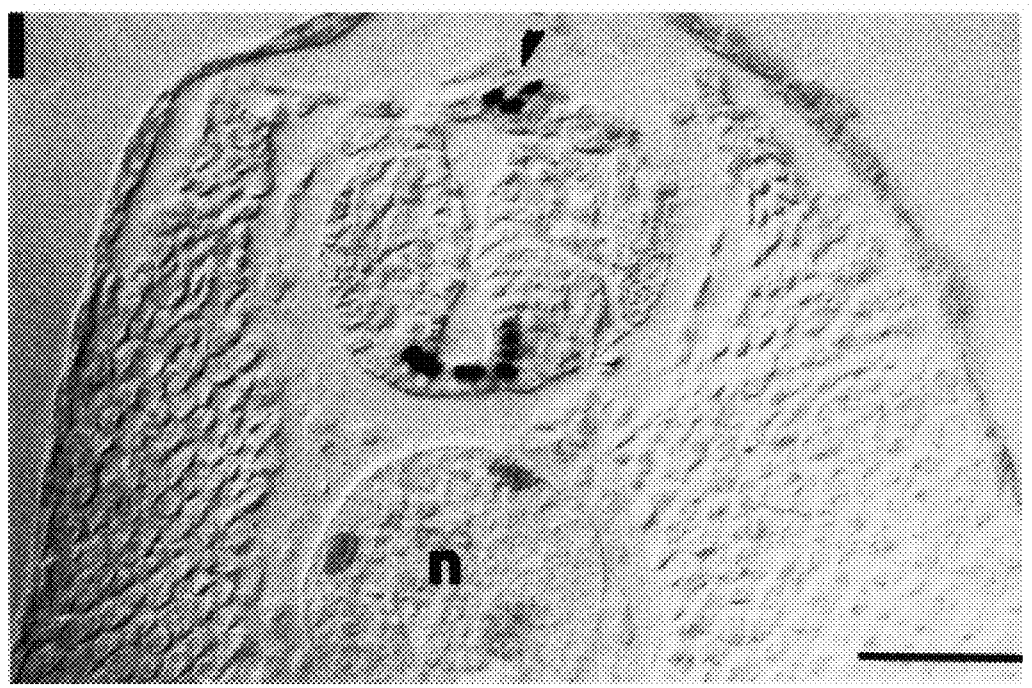

Applicants determined whether the widespread expression of vhh-1 RNA leads to the differentiation of floor plate cells in ectopic locations by monitoring the expression of two floor plate markers, the cell adhesion molecule F-spondin (Klar et al., 1992; Ruiz l Altaba et al., 1993a) (FIGS. 4B and 4D) and the transcription factor HNF-3β (19 of 153) were detected in regions other than the floor plate (FIGS. 4C, 4E, 4F, 4H and 4I). Ectopic expression of both markers was detected at midbrain, hindbrain, and spinal cord levels but not in forebrain regions (FIGS. 4E, 4F, 4H, and 4I). Embryos injected with a plasmid driving expression of vhh-1 cDNA in the antisense orientation showed a markedly lower incidence of ectopic F-spondin expression (2%; 4 of 198), and ectopic HNF-3β cells were not detected (0 of 53). Thus, the widespread expression of rat vhh-1 in developing frog embryos leads to the ectopic induction of floor plate marker. Although the ectopic expression of HNF-3β and F-spondin RNA was observed at all rostrocaudal levels of the neuraxis except the forebrain, the predominant location of ectopic markers expression was in cells at the dorsal midline, in or near the roof plate (FIGS. 4C, 4E, 4F, 4H, and 4I). In several embryos, the morphology of the neural tube in regions of ectopic floor plate markers expression was abnormal with marked constrictions or folds in the neural tube (data not shown).

Floor Plate Differentiation Induced in Vitro by vhh-1

To test more directly the ability to vhh-1 to induce ventral neural cell types, applicants used established in vitro assays of rat floor plate (Placzek et al., 1993) and chick motor neuron (Yamada et al., 1993) differentiation.

To detect floor plate differentiation, applicants monitored the induction of the floor plate antigens FP3 and FP4 (FIGS. 5A and 5B) in rat neural plate explants cultured in vitro. Notochord and floor plate induce the expression of FP3 and FP4 when grown in contact with E9–E10 rat neural plate tissue (FIGS. 5C and 5D) (Placzek et al., 1993) Expression vectors containing full-length vhh-1 cDNA in sense or antisense orientations were transiently transfected into COS cells. About 25% of COS cells expressed vhh-1 RAN (data not shown).

Figure 5J:
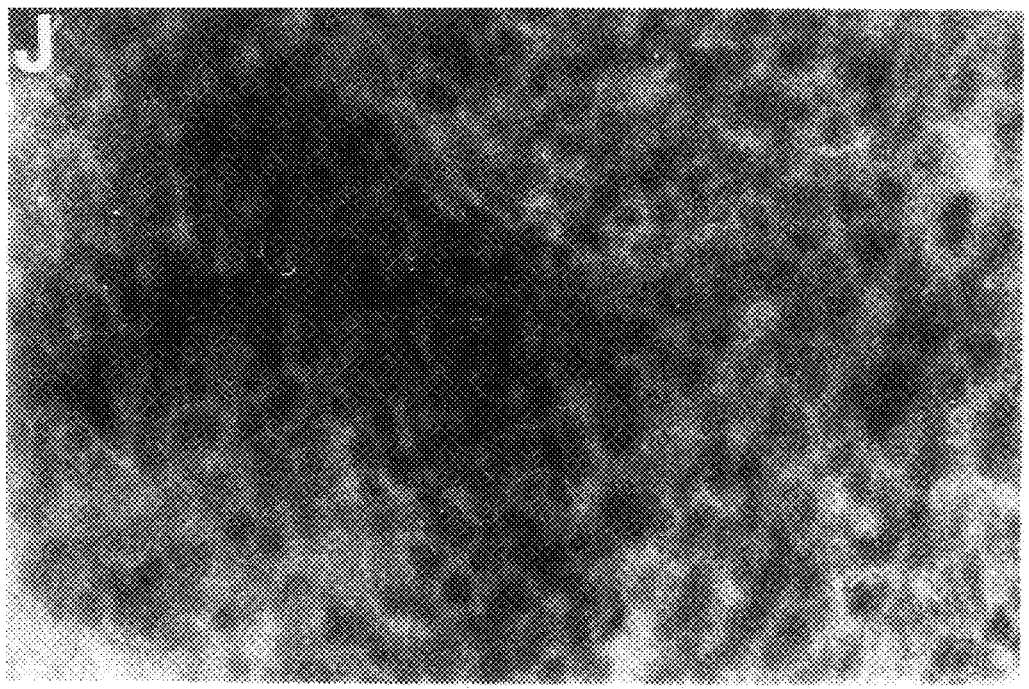
Figure 5K:
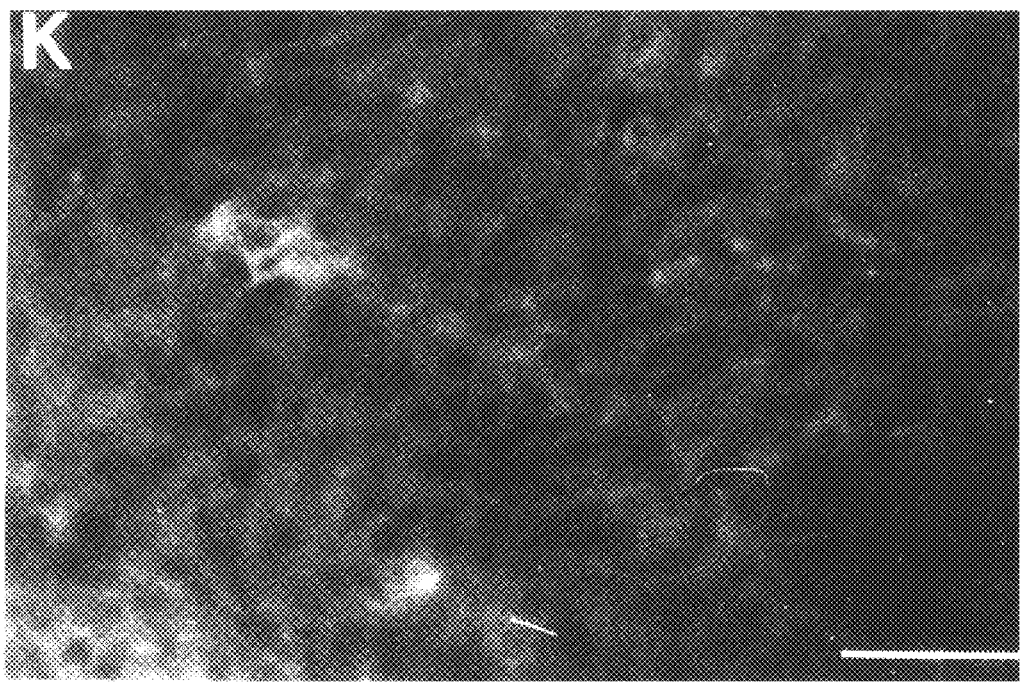

Of neural plate explants grown in contact with COS cells expressing sense vhh-1 cDNA, 70% expressed FP3 and 47% expressed FP4 (FIGS. 5E–5H; Table 1). As with floor plate induction by the notochord, not all explants that expressed FP3 also expressed FP4. This may reflect the later onset of FP4 expression in vivo (Placzek et al., 1993). The domain of FP3 and FP4 expression within neural plate explants was similar in size to that induced by the notochord, and labeled cells were located close to the junction of the COS cells aggregate and neural plate explant. Induction of floor plate differentiation by vhh-1 may thus be local and possibly contact-dependent process. Consistent with this, medium harvested from vhh-1 transfected COS cells did not induce FP3 or FP4 when added to neural plate explant grown alone (data not shown). It remains to be determined, however, whether vhh-1 activity can diffuse into the medium. Neural plate explants grown in contact with cells transfected with antisense vhh-1 cDNA did not express FP3 or FP4 (FIGS. 5J and 5K; Table 1).

The simplest explanation of these results is that vhh-1 protein is secreted from COS cells and interacts with neural plate cells to trigger, directly, floor plate differentiation. Nevertheless, it remains possible that expression of vhh-1 in COS cells induces the synthesis of a distinct factor that mediates floor plate induction. In addition, these results do not resolve whether the vhh-1 protein is sufficient to induce floor plate differentiation since COS cells could provide an accessory factor that acts in concert with the vhh-1 protein.

Motor Neuron Differentiation Induced In Vitro by vhh-1

In vitro studies have provided evidence that signals from the notochord can induce the differentiation of motor neurons as well as floor plate cells (Yamada et al., 1993). The expression of vhh-1 in the notochord therefore raises the questions of whether motor neurons can also be induced by vhh-1.

Figure 6A:
Figure 6B:
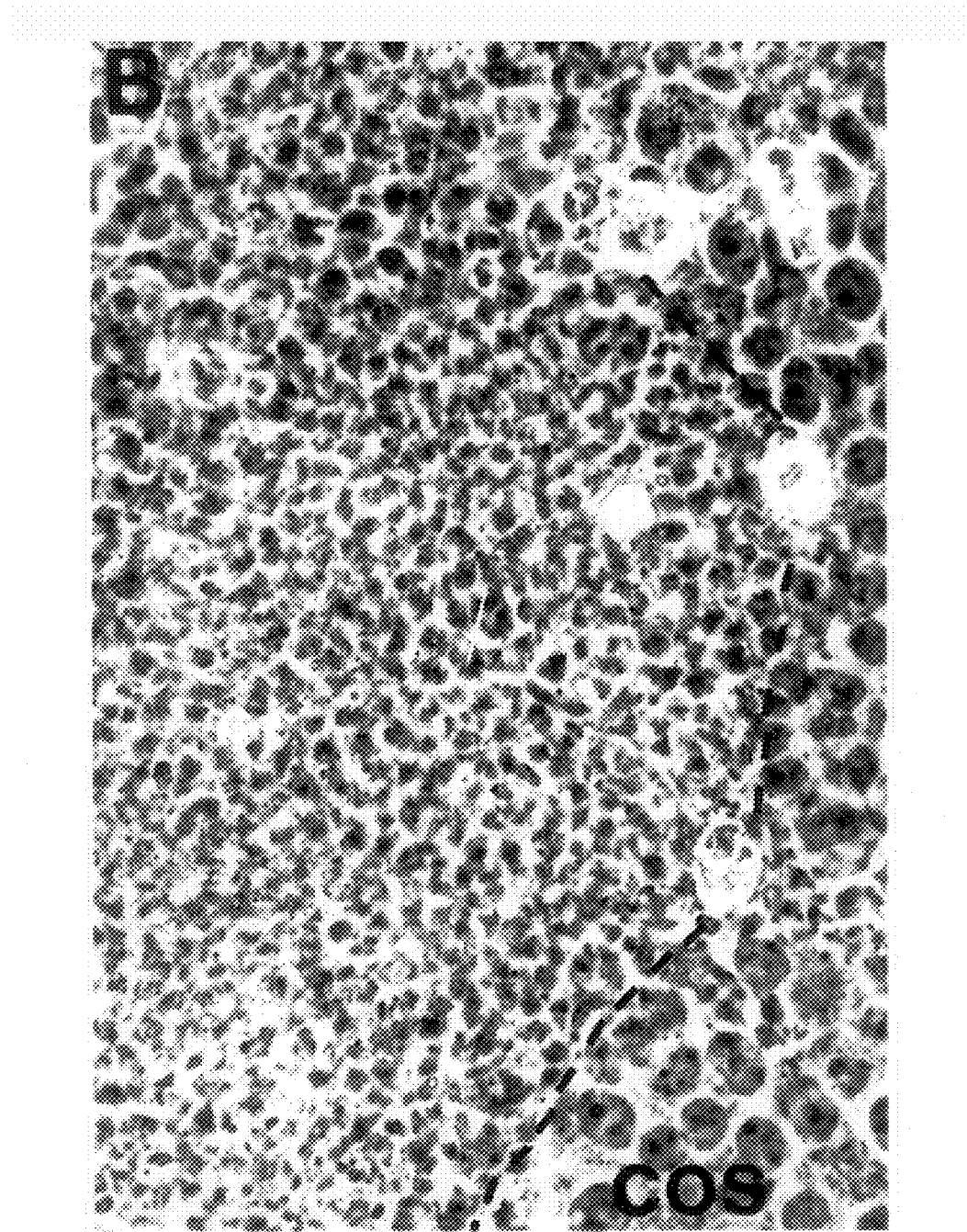
Figure 6C:
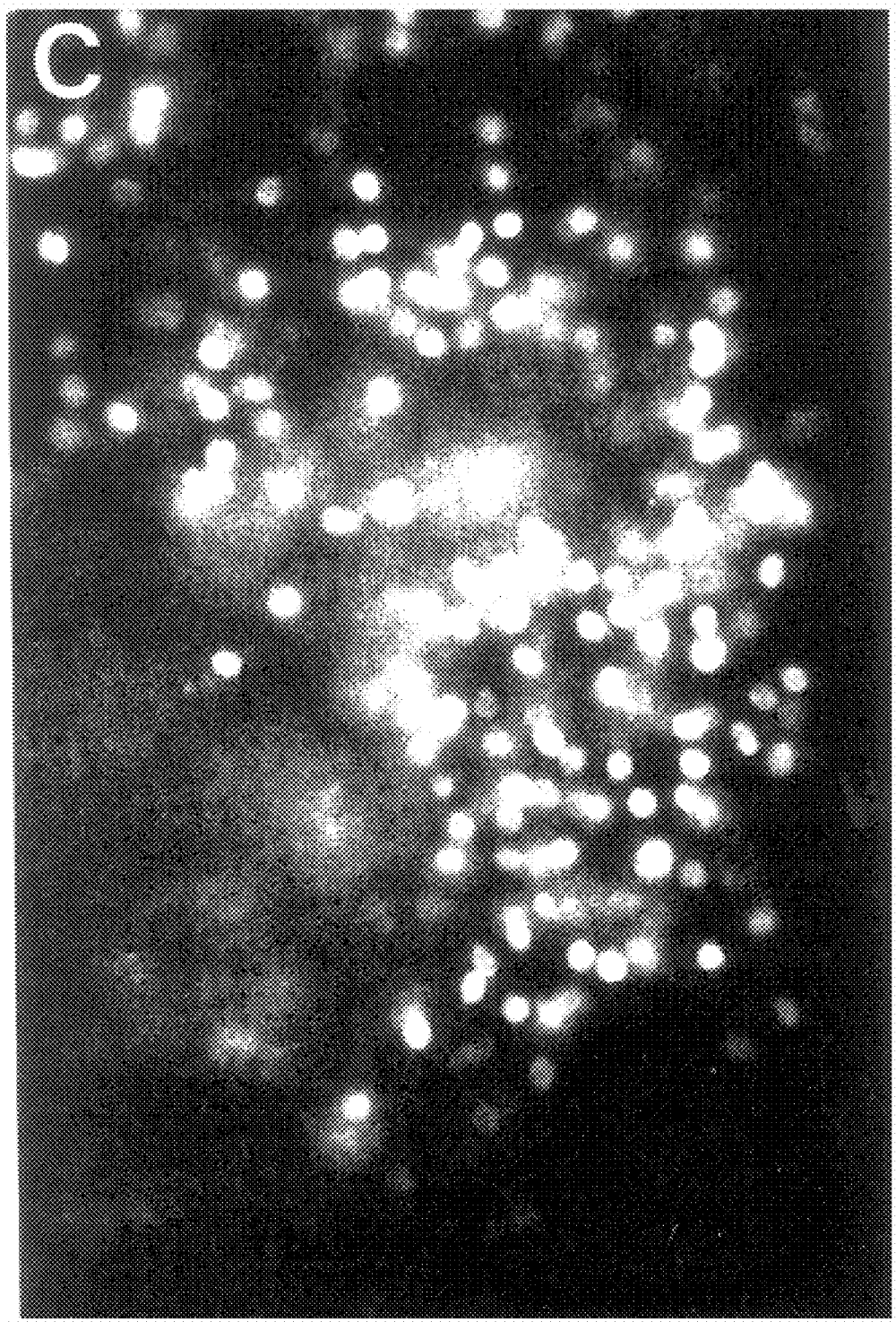
Figure 6D:
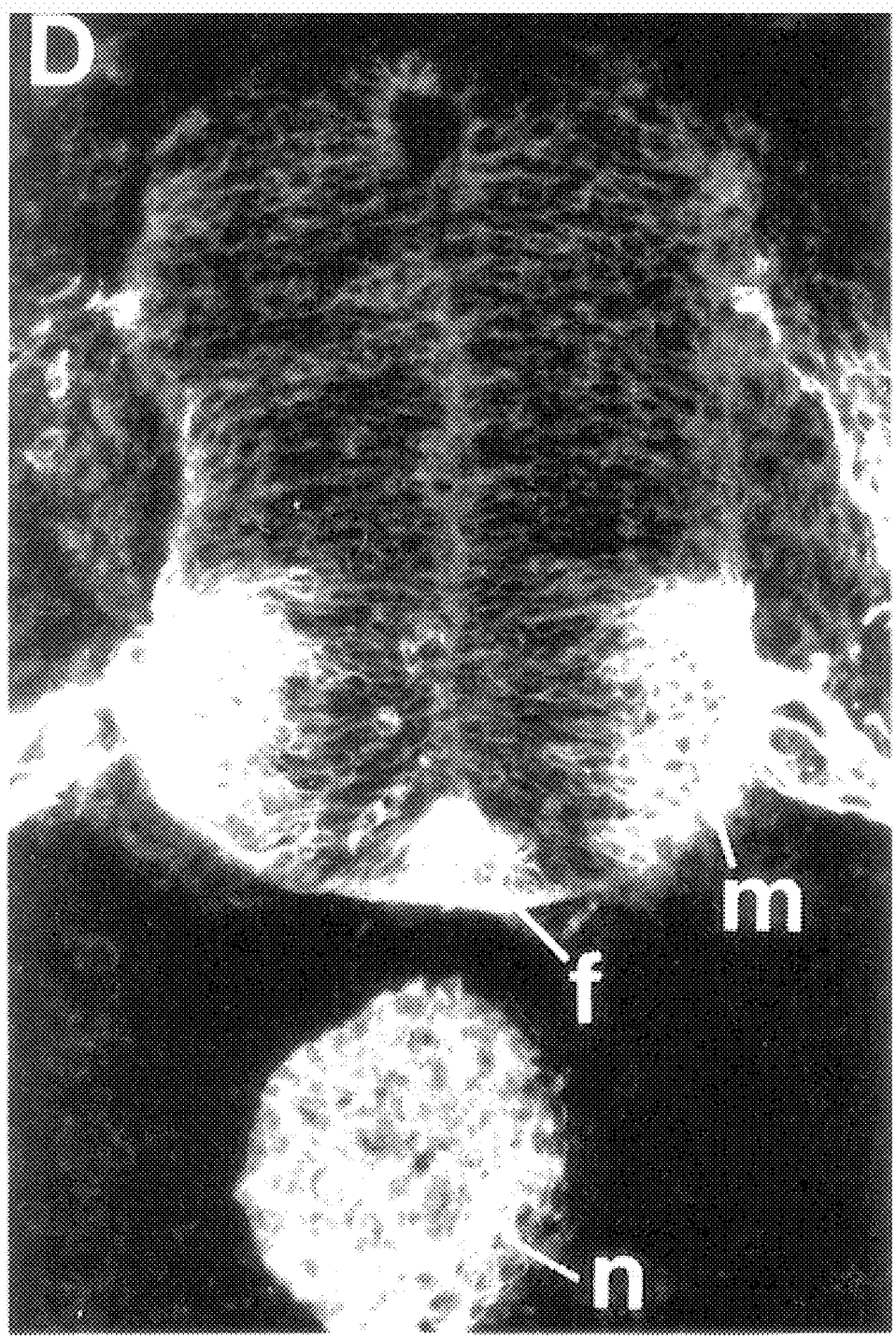
Figure 6E:
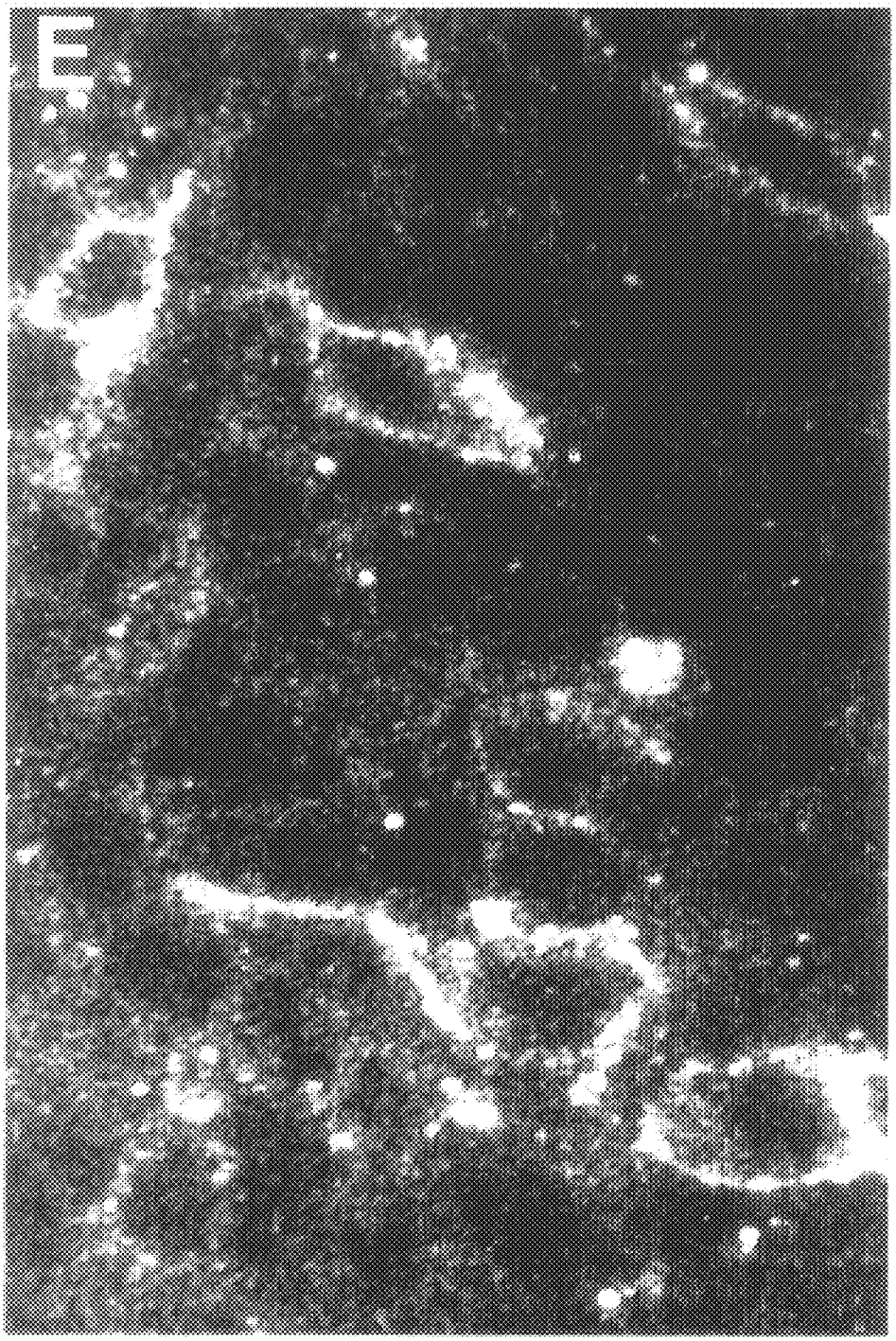
Figure 6F:
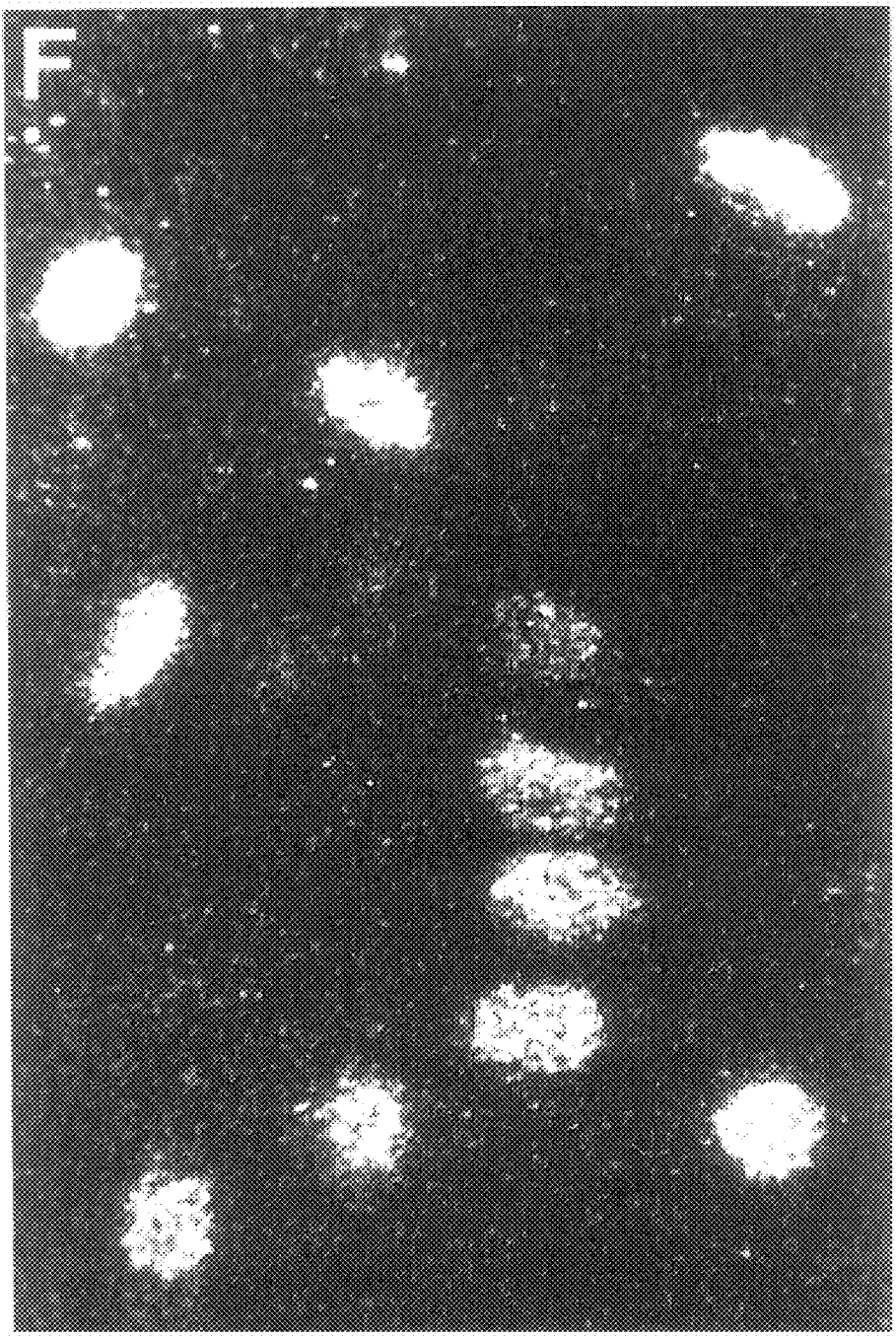
Figure 6G:
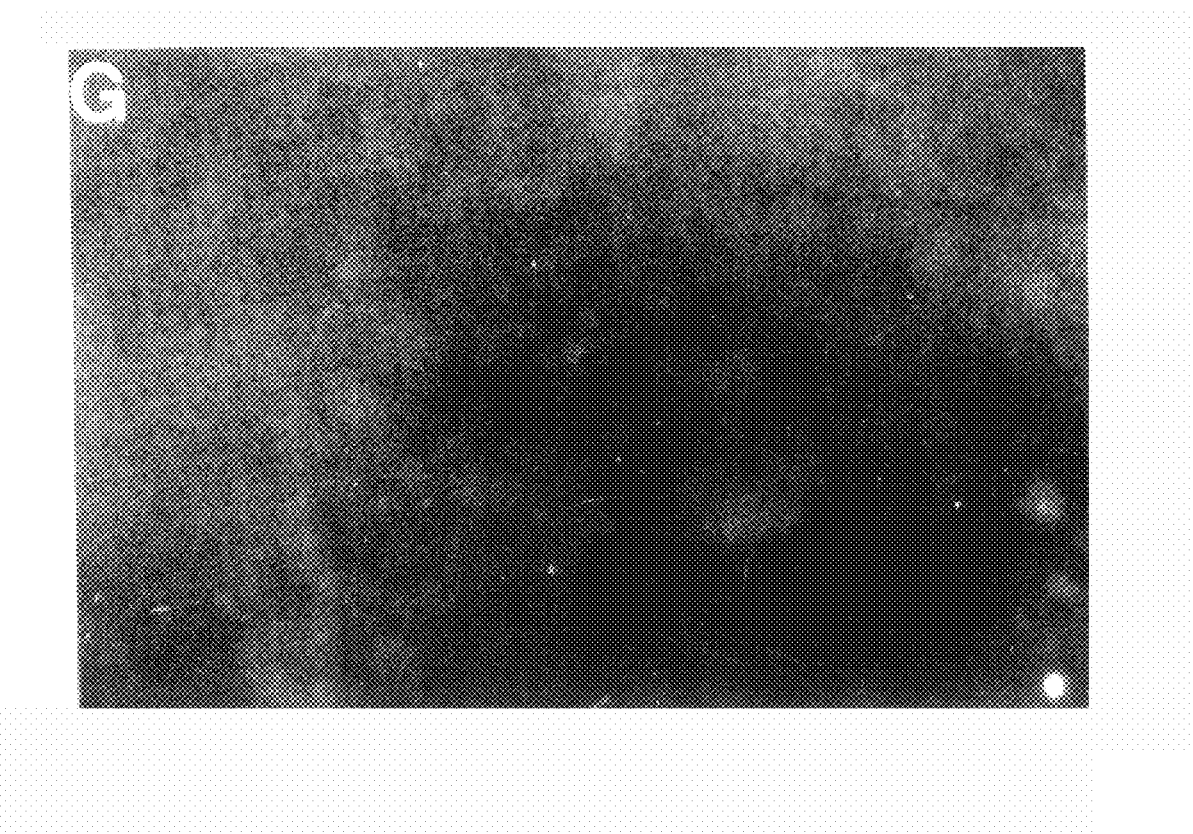
Figure 6H:
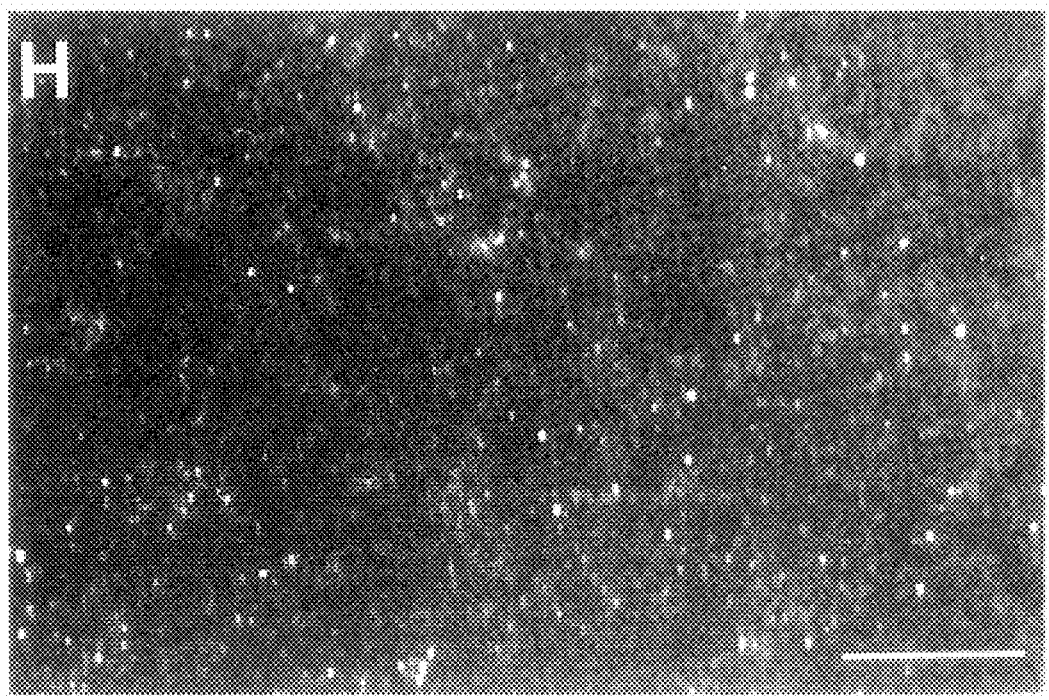

To determine whether vhh-1 can also induce motor neurons, applicants used chick neural plate explants in which motor neuron differentiation has been characterized (Table 1; Yamada et al., 1993). Motor neurons can be identified by the coexpression of two markers, the LIM homeodomain protein islet-1 (Thor et al., 1991; Ericson et al., 1992) (FIG. 6A) and the immunoglobulin-like protein SC1 (Tanaka and Obata, 1984) (FIG. 6D). Intermediate neural plate explants (Yamada et al., 1993) were grown for 44 hrs on a monolayer of COS cells transfected with sense or antisense vhh-1 expression plasmids. Neural plate explants grown on COS cells expressing the sense cDNA contained an average of 83 Islet-1' cells (FIGS. 6B and 6C; Table 1), whereas explants grown on COS cells transfected with antisense vhh-1 cDNA expressed at most one islet-1' (FIG. 6G, Table 1, motor neuron induction). Immunofluorescence labelling and confocal imaging revealed that most islet-1' cells expressed SC1 on their surface (FIGS. 6E and 6F) (n=27 explants), confirming their identity as motor neurons. Medium conditioned by COS cells transfected with sense vhh-1 cDNA did not induce islet-1' calls in intermediate neural plate explants (date not shown).

Since ambiguous markers of floor plate differentiation in chick neural plate explants are not available, applicants could not assay whether floor plate differentiation also occurs in chick neural plate explants in response to vhh-1.

Taken together, these in vitro assays provide evidence that COS cells expressing vhh-1 can induce both floor plate cells and motor neurons, although it is unclear whether motor neuron induction is a direct response to vhh-1.

TABLE 1

Induction of Floor Plate and Motor Neuron Differentiation in Neural Plate Explants in Vitro

| Inducer | Floor Plate Induction[a] | | | Motor Neuron Induction[b] | |
|---|---|---|---|---|---|
| | Percentage FP3+ Explants | Percentage FP4+ Explants | n (Explants) | Number of Islet-1+ Cells | n (Explants) |
| Notochord[c] | 85 | 63 | 65, 30 | 210 ± 12 | 22 |
| vhh-1 COS cells | 70 | 47 | 47 | 83 ± 8 | 24 |
| Antisense vhh-1 COS cells | 0 | 0 | 16 | 0–1 | 20 |
| Floor plate-conditioned medium | | | | 60 ± 4 | 20 |
| Posterior limb mesenchyme | 73 | 45 | 22 | | |
| Anterior limb mesenchyme | 0 | 0 | 22 | | |

[a]Numbers derive from three to six separate experiments.
[b]Values given are means ± SEM from 1 of 6 similar experiments; caudal stage 10 notochord was used. Floor plate-conditioned medium was prepared as described by Yamada et al. (1993).
[c]Data for floor plate induction from Placzek et al. (1993).

Floor Plate Differentiation Is Induced In Vitro by Posterior Limb Bud Calls

Figure 7A:
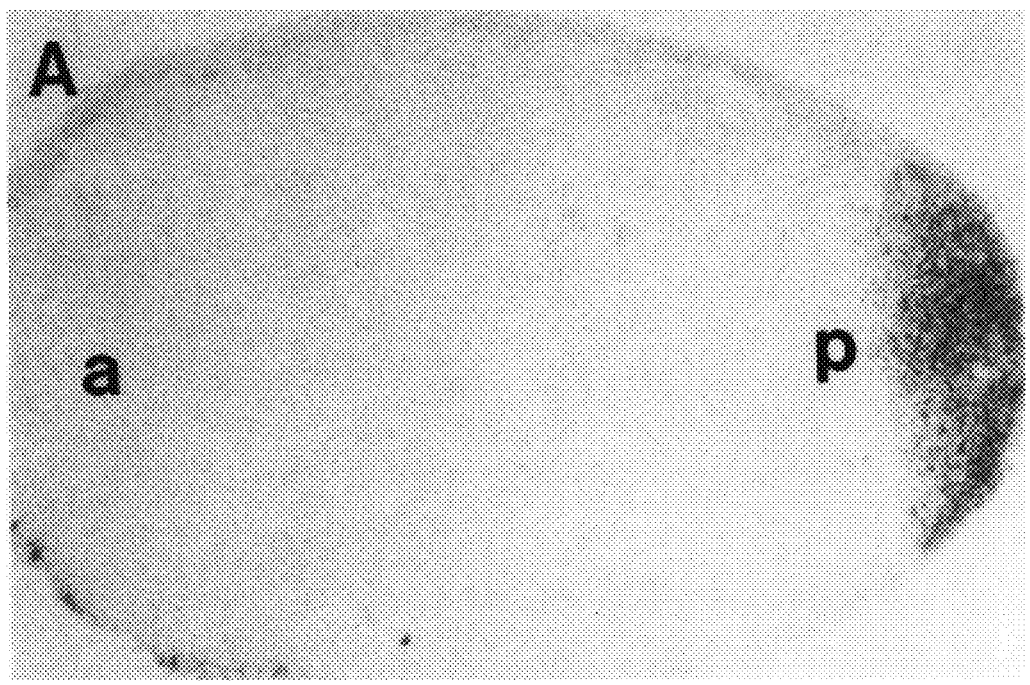
Figure 7B:
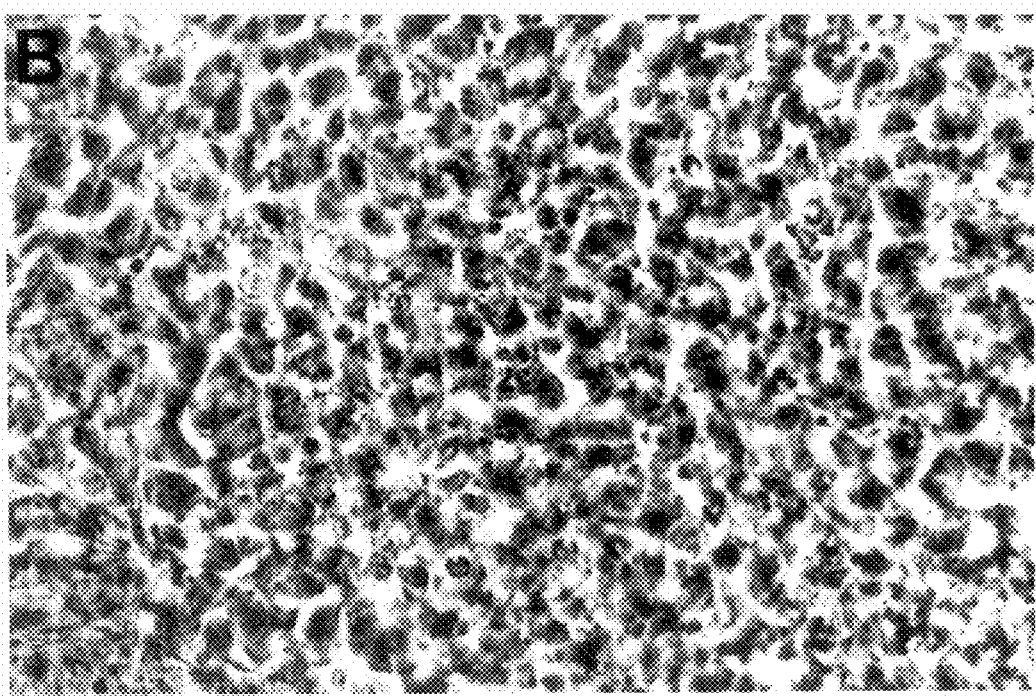
Figure 7C:
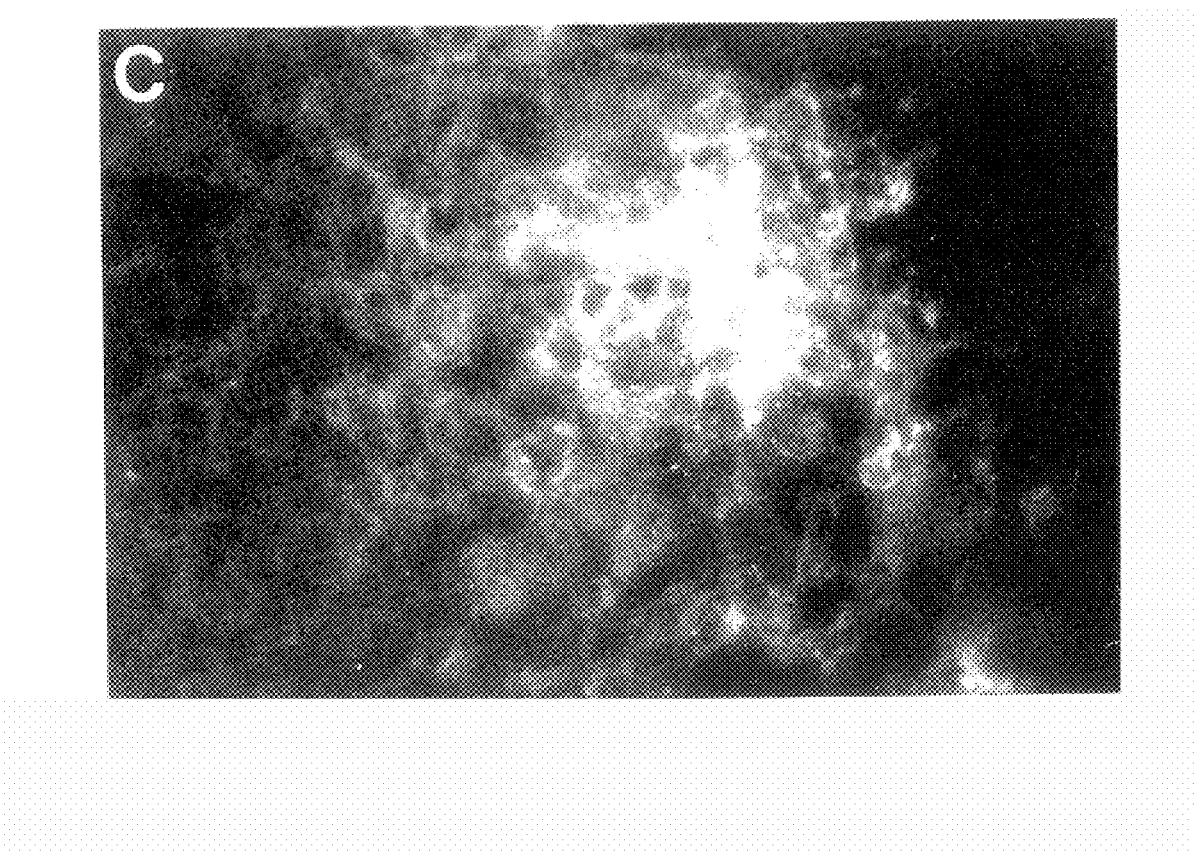
Figure 7D:
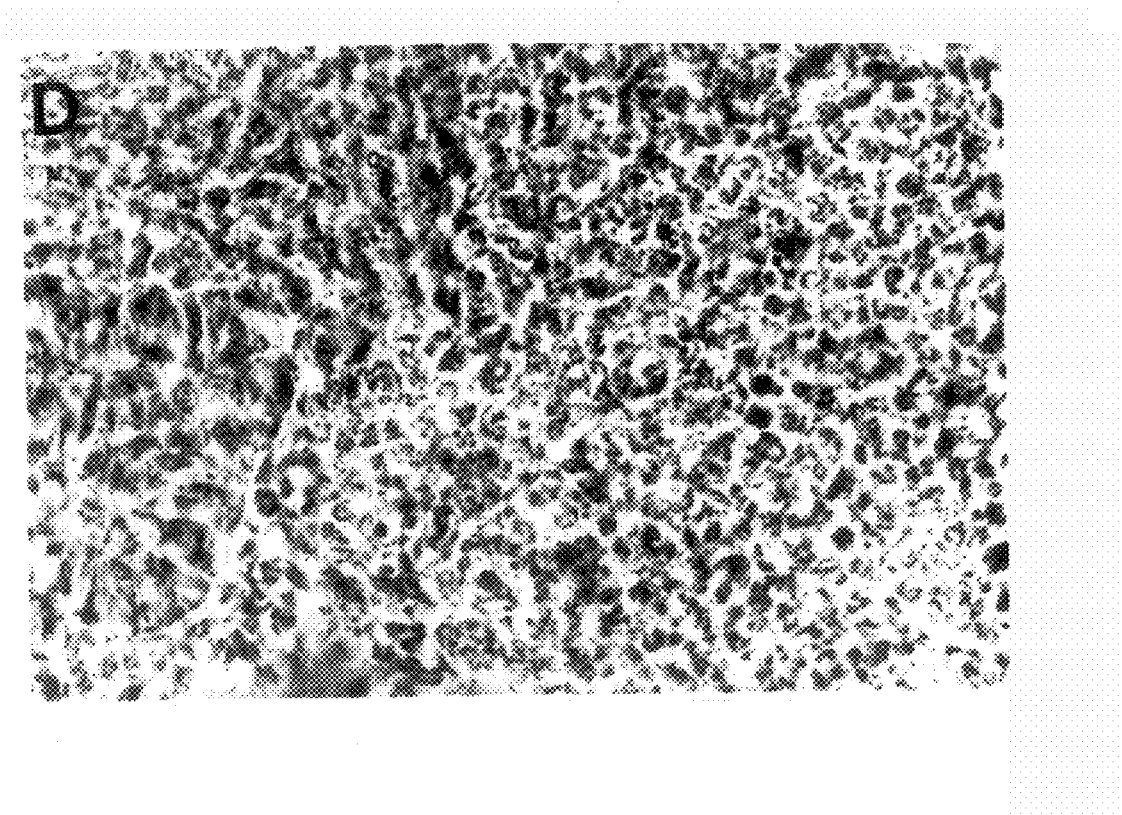
Figure 7E:
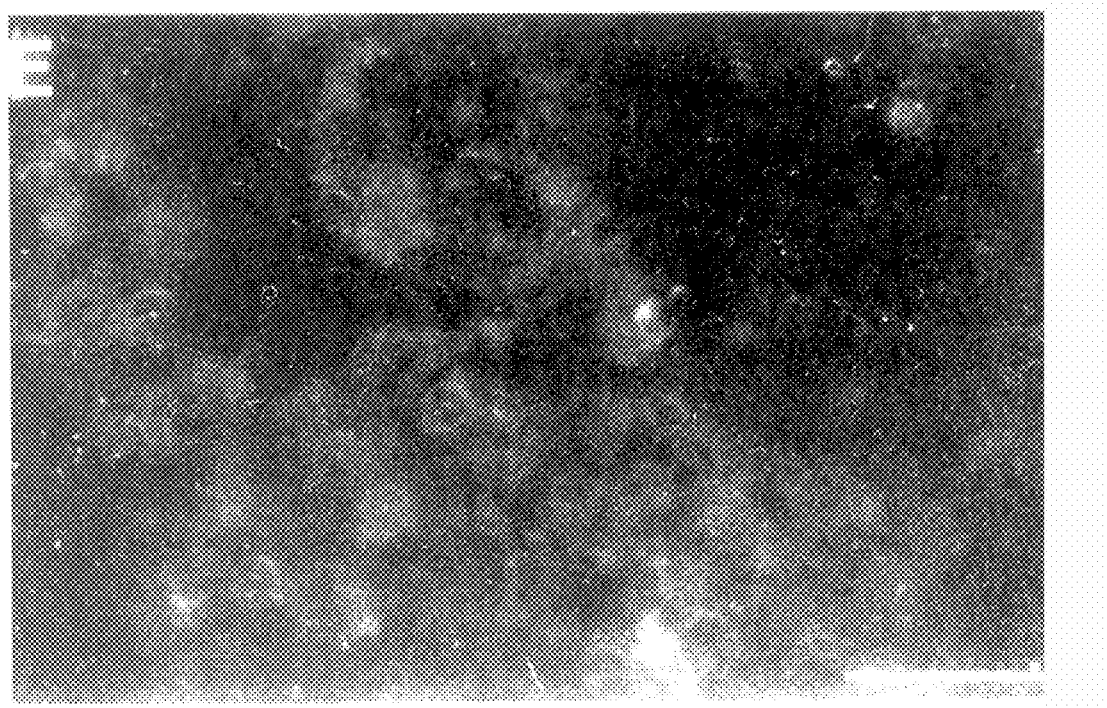

The node, notochord, and floor plate can induce floor plate differentiation (Placzek et al., 191, 1993) and can also mimic the ability of the ZPA to evoke digit duplications in the developing chick limb bud (Hornbruch and Wolpert, 1986; Wagner et al., 1990, Stoker and Carison, 1990; Hogan et al., 1992). The expression of vhh-1 in the ZPA region (see FIG. 3; FIG. 7A) raises the questions of whether the ZPA can mimic the ability of midline cells to induce floor plate differentiation. To test this, applicants assayed the ability of the ZPA to induce floor plate differentiation in rat neural plate explants in vitro. The ZPA region of the posterior limb mesenchyme (Honig and Summerbell, 1985) was isolated together with the adjacent apical ectoderm to provide factors that maintain ZPA activity in vitro (Anderson, et al., 1993; Vogel and Tickle, 1993; Niswander et al., 1993). Of neural plate explants grown in contact with posterior limb mesenchyme and ectoderm, 73% expressed FP3 and 45% displayed FP4 (Table 1, floor plate induction; FIGS. 7B and 7C). In contrast, neural plate explants grown in contact with anterior limb mesenchyme and ectoderm did not express FP3 or FP4 (FIGS. 7D and 7E; Table 1, floor plate induction). Neural plate explants grown in contact with posterior limb ectoderm in the absence of mesenchyme did not induce FP3 or FP4 (data not shown). These results support the idea that vhh-1 expression confers cells with floor plate inducing properties.

EXPERIMENTAL DISCUSSION

The differentiation of ventral cell types within the neural tube is controlled by signals that derive from the notochord. Applicants have identified a vertebrate homolog of the Drosophila hh gene, vhh-1, that is expressed in midline mesodermal and neural cells: the node, the notochord, and the floor plate. Widespread expression of the vhh-1 gene in frog embryos leads to ectopic floor plate differentiation, and COS cells expressing vhh-1 can induce floor plate and motor neuron differentiation in neural plate explants in vitro. Our results suggest that expression of vhh-1 by the notochord participates in the induction of floor plate and motor neuron differentiation in overlying neural plate cells.

Involvement of vhh-1 in Floor Plate and Motor Neuron Differentiation

In vitro studies have provided evidence for two distinct activities of the notochord, a contact mediated floor plate inducing activity and a diffusible motor neuron inducing activity (Placzek et al., 1990a, 1990b, 1993; Yamada et al., 1993). Both activities are also acquired by the floor plate after its induction by the notochord. Our results provide evidence that floor plate induction occurs as a direct response to vhh-1. Moreover, as with the notochord derived signal, floor plate induction by vhh-1 appears to be a local event and may be contact mediated.

Although vhh-1 can induce motor neurons as well as floor plate cells, our results do not resolve whether this induction is direct and thus whether vhh-1 could represent the diffusible motor neuron inducing activity present in notochord- and floor plate-conditioned medium. Since vhh-1 can induce floor plate differentiation, the induced floor plate could, in turn, secrete a motor neuron-inducing factor distinct from vhh-1. It is also unclear whether vhh-1 is present in medium conditioned by cells that secrete vhh-1. In Drosophila, hh is known to act nonautonomously (Mohler, 1988), and analysis of hh (or a downstream mediator of hh function) can act over a distance of a few cell diameters (Ingham, 1993; Heberlein et al., 1993; Ma et al., 1993; Heemskerk and Dinardo, 1994; Basier and Struhl, 1994). Consistent with this, hh protein has been detected beyond the domain of hh mRNA expression (Taylor et al., 1993).

The early expression of vhh-1 by the notochord is synchronous with its floor plate and motor neuron inducing activities. However, the persistent expression of vhh-1 by the notochord at later stages of embryonic development contrasts with in vitro studies showing that the notochord rapidly loses its ability to induce floor plate in vitro (Placzek et al., 1990a, 1990b, 1993). This difference could reflect the onset of expression of notochord factors that inhibit the action of vhh-1 or the loss of expression of a required cofactor. In rat, vhh-1 expression by floor plate cells can first be detected after neural tube closure, consistent with the time at which floor plate cells acquire floor plate and motor neuron inducing activity (Placzek et al., 1993; Yamada et al., 1993). By this time it appears that cells in the neural plate have been exposed to signals that initiate more neuron differentiation (Yamada et al., 1993). It is unlikely, therefore, that vhh-1 expression by the floor plate is involved in the initiation of motor neuron differentiation. Nevertheless, it is possible that later-born motor neurons (Hollyday and Hamburger, 1977) depend on floor plate-derived vhh-1 for their differentiation. A second function of vhh-1 in the floor plate may be to participate in the recruitment of additional cells to the floor plate as the neural tube grows (Placzek et al., 1993).

Pathway of Floor Plate Differentiation

The ability of vhh-1 to induce ectopic HNF-3β in the neural tube may be relevant to the steps involved in the normal development of the floor plate. Pintallavis and HNF-3β are expressed in the node, notochord, ad floor plate (Ruiz i Altaba and Jessell, 1992; Monaghan et al., 1993; Sasaki and Hogan, 1993; Ruiz i altaba et al., 1993b). The expression of both genes by the floor plate is dependent on inductive signals from the notochord (Ruiz i Altaba et al., 1992; A.R.A., MP., J.D., AND T.M.J., unpublished data), and expression occurs before other floor plate properties.

Widespread expression of Pintallavis and HNF-3β induces the expression of floor plate markers in the dorsal neural tube (Ruiz i Altaba et al., 1993a; A.R.A. et al., unpublished data; Sasaki and Hogan, 1994), suggesting that HNF-3β and Pintallavis are involved in the specification of floor plate fate in cells at the midline of the neural plate. The induction of HNF-3β by vhh-1, therefore, appears to mimic the ability of the notochord to trigger a program of floor plate differentiation that includes the transcription of genes such as vhh-1 itself and F-spondin.

Reauirements for Floor Plate Differentiation

Widespread expression of rat vhh-1 in frog embryos induces ectopic floor plate differentiation in vivo. The chick and zebrafish shh genes have also been shown to induce floor plate markers, although only in midbrain regions (Echelard et al., 1993; Krauss et al., 1993). Our in vivo studies show clearly that atopic expression of floor plate markers can also be obtained at hindbrain and spinal cord levels, although not in the forebrain. The absence of ectopic floor plate markers in the forebrain is consistent with in vitro studies showing that notochord cannot induce floor plate differentiation in anterior regions of the neural plate (Placzek et al., 1993).

Although widespread expression of vhh-1 in frog embryos induces ectopic floor plate differentiation in vivo. The chick and zebrafish shh genes have also been shown to induce floor plate markers, although only in midbrain regions (Echelard et al., 1993; Krauss et al., 1993). Our in vivo studies show clearly that atopic expression of floor plate markers can also be obtained at hindbrain and spinal cord levels, although not in the forebrain. The absence of ectopic floor plate markers in the forebrain is consistent with in vitro studies showing that notochord cannot induce floor plate differentiation in anterior regions of the neural plate (Placzek et al., 1993).

Although widespread expression of vhh-1 induces ectopic floor plate differentiation at all levels of the neuraxis caudal to the forebrain, applicants observed that ectopic floor plate markers were found primarily in the dorsal region of the neural tube. Notochord grafts can, however, induce floor plate differentiation at all dorsoventral positions within the neural tube (van Straaten et al., 1988; Yamada et all, 1991). Thus signals from the notochord may, in vivo, induce floor plate differentiation in regions of the neural tube that do not respond to vhh-1 alone. The observed differences in neural tube responses to vhh-1 and to the notochord could result from quantitative differences in vhh=1 levels provided by the notochord and by the vhh-1 expression plasmid. Alternatively, the notochord may provide additional signaling molecules, one function of which could be to regulate the expression of transcription factors that cooperate with Pintallavis and HNF-3β in the determination of floor plate fate.

Vhh-1 Expression and the Reciprocity of Neural Tube and Limb Polarizing Activities The expression of vhh-1 in the node, notochord, floor plate and posterior limb mesenchyme provides a possible molecular basis for the shared signaling properties of these cell groups (Jessell and Dodd, 1992; Ruiz 1 Altaba and Jessell, 1993). Grafts of Hensen's node, the notochord, or floor plate into the anterior region of the developing chick limb bud evoke digit duplications that mimic those of the ZPA (Hornbruch and Wolpert, 1986; Wagner et al., 1990; Stoker and Carlson, 1990; Hogan et al., 1992). The present results show that the ZPA can induce floor plate differentiation. Moreover, the common signaling properties of the node, notochord, floor plate, and ZPA appear to correlate more closely with the pattern of vhh-1 expression than with retinoid activity (Thaller and Eichele, 1987; Rossant et al., 1991; Wagner et al., 1992). Additional support for the idea that the limb and neural patterning have a common basis is provided by recent studies showing that chick shh can mimic ZPA activity when expressed in anterior regions of the limb bud (Riddle et al., 1993). Expression of the vhh-1 gene in the node, notochord, and floor plate is likely, therefore, to underlie the ability of these midline cell groups to mimic the activity of the ZPA in evoking digit duplications. Reciprocally, the expression of vhh-1 may underlie the ability of the ZPA to induce floor plate differentiation.

Hh-Related TGCβ and Wnt Proteins as Secreted Regulators of Cell Pattern

In Drosophila, dpp, wg, and hh regulate cell fate and pattern in embryonic and larval development. In vertebrates, members of the TGFβ and wnt gene families regulate cell differentiation during neural development. The wnt-1 gene is required for midbrain and anterior hindbrain development (McMahon and Bradely, 1990; Thomas and Capecchi, 1990), and dorsalin-1, a member of the TGFβ family, promotes the differentiation of dorsal cell types in neural plate explants in vitro (Blaser et al., 1993). Our results suggest that vhh-1 also contributes to neural patterning in vertebrates, acting to induce distinct cell types in the ventral region of the neural tube. Thus, dorsalin-1 dorsally and vhh-1 ventrally may provide polarizing signals with opposing actions that specify cell fates along the dorsoventral axis of the neural tube.

References of the First Series of Experiments

Aebischer, P., Winn, S. R., Tresco, P. A., Jaeger, C. B. and Greene, L. A. Transplantation of polymer encapsulated neurotransmitter secreting cells: effect of the encapsulation technique. J. Biomech. Eng. 113:178–183 (1991).

Anderson, R., Landry, M., and Muneoka, K. Maintenance of ZPA signaling in cultured mouse limb bud cells. Development. 117:1421–1433 (1993).

Baker, N. Transcription of the segment-polanty gene wingless in the imaginal discs of Drosophila, and the phenotype of a pupal-lethal wg mutation. Development. 102:489–497 (1988).

Basler, K., and Struhl, G. Hedgehog, a product of posterior compartment cells in Drosophila, organizes anterior compartment pattern. Nature. in press (1994).

Basler, K., Edmund, T., Jessell, T. M., and Yamada, T. Control of cell pattern in the neural tube: regulation of cell differentiation by dorsalin-1, a novel TGFβ family member. Cell. 73:687–702 (1993).

Bolce, M. E., Hammati-Brivanlou, A., and Harland, R. M. XFKH2, a Xenopus HNF-3α homologue, exhibits both activin inducible and autonomous phases of expression in early embryos. Dev. Viol. 160:413–423 (1993).

Bovolenta, P., and Dodd, J. Perturbation of neuronal differentiation and axon guidance in the spinal cord of mouse embryos lacking a floor plate analysis of Danforth's short-tall mutation. Development. 113:625–639 (1991).

Campbell, G., Weaver, T., and Tomlinson, A. Axis specification in the developing Drosophila appendage: the role of wingless, decapentaplegic, and the homeobox gene aristaless. Cell. 74:1113–1123 (1993).

Cardin, A. D., and Weintraub, H. J. R. Molecular modeling of protein-glycosaminoglycanInteractions. Arteriosclerosis. 9:21–32 (1989).

Clarke, J. D. W., Holder, N., Soffe, S. R. and Storm-Mathissen, J. Neuroanatomical and functional analysis of neural tube formation in notochordless Xenopus embryos laterally of the ventral spinal cord is lost. Development. 112:499–516 (1991).

Dale, L., and Slack, J. M. W. Fate map for the 32-cell stage of Xenopus laevis. Development. 99:527–551 (1987).

Dent, J. A. Poison, A. G., and Klymkowsky, M. W. A whole-mount immunocytochemical analysis of the expression of the intermediate filament vimentin in Xenopus. Development. 105:61–74 (1989).

Dirksen, M. L., and Jamrich, M. A novel activin-inducible, blastospore lip specific gene of Xenopus Laevis contains a fork head DNA-binding domain. Genes Dev. 6:599–608 (1992).

Echelard, Y., Epstein, D. J., St.-Jacques, B., Shen, L., Mohler, J., McMahon, J. A., and McMahon, A. P. Sonic hedgehog, a member of a family of putative signaling molecules is implicated in the regulation of CNS polarity. Cell. 75:1417–1430 (1993).

Erffert, H., Ohlenbusch, A., Fahling, W., Lottor, H., and Thomssen, R. Nucleotide sequence of the ospAg operon of a Borrella burgdoferi strain expressing OspA but not Ospe. Infect. Immun. 60:1654–1868 (1992).

Ericson, J., Thor, S., Edlund, T., Jessell, T. M., and Yamada, T. Early stages of motor neuron differentiation revealed by expression of homeobox gene Islet-1. Science. 258:155–1580 (1992).

Ferguson, E. L., and Anderson, K. V. decapontaplegic acts as a morphagen to organize dorsal-ventral pattern in the Drosophila embryo. Cell. 71:451–461 (1992).

Friden, P. T., Palmer, A. M., Sioms, N. R., Bowen, D. M., Davison, A. N., Esiri, M. M. and Neary, D. Neurochemical studies of early-onset Alzheimer's disease. Possible influence on treatment. Lancet, 4:7–11 (1985).

Goulding, M., Lumsden, A., and Gruss, P. Signals from the notochord and floor plate regulate the region-specific expression of two pax genes in the developing spinal cord. Development. 117:1001–1016 (1993).

Halpern, M. E., Ho. R. K., Walker, C., and Kimmel, C. B. Induction of muscle pioneers and floor plate is distinguished by the zebrafish no tail mutation. Cell. 75:99–111 (1993).

Hamburger, V., and Hamilton, H. A series of normal stages in the development of chick embryo. J. Morphol. 88:49–92 (1951).

Hartland, R. M. (1991) In situ hybridization: an improved whole mount method for Xenopus embryos. Meth. Enzymol 36:675–685 (1991).

Hatta, K., Kimmel, C. B., Ho, R. K., and Walker, C. The cyclops mutation blocks specification of the floor plate of the zebrafish central nervous system. Nature. 350:339–341 (1991).

Heberlain, U., Wolff, T., and Rubin, G. M. The TGFβ homolog dpp and the segment polarity gene hedgehog are required for propagation of a morphogenetic eave in the Drosophila retina. Cell 75:913–926 (1993).

Heemskerk, J., and DiNardo, S. Drosophila hedgehog acts as a morphogen in cellular patterning. Cell. 76:448–460 (1994).

Hidalgo, A., and Inqham, P. Cell patterning in the Drosophila segment spatial regulation of the segment polarity gene patched. Development. 110:291–301 (1990).

Hoffman, D., Wahlberg, L. and P. Aebischer. NGF released from a polymer matrix prevents loss of ChAT expression in basal forebrain neurons following a Fimbria-Fornix lesion. Exp. Neurol., 110:39–44 (1990).

Hogan, B. L. M., Thaller, C., and Eichele, G. Evidence that Hansen's node is a site of retinoic acid synthesis. Nature. 359:237–241 (1992).

Hollyday, M., and Hamburger, V. An autoradiographic study of the formation of the lateral motor column in the chick embryo. Brain Res. 132:197–208 (1977).

Honig, L. S., and Summerbell, D. Maps of strength of positional signaling activity in the developing chick wing bud. J. Embryol. Exp. Morphol. 87:163–174 (1985)

Hornbruch, A., and Wolpert, A. Positional signaling by Hensen's node when grafted to the chick limb bub. J. Embryol. Exp. Morphol. 94:257–265 (1986).

Ingham, P. W. Localized hedgehog activity controls sratial limits of wingless transcription in the Drosophila embryo. Nature 366:560–582 (1993).

Jessell, T. M., and Dodd, J. Floor plate-derived signals and the control of neural cell pattern in vertebrates. Harvey Lect. 85:87–128 (1992).

Klar, A., Baldassare, M., and Jessell, T. M. F-spondin: a gene expressed at high levels in the floor plate encodes a secreted protein that promotes neural cell adhesion and neurite extension. Cell 89:95–110 (992).

Knochel, S., Lef, J., Clement, J., Klocke, E., Hille, S., Koster, M., and Knochel, W. Activin A induced expression of a forkhead related gene in posterior chordamesoderm of Xenopus laevis embryos. Mech. Dev. 38:157–165 (1992).

Koliatsos, V. E., Clatterbuck, R. E., Nauta, H. J. W., Knusel, E., Burton, L. E., Hefti, F., Mobley, W. C. and Price, D. L. Human nerve growth factor prevents degeneration of basal forebrain chonlinergic neurons in primates. Ann. Neurol. 30:831–840 (1991b).

Korzh, V., edlund, T., and Thor, S. Zebrafish primary neurons initiate expression of the LIM homeodomain protein isl-1 at the end of gastrulation. Development. 118:417–425 (1993).

Krauss, S., Johansen, T., Korzh V., and Fjose, A. Expression pattern of zebrafish Pax genes suggests a role in early brain regionalization. Nature. 353:267–670 (1991).

Krauss, S., Concordel, J. P., and Ingham, P. W. A functionally conserved homolog of the Drosophila segment polarity gene hedgehog is expressed in tissues with polarizing activity in zebrafish embryos. Cell. 75:1431–1444 (1993).

Kyle, J., and Doolittle, R. F. A simple method for displaying the hydropathic character of a protein. J. Mol. Biol. 167:105–132 (9182).

Lai, E., Prezioso, V. R., Tao, W., Chen, W. S., and Darnell, J. E. Hepatocyte nuclear factor 3a belongs to a gene family in mammals that is homologous to the Drosophila homeotic gene fork head. Genes Dev. 5:416–427 (1992).

Lee, J. J., Von Kessler, D. P., Parks, S., and Beachy, P. A. Secretion and localization transcription suggest a role in positional signaling for products of the segmentation gene hedgehog. Cell. 71:33–50 (1992).

Ma, C., Zhou, Y., Beachy, P. A., and Moses, K. The segment polarity gene hedgehog is required for progression of the morphogenetic furrow in the developing Drosophila eye. Cell. 75:927–938 (1993).

Martinex-Arias, A., Baker, N., and Ingham, P. Role of Segment polarity genes in the definition and maintenance of cell states in the Drosophila embryo. Development. 103:157–170 (1988).

Maysinger, D., Jalsenjak, I. and Cuello, A. C. Microencapsulated nerve growth factor: effects on the forebrain neurons following devascularizing cortical lesions. Neurosci. Lett. 140:71–74 (1992).

McMahon, A. P. and Bradley, A. The Wnt-1 (int-1) protooncogene is required for development of a large region of the mouse brain. Cell 62: 1073–1085 (1990).

Mohler, J. Requirements for hedgehog, a segmental polarity gene, in patterning larval and adult cuticle of Drosophila. Genetic 120:1061–1072 (1988).

Mohler, J., and Vani, K Molecular. organization and embryonic expression of the hedgehog gene involved in cell-cell communication in segmental patterning of Drosophila. Development. 115:957–971 (1992).

Monaghan, A. P., Kasstner, K. H., Grau, E., and Schultz, G. Postimplantation expression patters indicate a role for the mouse forkhead/HNF-3 ($\alpha$, $\beta$, and $\gamma$ genes in determination of the definitive endoderm, chordamesoderm and neuroectoderm. Development. 119:567–578 (1993).

Morata, G., and Lawrence, P. A. The development of wingless, a homeotic mutation of Drosophila, Dev. Biol. 56:227–240 (1977).

Nieuwkoop, P. D., and Faber, J. Normal Table of Xenopus laevis (Daudin) (Amsterdam: North Holland) (1967).

Niswander, L., Tickle, C., Vogel, A., Booth, I., and Martin G. R. FGF-4 replaces the apical ectodermal ridge and directs outgrowth and patterning of the limb. Cell. 75:579–587 (1993).

Nusse, R. and Varmus, H. Wnt genes. Cell. 69:1073–1087 (1992).

Nussein-Volhard, C., and Wieschaus, E. Mutations affecting segment number and polarity in Drosophila. Nature. 287:795–801 (1992).

Olson, L., Nordberg, A., von Holst, H., Backman, L., Ebendahl, T., Alafuzoff, I., Amberla, K., Hartvig, P., Herlitz, A., Lilja, A. Lundquist, H. Langstron, B., Meyerson, B., Persson, A., Viitanen, M., Winblad, B. and Seiger, A. Nerve growth factor affects 11C-nicotine binding, blood flow, EEG and verbal episodic memory in an Alzheimer patient. J. Neurol. Transm. [P-D Sect] 4:79–95 (1992).

Parr, B. A., Shea, M. J., Vassileva, G., and McMahon, A. P. Mouse Wnt genes exhibit discrete domains of expression in its early embryonic CNS and limb buds. Development. 119:247–261 (1993).

Patel, N. H., Martin-Bianco, E., Coleman, K. G., Poole, S. J., Ellis, M. C., Kornberg, T. B., and Goodman, C. S. Expression of engrailed proteins in arthropods, annelids and chordates. Cell. 58:955–968 (1989).

Placzek, M., Tessler-Lavigne, M., Jessell, T. M., and Dodd, J. Orientation of commissural axons in vitro in response to a floor plate derived chemostractant. Development. 110:19–30 (1990a).

Placzek, M., Tessler-Lavigne, M., Yamada, T., Jessell, T. M. and Dodd, J. Mesodermal control of neural cell identity: floor plate induction by the notochord. Science. 250:985–988 (1990b).

Placzek, M., Yamada, T., Tessler-Lavigne, M., Jessell, T. M., and Dodd, J. control of dorso-ventral pattern in vertebrate neural development induction and polarizing properties of the floor plate. Development. 113(Suppl. 2):105–122 (1991).

Placzek, M., Jessell, T. M., and Dodd, J. Induction of floor plate differentiation by contact-dependent, homeogenetic signals. Development. 117:205–218 (1993).

Posakony, L. G., Raftery, L. A., and Gelbart, W. M. Wing formation in Drosophila melanogaster requires decapentalplegic gene function along the anterior-posterior compartment boundary. Mech. Dev. 33:69–82 (1991).

Riddle, R., Johnson, R. L., Laufer, E., and Tabin, C. Sonic hedgehog mediates the polarizing activity of the ZPA. Cell. 75:1401–1416 (1993).

Roelink, H., and Nusse, R. Expression of two members of the Wnt family during mouse development: restricted temporal and spatial patterns in the developing neural tube. Genes Dev. 5:381–388 (1991).

Rossant, J., Zirngibl, R., Cado, D., Shago, M., and Giguere, V. Expression of a retinoic acid response element-hsplacz transgene defines specific domains of transcriptional activity during mouse embryogenesis. Genes Dev. 5:1333–1344 (1991).

Ruiz i Altaba, A. Planar and vertical signals in the induction and patterning of the Xenopus nervous system. Development. 115: 67–80 (1992).

Ruiz i Altaba, A. Xenopus. In Essential Developmental Biology: A Practical Approach, C. D. Stern and P. W. H. Holland, eds. (Oxford: IRL Press) pp. 39–44 (1993).

Ruiz i Altaba, A., and Jessell, T. M. Pintallavis, a gene expressed in the organizer and midline cells of frog embryos: involvement in the development of the neural axis. Development. 116:81–93 (1992).

Ruiz i Altaba, A., and Jessell, T. M. Midline cells and the organization of the vertebrate neuraxis. Curr. Opin. Genet. Dev. 3:633–640 (1993).

Ruiz i Altaba, A., and Jessell, T. M. and Klar, A. Ectopic neural expression of a floor plate marker in frog embryos injected with the midline transcription factor Pintallavis. Proc. Natl. Acad. Sci. U.S.A. 90:8268–8272 (1993a).

Ruiz i Altaba, A., Prezioso, V. R., Darnell, J. E., and Jessell, T. M. Sequential expression of HNF-3$\beta$ and HNF-3$\alpha$ by embryonic organizing centers: the dorsal lip/node, notochord and floor plate. Mech. Dev. 44:91–108 (1993b).

Sanger, F., Nicklen, S., and Coulson, A. R. DNA sequencing with chain-terminating inhibitors. Proc. Natl. Acad. Sci. U.S.A. 74:5463 (1977).

Sasaki, H., and Hogan, B. L. M. Differentiation expression of multiple forkhead regrated genes during gastrulation and axial pattern formation in the mouse embryo. Development. 118:47–59 (1977).

Sasaki, H., and Hogan, B. L. M. HNG-3 as a regulator of floor plate development. Cell. 76:103–116

Schaeren-Wiemers, N., and Gerlin-Mosar, A. A single protocol to detect transcripts of various types and expression levels in neural tissue and cultured cells: in situ hybridization using digoxigeninlabeled cRNA probes. Histochemistry. 100:431–440 (1993).

Spencer, F. A., Hoffmann, F. M., and Gelbert, W. M. Decapentaplogic: a gene complex affecting morphogenesis in Drosophila metanogaster. Cell. 28:451–461 (1982).

Stoker, K. M., and Carlson, B. M. Hensen's node, but not other biological signallers can induce dupernumerary digits in the developing chick limb bud. Roux's Arch. Dev. Biol. 198:371–381 (1990).

Strahie, U., Blader, P., Henrique, D., and Ingham, P. Axial, a target gene of mesoderm and neural indication, shows altered expression in cyclops mutant zebrafish embryos. Genes. Dev. &:1438–1446 (1993).

Struhl, G., and Basler, K., Organizing activity of wingless protein in Drosophila. Cell. 72:527–540 (1993).

Tebata, T., Eaton, S., and Kornberg, T. B. The Drosophila hedgehog gene is expressed specifically in posterior compartment cells and is a target of engrailed regulation. Genes Dev. 6:2835–2646 (1992).

Tanaka, H., and Obata, K. Developmental changes in unique cell surface antigens of chick embryo spinal motor neurons and ganglion cells. Dev. Biol. 106:26–37 (1984).

Tashiro, S., Michiue, T., Higashijima, S., Zenno, S., Ishlmaru, S., Takahashi, F., Orlhara, M., Kojima, T., and Saigo, K. Structure and expression of hedgehog, a Drosophila segment-polarity gene required for cell-cell communication. Gene. 124:183–189 (1993).

Taylor, A. M., Nakano, Y., Mohler, J., and Ingham, P. W. Contrasting distributions of patched and hedgehog proteins in the Drosophila embryo. Mech. Dev. 42:89–96 (1993).

Tessler-Lavigne, M., Placzek, M., Lumsden, A. G. S., Dodd, J., and Jessell, T. M. Chemotropic guidance of developing axons in the mammalian central nervous system. Nature. 336:775–778. (1988).

Thalier, C., and Elchele, G. Identification and spatial distribution of retinoids in the developing chick limb bud. Nature 327:625–628 (1987).

Thomas, K. R., and Capecchi, M. R. Targeted disruption of the murine int-1 proto-oncogene resulting in severe abnormalities in midbrain and cerebellar development. Nature. 346:847–850 (1990).

Thor. S., Ericson, J., Brannstrom, T., and Edlund, T. The homeodomain LIM protein Isl-1 is expressed in subsets of neurons an dendocrine cells in the adult rat. Neuron. 7:881–889 (1991).

Van Straaten, H. M. W., and Hekking, J. W. M. Development of floor plate, neurons and axonal outgrowth pattern in the early spinal cord of the notochord-deficient chick embryo. Anat. Embryol. 184:55–63 (1991).

Van Straaten, H. M. W., Hekking, J. W. M., Wiertz-Hoesseis, E. L. Thors, F., and Drukker, J. Effect of the notochord on the differentiation of a floor plate area in the neural tube of the chick embryo. Anal. Embryol. 177:317–324 (1989).

Vogel, A., and Tickle, C. FGF-4 maintains polarizing activity of posterior limb bud cells in vivo and in vitro. Development. 119:199–206 (1993).

von Heijine, G. Signal sequences: the limits of variation. J. Mol. Biol. 184:99–105 (1985).

Wagner, M., Thaller, C., Jessell, T. M., and Elchele, G. Polarizing activity and retinoid synthesis in the floor plate of the neural tube. Nature. 345:819–822 (1990).

Wagner, M., Han, B., and Jessell, T. M. Regional differences in retinoid release from embryonic neural tissue detected by an in vitro reporter assay. Development. 116:55–66 (1992).

Welgel, D., and Jackie, H. The fork head domain: a novel DNA binding motif of eukaryotic transcription factor? Cell. 63:455–458 (1990).

Whiting, J., Marshall, H., Cook, M., Krumlauf, R., Rigby, P. W., Stolt, D., and Allemann, R. K. Multiple spatially specific enhancers are required to reconstruct the patter of Hox-2.6 gene expression. Genes Dev. 5:2048–2059 (1991).

Yamada, T., Placzek, M., Tanaka, H., Dodd, J., and Jessell, T. M. Control o cell pattern in the developing nervous system: polarizing activity of the floor plate and notochord. Cell 64:635–647 (1991).

Yamada, T., Plaff, S. L., Edlund, T., and Jossell, T. M.

Control of cell pattern in the neural tube: motor neuron induction by diffusible factors from notochord and floor plate. Cell. 73:673–686.

SECOND SERIES OF EXPERIMENTS

The vertebrate hedgehog-related gene, vhh-1/sonic hedgehog, is expressed in ventral domains along the entire rostrocaudal length of the neural tube, including the forebrain. Applicants show here that vhh-1/shh induces the differentiation of ventral neuronal cell types in explants derived from prospective forebrain regions of the neural plate. Neurons induced in explants derived from both diencephalic and telencephalic levels of the neural plate express the LIM homeodomain protein Islet-1, but these neurons possess distinct identities that match those of the ventral neurons normally generated in these two subdivisions of the forebrain. These results, together with previous studies of neuronal differentiation at caudal levels of the neural tube suggest that a single inducing molecule, vhh-1/shh, mediates the induction of distinct ventral neuronal cell types along the entire rostrocaudal extent of the embryonic central nervous system.

In vertebrate embryos, the patterning of the nervous system is initiated by inductive signals that act over short distances to direct the fate of neural progenitor cells. The complex pattern of cell types generated within the neural tube is though to involve the action of signals that impose regional character on cells at different rostrocaudal positions within the neural plate (Doniach et al., 1992; Ruiz i Altaba, 1992; Papalopulu, 1994) and that define the identity of cells along the dorsoventral axis of the neural tube (Jessell and Dodd, 1992; Basler et al. 1993; Smith, 1993). Thus, the fate of neural progenitor cells depends on their position along the rostrocaudal and dorsoventral axes of the neural tube.

The mechanisms that control the differentiation of cell types along the dorsoventral axis of the neural tube have been examined in most detail at caudal levels of the neuraxis. In the spinal cord, the differentiation of ventral cell types is initiated by signals transmitted from axial mesodermal cells of the notochord to overlying neural plate cells, inducing the differentiation of floor plate cells at the ventral midline and motor neurons more laterally within the neural tube (van Straaten et al., 1988; Placzek et al., 1990; 1991; Yamada et al., 1991, 1993; Goulding et al., 1993). At later stages, similar or identical signalling properties are acquired by floor plate cells (Hatta et al., 1991; Yamada et al. 1991; Placzek et al. , 1993) The specifxic identity of the ventral neuronal cell types that are generated in response to notochord- and floor plate-derived signals, however, appears to be defined by the position of origin of neuronal progenitor cells along the rostrocaudal axis. For example, serotonergic neurons are induced by midline-derived signals at the level of the rostral rhombencephalon (Yamada et al., 1991) whereas dopaminergic neurons are induced at the level of the mesencephalon (Hynes et al., 1995).

At caudal levels of the neuraxis, a vertebrate homolog of the secreted glycoprotein enoded by the Drosophila gene hedgehog (Nusslein-Volhard and Wieschaus 1980; Lee et al., 1992), vhh-1/sonic hedgehog (shh), has been implicated in the induction of ventral cell types. vhh-1/shh is expressed by the notochord and floor plate at the time that these two cell groups exhibit their inductive activities (Riddle et al., 1993; Krauss et al., 1993; Echelard et al., 1993; Chang et al., 1994; Roelink et al., 1994). Furthermore, exposure of neural plate explants to vhh-1/shh leads to the differentiation of motor neurons in addition to floor plate cells (Roelink et al., 1994), suggesting that vhh-1/shh participates in the induction of ventral neurons at caudal levels of the neuraxis.

At most levels of the embryonic forebrain, the notochord and floor plate are absent (Kingsbury, 1930; Puelles and Rubenstein, 1993) and neither the identity nor the source of inductive signals that trigger the differentiation of ventral neurons have been established. Studies of the zebrafish mutant cyclops (Hatta et al., 1991) have provided evidence that cells at the ventral midline of the embryonic diencephalon have a role in the patterning of the diencephalon (Hatta et al., 1994; Macdonald et al., 1994). vhh-1/shh is expressed by cells at the ventral midline of the embryonic forebrain (Echelard et al., 1993; Krauss et al., 1993; Chang et al., 1994; Roelink et al., 1994), raising the possibility that this gene participates in the specifications of neuronal identity within the forebrain as well as at more caudal levels in the neuraxis.

To address this issue, applicants first defined transcription factors and other molecular markers that permit the identification of ventral neuronal cell types generated in diencephalic and telencephalic subdivisions of the forebrain. Applicants then used these markers to assess the ability of vhh-1/shh to induce the differentiation of distinct ventral neuronal classes in explants derived from levels of the neural plate fated to give rise to the forebrain. Applicants' results show that vhh-1/shh induces ventral neuronal cell types normally found in the forebrain in addition to inducing motor neurons at more caudal levels of the neural tube. These findings suggest that a single inducing molecule, vhh-1/shh, is responsible for inducing ventral neuronal cell types along the entire rostrocaudal extent of the neuraxis. They also indicate that the repertoire of ventral neuronal cell types that can be induced by vhh-1/shh is defined by an earlier restriction in the rostrocaudal character of cells within the neural plate.

EXPERIMENTAL RESULTS vhh-1/shh and Islet-1 Occupy Adjacent Ventral Domains in the Embryonic CNS To begin to examine the involvement of vhh-1/shh in the patterning of the embryonic forebrain, it was necessary to identify early markers of ventral forebrain neurons. At caudal levels of the neuraxis, motor neurons constitute one prominent class of ventral neuron whose differentiation depends on inductive signals provided by the notochord and floor plate (Yamada et al., 1991, 1993). The earliest marker of differentiating motor neurons is Islet-1 (Karlsson et al., 1990), a LIM homeodomain protein that is expressed as motor neuron progenitors leave the cell cycle (Ericson et al., 1992; Korzh et al., 1993; Inoue et al., 1993; Tsuchida et al., 1994). Although motor neurons are absent from the forebrain, Islet-1 is expressed by ventral neurons in the adult forebrain (Thor et al., 1991). This observation prompted applicants to examine whether the embryonic expression of Islet-1 provides an early marker of the differentiation of ventral neuronal cell types at forebrain as well as at more caudal levels of the neuraxis.

Applicants therefore examined the pattern of expression of Islet-1 in the embryonic chick nervous system and compared it to that of vhh-1/shh. At Hamburger-Hamilton (HH) stage 18, Islet-1$^+$ cells were found in discrete domains along the rostrocaudal axis of the neural tube. Each Islet-1 cell group abutted the domain of expression of vhh-1/shh (FIG. 8, see FIG. 9Ai for a summary). In the spinal cord, rhombencephalon and mesencephalon, vhh-1/shh was expressed by floor plate cells at the ventral midline (FIGS. 8B, F, G and data not shown) and Islet-1 was expressed by cells located lateral to the floor plate (FIGS. 8B, F, G and data not shown). In the mid-diencephalon at the level of the infundibulum, vhh-1/shh was not expressed at the ventral midline but was located more laterally (FIGS. 8A, D). Islet-1$^+$ cells were also excluded from the ventral midline but were located immediately lateral to the zone of vhh-1/shh expression (FIG. 8D). In the rostral diencephalon, vhh-1/shh was expressed at the ventral midline of the neural tube and was restricted to the ventricular zone (FIGS. 8E, H, I). Within this region, Islet-1$^+$ cells were also located at the midline, immediately adjacent to the domain of expression of vhh-1/shh (FIG. 8I). In the telencephalon, the zone of vhh-1/shh expression also spanned the ventral midline of the neural tube (FIGS. 8J, K). Islet-1$^+$ cells were also restricted ventrally and were intermingled with cells expressing vhh-1/shh (FIG. 8K). These results indicate that Islet-1 expression defines ventral cell types at forebrain as well as at more caudal levels of the neural tube.

At all levels of the neuraxis, with the exception of the telencephalon, the expression of vhh-1/shh preceded the differential of Islet-1$^+$ cells. Expression of vhh-1/shh was detected in cells at the midline of the neural plate at prospective mesencephalic levels at HH stage 6 (FIG. 10A; and not shown). Between HH stages 6 and 10, midline expression of vhh-1/shh extended rostrally into the prospective diencephalon and caudally into the rhombencephalon and spinal cord (data not shown). The onset of Islet-1 expression at spinal cord, rhombencephalic, mesencephalic and diencephalic levels occurred between HH stages 13 and 15 (FIG. 8E; Ericson et al., 1992; Tsuchida et al., 1994; and data not shown), 18–24 hours after the onset of vhh-1/shh expression at similar axial levels. In the ventral telencephalon, however, expression of vhh-1/shh was not detected until late HH stage 17, about 30 hours after the gene was first expressed in ventral midline cells of the rostral diencephalon (data not shown) and coincident with the onset of Islet-1 expression.

Cells that Express Islet-1 at Different Axial Levels are Neurons with Distinct Identities To determine whether the ventral Islet-1$^+$ cells detected at different rostrocaudal levels of the neuraxis were neurons, applicants performed double-label immunocytochemistry with antibodies directed against Islet-1 and the neuron-specific markers β-tubulin and cyn-1. At all axial levels, Islet-1$^+$ cells expressed β-tubulin and/or cyn-1, confirming their identity as neurons (data not shown). Although all Islet-1+ cells were neurons, however, their identities at different rostrocaudal positions were distinct.

SC1 Expression Defines Islet-1+ Neurons as Motor Neurons:

In the rhombencephalon and mesencephalon, the location of Islet-1+ neurons coincided with the positions of somatic, visceral and brachial motor nuclei. At these levels, Islet-1+ neurons expressed the immunoglobulin-like surface protein SC1 (FIGS. 9Aii, B and data not shown), in common with spinal motor neurons (Yamada et al., 1991; Ericson et al.). The rostral-most group of motor neurons is generated in the mesencephalon (see Simon et al., 1994), thus Islet-1+ neurons found in the embryonic diencephalon and telencephalon are unlikely to give rise to motor neurons. Consistent with this, neither diencephalic nor telencephalic Islet-1+ neurons expressed SC1 (FIG. 9C and data not shown, see also Table 3).

Nkx 2.1 Expression Defines Ventral Forebrain Cells:

To identify a marker with which to distinguish cells in diencephalic and telencephalic regions from those found more caudally, applicants examined the pattern of expression of the homeodomain-containing protein Nkx 2.1. In mouse embryos, Nkx 2.1 mRNA is expressed at prospective diencephalic and telencephalic levels of the neural tube in a ventral domain that overlaps with that of vhh-1/shh, but the gene is not expressed at rhombencephalic or spinal cord levels (Lazzaro et al., 1991; Price et al., 1992; Rubenscein et al., 1994). In chick embryos examined at HH stages 14–18, antibodies directed against Nkx 2.1 labeled cells in a broad ventral domain of the mid and rostral diencephalon and telencephalon (FIGS. 9Aiii, D and data not shown) Nkx 2.1+ cells were not detected in the rhombencephalon or spinal cord (FIG. 9Aiii and data not shown). The onset of expression of Nkx 2.1 in the diencephalon occurred at HH stage 9 and in the telencephalon at HH stage 13/14 (data not shown). The expression of Nkx 2.1 in the ventral forebrain was transient, and by HH stages 19–20 the number of Nkx 2.1+ cells had decreased markedly (data not shown). Because of this, it was difficult to determine .accurately the extent of overlap between cells that expressed Nkx 2.1 and Islet-1. However, when examined at HH stage 18, about 10% of Nkx 2.1+ cells coexpressed Islet-1 (data not shown). Thus, the expression of Nkx 2.1 serves primarily as a marker of ventral forebrain cells but coexpression of Nkx 2.1 and Islet-1 can be used to distinguish Islet-1+ neurons generated in the diencephalon and telencephalon from those found at more caudal levels.

Lim-1 Expression Distinguishes Diencephalic and Telencephalic Cells:

To identify a marker with which to distinguish Islet-1 neurons in the diencephalon from those in the telencephalon, applicants examined the expression of the LIM homeodomain protein Lim-1 (Taira et al., 1992). In the embryonic mouse forebrain, Lim-1 mRNA is restricted almost exclusively to the diencephalon (Barnes et al., 1994, Fujii et al., 1994). In chick embryos examined from HH stages 14–18, antibodies directed against Lim-1 (Tsuchida et al., 1994) detected cells in the diencephalon in a pattern similar to that described for Lim-1 mRNA in mouse (see FIG. 9Aii). At these stages Lim-1+ cells were not detected in the telencephalon (FIG. 9A, and data not shown). Applicants next examined the relationship between Lim-1+ cells and Islet-1+ neurons in the diencephalon at HH stages 14–18. In the mid-diencephalon, but not at other levels of the diencephalon, Lim-1 was expressed by neuroepithelial cells (FIGS. 9Aii, F). At this axial level, Lim-1+ neurons were also present, moreover the majority of Islet-1+ neurons expressed Lim-1 (FIGS. 9E, F). In the rostral diencephalon, Lim-1 was expressed in the same population of ventral midline neurons that expressed Islet-1 (FIGS. 9G–I). In the intervening region of the diencephalon, Lim-1+ neurons were also present in a population distinct from, but intermingled with, Islet-1+ neurons (FIG. 9Aii) In the telencephalon, Islet-1+ neurons did not express Lim-1 (FIG. 9J). Thus, Lim-1 expression distinguishes diencephalic from telencephalic cells. Moreover, although Lim-1 is not a marker of all diencephalic Islet-1+ neurons, its coexpression with Islet-1 indicates the diencephalic origin of Islet-1+ forebrain neurons.

vhh-1/shh Induces Islet-1+ Neurons in ProsTective Forebrain Regions of the Neural Plate In order to isolate explants from regions of the neural plate that give rise to defined rostrocaudal domains of the neural tube, applicants constructed a coarse fate map of the neural plate of HH stage 6 chick embryos (see Experimental Procedures). This map was then used as a guide to isolate explants from lateral regions of the neural plate at three different levels of the neuraxis: i) a level ([T] in FIG. 10A) fated to give rise to the telencephalon; ii) a level ([D] in FIG. 10A) fated to give rise to the diencephalon, and iii) a level ([R] in FIG. 10A) fated to give rise to the rhombencephalon. Applicants then used the markers described above to examine whether vhh-1/shh can induce the differentiation of ventral neurons in explants derived from prospective forebrain levels of the neural plate as well as from more caudal levels.

Applicants examined first the expression of Islet-1 by cells in neural plate explants obtained from telencephalic, diencephalic and rhombencephalic levels grown in the absence of vhh-1/shh. Neural plate explants were grown for 60–66 hours in vitro, in the presence of COS cells transfected with antisense vhh-1 cDNA. Under these conditions, cells in explants derived from all three axial levels expressed the neuronal marker β-tubulin but Islet-1+ cells were not detected (FIGS. 10, B, C, F, G, J, K). In contrast, numerous Islet-1+ cells were induced in explants derived from each of the three axial levels of the neural plate when they were grown on COS cells transfected with sense vhh-1/shh cDNA (FIGS. 10D, E, H, I, L, M, Table 2). The proportion of Islet-1 neurons in induced explants derived from the three axial levels differed markedly. In telencephalic level explants, 96% of cells exposed to vhh-1/shh expressed Islet-1 (Table 2) whereas only 35% of cells in diencephalic level explants and 39% of cells in rhombencephalic level explants expressed Islet-1 (Table 2).

TABLE 2

Induction of Islet-1+ cells by vhh-1/shh in Neural Plate Explants

| Region of Neural Plate | Transfection construct | (%) Islet-1+ explants | (%) Islet-1+ neurons/ explant | (%) Islet-1+ neurons that express Lim-1 |
|---|---|---|---|---|
| Rhomben-cephalic: | Antisense vhh-1/shh | 0(49) | 0 | — |
| | Sense vhh-1/shh | 57(45) | 39(11) | 0(16) |
| Dien-cephalic: | Antisense vhh-1/shh | 0(28) | 0 | — |
| | Sense vhh-1/shh | 57(30) | 35(9) | 22(11) |

TABLE 2-continued

Induction of Islet-1+ cells by vhh-1/shh in Neural Plate Explants

| Region of Neural Plate | Transfection construct | (%) Islet-1+ explants | (%) Islet-1+ neurons/ explant | (%) Islet-1+ neurons that express Lim-1 |
|---|---|---|---|---|
| Telen-cephalic: | Antisense vhh-1/shh | 0(46) | 0 | 0 |
| | Sense vhh-1/shh | 78(42) | 96(7) | 0(15) |

Neural plate explants isolated from telencephalic, diencephalic and rhombencephalic levels of HH stage 6 chick embryos were cultivated for 60–66 hours in contact with COS cells transfected with a vhh-1 expression construct in sense or antisense orientation and the proportion of explants that express Islet-1 was determined by whole mount immunohistochemistry. The percentage of Islet-1+ and Lim-1+ cells in vhh-1/shh-induced explants was determined by sectioning explants and counting the number of labeled cells in individual sections. The total number of cells in explants was determined using DAPI nucleic staining. The number of explants analyzed is indicated in brackets.

Islet-1+ Neurons Induced by vhh-1/shh Have Distinct Axial Identities

To assess the rostrocaudal character of cells in neural plate explants derived from different axial levels and in particular to define the identity of induced Islet-1+ neurons, applicants examined the expression of SC1, Nkx 2.1 and Lim-1.

SC1 Expression:

Neural plate explants did not express SC1 when grown on COS cells transfected with antsense vhh-1/shh cDNA (Table 3). In rhombencephalic level explants that had been exposed to vhh-1/shh, Islet-1+ neurons expressed SC1 (FIGS. 11, A, B), indicating that these cells are motor neurons. However, Islet-1+ neurons accounted for only about 50% of the SC1+ cells induced by vhh-1/shh in rhombencephalic explants. The remaining, Islet-1−/SC1+ cells (FIGS. 11C, D) expressed the FP1 marker (data not shown) indicating that they are floor plate cells (Yamada et al., 1991). In diencephalic and telencephalic level explants, the Islet-1+ neurons induced by exposure to vhh-1/shh did not coexpress SC1 (FIGS. 11, E, F, J, I) providing evidence that they are not motor neurons. Floor plate cells, defined by expression of FPI, were no detected in diencephalic or telencephalic level explants exposed to vhh-1/shh (data not shown).

TABLE 3

Marker Expression in Explants Derived from Different Axial Levels of the Neural Plate

| Region of Neural Plate | Transfection Construct | Marker Expression | | | |
|---|---|---|---|---|---|
| | | Islet-1 | SC1 | Nkx2.1 | Lim-1 |
| Rhomben-cephalic: | Antisense vhh-1/shh | − | − | − | ++ |
| | Sense vhh-1/shh | ++ | ++ | − | + |
| Dien-cephalic: | Antisense vhh-1/shh | − | − | − | ++ |
| | Sense vhh-1/shh | ++ | − | + | ++ |
| Telen-cephalic: | Antisense vhh-1/shh | − | − | − | − |
| | Sense vhh-1/shh | +++ | − | + | − |

Analysis of neural plate explants grown for 60–66 hours in contact with COS cells transfected with either sense or antisense vhh-1 expression constructs. (−) sign indicates that fewer than 0.5%, (+) 5–35%, (++) 35–80%, (+++) >90% of cells expressed the marker, n.d. = not determined. Results were obtained from over 30 explants in each case.

Nkx 2.1 Expression:

Neural plate explants did not express Nkx 2.1 when grown on COS cells transfected with antisense vhh-1/shh cDNA (Table 3). Moreover, Nkx 2.1+ cells were not detected in rhombencephalic level explants exposed to vhh-1/shh (FIG. 12A) whereas induced diencephalic and telencephalic level explants contained Nkx 2.1+ cells (FIGS. 12B, C), and after 60–66 hours in vitro 5–10% of cells coexpressed Islet-1 (data not shown).

Lim-1 Expression:

Lim-1+ cells were detected in rhombencephalic (Table 3) and diencephalic (FIG. 12D) but not telencephalic (FIG. 12G) level explants grown on COS cells transfected with antisense vhh-1 cDNA. In diencephalic level explants exposed to vhh-1/shh, 22% of Islet-1+ neurons expressed Lim-1 (FIGS. 12, E, F, Table 2) and thus correspond phenotypically, to neurons characteristic of the diencephalon (FIG. 9Aii). In contrast, in both rhombencephalic and telencephalic level explants, the Islet-1+ neurons induced by vhh-1/shh did not express Lim-1 (FIGS. 12, H, I, Table 2).

Taken together, these in vitro experiments show that vhh-1/shh induces ventral neuronal cell types in prospective forebrain regions of the neural plate and that these neurons express marker combinations appropriate for distinct classes of ventral neurons that are generated ventrally in both the diencephalon and telencephalon.

Floor Plate and Midline Rostral Diencephalic Cells Mimic the Inductive Actions of vhh-1/shh The results described above leave open the possibility that the inducing activity of vhh-1/shh expressed in COS cells differs from the activities of neural cell groups implicated in the induction of ventral neurons in vivo. Applicants therefore determined whether the response of neural plate explants to vhh-1/shh was mimicked by potentially relevant neural sources of vhh-1/shh. Applicants assayed the activity of chick floor plate as a source of vhh-1/shh implicated in the induction of ventral cell types at spinal cord, rhombencephalic and mesencephalic levels (FIG. 8). Floor plate tissue induced Islet-1+ neurons in rhombencephalic level neural plate explants FIG. 13A) and these neurons coexpressed SC1 (data not shown. Nkx 2.1+ cells were not induced in rhombencephalic level explants by floor plant tissue (FIG. 13B). Thus, the inductive activity of floor plate was similar to that of vhh-1/shh expressed in COS cells.

Applicants also assayed the activity of cells at the ventral midline of the rostral diencephalon that express vhh-1/shh (FIG. 8) as a neural source of vhh-1/shh that might be involved in the patterning of the diencephalon (Hatta et al., 1994) and ventrol telensephalen (see Experimental Discussion). Since the midline of the rostral diencephalon itself expresses Islet-1+ neurons, midline diencephalic inducing tissue was derived from E11 mouse embryos and species-specific antibodies directed against the intermediate filament protein nestin (Dahlstrand et al., 1992) were used to define the murine inducing tissue. Midline rostral diencephalic tissue induced Islet-1+/SC1− neurons and Nkx 2.1+ cells in telencephalic level explants (FIG. 13C and data not shown). In contrast, ventral midline diencephalic tissue isolated at the level of the infundibulum, a region which does not express vhh-1/shh (FIGS. 8, 9Ai, Echelard et al., 1993), did not induce Islet-1+ cells in these explants (data not shown).

Finally, applicants tested whether the inductive activity of neural tissue sources of vhh-1/shh differed according to their rostrocaudal position. Conjugates were formed between floor plate tissue, a caudal source of vhh-1/shh, and telencephalic level neural plate explants. Floor plate tissue was effective in inducing Islet-1+/SC1− neurons (FIGS. 13D, E) and Nkx 2.1+ cells (FIG. 13F) in telencephalic level neural plate explants. Moreover, the Islet-1+ neurons did not express Lim-1 (data not shown) indicating that they have a characteristic telencephalic phenotype. Thus, the specific identities of ventral neurons that are induced by neural sources of vhh-1/shh appear to depend on rostrocaudal restrictions in the response properties of neural plate cells and not on the axial level of origin of the inducing tissue.

EXPERIMENTAL DISCUSSION

A vertebrate homolog of the Drosophila hedgehog gene, vhh-1/shh, is expressed by the notochord and floor plate and can mimic the ability of these two midline cell groups to induce motor neuron differentiation (Roelink et al., 1994). vhh-1/shh has, therefore, been implicated in the induction of ventral neuronal types at caudal levels of the neuraxis. The present studies and previous analyses show that vhh-1/shh is expressed by cells in the region of the diencephalon rostral to the floor plate and also in the ventral telencephalon (Echelard et al., 1993; Krauss et al., 1993; Chang et al., 1994; Roelink et al., 1994), raising the question of whether vhh-1/shh also participates in the induction of ventral neurons in the forebrain.

Applicants have found that vhh-1/shh induces the differentiation of ventral neuronal cell types characteristic of the diencephaion and telencephalon in regions of the neural plate that normally give rise to these two subdivisions of the forebrain. The LIM homeodomain protein Islet-1, an early marker of motor neuron differentiation at caudal levels of the neural tube, is also induced by vhh-1/shh early in the differentiation of these ventral diencephalic and telencephalic neurons. Islet-1$^+$ neurons, however, have distinct regional identities that appear to be constrained by the axial level of origin of cells within the neural plate. Thus, a single inducing molecule, vhh-1/shh, may participate in the differentiation and diversification of ventral neuronal cell types along the entire rostrocaudal extent of the neural tube acting on neural plate cells of predetermined rostrocaudal character.

One limitation of the present studies is that the eventual identity and function of the embryonic forebrain neurons induced by vhh-1/shh is not known. In the adult forebrain, Islet-1 is expressed by diencephalic neurons in the suprachiasmatic and arcuate nuclei of the hypothalamus, in the zona incerta, the septal and thalamic reticular nuclei and by basal telencephalic neurons (Thor et al., 1991). It is likely, therefore, that neurons in these ventral forebrain nuclei represent the mature derivatives of the Islet-1$^+$ neurons that are induced by vhh-1/shh at prospective forebrain levels of the neural plate.

vhh-1/shh as a Direct Inducer of Ventral Neurons

In neural plate explants obtained from spinal cord and rhombencephalic levels, vhh-1/shh induces motor neurons (FIGS. 10, 11; Roelink et al., 1994). Since floor plate cells are also induced under these conditions, this observation does not resolve whether motor neuron differentiation results from the activity of vhh-1/shh directly or from the actions of a distinct floor plate-derived inducing molecule. In diencephalic level explants, only approximately 35% of cells were induced to differentiate into Islet-1$^+$ neurons and it is possible that diencephalic cells with specialized midline signalling properties are also induced in these explants. Thus, at diencephalic as well as at more caudal levels, vhh-1/shh could induce the production of a distinct midline-derived factor that is responsible for the generation of ventral neurons. In contrast, in telencephalic level neural plate explants, vhh-1/shh caused virtually all cells to differentiate into Islet-1$^+$ neurons of telencephalic character. This result provides strong evidence that vhh-1/shh can induce ventral neurons by an action on neural plate cells that is independent of the induction of specialized midline cells.

Early Restriction in the Rostrocaudal Character of Neural Plate Cells

Embryological studies have provided evidence that the rostrocaudal and dorsoventral character of cells within the neural plate and neural tube is controlled by independent patterning systems (Doniach et al., 1992; Ruiz i Altaba, 1992; Jessell and Dodd, 1992; Smith, 1993). The early rostrocaudal character of neural cells appears to be established prior to the definition of cell identity along the dorsoventral axis of the neural tube (Roach, 1945; Jacobson, 1964; Simon et al., 1995). Applicants' in vitro results support this idea and in addition show that the rostrocaudal character of neural cells that has been defined at the neural plate stage is maintained in vitro, both in the absence and presence of ventralizing signals mediated by vhh-1/shh. Thus, an early and stable restriction in the potential of cells located at different rostrocaudal positions within the neural plate appears to define the repertoire of ventral neuronal cell types that can be generated upon exposure of cells to vhh-1/shh.

The signals that establish which the early rostrocaudal character of neural plate cells have not been identified. However, studies in several vertebrate species have provided evidence that the action of these signals subdivides the neural tube along its rostrocaudal axis, into discrete domains or segments (Vaage, 1969; Figdor and Stern, 1993; Lumsden and Keynes 1989). Many or all of these segmental domains coincide with the boundaries of expression of transcription factors (Rubenstein et al., 1994; Macdonald et al., 1994; Papalopulu, 1994). The intrinsic restriction in the potential fates of neural plates cells might, therefore, be established by the early and regionalized expression of transcription factors that later reveal segmental subdivisions of the neural tube.

Homeobox Gene Expression and a Common Program for the Generation of Ventral Neurons The detection of Islet-1 in ventral neuronal cell types generated at many different positions along the rostrocaudal extent of the neural tube suggests that the expression of this gene is more closely associated with the differentiation of neurons of ventral character than with the generation of any specific class of ventral neuron. However, at rhombencephalic and mesencephalic levels, the differentiation of serotonergic and dopaminergic neurons can be induced by the notochord and floor plate but these neurons do not express Islet-1 (Yamada et al. 1991; Hynes et al., 1995 and applicants' unpublished observations). Thus, although Islet-1 expression is a prominent marker of ventral neuronal differentiation, its expression is not always associated with the generation of ventral neuronal cell types that depend on notochord- and floor plate-derived signals.

Nevertheless, the expression of Islet-1 by many distinct classes of ventral neurons raises the possibility that elements of the response of neural plate cells to vhh-1/shh may be conserved along the rostrocaudal axis. In support of this, members of the Nkx 2 family of homeobox genes, notably Nkx 2.1 and Nkx 2.2 are expressed in the ventral neural tube at all rostrocaudal levels, in a domain that overlaps closely with that of vhh-1/shh (Price et al., 1992; Lazzaro et al., 1991; Rubenstein et al., 1994). Moreover, at forebrain levels the expression of Nkx 2.1 is induced by vhh-1/shh. Thus, the Nkx 2 and Islet-1 homeodomain proteins might represent elements of a common vhh-1/shh-response program that is activated in neural plate cells independent of their rostrocaudal position.

The Source of Signals that Induce Ventral Neurons In Vivo

Cells in the floor plate and at the ventral midline of the rostral diencephalon represent likely neural sources of signals involved in the induction of ventral neurons in vivo. However, the notochord and prechordal plate express vhh-1/shh (Riddle et al., 1993; Echelard et al., 1993; Krauss et al., 1993; Roelink et al., 1994), and could, therefore, also participate in the induction of ventral neuronal cell types. Indeed, in vitro studies of motor neuron differentiation at spinal cord levels have provided evidence that the signals responsible for induction of the earliest-born motor neurons derive from the notochord, with the floor plate acquiring a more prominent role in the differentiation of motor neurons only at larger stages (Yamada ez al., 1993).

At telencephalic levels, however, the induction of ventral neurons is unlikely to depend on signals from the axial mesoderm, since the region of the neural plate that gives rise to the floor of the telencephalon is never contacted by prechordal plate mesoderm (Couly and Le Douarin, 1987; Placzek, M., unpublished data). Moreover, Islet-1$^+$ neurons of the ventral forebrain are not specified until HH stage 14 (Muhr, unpublished data). It is possible that telencephalic Islet-1$^+$ neurons or their precursors migrate from the rostral diencephalon into the telencephalon. Alternatively, neural tissue might be a source of vhh-1/shh involved in the induction of the Islet-1$^+$ neurons in the ventral telencephalon. This neural source is unlikely to derive from the telencephalon itself, however, since vhh-1/shh is not expressed by cells at the floor of the telencephalon until HH stages 17–18, coincident with the appearance of telencephalic Islet-1$_+$ neurons.

Cells at the ventral midline of the rostral diencephalon could provide a source of signals that induce Islet-1$^+$ neurons in the ventral telencephalon since they express vhh-1/shh at HH stage 9. Consistent with this, in vitro studies show that midline rostral diencephalic cells that express vhh-1/shh can induce Islet-1$^+$ neurons in telencephalic regions of the neural plate. It remains possible that rostral diencephalic cells secrete other factors that cooperate with vhh-1/shh to define the number and diversity of ventral cell types generated at the floor of the telencephalon. This might account for the difference between in vitro results, in which vhh-1/shh induced virtually all cells in telencephalic neural plate explants to differentiate into Islet-1$^+$ neurons, and in vivo analyses showing a sparse scattering of Islet-1$^+$ neurons at the ventral midline of the telencephalon. Alternatively, expression of vhh-1/shh in COS cells could expose telencephalic neural plate explants to a higher level of inducer than is provided in vivo and in vitro by rostral diencephalic cells. Independent of the identity of the endogenous diencephalic inducers, these observations suggest that the differentiation of neurons in the ventral telencephalon is normally dependent on signals provided in a planar manner by midline cells of the rostral diencephalon.

Taken together, these studies implicate vhh-1/shh in the induction of ventral neuronal types along the entire rostrocaudal extent of the embryonic central nervous system. Several prominent classes of neurons that are depleted in neurodegenerative diseases derived from ventrally-located progenitors at different axial levels of the neural tube: motor neurons at spinal levels, dopaminergic neurons at mesencephalic levels and striatal and basal forebrain neurons at telencephalic levels. Since vhh-1/shh appears to direct the ventral neuronal fates of progenitor cells during embryogenesis, the protein might exert a similar activity on neuronal progenitors present in the adult (Reynolds and Weiss, 1992) and thus could repopulate the central nervous system with classes of ventral neurons depleted in neurodegenerative disease.

EXPERIMENTAL PROCEDURES

Animals

Fertilized white leghorn chicken eggs were obtained from Agrisera AB, Sweden. Chick embryos were staged according to Hamburger and Hamilton (1951). Time mated mouse embryos (C57/bl) were obtained from the animal facility, University of Umea.

Neural Plate Fate Mapping

Glass micropipettes with fine tip diameters were filled with Di-I (1,1'-dioctadecyl-3,3,3',3'-tetramethylindocarbocyanine perchlorate) (Molecular Probes; 2.5 mg ml$^{-1}$ in DMSO). 1–5 nl of Di-1 was injected into defined regions of the neural plate of HH stage 6 chick embryos using an automated microinjection system. Embryos were permitted to develop until HH stages 10/11 or stage 15 and the neural tube was then isolated. The position of Di-I labeled cells was mapped using phase contrast and epifluoresecnce optics and compared to the fate map of Couly and Le Douarin (1987) or assessed using morphological landmarks.

In Situ Hybridization and Immunohistochemistry

In situ hybridization analysis of mRNA expression of cryostat sections was performed using a 1.7 kb digoxigenin-labeled chick vhh-1/shh riboprobe (T. Lints and J. Dodd, unpublished data) essentially as described (Schaeren-Wiemers and Gerfin-Moser, 1993). Sections processed for in situ hybridization were washed for 4×10 minutes in Tris-buffered saline containing 0.1% Triton X-100 (TBST), blocked in TBST containing 10% normal goat serum and incubated with primary rabbit anti-Islet-1 antibodies (1:250) overnight at 22° C. Islet-1 was detected using an avidin/biotin-complex as described (Thor et al., 1991), except that the incubation times were doubled and the slides were mounted in a glycerol-based mounting media. Whole-mount in situ hybridization was performed as described (Francis et al., 1994).

Islet-1 was detected using rabbit and anti-Islet-1 antibodies (Thor et al., 1991; Ericson et al., 1992) or MAb 4D5 (Roelink et al., 1994). Lim-1 (Taira et al., 1992) was detected with MAb 4F2 which also recognizes Lim-2 (Tsuchida et al., 1994). In situ hybridization studies indicate that the patterns of expression of Lim-1 and Lim-2 mRNAs in embryonic forebrain are similar (data not shown). Thus, applicants cannot resolve whether Lim-1 and/or Lim-2 are expressed by individual cells labeled with MAb 4F2. This does not affect the use of the antibody to distinguish Islet-1$^+$ neurons at different forebrain levels. The SC1 glycoprotein was detected with MAb SC1 (Tanaka and Obata, 1984), the homeodomain protein Nkx-2.1 with rabbit and anti-Nkx-2.1 antibodies (Lazzare et al., 1991), the floor plate marker FP1 with MAb FP1 Yamada et al., 1991), anti-nestin with antisera 129/130 (Dahlstrand et al., 1992), anti-acetylated β tubulin was detected using the monoclonal antibody T6793 (Sigma immunochemicals) and neuronal cytoplasm using the anti-cyn-1 antibody (S. B. Morton and T. Jessell, unpublished) The number of Islet-1 and Lim-1 cells in explants was determined by sectioning explants and counting the number of labeled cells in every fifth section. The total number of cells in these sections was determined by nuclear labeling DAPI (Boehringer Mannheim). Other markers used were analyzed by whole-mount immunohistochemistry as described (Yamada et al., 1993).

Isolation and Culture of Neural Plate Explants

Eggs were incubated at 38° C. in a humidified incubator. HH stage 6 embryos were collected in L15 (GIBCO-BRL) medium at 4° C., incubated in dispase solution (Boehringer Mannheim, 2 mg/ml in L15) at 22° C. for 4 minutes and transferred into L15 at 4° C. containing 5% heat-inactivated fetal calf serum. Embryos were washed three times in L-15 and neural tissue was separated from adherent mesoderm and endoderm. Neural plate explants corresponding to presumptive telencephalic, diencephalic and rhombencephalic regions were dissected using tungsten needles. Floor plate from HH stage 25 chick embryos was isolated as previously described (Yamada et al., 1993). Midline rostral diencephalic tissue expressing vhh-1/shh (Echelard et al., 1993) was dissected from E11 mouse embryos. Neural plate explants were cultured for 60–66 hours in contact with COS cell aggregates, floor plate fragments or diencephalic tissue in three-dimensional collagen gels (Vitrogen 100, Celtrix Laboratories) in 600 μl of OPTIMEM-1 supplemented with N2-supplement, human fibronectin (5 μg/ml and penicillin/streptomycin (media and additives from GIBCO-BRL, Inc.).

Expression of rat vhh-1 in COS Cells

COS cells were grown until 90% confluency and transfected with 1 μg of DNA per 35 mm dish with 12 μg/ml lipofectamine reagent (GIBCO BRL) in Dulbecco's modified Eagle's medium (DMEM). After a 5 hour incubation, medium was replaced with DMEM containing 10% FCS and cells were incubated for additional 18 hours. COS cells were then dissociated using PBS containing 2 mM EDTA, pelleted and resuspended in DMEM containing 10% FCS and antibiotics. Cell aggregates were made by hanging a 20 μl drop containing about 1000 cells on the lid of a tissue culture plate as described (Roelink et al., 1994). After 24 hours, aggregates were washed in OPTIMEM-1 and placed contact with chick neural plate explants.

References of the Second Series of Experiments

Barnes, J. B., Crosby, J. L., Jones, C. M., Wright, C. V. E. and Hogan, B. L. (1994) Embryonic expression of Lim-1, the mouse homolog of Xenopus Xlim-1, suggests a role in lateral mesoderm differentiation and neurogenesis, *Dev. Biol.*, 161:168–178.

Basler, K., Edlund, T., Jessell, T. M., and Yamada, T. (1993) Control of cell pattern in the neural tube: regulation of cell differentiation by dorsalin-1, a novel TGFβ family member, *Cell*, 73:687–702.

Chang, D. T., Lopez, A., von Kessler, D. P., Chang, C., Simandl, B. K., Zhao, R., Seldin, M. F., Fallon, J. F., and Beachy, P. A., (1994) Products, genetic linkage and limb patterning activity of a murine hedgehog gene, *Development*, 120:3339–3353.

Couly, F. and Le Douarin, M. (1987) Mapping of the Early Primordium in Quail-Chick Chimeras, II. The Prosencephalic Neural Plate and Neural Folds: Implications for the Genesis of Cephalic Human Congenital Abnormalities. *Dev. Biol.*, 120:198–214.

Dahlstrand, J., Collins, V. P. and Lendahl, U. (1992) Expression of the class VI intermediate filament nestin in human central nervous system tumors, *Cancer Research*, 52:5334–5341.

Doniach, T., Phillips, C. R., and Gerhart, J. C., (1992) Planar induction of anteroposterior pattern in the developing central nervous system of Xenopus laevis, *Science*, 257:542–545.

Echelard, Y., Epstein, D. J., St-Jacques, B., Shen, L., Mohler, J., McMahon, J. A., and McMahon, A. P. (1993), Sonic hedgehog, a member of a family of putative signaling molecules, is implicated in the regulation of CNS polarity, *Cell*, 75:1417–1430.

Ericson, J., Thor, S., Edlund, T., Jessell, J. M., and Yamada, T. (1992) Early stages of motor neuron differentiation revealed by expression of homeobox gene Islet-1, *Science*, 256:1555–1560.

Figdor, M. C., and Stern, C. F., (1993) Segmental organization of embryonic diencephalon, *Nature*, 363:630–634.

Francis, P. H., Richardson, M. K., Brickell, P., and Tickle, C. (1994) Bone morphogenetic proteins and a signalling pathway that controls patterning in the developing chick limb, *Development*, 120:209–218.

Fujii, T., Pichel, J. G., Taira, M., Toyama, R., Dawid, I. B. and Westphal, H., (1994) Expression patterns of the murine LIM class homeobox gene lim1 in the developing brain and excretory system, *Developmental Dynamics*, 199:73–83.

Goulding, M., Lumsden, A., and Gruss, P. (1993) Signals from the notochord and floor plate regulate the region-specific expression of two pax genes in developing spinal cord, *Development*, 117:1001–1016.

Hamburger, H., and Hamilton, R. (1951) A series of normal stages in the development of the chick embryo, *J. Morphol.*, 88:49–92.

Hatta, K., Kimmel, C. B., Ho, R. K., and Walker, C. (1991) The cyclops mutation blocks specification of the floor plate of the zebrafish central nervous system, *Nature*, 350:339–341.

Hatta, K., Puschel, A. W., and Kimmel, C. B., (1994) Midline signaling in the primordium of the zebrafish anterior central nervous system, *Proc. Natl. Acad. Sci.*, 91:2061–2065.

Hynes, M., Poulsen, K., Tessier, Lavigne, M., Rosenthal, A., (1995) Control of neuronal diversity by the floor plate: contact-mediated induction of midbrain dopaminergic neurons, *Cell*, 80: In Press.

Inoue, A., Takahashi, M., Hatta, D., Hotta, Y. and Okamoto, H. (1994) Developmental regulation of Islet-1 mRNA expression during neuronal differentiation in embryonic zebrafish, *Dev. Dyn.*, 199:1–11.

Jacobson, C. O. (1964) Motor nuclei, cranial nerve roots, and fibre pattern in the medulla oblongata after reversal experiments on the neural plate of axolotl larvae. I. Bilateral operations, *Zool. Bidr. Uppsala*, 36:73–160.

Jessell, T. M., and Dodd, J. (1992) Floor plate-derived signals and the control of neural cell pattern in vertebrates, *Harvey Lect.*, 86:87–128.

Karlsson, O., Thor, S., Norberg, T., Ohlsson, H., and Edlund, T., (1990) Insulin gene enhancer binding protein Isl-1 is a member of a novel class of proteins containing both a homeo- and a Cys-His domain, *Nature*, 344:879–882.

Kingsbury, B. F., (1930), The development significance of the floor plate of the brain and spinal cord, *J. Comp. Neurol.*, 50:177–2077.

Korzh, V., Edlund, T. and Thor, S., (1993) Zebrafish primary neuron initiate expression of the LIM homeodomain protein Isl-1 at the end of gastrulation, *Development*, 188:417–425.

Krauss, S., Concordet, J. P., and Ingham, P. W. (1993), A functionally conserved homolog of the Drosophila segment polarity gene hedgehog is expressed in tissues with polarizing activity in zebrafish embryos, *Cell*, 75:1431–1444.

Lazzaro, D., Price, M., De Felice, M., and Di Lauro, R. (1991) The transcription factor TTF-1 is expressed at the onset of thyroid and lung morphogenesis and in restricted regions of the foetal brain, *Development*, 113:1093–1104.

Lee, J. J., von Kessler, D. P., Parks, S., and Beachv, P. A., (1992) Secretion and localized transcription suggest a role in positional signaling for products of the segmentation gene hedgehog, *Cell*, 71:33–50.

Lumsden, A. and Keynes, R., (1989), Segmental patterns of neuronal development in the chick hindbrain, *Nature*, 337:424–428.

Macdonald, R., Xu, Q., Barth, K. A., Mikkola, I., Holder, N., Fjose, A. Krauss, S. and Wilson, S. W. (1994), Regulatory gene expression boundaries demarcate sites of neuronal differentiation and reveal neuromeric organization of the zebrafish forebrain, *Neuron.*, 13:1039–1053.

Nusslein-Volhard, C., and Weischaus, E. (1980), Mutations affecting segment number and polarity in Drosophila, *Nature*, 287:795–801.

Papalopulu, N., (1994), Regionalization of the forebrain: from neural plate to neural tube, *Perspect. Dev. Neurobiol.*, In press.

Placzek, M., Tessier-Lavigne, M., Yamada, T., Jessell, T. M., and Dodd, J. (1990), Mesodermal control of the neural cell identity: floor plate induction by the notochord, *Science*, 250:985–988.

Placzek, M., Yamada, T., Tessier-Lavigne, M., Jessell, T. M., and Dodd, J., (1991), Control of dorso-ventral pattern in vertebrate neural development: Induction and polarizing properties of the floor plate, *Develonment*, 113(Suppl. 2):105–122.

Placzek, M., Jessell, T. M., and Dodd, J. (1993), Induction of floor plate differentiation by contact-dependent, homeogenetic signals, *Development*, 117:205–218.

Price, M., Lazzaro, D., Pohl, T., Mattei, M-G., Ruther, U., Olivo, J-C., Duboule, D., and DiLauro, R., (1992), Regional expression of the homeobox gene Nkx-2.2 in the developing mammalian forebrain, *Neuron.*, 8:241–255.

Puelles, L., Amat, J. A., and Martinez-de-la-Torre, M. (1987), Segment-related, mosaic neurogenetic pattern in the forebrain and mesencephalon of early chick embryos: I. Topography of AChE-positive neuroblasts up to stage HH18, *J. Comp. Neurol.*, 266:247–268.

Puelles, L. and Rubenstein, J. L. R., (1993) Expression patterns of homeobox and other putative regulatory genes in the embryonic mouse forebrain suggest a neuromeric organization, *TINS*, 16:472–479.

Reynolds, B. A., and Weiss, S. (1992), Generation of neurons and astrocytes from isolated cells of the adult mammalian central nervous system, *Science*, 255:1707–1710.

Riddle, R., Johnson, R. L., Laufer, E., and Tabin, C., (1993) Sonic hedgehog mediates the polarizing activity of the ZPA, *Cell*, 75:1401–1416.

Roach, F. C., (1945) Differentiation of the central nervous system after axial reversals of the medullary plate of amblystoma, *J. Exp. Zool.*, 99:53–77.

Roelink, H., Augsberger, A., Heemskerk, J., Korzh, V., Norlin, S., Ruiz i Altaba, A., Tanabe, Y., Placzek, M., Edlund, T., Jessell, T. M. and Dodd, J., (1994), Floor plate and motor neuron indication by vhh-1, a vertebrate homolog of hedgehog expressed by the notochord, *Cell*, 76:761–775.

Rubenstein, J., Martinez, S., Shimamura, K., and Puelles, L., (1994), The embryonic vertebrate forebrain: the prosomeric model, *Science*, 266:578–580.

Ruiz i Altaba, A. (1992), Planar and vertical signals in the induction and patterning of the Xenopus nervous system, *Development*, 115:67–80.

Schaeren-Wiemers, N., and Ferfin-Moser, A. (1993), A single protocol to detect transcripts of various types and expression levels in neural tissue and cultured cells: in situ hybridization using digoxigenin-labeled cRNA probes, *Histochemistry*, 100:431–440.

Simon, H., Guthrie, S., and Lumsden, A., (1994), Regulation of SC1/DM-GRASP during the migration of motor neurons in the chick embryo brain stem, *J. of Neurobiol.*, 25:1129–1143.

Simon, H., Guthrie, S., and Lumsden, A., (1995), Pattern formation in the hindbrain independent assignment of positional values on antero-posterior and dorso-ventral axes, *Current Biol. In Press.*

Smith, J. C., (1993) Dorso-ventral patterning in the neural tube, *Current Biology*, 3:582–585.

Taira, M., Jamrich, M., Good, P. J., and Dawid, I. B., (1992), The LIM domain-containing homeobox gene Xlim-1 is expressed specifically in the organizer region of Xenopus gastrula embryos, *Genes Dev.*, 6:356–366.

Tanaka, H. and Obata, K., (1984), Developmental changes in unique cell surface antigens of chick embryo spinal motor neurons and ganglion cells, *Dev. Biol.*, 106:26–37.

Thor, S., Ericson, J., Brannstrom, T., and Edlund, T., (1991), The homeodomain LIM proteins Isl-1 is expressed in subsets of neurons and endocrine cells in the adult rat, *Neuron.*, 7:881–889.

Tsuchida, T., Ensini, M., Morton, S.B., Baldassare, M., Edlund, T., Jessell, T. M., and Pfaff, S. L., (1994), Topographic organization of embryonic motor neurons defined by expression of LM homeobox genes, *Cell*, 79:957–970.

Vaage, S., (1969), The segmentation of the primitive neural tube in chick embryos (Gallus domesticus) : A morphological, histochemical and autoradiographical investigation, *Adv. Anat. Embryol. Cell Biol.*, 41:1–88.

van Straaten, H. M. W., Hekking, J. M. W., Wiertz-Hoessels, E. L., Thors, F., and Drukker, J., (1988), Effect of the notochord on the differentiation of a floor plate area in the neural tube of the chick embryo, *Anat. Embryol.*, 177:317–324.

Yamada, T., Placzek, M., Tanaka, H., Dodd, J., and Jessell, T. M., (1991), Control of cell pattern in the developing nervous system: polarizing activity of the floor plate and notochord, *Cell*, 64:635–647.

Yamada, T., Pfaff, S. L., Edlund, T., and Jessell, T. M., (1993), Control of cell pattern in the neural tube: motor neuron induction by diffusible factors from notochord and floor plate, *Cell*, 73:673–686.

THIRD SERIES OF EXPERIMENTS

During vertebrate development, the generation of cell types in the ventral half of the neural tube depends on signals provided by axial mesodermal cells of the notochord (1–6). The notochord appears to be the source of a contact-dependent signal that induces floor plate cells at the ventral midline of the neural tube and a diffusible signal that induces motor neurons independent of floor plate differentiation (2,7,8,9). Floor plate cells subsequently acquire both these Inducing activities (5,7,9). Sonic hedgehog (shh)/vhh-1, a vertebrate homolog of the secreted glycoprotein encoded by the Drosophila gene, hedgehog (10,11), is expressed by the notochord and floor plate at the time that these midline cell groups exhibit their inductive activities (12–16). Shh/vhh-1 can induce ectopic floor plate differentiation in the neural tube in vivo (13–15) and in neural plate explants in vitro (15) suggesting that it participates normally in floor plate induction. Whether the notochord- and floor plate-derived diffusible factor that induces motor neurons is also shh/vhh-1, however, remains unclear. Motor neurons are induced in neural plate explants grown in contact with cells that express shh/vhh-1 (15), but this could reflect the activity of a distinct factor secreted by the floor plate cells that are also induced in these explants. Applicants show here that: i) COS cells transfected with shh/vhh-1 acquire a diffusible activity that is sufficient to induce motor neurons in neural plate explants in the absence of floor plate differentiation, ii) that shh/vhh-1 itself can act on cells in neural plate explants to induce, independently, motor neurons and floor plate cells. These results. suggest that shh/vhh-1 provided by the notochord normally initiates the differentiation of motor neurons as well as floor plate cells in the neural tube of vertebrate embryos.

Floor plate and motor neuron differentiation was monitored in explants derived from the intermediate region of the neural plate of Hamburger Hamilton (HH) stage 10 chick embryos (8) using immunocytochemical and reverse transcription-polymerase chain reaction (RT-PCR) assays. Floor plate differentiation was assessed primarily by expression of the winged helix transcription factor HNF3β (Table 4). HNF3β is an early marker of floor plate differentiation in vivo (17,18) and its transcription in neural plate cells in vitro is a direct response to notochord-derived signals since it can occur in the absence of protein synthesis (17). Moreover, misexpression of HNF3in the neural tube is sufficient to trigger ectopic floor plate cells (19,20) which, in turn, can induce ventral neurons in adjacent dorsal regions of the neural tube (19). Thus, HNF3β expression provides an early and reliable indicator of floor plate differentiation. As an independent marker of floor plate differentiation, applicants monitored expression of mRNA encoding the chemoattractant, Netrin-1 (Table 4). Motor neuron differentiation was assessed by expression of the LIM homeodomain proteins Isl-1 and Isl-2 (21), by coexpression of SC1 with Isl-1 and Isl-2 and by expression of Isl-1, Isl-2 and choline acetyltransferase (ChAT) mRNAs (Table 4).

TABLE 4

Markers of Floor Plate and Motor Neuron Differentiation in Chick Neural Plate Tissue.

| Floor Plate Cells | Reference | Motor Neurons |
|---|---|---|
| HNF3β | (18, 19) | Isl-1/SC1 |
| (5, 8, 20, 34) | | |
| Netrin-1 | (32, 33) | Isl-2 (20) |
| | | ChAT (8) |

Neural plate explants (8) that were grown alone in vitro for 36 h did not express floor plate or motor neuron markers (FIGS. 14A, E, F, Table 5A). In contrast, neural plate explants grown in contact with notochord for 36 h expressed HNF3β mRNA and protein (FIGS. 14B, D, E) and Netrin-1 mRNA (FIG. 14E) indicating the differentiation of floor plate cells. The same explants contained cells that expressed Isl-1 and/or Isl-2 (termed Isl+cells) in combination with SC1 (FIGS. 14B, C, D, F), and Isl-1, Isl-2 and ChAT mRNAs (FIG. 14F) indicating the differentiation of motor neurons. To separate experimentally, the motor neuron- and floor plate-inducing activities of the notochord, applicants prevented contact between the notochord and neural plate explants by interposing a membrane filter. In the absence of contact, the notochord induced motor neuron differentiation (FIGS. 14G, H), albeit less effectively, as assessed by the number of Isl+ neurons (Table 5A).

TABLE 5

Induction of Floor Plate and Motor Neuron Markers in Neural Plate Explants.

| (Number of explants) | HNF3β⁺ cells/explant | Isl⁻ cells/ explant |
|---|---|---|
| A. Induction by notochord | | |
| neural plate | 0 | <1 |
| notochord + neural plate | 286 ± 40 | 215 ± 8 |
| notochord/filter/ neural plate | 0 | 38 ± 10 |
| B. Induction by shh/vhh-1 | | |
| antisense vhh-1 + neural plate | 0 | 0 |
| sense vhh-1 + neural plate | 100 ± 23 | 182 ± 28 |
| sense vhh-1/filter/ neural plate | 0 | 47 ± 8 |
| sense vhh-1/collagen/ neural plate | 0 | 49 ± 5 |

Neural plate explants were grown for 36 h with the notochord (A) or vhh-1-transfected COS cells (B) either in contact (indicated by+sign) or separated by membrane filters or by a strip of collagen gel (indicated by //) Values are mean±s.e.m.

In contrast, the notochord did not induce floor plate differentiation across a filter, as assessed by the absence of HNF3β expression at 24 h (data not shown) or 36 h (FIG. 14G, Table 5A). These results extend previous observations (7,8) in that they show that a notochord-derived diffusible factor can induce motor neurons in the absence of floor plate differentiation within the same neural plate explant.

To examine whether shh/vhh-1 can mimic the contact-dependent and diffusible activities of the notochord, applicants grew neural plate explants for 36 h either in contact with, or separated from, COS cells transfected with sense or antisense cDNA constructs encoding the rat shh homologue, vhh-1 (15). Neural plate explants grown in contact with COS cells transfected with sense vhh-1 contained both floor plate cells, assessed by expression of HNF3β (FIGS. 15A, G lane 1, Table 4) and Netrin-1 (FIG. 15G lane 1) and motor neurons, assessed by expression of Isl⁺/SC1⁺ neurons (FIGS. 15A, B, C), Isl-1 and ChAT (FIG. 15H lanes 1). Neural plate plants grown in the absence of contact with COS cells transfected with sense vhh-1 did not express (FIGS. 15D, G lane 3) or Netrin-1 (FIG. 15G lane 3). In contrast, motor neuron differentiation was induced in the absence of contact, as assessed by expression of Isl+/SCl+ neurons (FIGS. 15D, E, F, Table 5B), Isl-1 and ChAT (FIG. 15H lanes 1). Neural plate explants grown in the absence of contact with COS cells transfected with sense vhh-1 did not express HNF3β (FIGS. 15D, G lane 3) or Netrin-1 (FIG. 15G lane 3). Medium conditioned by vhh-1-transfected COS cells does not induce floor plate or motor neuron differentiation in neural plate explants (15). In the present experiments, the differentiation of motor neurons in neural plate explants grown at a distance from vhh-1-transfected COS cells may result from the provision of a higher concentration or of a constant source of shh/vvh-1. COS cells transfected with antisense vhh-1 did not induce floor plate or motor neuron differentiation under any condition (FIGS. 15G, H lanes 2 and 4 and data not shown). Expression of vhh-1, therefore, confers COS cells with a contact-dependent floor plate-inducing activity and a diffusible motor neuron inducing-activity that does not elicit floor plate differentiation. The most likely explanation of these results is that shh/vhh-1 itself mediates both these activities. A diffusible form of shh/vhh-1 has also been implicated in the introduction of Pax-1 expression in segmental plate mesoderm (22).

To examine whether shh/vhh-1 can itself induce motor neuron differentiation, applicants transfected vhh-1 expression constructs directly into cells within neural plate explants. Neural plate explants assayed 48 h after transfection with vhh-1 expressed HNF3β, Netrin-1, Isl-1 and Isl-2 (FIG. 16A). Shh/vhh-1 is, therefore, sufficient to induce floor plate and motor neuron differentiation in neural plate explants. To determine whether the induction of motor neurons in neural plate explants transfected with vhh-1 occurs independently of floor plate differentiation, applicants analyzed the time course of expression of HNF3β and Isl-1. Expression of Isl-1 in neural plate explants transfected with vhh-1 was first detected after ~22 h and either preceded (FIG. 16Bii) or occurred coincidentally (FIG. 16Bi) with that of HNF3β, depending on the particular experiment. Thus, motor neuron differentiation in neural plate explants transfected with vhh-1 occurs prior to or synchronously with floor plate differentiation. Shh/vhh-1, therefore, appears to act on neural plate cells to induce the differentiation of motor neurons in a manner that does not require the prior differentiation of floor plate cells (15) Previous studies in chick embryos have shown that cells in lateral regions of the neural plate are exposed to a motor neuron-inducing signal from the notochord prior to the differentiation of floor plate cells (8). The early expression of motor neuron markers in neural plate explants transfected with vhh-1 provides evidence that this signal is shh/vhh-1.

Taken together, applicants' results suggest that the ability of the notochord to induce floor plate differentiation in a contact-dependent manner and motor neuron differentiation via a diffusible factor can be attributed to independent activities of shh/vhh-1. They do not exclude that the induction of motor neurons by shh/vhh-1 involves the synthesis by neural plate cells of a distinct secreted factor, in a manner similar to the proposed involvement of dpp and wg as mediators of the long-range patterning activities of hedgehog in the imaginal disc epithelia of Drosphila (23–25). In the neural tube, however, vertebrate homologs of dpp (BMP proteins) and wg (wnt proteins) have dorsalizing actions (26, 27), and are, therefore, unlikely to act as mediators of the ventralizing actions of shh/vhh-1.

The mechanism by which shh/vhh-1 induces the differentiation of floor plate cells and motor neuron remains unclear. Drosophila and vertebrate hedgehog proteins undergo autoproteolysis to generate an amino-terminal fragment (N) which is associated with the cell surface and a carboxy-terminal (C) fragment which is freely diffusible (28). The induction of floor plate and motor neuron differentiation could, therefore, result from distinct biological activities that reside in the processed N and C fragments of shh/vhh-1 (FIG. 17A). Alternatively, floor plate and motor neuron fates could be specified by different concentrations of a single shh/vhh-1 fragment (FIG. 17B), in a manner similar to that proposed for TGFβ-related proteins in the patterning of mesodermal tissues in vertebrate embryos (29–31).

MATERIALS AND METHODS

Intermediate neural plate explants were dissected from the caudal region of the neural plate of Hamburger-Hamilton (36) (HH) stage 10 chick embryos as described (8) Notochord explants were dissected after dispase treatment from the caudal region of HH stage 10 chick embryos. Conjugates between notochord and neural plate explants were prepared in collagen gels. When required, notochord and neural plate explants were separated by Nucleopore polycarbonate (pore size 0.1 μm, COSTAR) or dialysis membrane (Spectrum, Spectra/Por membrane MW cut off: 50,000) filters. Explants were grown in defined medium as described (8).

Detection of Neural Markers: HNF3β was detected with rabbit antibodies(18,19), Isl-proteins were detected by antibodies that recognize both Islet-1 and Islet-2 (Isl$^+$ cells), or by Isl-1-specific or Isl-2-specific monoclonal antibodies (20,34) (Morton, S., unpublished data). The SC1 glycoprotein was detected with MAb SC1 (35). Neural plate explants were fixed with 4% paraformaldehyde at 4° C. ror 1–2 h and washed with phosphate-buffered saline (pH 7.4) at 4° C. for 1–2 h. Explants were incubated with primary antibodies overnight at 4° C., then with FITC-conjugated goat anti-mouse lgG (Boehringer Mannheim) or Texas red-conjugated goat anti-rabbit 1 g G (Molecular Probes) for 1–2 h at 22° C. The explants were then washed and mounted on slides in 50% glycerol: 50% 0.1 M carbonate buffer, pH 9.0 containing paraphenylene diamine (0.4 mg/ml). Explants were examined on a Zeiss Axiophot microscope equipped with epifluorescence optics. Optical sectioning of explants was performed on a Bio-Rad MRC-500 confocal microscope.

Competitive PCR analysis: RT-PCR analysis was performed essentially as described (8) Total RNA was extracted from 10–20 explants cultured in collagen gel with 5 ug of glycogen as carrier (37). An internal standard for competitive PCR analyses was prepared by deleting (in HNF3β, Isl-1) or inserting (in Isl-2, Netrin-1, ChAT) a 200–300 bp fragment within the sequence to be amplified. Plasmid DNAs were linearized and transcribed in vitro to prepare sense-oriented RNA. 100 fg of competitive template RNA was added to the total RNA of each sample and was reverse transcribed using MOMLV-RT (Gibco BRL). One tenth of each reaction product was subjected to PCR using specific primers flanking the deleted or inserted site of each clone. HNF3β: 5'-TCA CCA TGG CCA TCC AGC AGT CG SEQ ID NO:9 and 5' -CAG CAG GTG CTG CGC TGG AGA GG SEQ ID NO:10, Netrin-1: 5'-TGG GCA GCA CCG AGG AC SEQ ID NO:11 and 5'-CCT TCC ATC CCT CAA TA SEQ ID NO:12, Isl-1: 5'-TCA AAC CTA CTT TGG GGT CTT A SEQ ID NO:13 and 5'-ATC GCC GGG GAT GAG CTG GCG GCT SEQ ID NO:14 Isl-2: 5'-TGC TGA ACG AGA AGC AG SEQ ID NO:15 and 5'-TGG TAG GTC TGC ACC TCC A SEQ ID NO:16, ChAT: 5'-TCC ATA CGC CGA TTT GAT GAG GGC SEQ ID NO:17 and 5'-CTA TTG CTT GTC AAA TAG GTC TCA SEQ ID NO:18. Each PCR cycle was at 94° C. for 1 min., 54° C. for 1 min. and 72° C. for 1 min. Twenty two cycles were used for amplifying Isl-2, Isl-1, HNF3β and Netrin-1 and twenty cycles for ChAT. The PCR products were detected by Southern Blot hybridization with $^{32}$P-labeled DNA probes. Blots are aligned such that the tissue-derived band is above the internal standard. Sizes of tissue-derived PCR bands are: HNF3β: 510 bp, Netrin-1: 232 bp, Isl-1: 427 bp, Isl-2: 304 bp, ChAT: 283 bp.

COS cell transfections: Transfections with sense or antisense vhh-1 expression plasmids were performed as described (15). Briefly, 1 ug of DNA and 12 ug/ml or Lipofectamine (GIBCO BRL) in Dulbecco's modified Eagles medium (DMEM) supplemented with 1% glutamine was added to the 80–90% confluent COS cells in 35 mm dishes. After 5 h of incubation, the transfection reaction was stopped by replacing the medium with DMEM-supplemented with 10% calf serum. Induction assays were carried out after 36 h of incubation. For induction of floor plate cells and motor neurons by vhh-1-transfected COS cells, intermediate neural plate explants were placed on a monolayer of transfected COS cells, embedded in the collagen gel and cultured for 36 h in F12/N3 medium. To prepare transfilter assays, intermediate neural plate explants were separated from COS cells by a polymerized collagen gel, by Nucleopore Polycarbonate filter or by dialysis membrane. (See FIG. 14 legend.)

Neural Plate Transfections: CMV- or RSV-LTR-based vhh-1 expression plasmids were transfected directly into intermediate neural plate explants using LIpofectamine (GIBCO BRL). 400 ng of DNA and 2 ug of Lipofectamine were mixed in 100 $\mu$l of F12/N3 and added to neural plate explants. The explants were incubated for 5 h, rinsed and cultured in collagen gels as described (8). In experiments on vhh-1-transfected explants, 28 cycles of amplification were used on 1/100th of the tissue-derived cDNA product. The viability of neural plate explants subjected to the transfection protocol was impaired (data not shown). Applicants therefore supplemented the culture medium with neurotrophin 3 (NT3; 10 ng/ml: Genentech, Inc.) which has no floor plate or motor neuron-inducing activity (FIG. 14A and data not shown), but which enhances the number of motor neurons that differentiate in dissociated neural tube cultures (38).

References of the Third Series of Experiments 1. van Straaten, H. W. M. et al., Anat. Embryol. 177, 317–324 (1988).
2. Placzek, M. et al., Science 250, 985–988 (1990).
3. Bovolenta, P. and Dodd, J., Development 113, 625–639 (1991).
4. Hirano, S., Fuse, S. and Sohal, G. S., Science 251, 310–313 (1991).
5. Yamada, T. et al., Cell 64, 635–647 (1991).
6. Goulding, M., Lumsden, A. and Gruss, P. Development 117, 1001–1016 (1993).
7. Placzek, M., Jessell, T. M. and Dodd, J., Development 117, 205–218 (1993).
8. Yamada, T., Pfaff, S. L., Edlund, T. and Jessell, T. M., Cell 73, 673–686 (1993).
9. Hatta, K., Kimmell, C. B., Ho, R. K. and Walker, C., Nature 350, 339–341 (1991).
10. Nusslein-Vollhard, E. and Wieschaus, E. Nature 287, 795–801 (1980).
11. Lee, J. J., von Kessler, D. P., Parks, S. and Beachy, P. A. Cell 71, 33–50 (1992).
12. Riddle, R. D., Johnson, R. L., Laufer, E. and Tabin, C. Cell 75, 1401–1416 (1993).
13. Echelard, Y. et al., Cell 75, 1417–1430 (1993).
14. Krauss, S., Concordet, J.-P. and Ingham, P. W. Cell 75, 1431–1444 (1993).
15. Roelink, H. et al., Cell 76, 761–775 (1994).
16. Chang, D. T. et al., Development, 120, 3339–3353 (1994).
17. Ruiz i Altaba, A. et al., Submitted (1995).
18. Ruiz i Altaba, A., Prezioso, V. R., Darnell, J. E. and Jessell, T. M., Mech. of Development, 44, 91–108 (1993).
19. Sasaki, H. and Hogan, B. Cell 76, 103–115 (1994).
20. Ruiz i Altaba, A., Roelink, H. and Jessell, T. M. Submitted (1995).
21. Tsuchida, T. N. et al., Cel: 79, 957–970 (1994).
22. Fan, C. M. and Tessier-Lavigne, M. L., Cell 79, 1175–1186 (1994).
23. Capdevila, J., Estrada, M. P., Sanchez-Herrero, E. and Guerrero, I. EMBO J. 13, 71–82 (1994).
24. Basler, K. and Struhl, G., Nature 368, 208–214 (1994).
25. Tabata, T. and Kornberg, T., Cell 76, 89–102 (1994).
26. Basler, K., Edlund, T. Jessell, T. M. and Yamada, T., Cell 73, 687–702 (1993).
27. Dickinson, M., Krumlauf, R. and McMahon, A. P., Development 120, 1453–1471 (1994).
28. Lee, J. J. et al., Science 266, 1528–1537 (1994).
29. Ruiz i Altaba, a. and Melton, D. Nature 341, 33–38 (1989).
30. Green, J., New, H. V. and Smith, J. Cell 71, 731–739 (1992).
31. Gurdon, J. B., Harger, P., Mitchell, A. and Lemaire, P., Nature, 371, 487–492 (1994).
32. Serafini, T. E. et al., Cell 78, 409–424 (1994).
33. Kennedy, T. E., Serafini, T., de la Torre, J. R. and Tessier-Lavigne, M., Cell, 78, 425–435 (1994).
34. Ericson, J. et al., Science 256, 1555–1560 (1992).
35. Tanaka, H. and Obata, K., Dev. Biol. 106, 26–37 (1984).
36. Hamburger, V. and Hamilton, H., J. Morphol. 88, 49–92 (1951).
37. Chomczymski, P. and Sacchi, N., Analytical Biochem. 162, 156–159 (1987).
38. Averbuch-Heller, L. et al., Proc. Natl. Acad. Sci. USA 91, 3247–3251 (1994).

FOURTH SERIES OF EXPERIMENTS

Intercellular signaling molecules of the vertebrate hedgehog family and transcription factors of the winged-helix family have been implicated in floor plate development. Applicants have examined the consequences of misexpressing the vertebrate hedgehog gene vhh-1 (sonic hedgehog, shh) and the winged-helix gene HNF-3$\beta$ in the neural plate and neural tube of frog embryos. Misexpression of either of these genes induces floor plate differentiation at ectopic locations. However, ectopic floor plate induction in response to both vhh-1 and HNF-3$\beta$ was temporally and spatially restricted. At neural plate stages, ectopic floor plate differentiation was not detected. After neural tube closure, ectopic floor plate differentiation, was detected, but was restricted predominantly to the dorsal region of the neural tube. The ability of winged-helix and vertebrate hedgehog genes to induce floor plate differentiation in vibo may, therefore, be constrained by additional signals that specify the time and position of floor plate differentiation.

Introduction

Cells at the midline of the vertebrate embryo act as organizing centers, providing local signals that control the pattern of mesodermal and neural cell differentiation. Axial mesodermal cells of the notochord influence the pattern of cell types generated along the dorsoventral (D–V) axis of the neural tube. In chick embryos, notochord grafts can induce the differentiation of floor plate cells and motor neurons at ectopic locations in the neural tube (van Straaten et al., 1988; Placzek et al., 1990, 1993; Yamada et al, 1991, 1993). Inversely, removal of the notochord prevents the differentiation of floor plate cells and motor neurons (van Straaten and Hekking, 1991; Placzek et al., 1990; Yamada et al., 1991; Ericson et al., 1992; Goulding et al., 1993; but see Artinger and Bronner-Fraser, 1993). In mouse, mutations that eliminate the notochord also prevent floor plate and motor neuron differentiation (Bovolenta and Dodd, 1991; Ang and Rossant, 1994; Weinstein et al., 1994). Similarly, in frog embryos the differentiation of floor plate cells and motor neurons is inhibited if notochord formation is prevented (Clarke et al., 1991) or if the notochord develops at a distance from the neural ectoderm (Ruiz i Altaba, 1994). The organizer region and the floor plate can mimic the inductive actions of the notochord (Wagner et al., 1990; Yamada et al., 1991, 1993; Hatta et al., 1991; Placzek et al., 1993), raising the possibility that signalling molecules expressed by these three midline cell groups may be conserved (Ruiz i Altaba and Jessell, 1993). Intercellular signalling molecules and transcription factors that appear to participate in floor plate development have been identified. A vertebrate homolog of the Drosophila gene hedgehog, vhh-1/shh, encodes a putative secreted protein and is expressed by cells in the organizer region, the notochord and the floor plate at the time that these cell groups exhibit their inductive activities (Riddle et at., 1993; Krauss et al., 1993; Echelard et al., 1993; Roelink et al., 1994). The same three cell groups also express members of the winged-helix (HNF-3/fork head) family of DNA-binding transcription factors (Lai et al., 1990; 1991; Weigel and Jäckle, 1990; Clark et al., 1993): Pintallavis (also known as XFKH1 or XFD1/1'), HNF-3β (also known as axial) and HNF-3α (also known as XFKH2) (Ruiz i Altaba and Jessell, 1992; Dirksen and Jamrich, 1992; Knöchel et al., 1992; Ruiz i Altaba et al., 1993b; Bolce et al., 1993; Sasaki and Hogan, 1993; Ang et al., 1993; Monoghan et al., 1993; Strahle et al., 1993). In frog embryos, Pintallavis appears to be the functional homolog of mammalian HNF-3β at gastrula stages: Pintallavis is expressed transiently in the organizer, notochord and floor plate whereas HNF-3β does not appear until neurula stages.

Evidence for the involvement of vertebrate hedgehog and winged-helix genes in neural patterning has derived from an analysis of cell differentiation in the neural tube after misexpression of these genes. Misexpression of vhh-1/shh in mouse, frog or zebrafish embryos leads to the ectopic expression of floor plate markers in the neural tube in vivo (Echelard et al., 1993; Krauss et al., 1993; Roelink et al., 1994) and vhh-1 expression in COS cells induces floor plate and motor neuron differentiation in rat and chick neural plate explants in vitro (Roelink et al., 1994). Misexpression of Pintallavis in frog embryos also leads to the appearance of floor plate markers in dorsal regions of the neural tube and to a reduction in the number of dorsal sensory neurons (Ruiz i Altaba and Jessell, 1992; Ruiz i Altaba et al., 1993a). Similarly, transgenic mice that express HNF-3β throughout the midbrain express floor plate markers ectopically (Sasaki and Hogan, 1994). Moreover, mice in which the HNF-3β gene has been inactivated by targeted mutation display a perturbation in node development, lack a notochord and exhibit a loss of floor plate cells and motor neurons (Weinstein et al., 1994; Ang and Rossant, 1994). These results suggest that the vertebrate hedgehog gene vhh-1/shh and members of the winged-helix transcription factor family participate in the specification of midline fates and in the patterning of the neural tube by axial midline cell groups.

Clarification of the mechanisms by which vertebrate hedgehog and winged-helix genes normally act in midline neural plate and neural tube cells requires the determination of their sufficiency in eliciting floor plate differentiation. To address this issue applicants have analyzed, in parallel, the actions of vhh-1/shh and HNF-3β on neural cell patterning in frog embryos in vivo. Applicants show here that vhh-1 and HNF-3β can each activate expression of the other gene and that both genes can cause ectopic floor plate differentiation in the neural tube. However, applicants have found marked temporal and spatial constraints on the ability of vhh-1 and HNF-3β to induce ectopic floor plate cells. These findings suggest that the ability of vhh-1, Pintallavis and HNF-3β to promote floor plate differentiation in vivo is constrained by additional factors.

EXPERIMENTAL RESULTS isoiacion and Pattern of Expression of Frog vhh-1

To examine the effects of deregulated expression of the endogenous vhh-1 gene in frog embryos, applicants cloned several Xenopus laevis vhh-1 cDNAs (see Experimental Procedures) one of which contained a ~1.4 kb open reading frame, encoding a protein with ~70% identity vhh-1/shh genes identifies in other vertebrate species (Genbank accession number L35248).

The pattern of expression of vhh-1 in early frog embryos was analyzed by in situ hybridization and compared to that of the winged-helix genes Pintallavis and HNF-3β and to the homeobox gene goosecoid. Expression of vhh-1 mRNA in frog embryos was first detected at early gastrula stages (stage 10+) in cells within the medial region of the dorsal blastopore lip (FIG. 18A, stage 10 and not shown) and occurred after that of Pintallavis and goosecoid (FIGS. 18B, C; Cho et al., 1991; Dirksen and Jamrich, 1992; Ruiz i Altaba and Jessell, 1992). During gastrulation (stage 11–13), vhh-1 expression was detected in the prechordal plate and notochord with the exception of the posterior region near the blastopore (FIG. 18D). At these stages, expression of vhh-1 in the notochord was higher dorsally than ventrally (FIGS. 18F, G) in contrast to the uniform expression of Pintallavis, brachyury, Xlim-1 and Xnot mRNAs (FIG. 18I; Smith et al., 1991; Ruiz i Altaba and Jessell, 1992; Taira et al., 1992; von Dassow et al., 1993) At gastrula stages, Pintallavis was also expressed in the prechordal plate (FIGS. 18E). By the early neurula stage (stage 15), the level of vhh-1 in the notochord decreased markedly (FIGS. 18H, J) in, parallel with the decrease in Pintallavis expression (Ruiz i Altaba and Jessell, 1992). At early neural tube stages (~stages 20–26) there was little or no expression of vhh-1 in the notochord, but expression in the prechordal plate was maintained at high levels until tailbud stages (FIGS. 18K, L). At tadpole stages, vhh-1 was reexpressed transiently in the notochord (stage 36; FIGS. 18M, N), when low levels of HNF-3β are detected (FIG. 18O; Roelink et al., 1994 and not shown).

Neural expression of vhh-1 was first detected along the entire anteroposterior (A–P), later rostrocaudal, axis (FIG. 18J) in median deep (md) but not median superficial (ms) cells (Schroeder, 1970, ~stage 12–15, FIGS. 18G, H). The onset of vhh-1 expression occurred after that of Pintallavis (compare FIGS. 18F, G and I). From the early tailbud stage (stage ~24) onwards, however, vhh-1 was expressed in all floor plate cells at the ventral midline of the midbrain, hindbrain and spinal cord (stage ~36, FIGS. 18M, N). Expression of vhh-1 in the floor plate persisted at high levels up to stage 51, the latest stage examined (not shown). At tadpole stages, floor plate cells expressed both vhh-1 and HNF-3β (FIGS. 18M–P). However, unlike HNF-3β (FIG. 18P; see also Ruiz i Altaba et al., 1993b), vhh-1 was not expressed in ventricular zone cells immediately adjacent to the floor plate (FIG. 18N).

In the prospective forebrain, expression of vhh-1 was first detected at neurula stages (-stage 15) initially at the ventral midline of the diencephalon (FIG. 18J and not shown). At tailbud stages, vhh-1 was expressed throughout the ventral diencephalon (FIG. 18K) extending more dorsally in caudal regions (unlabeled arrow in FIG. 18L, M) paralleling that of HNF-3β (unlabeled arrow in FIG. 18O; Ruiz i Altaba et al., 1993b). By the late tailbud to tadpole stages (stages ~28–41) expression of vhh-1 in the mid-diencephalon was no longer detected at the ventral midline, and instead occupied a more dorsal position (FIGS. 10L, M and not shown). In the most rostral diencephalon, the ventral midline expression of vhh-1 was maintained (FIG. 18M) and a new site of expression of vhh-1 was detected in ventral telencephalic cells, beginning at stage ~41 (not shown).

vhh-1 was also expressed in the anterior and posterior endoderm, hypochord, olfactory placode, ventral cells posterior to the heart (FIGS. 18L, M and not shown) and in the posterior mesenchyme of the limb buds (not shown), consistent with the pattern of expression of vhh-1/shh in other species (Riddle et al., 1993; Echelard et al., 1993; Krauss et al., 1993; Roelink et al., 1994).

Lack of Neural Expression of vhh-1 in Exogastrulae

The expression of vhh-1 by the floor plate (FIGS. 18H, N) suggested that vhh-1 expression in midline cells depends on induction by the notochord. To examine this, complete exogastrula embryos, in which the notochord develops at a distance from the neural ectoderm, were assayed for vhh-1 expression. In complete exogastrulae (stages ~15 and ~36), vhh-1 was detected in the notochord and anterior endodermal cells, but not in neural ectoderm (FIG. 18Q and not shown). Vhh-1 expression by midline neural cells, therefore, appears to depend on signals from the axial mesoderm, consistent with the dependency of Pintallavis and HNF-3β expression in floor plate cells on signals from the notochord (Ruiz i Altaba and Jessell, 1992; Dirksen and Jamrich, 1992; Ruiz i Altaba et al., 1993a, 1993b).

Localized Plasmid Injections Target Gene Expression to Neural Cells

To examine the effects of vhh-1 and HNF-3β expression on neural cell patterning, applicants first attempted to establish an injection protocol that would consistently achieve ectopic gene expression in prospective neural cells. The vhh-1 and HNF-3β genes were inserted into plasmids under the control of a CMV promoter and injected into different regions of frog embryos at the one or two cell stage (Table 6).

TABLE 6

Localization of ectopic HNF-3β neural plate stages (stage approximately 15) after targeted injection of plasmids driving the expression of HNF-3β

| Injected Region | Ectoderm | Neural | Mesoderm | (Axial) | (Paraxial) | n |
|---|---|---|---|---|---|---|
| Equatorial | 83% | 45% | 90% | 13% | 66% | 24 |
| Animal | 80% | 33% | 20%[1] | 7% | 13% | 61 |
| Animal pole | 90% | 70% | 19%[2] | n.d. | n.d. | 36 |

Numbers represent percentage of the total number of embryos (n). Expression in ectoderm includes expression in neural tissue. Percentage of embryos showing expression in axial and paraxial mesoderm, but not in more ventral mesoderm, are shown. This value was not determined for injections into the animal pole under the cellular membrane (see text) since only single scattered cells were detected in mesoderm per embryo. Expression of HNF-3β from injected plasmids was driven by a CMV promoter (see Materials and Methods).
[1]Large patches of expression in all embryos examined.
[2]Only scattered single cells detected in mesoderm.
nd: not determined To direct ectopic expression of genes to the neural ectoderm, recombinant plasmids were injected into the extreme animal pole of one or two cell embryos, under the cellular membrane. At gastrula and neural plate stages, ectopic expression of vhh-1 and HNF-3β was mosaic and detected in large patches in both neural and non-neural ectoderm (FIGS. 19A, B, D, E; Tables 6, 7). Targeting of plasmids to the animal pole resulted in expression of the injected genes, predominantly in anterior regions of the embryo (FIG. 19C and not shown). As expected for plasmid injections, ectopic expression of vhh-1 and HNF-3β was highly mosaic (FIGS. 19C, F). Analysis of over 100 injected embryos showed that cells that expressed vhh-1 or HNF-3β could be found at tadpole stages at any position along the D–V axis of the neural tube (Table 8, FIG. 24 and not shown). Thus, injection under the cellular membrane of the animal pole is effective in achieving the expression of genes in the neural ectoderm of frog embryos. Moreover, although the expression of injected vhh-1 and HNF-3β is mosaic there is no consistent spatial restriction within the neural tube. In these experiments, applicants have assayed mRNA and not protein, and it remains to be established that all cells that express vhh-1 mRNA can express functional protein.

To determine the effects of misexpression of vhh-1 and HNF-3β on floor plate differentiation, applicants monitored the expression of four floor plate markers that exhibit distinct temporal patterns of expression. Pintallavis is expressed transiently at neural plate stages (FIG. 18; Ruiz i Altaba and Jessell, 1992; Dirksen and Jamrich, 1992) whereas, vhh-1 is expressed continually from neural plate stages (FIG. 18). F-spondin, a gene encoding a floor plate adhesion molecule (Klar et al., 1992), and HNF-3β are expressed only after neural tube closure (FIG. 18, Ruiz i Altaba et al., 1993a; Ruiz i Altaba et al., 1993b). Since HNF3: expression appears sufficient to confer floor plate properties to neural tube cells (Sasaki and Hogan, 1994) the combined use of HNF3β with other markers provides a strong case that the induced cells possess floor plate properties. With these markers applicants have examined the timing of ectopic floor plate differentiation and the position at which ectopic floor plate cells appear.

Temporal and Spatial Constraints on Floor Plate Induction by vhh-1 vhh-1 Does not Induce the Ectopic Expression of Floor Plate Markers at Neural Plate Stages After injection of a plasmid expressing frog or rat vhh-1, large patches of cells expressing vhh-1 were detected in the ectoderm at late blastula/early gastrula stages and in the neural plate at neurula stages (FIGS. 19A, B and not shown). At neural plate stages, however, ectopic expression of Pintallavis was not detected in the neural ectoderm (Table 7) even though at this time endogenous Pintallavis expression occurs in cells at the midline of the neural plate (Ruiz i Altaba and Jessell, 1992; FIGS. 18E, I). Similarly, injection of frog vhh-1 plasmids did not induce the expression of HNF-3β at neural plate stages (Table 7).

TABLE 7

Summary of the incidence of ectopic expression of floor plate markers in injected embryos

| Injected Plasmid | Pintallavis | vhh-1 | HNF-3β | F-spondin |
|---|---|---|---|---|
| Neural Plate | | | | |
| vhh-1 s | 0/108 | 12/14 | 0/42 | |
| vhh-1 a | 0/93 | n.d.[1] | n.d. | |
| R vhh-1 s | 0/53 | 5/21[3] | n.d. | |
| R vhh-1 a | 0/147 | 0/72 | n.d. | |
| HNF-3β | 0/85 | 0/59 | 32/36 | |
| HNF-3β^Δ | 0/43 | 0/62 | +[6] | |
| Neural Tube | | | | |
| vhh-1 s | | n.d. | 27/164[2] | n.d. |
| vhh-1 a | | n.d. | 0/108 | n.d. |
| R vhh-1 s | | 23/128[4] | 19/153[5] | 22/179[5] |
| R vhh-1 a | | 3/112 | 0/57[5] | 4/198[5] |

TABLE 7-continued

Summary of the incidence of ectopic expression
of floor plate markers in injected embryos

| Injected Plasmid | Pintallavis | vhh-1 | HNF-3β | F-spondin |
|---|---|---|---|---|
| HNF-3β | | 80/134 | 49/61 | 8/40 |
| HNF-3βΔ | | 5/122 | +[6] | 0/55 |

Fractions refer to the number of embryos showing ectopic expression as a function of the total number of embryos assayed. Injected embryos were assayed at neural plate (stages 14–16) or neural tube stages (stages 28–38). The markers assayed in each case are shown on top of each column. The injected genes, cloned in CMV plasmids, are shown at the left of each row. See text for other details.
s = sense construct,
a: antisense construct,
HNF-3βΔ = denotes a truncated HNF-3β gene (see Experimental Methods).
The few ectopic sites of vhh-1 and HNF-3β expression detected in embryos injected with CMV plasmids driving the expression of antisense vhh-1 or HNF-3βΔ are detected in dorsal regions. The majority of affected embryos displayed more than 1 site of ectopic floor plate marker expression.
[1]40/48 embryos expressed the injected antisense vhh-1 plasmid.
[2]27/164 embryos expressed ectopic HNF-3β in the neural tube. An additional 40/164 embryos expressed ectopic HNF-3β exclusively in the otic vesicle. Expression in cells located between the dorsal hindbrain and the otic vesicle was detected rarely (2/16 embryos). Within the neural tube there was only one ectopic site in the telencephalon.
[3]Only scattered single cells in the neural plate and adjacent ectoderm (see text).
[4]23/128 embryos expressed vhh-1 both in the ectoderm and neural tube. An additional 61/128 embryos expressed ectopic vhh-1 in non-neuronal ectoderm exclusively.
[5]Data from Roelink et al. (1994). Injected rat vhh-1 expression was detected in 11/11 embryos at neural plate stages and in 23/74 embryos at tadpole stages.
[6]HNF-3β protein is detected in the nucleus. HNF-3βΔ protein is detected both in the cytoplasm and nucleus.
nd: not determined.

Since vhh-1 is expressed by cells at the midline of the neural plate (FIGS. 18G, H), applicants tested whether vhh-1 could induce its own expression by injecting rat vhh-1 plasmids and assaying for the expression of frog vhh-1. In the vast majority of embryos no ectopic expression of vhh-1 was apparent, but in a few embryos, scattered cells that expressed vhh-1 were detected in the neural plate and in the adjacent ectoderm (FIG. 21A; Table 7).

These results provide evidence that floor plate genes are not induced ectopically at neural plate stages in response to widespread expression of vhh1.

Ectopic induction of Floor Plate Markers occurs at Neural Tube Stages in Response to vhh-1

Expression of floor plate markers was detected ectopically in injected embryos that developed to neural tube stages. Ectopic expression of HNF-3β was detected after injection of frog (FIG. 20; Table 7) or rat vhh-1 plasmids (Roelink et al., 1994; Table 7). Injection of plasmid constructs driving the expression of vhh-1 in the antisense orientation did not lead to the ectopic expression of HNF-3β (Table 7). Injection of rat vhh-1 also resulted in the ectopic expression of frog vhh-1 within the neural tube (FIG. 21, Table 7) and in the non-neural ectoderm (Table 7). Injection of an antisense rat vhh-1 plasmid resulted in only a very low incidence of ectopic expression of frog vhh-1 mRNA (Table 7). Previous studies have shown that widespread expression of rat vhh-1 also leads to the ectopic expression of F-spondin (Roelink et al., 1994).

The ectopic dorsal expression of vhh-1 and HNF-3β was observed in the spinal cord, hindbrain, midbrain and diencephalon but only rarely in the telencephalon (data not shown). The low incidence of ectopic floor plate marker expression in the telencephalon is striking since anterior regions of the embryo displayed a high incidence of expression of injected plasmids (FIGS. 19B, C).

Taken together, these results indicate that widespread expression of vhh-1 leads to the ectopic differentiation of floor plate cells within the neural tube.

Ectopic Floor Plate Differentiation Induced by vhh-1 is Restricted

Although both HNF-3β and vhh-1 are expressed ectopically in the neural tube of injected embryos there were marked spatial restrictions in the pattern of ectopic gene expression. Analysis by whole-mount showed that all affected embryos exhibited dorsal sites of ectopic gene expression (FIGS. 20, 21). In addition, HNF-3β and vhh-1 expression occasionally occupied the D–V extent of the neural tube (23% of vhh-1 sites, n=35 sites; see FIG. 21D and 10% of HNF-3β sites, n=40 sites; not shown). In a lower proportion of sites, ectopic floor plate marker expression appeared as an expansion of the normal ventral midline domain of expression of floor plate genes (9% of vhh-1 sites, not shown and 10% of HNF-3β sites; see FIG. 20B).

Figure 24:
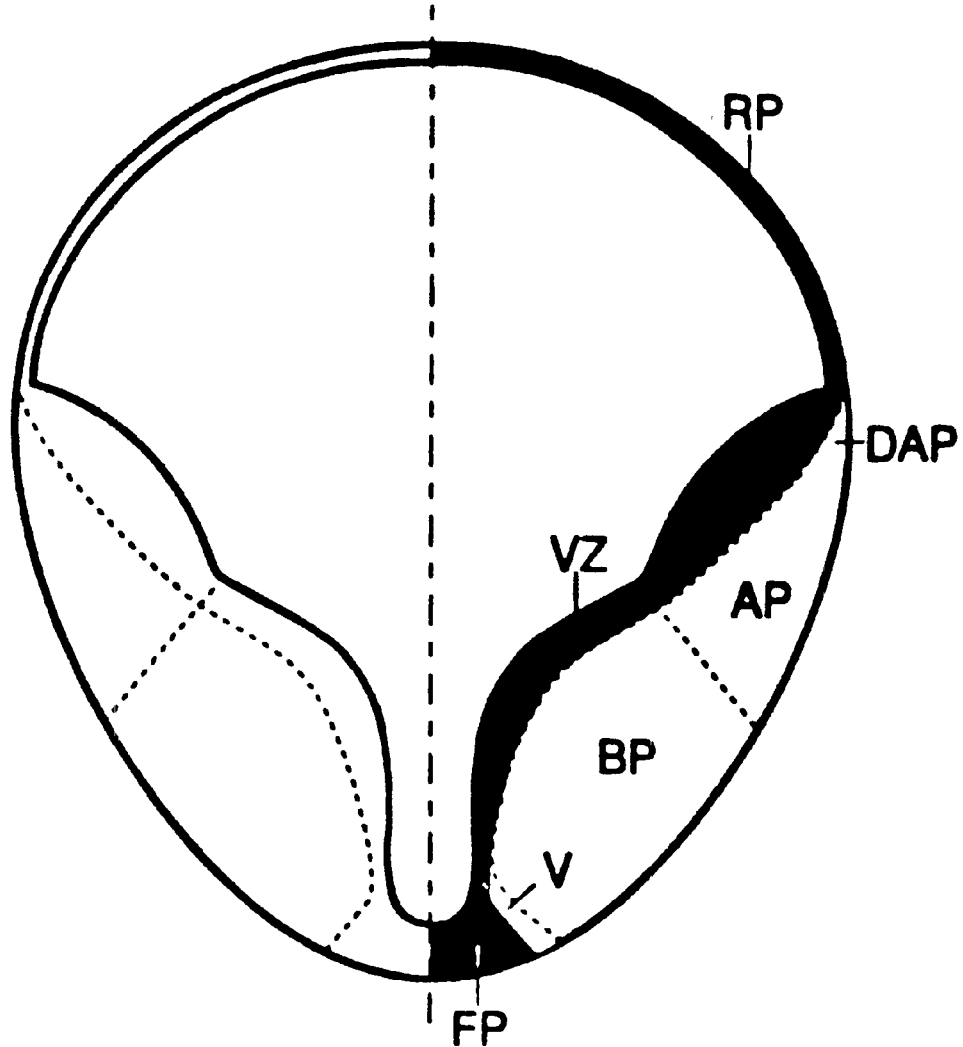

To determine more precisely the sites of ectopic floor plate marker expression, transverse sections of the neural tube of injected embryos were examined (Table 8 and FIG. 24). The majority of ectopic sites were found in and around the roof plate (FIGS. 20A–E; 20B–D, F) Cells in the most dorsal region of the alar plate immediately adjacent to the roof plate also expressed floor plate markers at a lower incidence (arrow in FIG. 20D). In more ventral regions of the neural tube, ectopic floor plate markers were often expressed along the ventricular zone (Table 8 and FIG. 24). Ectopic floor plate marker expression was not detected in lateral regions of the alar of basal plates (FIGS. 20D–F, 21D, F; Table 8 and FIG. 24). Embryos in which ectopic expression of vhh-1 or HNF-3β were detected often exhibited changes in neural tube morphology, most frequently a branched neural tube (FIGS. 20E, 21E, 21F).

TABLE 8

Localization of ectopic sites of floor plate
marker expression within the neural tube of injected
embryos

| Injected Plasmid | Marker | RP | DAP | AP/BP | VZ | V | FP | n |
|---|---|---|---|---|---|---|---|---|
| Rvhh-1 | vhh-1 | 71 | 18 | 0 | 29 | 6 | + | 17 |
| vhh-1 | HNF-3β | 74 | 26 | 0 | 9 | 11 | + | 35 |
| HNF-3β | vhh-1 | 81 | 0 | 0 | 23 | 4 | + | 26 |
| HNF-3β | HNF-3β | 47 | 3 | 87 | 0 | 0 | + | 30 |
| Percentage | of Cells | 7 | 8 | 57 | 22 | 4 | 2 | 171 |

Numbers refer to percentage of cases in each zone (see FIG. 24) as a function of the total number of cases (n). Some sites of expression spanned two or more zones. Each row shows the results of expression of the specified marker (top right columns), vhh-1 mRNA or HNF-3β protein, after injection of CMV plasmids driving the expression of rat vhh-1 (Rvhh-1), frog vhh-1 or frog HNF-3β (left of each row). The localization of ectopic F-spondin sites is not shown since only a small number of sites were analyzed. Number of cells (bottom row) represent the average percentage of cells located within each zone unilaterally. Average were determined counting the numbers of DAPI stained nuclei in one half of 3 different sections. Numbers were obtained by inspection of transverse sections.

Temporal and Spatial Constraints on Floor Plate Induction by HNF-3β

The temporal and spatial restrictions in floor plate induction observed after widespread expression of vhh-1 described above, could in principle occur upstream of, or in parallel with the induction of Pintallavis and HNF-3β expression. If such restrictions occur upstream of Pintallavis or HNF-3β activation, they might not be evident in response to widespread expression of HNF-3β. Applicants therefore assessed possible restrictions in floor plate induction by HNF-3β.

HNF-3β does not Induce the Ectopic Expression of Floor Plate Markers at Neural Plate Stages Ectopic expression of Pintallavis or vhh-1 was not detected in the neural plate of embryos injected with HNF-3β plasmids (Table 7). The temporal restriction in floor plate marker expression observed in response to vhh-1 are, therefore, also evident after widespread expression of HNF-3β.

Ectopic Induction of Floor Plate Markers Occurs at Neural Tube Stages in Response to HNF-3β

Ectopic expression of vhh-1 and F-spondin was detected in the neural tube in a high proportion of embryos that expressed injected HNF-3β (FIGS. 22A, B, D, F; Table 7). Injection of plasmids driving the expression of a truncated HNF-3β gene (see Experimental Methods) did not result in ectopic expression of vhh-1 or F-spondin (Table 7). These results are consistent with previous studies showing that widespread expression of Pintallavis induces the ectopic expression of F-spondin at tadpole stages (Ruiz i Altaba et al., 1993a). Widespread expression of HNF-3β was able to induce ectopic floor place marker expression along the A–P axis of the neural tube (FIG. 22A). In the telencephalon however, only a single ectopic site was found. Thus, HNF-3β can induce the ectopic expression of vhh-1 and other floor plate markers within the neural tube.

Ectopic Floor Plate Differentiation Induced by HNF-3β is Spatially Restricted

The ectopic expression of both vhh-1 or F-spondin detected after widespread expression of HNF-3β showed marked restrictions within the neural tube. Wholemount analysis showed that widespread expression of HNF-3β resulted in the preferential localization of ectopic floor plate markers to the dorsal neural tube (FIG. 22; Table 8 and FIG. 24) with all affected embryos showing dorsal ectopic expression sites. In addition, at 23% of sites, vhh-1 expression spanned the D-V extent of the neural tube and at 8% of sites vhh-1 was expressed in an expanded ventral region (n=60 sites; not shown; see also Ruiz i Altaba et al., 1993a).

Examination of transverse sections revealed that most of the ectopic vhh-1 sites were found dorsally (Table 8 and FIG. 24). In more ventral regions of the neural tube, ectopic vhh-1 expression was restricted either to the ventricular zone, often unilaterally, or to cells immediately adjacent to the floor plate, usually in the ventricular zone (Table 8 and FIG. 24). Ectopic vhh-1 or F-spondin expression was not detected in lateral regions of the alar or basal plates (FIG. 22D, F; Table 8 and FIG. 24 and not shown). Neural tube malformations were often accompanied by ectopic vhh-1 expression (not shown).

These results demonstrate that HNF-3β can activate the transcription of vhh-1 and other floor plate markers in neural tube cells and that the spatial restrictions in floor plate marker expression detected in response to vhh-1 are also evident after widespread expression of HNF-3β.

EXPERIMENTAL DISCUSSION

Reciprocal Activation of vhh-1 and Winged-Helix Genes and the Homeogenetic Nature of Floor Plate Induction The differentiation of floor plate cells at the midline of the neural plate is induced by signals from the notochord (van Straaten et al., 1988; Placzek et al., 1990, 1993; Hatta, 1991; Yamada et al., 1991; Ruiz i Altaba, 1992; Jessell and Dodd, 1992). Once induced, floor plate cells acquire the ability to induce the differentiation of additional floor plate cells (Placzek et al., 1990; 1993; Yamada et al., 1991; Hatta et al., 1991). Thus, induction of floor plate differentiation is a homeogenetic process in which cells of the notochord confer similar signalling properties to midline neural plate cells. The present studies on vhh-1 and HNF-3β, taken together with previous findings (Ruiz i Altaba et al., 1993a; Sasaki and Hogan, 1994; Krauss et al., 1993; Echelard et al., 1993; Roelink et al., 1994) suggest a molecular pathway for floor plate induction and mechanisms that could underly the propagation and eventual restriction of this inductive process (FIG. 23).

Pintallavis is expressed in the organizer region and the notochord prior to the onset of vhh-1 expression. In frog embryos Pintallavis appears to assume the early functions ascribed to HNF-3β in the mouse (Ruiz i Altaba et al., 993b) and thus may be required for the expression of vhh-1 in the notochord. It remains unclear, however, whether vhh-1 represents a direct target of winged-helix transcription factors. vhh-1 expression in the notochord precedes that of floor plate markers in cells at the midline of the neural plate (FIG. 18; Ruiz i Altaba and Jessell, 1992) and vhh-1 can induce ectopic expression of floor plate markers (FIGS. 20, 21; Echelard et al., 1993; Krauss et al., 1993; Roelink et al., 1994). Thus, it is likely vhh-1/shh secreted by the notochord particpates normally in the induction of floor plate differentiation.

Three lines of evidence indicate that the induction of Pintallavis and HNF-3β in midline neural cells is required for floor plate differentiation. First, the expression of Pintallavis in frog and HNF-3β in chicks appear to be direct responses of neural plate cells to notochord-derived inductive signals (Ruiz i Altaba et al., 1993a; 1995). Second, both Pintallavis and HNF-3β can induce the ectopic expression of floor plate markers in the neural tube (FIG. 22; Ruiz i Altaba et al., 1993a, Sasaki and Hogan, 1994) including vhh-1/shh (FIG. 22. Third, separating the notochord from the ectoderm leads to the lack of expression of Pintallavis and HNF-3β and other floor plate markers in the neural ectoderm (FIG. 1Q; Ruiz i Altaba, 1994). The floor plate attains autonomy from the notochord around the time of neural tube closure (Yamada et al., 1991; Placzek et al., 1991). Such autonomy may be established by the autoregulation of HNF-3β which has been shown to occur in vitro (Pani et al., 1992) and in the neural tube in vivo (FIGS. 19F, 22C; Sasaki and Hogan, 1994).

Taken together, these experimental observations are consistent with a model in which the sequential expression of winged-helix transcription factors and vertebrate hedgehog genes by the notochord underlies the initial phase of floor plate induction. The sequential expression of these genes in the floor plate may also participate in the homeogenetic induction of additional floor plate cells. In vivo, however, this signalling cascade is not propagated indefinitely throughout the neural plate and neural tube. The extent of floor plate differentiation may be limited in part by the range of action of secreted vhh-1 and, as discussed below, by restrictions in the ability of neural cells to respond to by vhh-1 and winged-helix factors.

Constraints on Ectopic Floor Plate Induction

The main finding of the present work is that there are marked temporal and spatial constraints on the ability of vhh-1 and winged-helix transcription factors to induce floor plate differentiation.

During normal development, floor plate markers are first expressed by cells at the midline of the neural plate (FIGS.

18, 23). In contrast, misexpression of vhh-1 or HNF-3β fails to induce ectopic expression of floor plate markers in neural plate cells (FIG. 24). It is unlikely that lateral neural plate cells express vhh-1 or HNF-3β and then die since these cells can express the same genes driven by a plasmid vector (Table 8, FIG. 24 and not shown). One possible explanation for the observed restrictions in floor plate differentiation is that the notochord provided two signals, a vertebrate hedgehog protein and a distinct factor, with the combined action of both signals being required to trigger floor plate differentiation at neural plate stages. A second possibility is that the inability of lateral neural plate cells to respond to vhh-1 and HNF-3β is imposed by signals derived from non-neural tissues, in particular, from paraxial mesoderm that underlies the lateral region of the neural ectoderm. The only neural plate cells capable of responding to vhh-1 and HNF-3β would, therefore, be those at the midline which are removed from a local inhibitory influence of paraxial mesoderm by virtue of their apposition with the notochord. In either case, these temporal restrictions in floor plate differentiation are observed when the extopic expression of HNF-3β is induced by vhh-1 and when the expression vhh-1 is induced by HNF-3β. Thus, these restriction appear to act both upstream and downstream of HNF-3β.

After neural tube closure, neural cells can respond to widespread expression of vhh-1 and HNF-3β with ectopic floor plate differentiation. Ectopic floor plate cells are, however, confined primarily to the dorsal neural tube and to cells in the ventricular zone (FIG. 24). The constraints that operate at neural plate stages might, therefore, be maintained after neural tube closure with the exception of cells in the most dorsal region of the neural tube stages and in the ventricular zone. An additional constraint that could contribute to the spatial restrictions on ectopic floor plate differentiation at neural tube stages is neuronal differentiation. The exclusion of floor plate gene expression from neurons might confine ectopic floor plate differentiation primarily to ventricular zone cells and to the non-neural cells of the roof plate.

The absence of ectopic floor plate differentiation in intermediate regions of the neural tube of frog embryos contrasts with the ability of a secondary notochord to induce a floor plate in this region of the chick and frog neural tube (Yamada et al., 1991; ARA and TMJ, unpublished) and with the ability of vhh-1 expressed in COS cells to induce floor plate differentiation in rat lateral neural plate explants in vitro (Roelink et al., 1994). These differences could be explained by the action in vivo of a repressive signal that derives from paraxial mesoderm. Notochord grafts physically separate the neural plate from the somites, removing neural plate cells from the local influence of such a signal. Similarly, isolation of neural plate explants in vitro removes neural cells from signals derived from surrounding tissues and thus may permit floor plate differentiation in response to vhh-1.

Contribution of Spatial Restrictions to Normal Floor Plate Differentiation

Floor plate cells differentiate in a restricted domain at the ventral midline of the neural tube (FIG. 23). The initial induction of floor plate differentiation by the notochord appear to be mediated by a contact-dependent signal (Placzek et al, 1993). Thus, the spatial restriction in floor plate differentiation could depend on the limited extent of contact between the notochord and neural plate cells. However, induced floor plate cells acquire the capacity to induce new floor plate cells through homeogenetic induction (Hatta et al., 1991; Yamada et al., 1991; Placzek et al., 1993). Restriction on the spread of floor plate differentiation, therefore, appear to operate during normal development.

In vivo an in vitro studies have shown that neural cells have a limited period of competence to respond to floor plate inducing signals (van Straaten et al., 1988; Yamada et al., 1991; Placzek et al., 1993). Thus, the spread of floor plate induction may be limited, in part, by the loss of competence of neural cells to respond to inductive signals. Applicants' in vivo studies show, however, that the widespread expression of vhh-1 or HNF-3β cannot drive the ectopic expression of floor plate markers in the neural plate. In vivo, therefore, there be constraints on the propagation of floor plate differentiation that act prior to and independent of the loss of competence of neural cells (FIG. 23).

vhh-1, Winged-Helix Genes and Forebrain Patterning

In the neural tube, the expression vhh-1 includes floor plate cells and midline cells of the forebrain. One possible source of. inductive signals responsible for vhh-1 expression in the rostral forebrain is the prechordal plate, which has been implicated in the progression of forebrain differentiation (Dixon and Kintner, 1989; Ruiz i Altaba, 1992). Both Pintallavis and vhh-1 are expressed in the prechordal plate. Thus, expression of vhh-1 in the prechordal plate mesoderm might be regulated by winged-helix transcription factors in a manner similar to that occuring in the notochord. In view of the participation of notochord-derived vhh-1 in the induction of floor plate properties at posterior levels of the neuraxis, it is also possible that vhh-1 secreted by the prechordal plate is involved in the induction of vhh-1 in midline cells of the rostral forebrain. However, neither Pintallavis, HNF-3β nor HNF-3α are expressed in the rostral forebrain at the time when vhh-1 mRNA first appears. Thus, vhh-1 expression this region is likely to be regulated by a pathway distinct from that operating to induce vhh-1 expression in floor plate cells.

EXPERIMENTAL METHODS

Frogs, Embryos and Microinjection

Xenopus laevis female frogs were induced to lay eggs by injection of 1000 u. of human chorionic gonadotropin. Eggs were fertilized with testis homogenates and reared under standard conditions (Ruiz i Altaba, 1993). Staging of embryos was according Go Nieuwkoop and Faber (1967).

Fertilized eggs were dejellied in 306 cysteine pH 7.6 before first cleavage and transferred to injection solution (3% ficoll, 1×MMR). Injection was performed as described (Ruiz i Altaba, 1993) before or after first cleavage. In the majority of cases injection was targeted to the animal pole (see text) Because the formation of the first cleavage furrow begins in this area, embryos frequently received an injection into a single blastomere which resulted in the unilateral distribution of injected materials. Injected embryos were cultured in injection solution for about 1 hour and then transferred gradually to 0.1×MMR.

100–200 pg of supercoiled plasmid DNA in water was injected into frog embryos and was not detrimental for embryonic development. Large amounts of plasmid DNA were toxic.

Library Screens and Clones

To isolate a frog vhh-1 cDNA, $10^6$ recombinant phages of a Xenopus laevis stage 17 whole embryo library (Kintner and Melton, 1987) were screened with the full-length rat vhh-1 cDNA (Roelink et al., 1994) at moderate stringency in HM: 10% dextran sulphate, 3×SSC, 3×SSPE, 5×Denhardt's, 0.5% SDS and 100 μg/ml denatured herring sperm DNA at 60° C. Nitrocellulose filters were washed in 1×SSC, 0.1% SDS for 2–4 h. Of 50 positive plaques 10 were analysed further. Applicants isolated the two copies of the vhh-1 gene in the Xenopus tetraploid genome and other members of the hh gene family.

Lambda clone #4 was digested with EcoRI and the ~2.4 Kb insert subcloned into pBluescript SK yielding pfhh #4. The nucleotide sequence of this insert was determined on both strands by the chain termination method using dsDNA as template and Sequenase (USB). Sequence analysis was performed with a VAX computer.

For injection, the EcoRI vhh-1 cDNA insert of pfhh #4 was cloned into pcDNAI-Amp (Invitrogen) which contains a cytomegalovirus (CMV) promoter 5' to the polylinker and SV40 polyandenylation sequences 3' to the polylinker. Two clones were made with vhh-1 in the sense and antisense orientations and named pCMV-vhh-1 S and pCMV-vhh-1 A. Similarly, the EcoRI-Not I HNF-3β cDNA fragment of Xβ1 (Ruiz i Altaba et al., 1993b) was cloned into pcDNA1-Amp yielding pCMV-Xβ. As control, pCMV-Xβ was cut at the single BglII site, filled-in and religated yielding pCMV-XβΔ. This mutation changes the reading frame downstream of the BglII site adding 30 amino acids before terminating prematurely. The XβΔ protein product lacks most of the DNA-binding domain conserving only helix 1 and two amino acids of helix 2 (see Clark et al., 1993 and Ruiz i Altaba et al., 1993b). The XβΔ protein is predicted to lack DNA-binding activity.

In Situ Hybridization

Frog embryos were processed for whole-mount in situ hybridization as described by Harland (1991). The vitelline membrane of young embryos was removed manually and holes were made into the blastocoel and archenteron to prevent background labelling. Embryos were fixed in MEMFA (3.7% formaldehyde, 1 mMEGTA, 2 mM $MgCl_2$, 0.1M MOPS; Patel et al., 1989) for 2 h, dehydrated and stored in 100% methanol at −20° C. Embryos were not prehybridized and the RNA probes were not hydrolized. Detection of pecific hybridization was performed with an anti-digoxygenin antibody coupled to alkaline phosphatase and reacted with nitro blue t-etrazolium and 5-bromo-4-chloro-3-indolyl-phosphate.

Single-stranded digoxygenin-labelled antisense and sense RNA probes were generated by in vitro transcription of the appropriate plasmid clones in the presence of digoxygenin-UTP and a trace of $^{32}P$-UTP to measure incorporation. An antisense frog vhh-1 RNA probe spanning the entire cDNA clone was generated by transcribing NotI cut pfhh#4 with T3 RNA polymerase. An identical pattern of vhh-1 expression was observed with an antisense probe spanning only the 3' untraslated region. A sense frog vhh-1 RNA probe was generated by transcribing SalI cut pfhh#4 with T7 RNA polymerase. An antisense rat vhh-1 RNA probe was generated by transcribing Bam HI cut pRvhh-1#7 (Roelink et al., 1994) with T3 RNA polymerase. Hybridization of embryos at different stages with the rat vhh-1 antisense probe did not reveal the pattern of expression of frog vhh-1 mRNA showing that the frog and rat probes do not cross-hybridize. An antisense Pintallavis RNA probe was generated by transcribing HindIII cut of5 (Ruiz i Altaba and Jessell, 1992) with T7 RNA polymerase. An antisense goosecoid RNA probe was generated by transcribing an EcoRI cut 0.9 Kb PCR clone derived from stage 10 dorsal lip cDNA with T7 RNA polymerase.

Immunochemistry

Whole-mount antibody labelling was performed as described by Dent et al. (1989) and Patel et al. (1989). Embryos were fixed for ~20 min. in MEMFA and bleached in 10% $H_2O_2$ in methanol overnight under fluorescent light at 4° C. Embryos were gradually trasferred to PBS, washed extensively in PBS plus 0.1% Triton X-100 (PBT) and blocked in PBT plus 10% heat-inactivated goat serum a room temperature for ~1 h. Primary antibody incubation was carried out at 4° C. overnight on a nutator (Adams). After four to five 30 min. washes in PBT at room temperature, embryos were incubated with goat anti-rabbit secondary antibodies coupled to horseradish peroxidase (1/100; Boehringer Mannheim) and reacted for 2 h. at room temperature on a nutator. Embryos were then washed at least five times, for a total of 2–3 h, and reacted with $H_2O_2$ in the presence of diaminobenzidine. Embryos were dehydrated and cleared in benzyl alcohol/benzy benzoate (1/2) before viewing with an axiophot (Zeiss) microscope under Nomarski optics.

Rabbit anti-HNF-3β antibodies were generated by immunizing female New Zealand white rabbits with a 30 amino acid peptide corresponding to the amino terminal end of the frog HNF-3β protein (Ruiz i Altaba et al., 1993b) containing a C-terminal cysteine coupled to activated keyhole limpet hemocyanin (Pierce).

References of the Fourth Series of Experiments

Ang, S.-L., Wierda, A., Wong, D., Stevens, K. A., Cascio, S. Roassant, J. and Zaret, K. S. 1993. The formation and maintenance of the definitive endoderm lineage in the mouse: involvement of HNF-3/fork head proteins. *Development* 119, 1301–1315.

Ang, S.-L. and Rossant J. 1994. HNF-3β is essential for node and notochord formation in mouse develoment. *Cell* 78, 561–574.

Artinger, K. B. and Bronner-Fraser, M. 1993. Delayed formation of the floor plate after ablation of the avian notochord. *Neuron* 11, 1147–1161.

Bolce, M., Hemmati-Brivanlou, A., and Harland, R. 1993. XFKH2, a Xenopus HNF-3α homologue exhibits both activin-inducible and autonomous phases of expression in early embryos. *Dev. Biol.* 160: 413–423.

Bovolenta, P. and Dodd, J. 1991. Perturbation of neuronal differentiation and axon guidance in the spinal cord of mouse embryos lacking a floor plate: analysis of Danforth's short-tail mutation. *Devlopment* 113, 625–639.

Bradley, L. C., Snape, A., Bhatt S., and Wilkinson, D. G. 1992. The structure and expression of the Xenopus Krox-20 gene: conserved and divergent patterns of expression in rhombomeres and neural crest. *Mech. Dev.* 40, 73–84.

Cho, K. W. Y., Blumberg, B., Steinbeisser, H., and De Robertis, E. M. 1991. Molecular nature of Spemann's Organizer: the role of the Xenopus homeobox gene goosecoid. *Cell* 67: 1111–1120.

Clark, K. L., Halay, E. D., Lai, E., and Burley, S. K. 1993. Co-crystal structure of the HNF-3/fork head DNA-recognition motif resembles histone H5. *Nature* 364: 412–420.

Clarke, J. D. N., Holder, N., Soffe, S. R., and Storm-Mathisen, J. 1991. Neuroanatomical and functional analysis of neural tube formation in notochordless Xenopus embryos: laterality of the spinal cord is lost *development* 112: 499–516.

Dent, J. A., Polson, A. G., and Klymkowsky, M. W. 1989. A whole-mount immunocytochemical analysis of the expression of the intermediae filament vimentin in *Xenopus*. *Development* 105: 61–74.

Dirksen, M. L., and Jamrich, M. 1992. A novel, activin-inducible, blastopore lip-specific gene of Xenopus laevis contains a fork head DNA-bindina domain. *Genes Dev.* 6: 599–608.

Dixon, J., and Kintner, C. R. 1989. Cellular contacts required for neural induction in Xenopus embryos: evidence for two signals. *Development* 106: 749–757.

Echelard, Y., Epstein, D. J., St-Jacques, B., Shen, L., Mohler, J., McMahon, J. A., and McMahon, A. P. 1993. Sonic hedgehog, a member of a family of putative signaling molecules, is implicated in the regulation of CNS polarity. *Cell* 75: 1417–1430.

Ericson, J., Thor, S., Edlund, T., Jessell, T. M., and Yamada, T. 1992. Early stages of motor neuron differentiation revealed by expression of homeobox gene Islet-1 *Science* 256, 1555–1560.

Goulding, M., Lumsden, A., and P. Gruss. 1993. Signals from the notochord and floor plate regulate the region-specific expression of two Pax genes in the developing spinal cord. *Development* 117: 1001–1016.

Harland, R. 1991. In situ hybridization: an improved whole-mount method to Xenopus embryos. *Meth. in Cell Biol.* 36: 675–685.

Hatta, K., Kimmel, C. B., Ho, R. K., and Walker, C. 1991. The cyclops mutation blocks specification of the floor plate of the zebrafish central nervous system. *Nature* 350: 339–341.

Jessell, T. M. and Dodd, J. 1992. Floor plate-derived signals and the control of neural cell pattern in vertebrates. *Harvey Lectures.* 86, 67–128.

Kintner C. R. and Melton, D. A. 1987. Expression of the Xenopus N-CAM RNA in octoderm an early response to neural induction. *Development* 99: 311–325.

Klar, A., Baldassare, M. and Jessell, T. M. 1992. F-spondin: a gene expressed at high levels in the floor plate encodes a secreted protein that promotes neural cell adhesion and neurite extension. *Cell* 69: 95–110.

Knöckel S., Lef, J., Clement, J., Klocke, B., Hille, S., Koster, M., and Knöckel, W. 1992. Activin A induced expression of a fork head related gene in posterior chordamesoderm (notochord) of Xenopus laevis embryos. *Mech. Dev.* 38: 157–165.

Krauss, S., Concordet, J.-P., and Ingham, P. W. 1993. A functionally conserved homolog of the Drosophila segment polarity gene hh is expressed in tissues with polarizing activity in zebrafish embryos. *Cell* 75: 1431–1444.

Lai, E., Prezioso, V. R., Smith, E., Litvin, O., Costa, R. H., and Darnell, J. E. Jr. 1990. HNF-3α, a hepatocyte-enriched transcription factor of novel structure is regulated transcriptionally. *Genes Dev.* 4: 1427–1436.

Lai, E., Prezioso, V. R., Tao, W., Chen, W. S. and Darnell, J. E. Jr. 1991. Hepatocyte nuclear factor 3α belongs to a gene family that is homologous to the Drosophila homeotic gene fork head. *Genes Dev.* 5: 416–427.

Lumsden, A. and Keynes, R. 1989. Segmental patterns of neural development in the chick hindbrain. *Nature* 337: 424–428.

Monaghan, A. P., Kaestner, K. H., Grau, E., and Schutz, G. 1993. Postimplantation expression patterns indicate a role for the mouse fork head/HNF-3α, β, and γ genes in determination of the definitive endoderm, chordamesoderm, and neuroectoderm. *Development* 119: 567–578.

Nieuwkoop, P. D., and Faber, J. 1969. Normal Table of Xenopus laevis (Daudin). North Holland, Amsterdam.

Pani, L., Qian, X., Clevidence, D., and Costa, R. H. 1992. The restricted promoter activity of the liver transcription factor hepatocyte nuclear factor 3β involves a cell-specific factor and positive autoactivation. *Mol. Cell. Biol.* 12: 552–562.

Patel, N. H., Martin-Blanco, E., Coleman, K. G., Poole, S. J., Ellis, M. C., Kornberg, T. B., and Goodman, C. S. 1989. Expression of engrailed proteins in arthropods, anelids and chordates. *Cell* 58: 955–968.

Placzek, M., Tessier-Lavigne, M., Yamada, T., Jessell, T. M., and Dodd, J. 1990. Mesodermal control of neural cell identity: floor plate induction by the notochord. *Science* 250: 985–988.

Placzek, M., Jessell, T. M. and Dodd, J. 1993. Induction of floor plate differentiation by contact-dependent, homeogenetic signals. *Development* 117: 205–218.

Riddle, R. D., Johnson, R. L., Laufer, E., and Tabin, C. 1993. Sonic hedgehog mediates the polarizing activity of ZPA. *Cell* 75: 1401–1416.

Roelink, H., Augsburger, A., Heemskerk, J., Korzh, V., Norlin, S., Ruiz i Altaba, A., Tanabe, Y., Placzek, M., Edlund, T., Jessell, T. M., and Dodd, J. 1994. Floor plate and motor neuron induction by vhh-1, a vertebrate homolog of hedgehog expressed by the notochord *Cell* 75: 761–775.

Ruiz i Altaba, A. 1992. Plannar and vertical signal in the induction and patterning of the Xenopus nervous system. *Development* 115: 67–80.

Ruiz i Altaba, A. 1993. In Essential Developmental Biology—A Practical Approach, C. Stern and P. W. H. Holland, Eds. IRL Press, Oxford.

Ruiz i Altaba, A. 1994. Pattern formation in the vertebrate neural plate. *Trends in Neurosci.* 17: 233–243.

Ruiz i Altaba, A., Cox, C., Jessell, T. M., and Klar, A. 1993a. Ectopic neural expression of floor plate marker in frog embryos injected with the midline transcription factor Pintallavis. *Proc. Natl. Acad. Sci. USA* 90: 8268–8272.

Ruiz i Altaba, A., and Jessell, T. M. 1992. Pintallavis, a gene expressed in the organizer and midline cells of frog embryos: involvement in the development of the neural axis. *Development* 116: 81–93.

Ruiz i Altaba, A., and Jessell, T. M. 1993. Midline cells and the organization of the vertebrate neuraxis. *Curr. Opin. Genet. Dev.* 3: 633–640.

Ruiz i Altaba, A., Prezioso, V. R., Darnell, J. E., and Jessell, T. M. 1993b. Sequential expression of HNF-3α and HNF-3β by embryonic organizing centers: the dorsal lip/node, notochord, and floor plate. *Mechanisms of Development* 44: 91–108.

Ruiz i Altaba, A., Placzek, M., Baldassare, M., Dodd, J. and Jessell, T. M. (1995). Early stages of notochord and floor plate development in the chick embryo defined by normal and induced expression of HNF-3β (Submitted).

Sasaki, H., and Hogan, B. L. M. 1993. Differential expression of multiple fork head related genes during gastrulation and axial pattern formation in the mouse embryo. *Development* 118: 47–59.

Sasaki, H., and Hogan, B. L. M. 1994. HNF-3β as a regulator of floor plate development. *Cell* 76: 103–115.

Schroeder, T. E. 1970. Neurulation in Xenopus laevis. An analysis and model based upon light and electron microscopy. *J. Embryol. Exp. Morph.* 23: 427–462.

Smith, J.c., Price, B. M. J., Greenm J. B. A, Weigel, D. and Herrmauu, B. G. 1991. Expression of a Xenopus homolog of Brachyury (T) is an immediate-early response to mesoderm induction. *Cell* 67: 79–87.

Strahle, U., Blader, P., Henrique, D., and Ingham, P. W. 1993. Axial, a zebrafish gene expressed along the developing body axis, shows altered expression in cyclops mutant embryos. *Genes and Dev.* 7: 1436–1446.

Taria, M., Jamrich, M., Good, P. J. and Dawid, I. B. 1992. The LIM domain-containing homeobox gene XLim-1 is expressed specifically in the organizer region of Xenopus gastrula embryos. *Genes Dev.* 6: 356–366.

van Straaten, H. W. M., Hekking, J. W. M., Wiertz-Hoessels, E. L., Thors, F., and Drukker, J. 1988. Effects of the notochord on the differentiation of the floor plate area in the neural tube of the chick embryo. *Anat. Embryol.* 177: 317–324.

van Straaten, H. W. M., and Hekking, J. W. M. 1991. Development of a floor plate, neurons and axonal outgrowth pattern in the early spinal cord of the notochord-deficient chick embryo. *Anat. Embryol.* 184: 55–63.

von Dassow, G., Schmidt, J. E. and Kimelman, D. 1993. Induction of the Xenopus organizer. Expression and regulation of Xnot, a novel FGF and activin-regulated homeobox gene. *Genes Dev.* 7: 355–366.

Wagner, M., Thaller, C., Jessell, T. M., and Eichele, G. 1990. Polarizing activity and retinoid synthesis in the floor plate of the neural tube. *Nature* 345: 819–822.

Weigel, D. and Jackle, H. 1990. The fork head domain: a novel DNA-binding motif of eukaryotic transcription factors? *Cell* 63: 455–456.

Weinstein, D. C., Ruiz i Altaba, A., chen, W. S., Hoodless, P., Prezioso, V. R., Jessell, T. M., and Darnell, J. E. Jr. 1994. The winged-helix transcription factor HNF-3β is required for notochord development in the mouse embryo. *Cell* 78, 575–588.

Winning, R. S., and Sargent, T. D. 1994. Pagliaccio, a member of the Eph family of receptor tyrosine kinase genes, has localized expression in a subset of neural crest and neural tube tussues in *Xenopus laevis* embryos. *Dev.* 46: 219–229.

Yamada, T., Placzek, M., Tanaka, H., Dodd J., and Jessell, T. M. 1991. Control of cell pattern in the developing nervous system: polarizing activity of the floor plate and notochord. *Cell* 64: 635–647.

Yamada, T., Pfaff, S. L., Edlund, T., and Jessell, T. M. 1993. Control of cell pattern in the neural tube: motor neuron induction by diffusible factors from notochord and floor plate. *Cell* 73: 673–686.

What is claimed is:

1. An isolated nucleic acid, the nucleotide sequence of which comprises nucleotides which correspond to codons which encode a protein, the amino acid sequence of which protein is set forth in SEQ ID NO: 2.

2. The isolated nucleic acid of claim 1, wherein the nucleic acid is cDNA.

3. The isolated nucleic acid of claim 1, wherein the nucleic acid is mRNA.

4. An isolated nucleic acid comprising nucleotides, the nucleotide sequence of which is set forth in SEQ ID NO: 1.

5. A replicable vector which comprises an isolated nucleic acid, the nucleotide sequence of which nucleic acid comprises nucleotides which correspond to codons which encode a protein, the amino acid sequence of which protein is set forth in SEQ ID NO: 2.

6. The vector of claim 5, wherein the vector is a plasmid.

7. The vector of claim 6, wherein the plasmid is designated pMT21 2hh #7 (ATCC Accession No. 75686).

8. The vector of claim 5, wherein the plasmid is designated CMV vhh #7 (ATCC Accession No. 75685).

9. A method of producing a protein which comprises:

a. introducing a replicable vector which comprises an isolated nucleic acid, the nucleotide sequence of which nucleic acid comprises nucleotides which correspond to codons which encode a protein, the amino acid sequence of which protein is set forth in SEQ ID NO: 2 into a suitable host cell;

b. growing the host cell under suitable conditions permitting production of the protein; and c. recovering the protein so produced, so as to thereby produce the protein.

10. The method of claim 9, wherein the host cell is a mammalian cell.

11. The method of claim 9, wherein the host cell is a Cos cell.

12. An isolated nucleic acid, the nucleotide sequence of which is complementary to the entire sequence of a nucleic acid whose nucleotide sequence comprises nucleotides which correspond to codons which encode a protein, the amino acid sequence of which protein is set forth in SEQ ID NO: 2.

* * * * *